United States Patent
Huang et al.

(10) Patent No.: US 12,378,278 B2
(45) Date of Patent: Aug. 5, 2025

(54) MIMETICS OF HEPARIN OLIGOSACCHARIDES

(71) Applicant: Board of Trustees of Michigan State University, East Lansing, MI (US)

(72) Inventors: Xuefei Huang, Okemos, MI (US); Jicheng Zhang, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 811 days.

(21) Appl. No.: 17/761,857

(22) PCT Filed: Sep. 21, 2020

(86) PCT No.: PCT/US2020/051775
§ 371 (c)(1),
(2) Date: Mar. 18, 2022

(87) PCT Pub. No.: WO2021/055933
PCT Pub. Date: Mar. 25, 2021

(65) Prior Publication Data
US 2023/0012702 A1     Jan. 19, 2023

Related U.S. Application Data

(60) Provisional application No. 62/968,062, filed on Jan. 30, 2020, provisional application No. 62/903,432, filed on Sep. 20, 2019.

(51) Int. Cl.
| | | |
|---|---|---|
| C07H 15/04 | (2006.01) | |
| C07H 1/00 | (2006.01) | |
| C07H 15/203 | (2006.01) | |
| C08B 37/00 | (2006.01) | |

(52) U.S. Cl.
CPC .............. *C07H 15/04* (2013.01); *C07H 1/00* (2013.01); *C07H 15/203* (2013.01); *C08B 37/0075* (2013.01)

(58) Field of Classification Search
CPC ................................................ C08B 37/0075
See application file for complete search history.

(56) References Cited

U.S. PATENT DOCUMENTS

2015/0038455 A1    2/2015   Sheng et al.

FOREIGN PATENT DOCUMENTS

| WO | WO-2009/046314 A2 | 4/2009 |
| WO | WO-2021/055933 A1 | 3/2021 |

OTHER PUBLICATIONS

Dulaney, S. et al., Journal of Organic Chemistry, "Divergent Synthesis of Heparan Sulfate Oligosaccharides", 2015, vol. 80, pp. 12265-12279 (Year: 2015).*
Miller, G. et al., Organic & Biomolecular Chemistry, "A latent reactive handle for functionalizing heparin-like and LMWH deca- and dodecasaccharides", 2015, vol. 13, pp. 11208-11219 (Year: 2015).*
Dulaney et al., "Chapter 3—Strategies in Synthesis of Heparin/Heparan Sulfate Oligosaccharides: 2000-Present," Advances in Carbohydrate Chemistry and Biochemistry, 67: 95-136 (2012).
International Preliminary Report on Patentability for International Application No. PCT/US2020/051775 mailed Mar. 31, 2022.
International Search Report and Written Opinion for International Application No. PCT/US20/51775 mailed Feb. 2, 2021.
Kanno et al., "Synthesis of Glycosaminoglycan-Like Copolysaccharide Derivative. The System of Anhydroglucosamine Monomer and Carboxyl-Containing Monomer Has a Tendency to Alternate," Polymer Journal, 29(9): 773-774 (1997).
Maza et al., "Synthesis of amine-functionalized heparin oligosaccharides for the investigation of carbohydrate-protein interactions in microtiter plates," Organic & Biomolecular Chemistry, 10: 2146-2163 (2012).
Tiruchinapally et al., "Divergent Heparin Oligosaccharide Synthesis with Preinstalled Sulfate Esters," Chemistry, 17(36): 10106-10112 (2011).

* cited by examiner

*Primary Examiner* — Bahar Craigo
(74) *Attorney, Agent, or Firm* — Foley Hoag LLP; DeAnn F. Smith

(57) ABSTRACT

The present disclosure relates to disaccharides with defined sulfation patterns, and oligosaccharide mimetics comprising the disaccharides as repeating units linked in a head to tail fashion. The present disclosure further relates to methods of making the same, and to methods of using the same to mediate cell proliferation, cell differentiation, amyloid plaque formation, anti-coagulation, and neuronal growth.

16 Claims, 8 Drawing Sheets

MIMETICS OF HEPARIN OLIGOSACCHARIDES

CROSS-REFERENCE TO RELATED APPLICATIONS

This application is a National Stage Entry of International Patent Application No. PCT/US20/51775, filed Sep. 21, 2020, which claims the benefit of U.S. Provisional Application No. 62/903,432, filed Sep. 20, 2019, and U.S. Provisional Application No. 62/968,062, filed Jan. 30, 2020, the contents of each of which are incorporated herein by reference in their entirety.

STATEMENT REGARDING FEDERALLY SPONSORED RESEARCH

This invention was made with government support under GM072667 and GM116262 awarded by the National Institutes of Health. The government has certain rights in the invention.

BACKGROUND OF THE INVENTION

Heparin and heparan, a heterogeneously sulfated glycosaminoglycan (GAG), consists of α-1,4-linked glucosamine (GlcN) and uronic acid [either D-glucuronic acid (GlcA) or L-iduronic acid (IdoA)] disaccharide repeating units. It has been used as an anticoagulant drug for over 80 years. In addition, it plays significant roles in various biological processes such as inflammation, growth factor regulation, bacterial and viral infection, cell adhesion, cell growth, tumor metastasis, lipid metabolism and diseases of the nervous system. However, the complex heterogeneity of natural heparin polysaccharides has hindered efforts to understand the relationship between their diverse structures and biological functions. While chemical and enzymatic syntheses of heparin oligosaccharides have seen tremendous advances in recent years, it is still challenging to prepare heparin analogs approaching the length of polysaccharides with distinct backbone structures and sulfation patterns. Thus, there is a need for novel heparin analogs and methods to prepare them.

SUMMARY OF THE INVENTION

The invention disclosed herein is based, in part, on the novel discovery of heparin and heparan sulfate mimetics that can be used to mimic the functions of native heparin and heparan sulfate, and the discovery of synthetic methodology to access such mimetics.

In some aspects, the present invention is directed to compounds of Formula (I) or a pharmaceutically acceptable salt thereof:

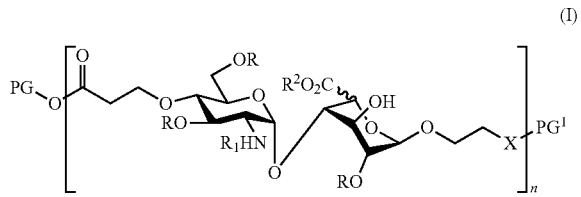

(I)

wherein:
n is an integer from 1 to 40;
R is H, $SO_3H$, or $SO_3^-$;
$R_1$ is $SO_3H$, $SO_3^-$, or $-C(O)CH_3$;
$R^2$ is $C_{1-6}$ alkyl, H, or is a negative charge;
X is NH, S, or O;
$PG^1$ is H, Fmoc, $-C(O)CH_3$, $-C(O)CF3$, and Boc;
PG is H, $C_{1-6}$ alkyl, allyl or benzyl.

In some aspects, the present invention is directed to a pharmaceutical composition comprising a compound of the invention.

In other aspects, the present invention is directed to a method of mediating cell proliferation, cell differentiation, amyloid plaque formation, anti-coagulation, or neuronal growth in a subject in need thereof, comprising administering to the subject a therapeutically effective amount of a compound of the invention.

In other aspects, the present invention is directed to a method of enhancing FGF-2 binding to FGF-R, the method comprising contacting a cell containing FGF-2 and FGF-R with a compound of the invention.

In other aspects, the present invention is directed to a method of stimulating cell proliferation, the method comprising contacting a cell with a compound of the invention.

In other aspects, the present invention is directed to a method of inhibiting blood coagulation, the method comprising contacting a blood sample with a compound of the invention.

In other aspects, the present invention is directed to heparin mimetic comprising a compound of the invention or a pharmaceutically acceptable salt thereof.

In other aspects, the present invention is directed to heparan mimetic comprising a compound of the invention or a pharmaceutically acceptable salt thereof.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2A: heparin as the inhibitor. Concentrations from top to bottom: 0, 3.2, 6.5, 13.1, 26.1, 51.7, 77.8 nM. FIG. 2B: compound 50k. Concentrations from top to bottom: 0, 12.5, 25, 50, 100, 500, 1000 uM. FIG. 2C: fondaparinux. Concentrations from top to bottom: 0, 1.0, 10.0, 25, 50, 1000, 2000 uM.

FIG. 3A: Compound 50. FIG. 3B: Compound 50z. FIG. 3C: Compound 50m.

DETAILED DESCRIPTION OF THE INVENTION

Figure 1:
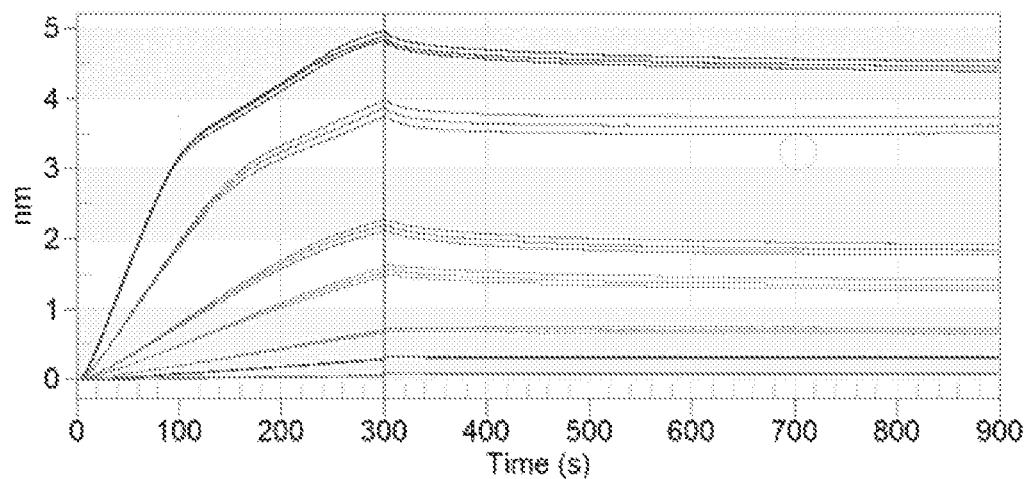
FIG. 1 shows a sensorgram of heparin-FGF-2 interaction as described in Example 3.

In some aspects, the present invention is directed to compounds of Formula (I) or a pharmaceutically acceptable salt thereof:

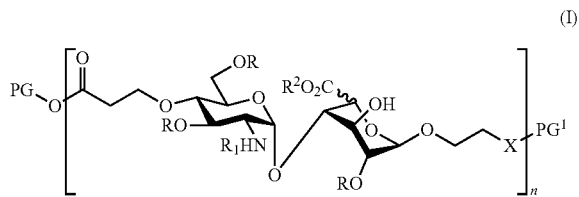
(I)

wherein, independently at each occurrence:
n is an integer from 1 to 40;
R is H, $SO_3H$, or $SO_3^-$;
$R_1$ is $SO_3H$, $SO_3^-$, or —$C(O)CH_3$;
$R^2$ is $C_{1-6}$ alkyl, H, or is a negative charge;
X is NH, S, or O;
$PG^1$ is H, Fmoc, —$C(O)CH_3$, —$C(O)CF3$, and Boc;
PG is H, $C_{1-6}$ alkyl, allyl or benzyl.

In certain embodiments, PG is $C_{1-6}$ alkyl, such as methyl; X is NH; and $PG^1$ is H.

In certain embodiments, R is H and $R_1$ is $SO_3$— or $SO_3H$.

In certain embodiments, R is $SO_3$— or $SO_3H$, and $R_1$ is —$C(O)CH_3$.

In certain embodiments, R is $SO_3$— or $SO_3H$ and $R_1$ is $SO_3$— or $SO_3H$.

In certain embodiments, PG is H; X is NH; and $PG^1$ is Fmoc.

In certain embodiments, R is H and $R_1$ is $SO_3$— or $SO_3H$.

In certain embodiments, R is $SO_3$— or $SO_3H$, and $R_1$ is —$C(O)CH_3$.

In certain embodiments, R is $SO_3$— or $SO_3H$ and $R_1$ is $SO_3$— or $SO_3H$.

In certain embodiments, PG is H; X is NH; and $PG^1$ is acetyl.

In certain embodiments, R is H and $R_1$ is $SO_3$— or $SO_3H$.

In certain embodiments, R is $SO_3$— or $SO_3H$, and $R_1$ is acetyl.

In certain embodiments, R is $SO_3$— or $SO_3H$ and $R_1$ is $SO_3$— or $SO_3H$.

In certain embodiments, n is 1-20. In some such embodiments, n is 1-10, such as n is 1, 2, 3, 10, or 20. In certain preferred embodiments, n is 1. In other preferred embodiments, n is 2. In still other preferred embodiments, n is 3. In some such embodiments, the compound

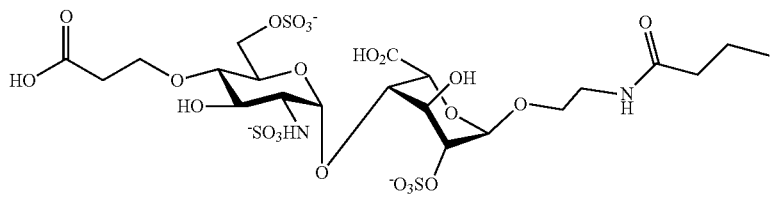
19b

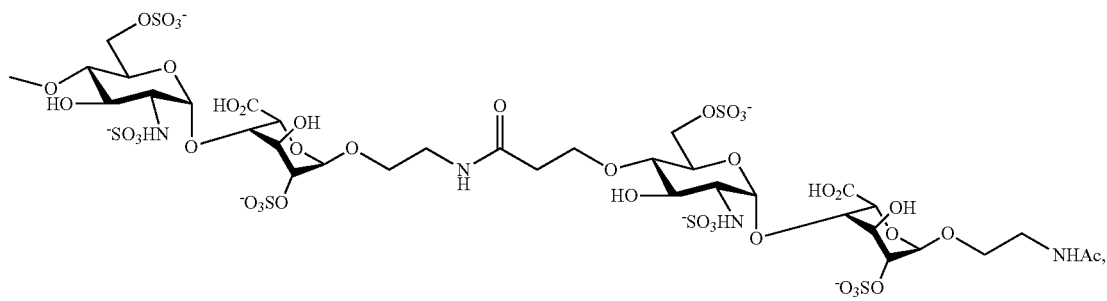

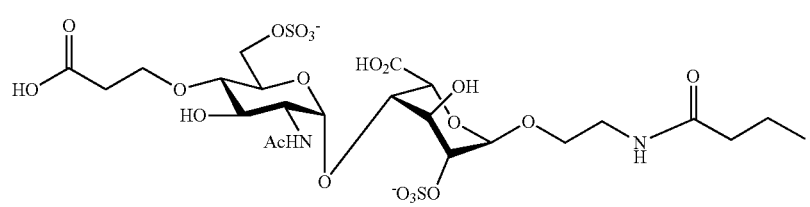
19y

-continued

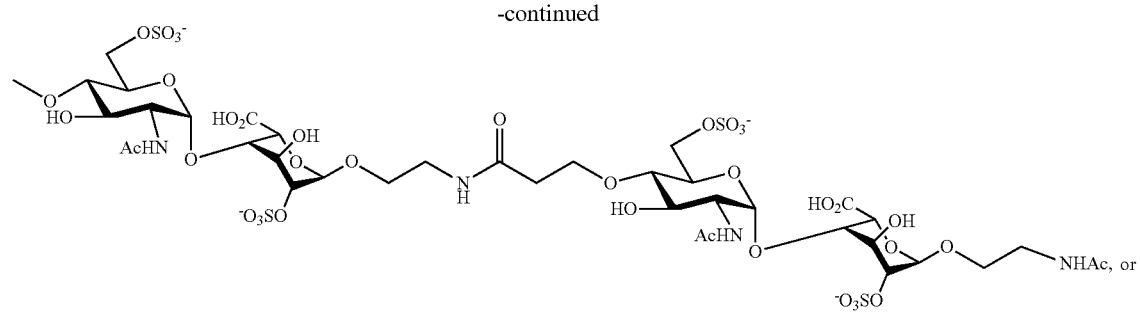

191

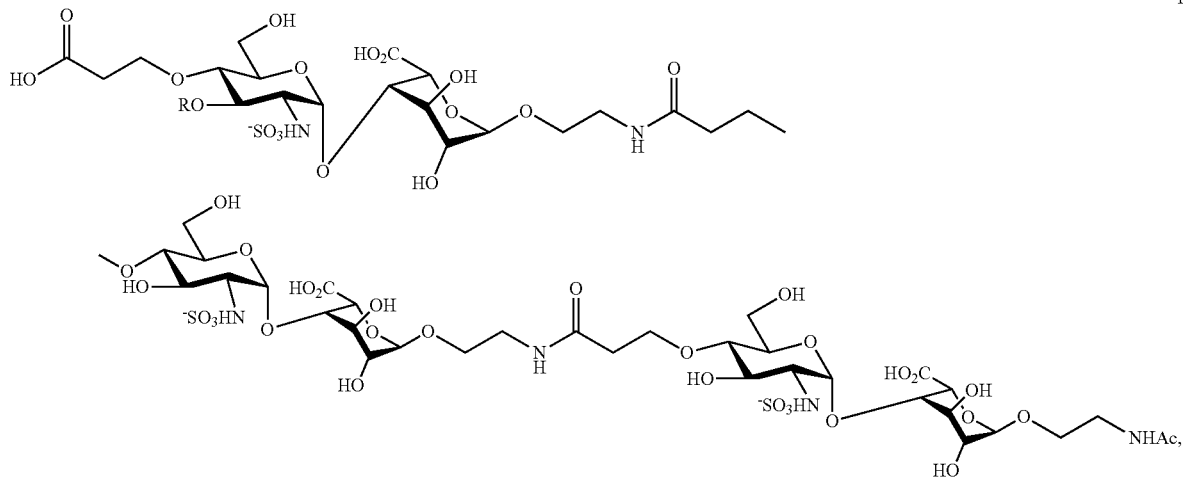

or a pharmaceutically acceptable salt thereof.

In other aspects, the present invention is directed to pharmaceutical compositions comprising a compound as described herein and a pharmaceutically acceptable excipient.

In still other aspects, the present invention is directed to methods of mediating cell proliferation, cell differentiation, amyloid plaque formation, anti-coagulation, or neuronal growth in a subject in need thereof, comprising administering to the subject a therapeutically effective amount of a compound as described herein.

In still other aspects, the present invention is directed to methods of enhancing FGF-2 binding to FGF-R, the methods comprising contacting a cell containing FGF-2 and FGF-R with a compound as described herein.

In still other aspects, the present invention is directed to methods of stimulating cell proliferation, the methods comprising contacting a cell with a compound as described herein.

In still other aspects, the present invention is directed to methods of inhibiting blood coagulation, the methods comprising the step of contacting a blood sample with a compound as described herein. In certain embodiments, the step of contacting the blood sample with the compound comprises administering to a subject in need of inhibiting blood coagulation a therapeutically effective amount of the compound.

In still other aspects, the present invention is directed to a heparin mimetic comprising a compound as described herein or a pharmaceutically acceptable salt thereof.

In still other aspects, the present invention is directed to a heparan mimetic comprising a compound as described herein or a pharmaceutically acceptable salt thereof.

In still other aspects, the present invention is directed to a method of synthesizing a compound of formula 34

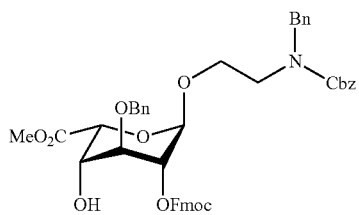

34 the method comprising:

(i) treating a compound of formula 32

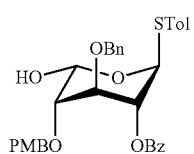

32 with TEMPO and BAIB in a first solvent, to provide a first product mixture;

(ii) treating the first product mixture with potassium carbonate and methyl iodide in a second solvent, to provide a second product mixture comprising a compound of formula 33

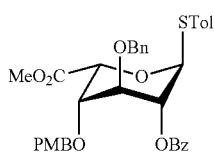

33

(iii) treating the compound of formula 33 with silver triflate, p-toluenesulfonyl chloride, and

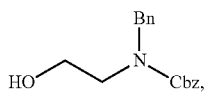

at a temperature from −78° C. to 0° C., to provide a third product mixture;

(iv) treating the third product mixture with NaOMe in a third solvent to provide a fourth product mixture;

(v) treating the fourth product mixture with FmocCl and pyridine in a fourth solvent, to provide a fifth product mixture; and (vi) treating the fifth product mixture with DDQ in a fifth solvent to afford a sixth product mixture comprising the compound of formula 34.

In certain embodiments, the method further comprises isolating the compound of formula 33 from the second product mixture, thereby obtaining substantially pure

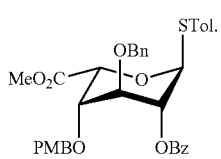

33

In certain embodiments, the method further comprises isolating the compound of formula 34 from the sixth product mixture, thereby obtaining substantially pure

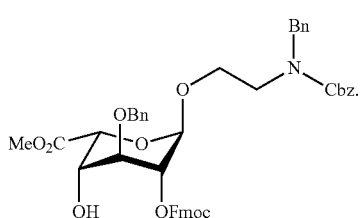

34

In certain embodiments, the first, second, third, fourth, and fifth solvents are each independently selected from dichloromethane, water, N,N-dimethylformamide (DMF), methanol, and mixtures thereof.

In still other aspects, the present invention is directed to a method of synthesizing a compound of formula 35

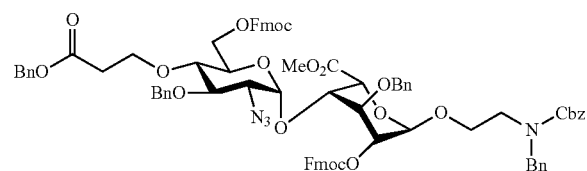

35 the method comprising:

treating a compound of formula 31

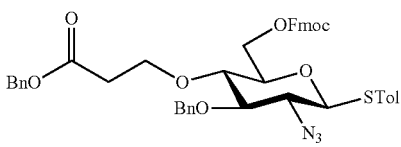

31 with a compound of formula 34

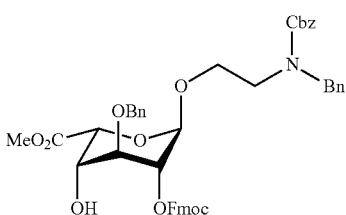

34 in the presence of silver triflate and p-toluenesulfonyl chloride, at a temperature from −78° C. to 0° C., to provide the compound of formula 35.

In certain embodiments, the method further comprises treating the compound of formula 35 under conditions for Fmoc deprotection and azide reduction, to provide a compound of formula 36

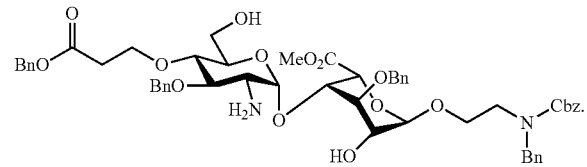

36

In certain embodiments, the treating the compound of formula 35 under the conditions for Fmoc deprotection and azide reduction comprises treating the compound of formula 35 with 1,3-propanedithiol and triethylamine in a sixth solvent. In certain embodiments, the sixth solvent comprises pyridine, water, or a mixture thereof.

In still other aspects, the present invention is directed to a method of making a compound of formula (Ia)

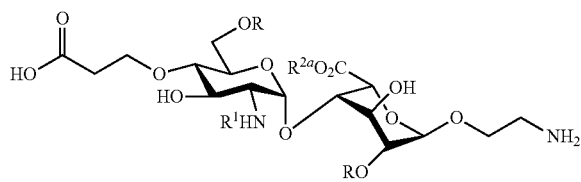

(Ia)

wherein, independently at each occurrence:

R is H, SO$_3$H, or SO$_3^-$;

R$^1$ is SO$_3$H, SO$_3^-$, or C(O)CH$_3$;

R$^{2a}$ is C$_{1-6}$ alkyl;

the method comprising:

(i) treating a compound of formula 36

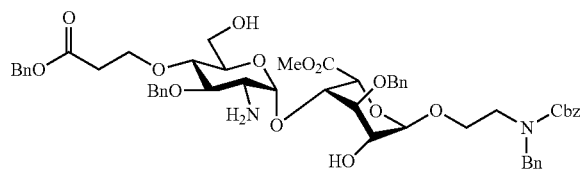

36 under sulfation conditions, to provide a seventh product mixture; and (ii) treating the seventh product mixture under deprotection conditions to afford an eighth product mixture comprising the compound of formula (Ia).

In certain embodiments, the treating with sulfation conditions comprises treating the compound of formula 36 with SO$_3$·NEt$_3$ and NaHCO$_3$ in a seventh solvent (such as water, tetrahydrofuran, or a mixture thereof), and the seventh product mixture comprises a compound of formula 37

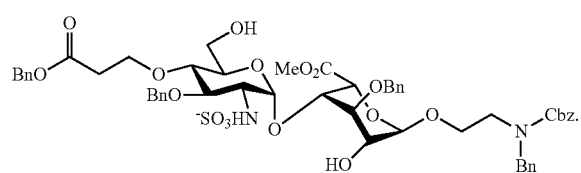

37

In certain embodiments, the treating with sulfation conditions comprises:

(ia) treating the compound of formula 36 with acetic anhydride in an eighth solvent (such as methanol, DMF, or a mixture thereof) to afford a ninth product mixture; and (ib) treating the ninth product mixture with SO$_3$·NEt$_3$ and NaHCO$_3$ in a ninth solvent (such as DMF);

and wherein the seventh product mixture comprises a compound of formula 38

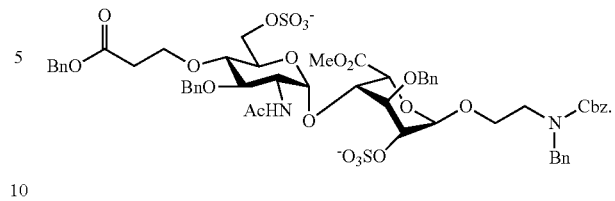

38

In certain embodiments, the treating the compound of formula 36 under sulfation conditions comprises:

(ic) treating the compound of formula 36 with SO$_3$·NEt$_3$ to afford a tenth product mixture; and (id) treating the tenth product mixture with SO$_3$·pyridine in a tenth solvent;

and wherein the seventh product mixture comprises a compound of formula 39

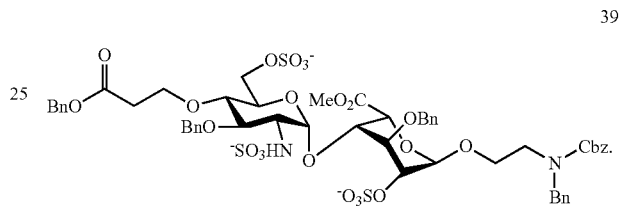

39

In certain embodiments, the tenth solvent comprises pyridine, triethylamine, or a mixture thereof.

In certain embodiments, the treatment under deprotection conditions comprises treatment with (Pd(OH)$_2$/C in an eleventh solvent. In certain embodiments, the eleventh solvent comprises water, tert-butanol, or a mixture thereof.

In certain embodiments, the compound of formula (Ia) is selected from

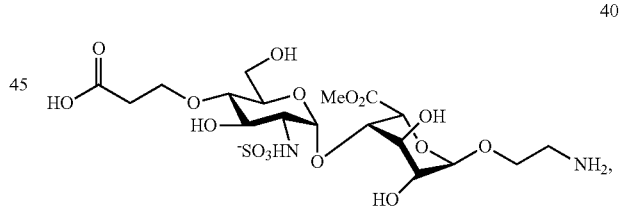

40

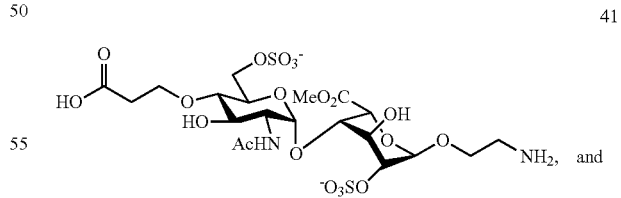

41 and

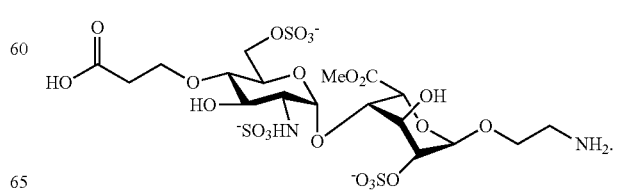

42

In certain embodiments, the method further comprises:
(iii) reaction of the compound of formula (Ia) under protection conditions, to provide an eleventh product mixture comprising a compound of formula (Ib)

(Ib)

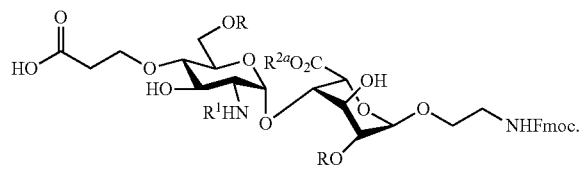

In certain embodiments, the reaction under protection conditions comprises treatment with Fmoc-OSu and DIPEA, in the presence of water and DMF.

In certain embodiments, the compound of formula (Ib) is selected from 43
44
45

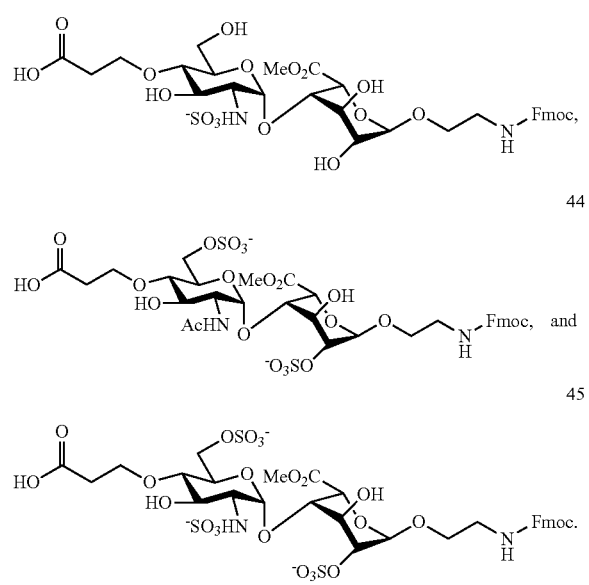

(Ic)

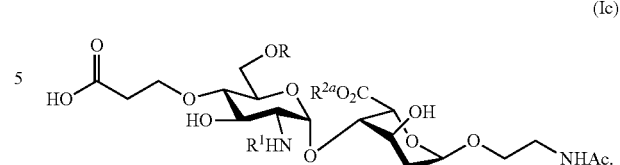

In certain embodiments, the treatment under acetylation conditions comprises treating the compound of formula (Ia) with acetic anhydride in methanol.

In certain embodiments, the compound of formula (Ic) is selected from 46
47
48

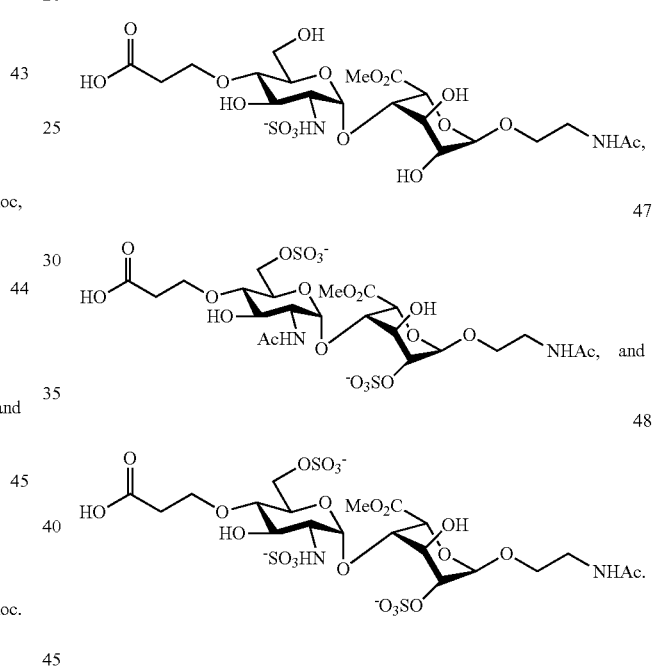

In still other aspects, the present invention is directed to a method of synthesizing a compound of formula (Id)

(Id)

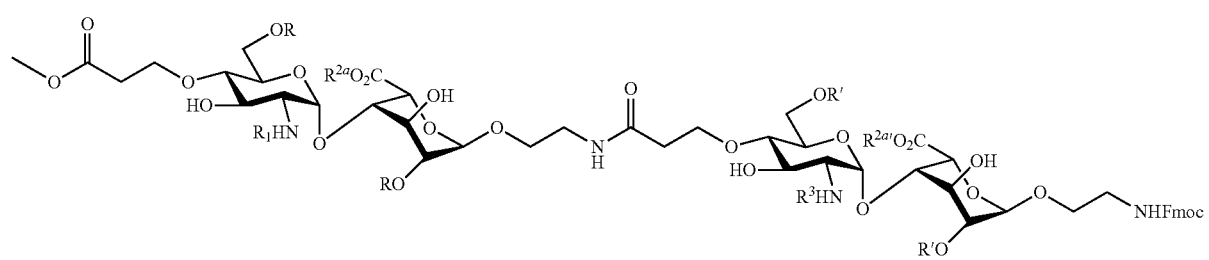

In certain embodiments, the method further comprises:
(iv) reacting the compound of formula (Ia) under acetylation conditions to afford a twelfth product mixture comprising a compound of formula (Ic):

wherein, independently at each occurrence:
R is H, $SO_3H$, or $SO_3^-$;
R' is H, $SO_3H$, or $SO_3^-$;
$R^1$ is $SO_3H$, $SO_3^-$, or $C(O)CH_3$;
$R^3$ is $SO_3H$, $SO_3^-$, or $C(O)CH_3$;

$R^{2a}$ is $C_{1-6}$ alkyl;
$R^{2a\prime}$ is $C_{1-6}$ alkyl;
the method comprising:
(v) reacting a compound of formula (Ib)

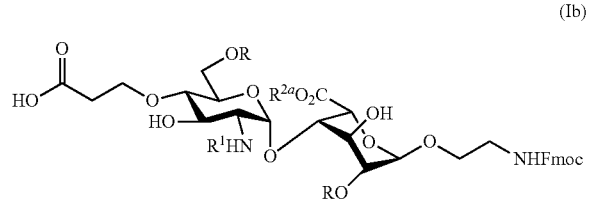

(Ib)

under esterification conditions to afford a thirteenth product mixture;
(vi) reacting the thirteenth product mixture under deprotection conditions, to afford a fourteenth product mixture; and
(vii) reacting the fourteenth product mixture with the compound of formula (Ib) under coupling conditions, to provide a fifteenth product mixture comprising the compound of formula (Id).

In certain embodiments, the reacting under esterification conditions comprises treatment with a methyl halide and a base in a twelfth solvent. In some such embodiments, the methyl halide is selected from methyl iodide, methyl bromide, and methyl chloride. In certain such embodiments, the methyl halide is methyl iodide. In certain embodiments, the base is potassium carbonate. In certain embodiments, the solvent is dimethylformamide (DMF).

In certain embodiments, deprotection conditions comprise DBU in a thirteenth solvent. In some such embodiments, the thirteenth solvent comprises DMF.

In certain embodiments, coupling conditions comprise HATU or HBTU, and DIPEA, in a fourteenth solvent. In some such embodiments, the fourteenth solvent comprises DMF.

In certain embodiments, the compound of formula (Id) is a compound of formula (Id')

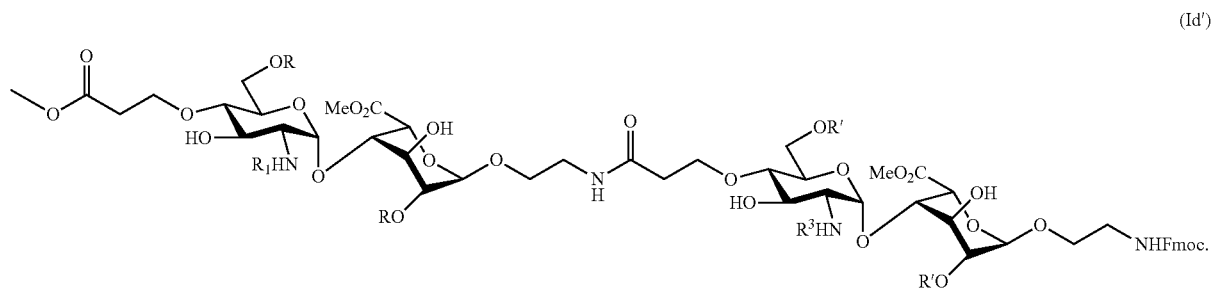

(Id')

In certain embodiments, the compound of formula (Id') is selected from the group consisting of:
49a (R, $R^1$, R', $R^3$=$SO_3^-$);
49b (R, $R^1$, $R^3$=$SO_3^-$; R'=H);
49c (R, $R^1$, R'=$SO_3^-$; $R^3$=C(O)CH$_3$);
49d (R=H; $R^1$, R', $R^{1\prime}$=$SO_3^-$);
49e (R, R'=H; $R^1$, $R^3$=$SO_3^-$);
49f (R=H; $R^1$, R'=$SO_3^-$, $R_3$=C(O)CH$_3$);
49g (R, R', $R^3$=$SO_3^-$; $R^1$=C(O)CH$_3$);
49h (R, $R^3$=$SO_3^-$; $R^1$=C(O)CH$_3$; R'=H); and
49i (R, R'=$SO_3^-$; $R^1$, $R^3$=C(O)CH$_3$).

In still other aspects, the present invention is directed to a method of making a compound of formula (If)

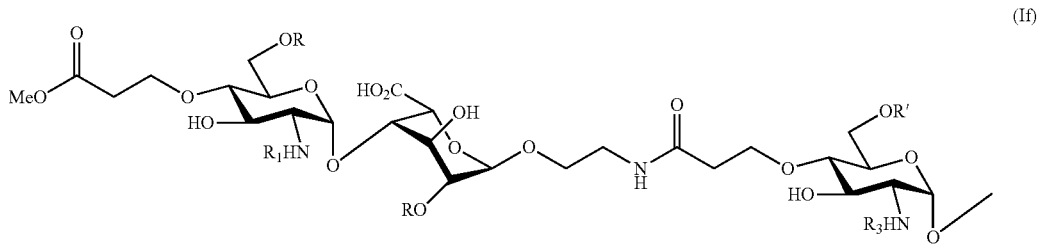

(If)

-continued

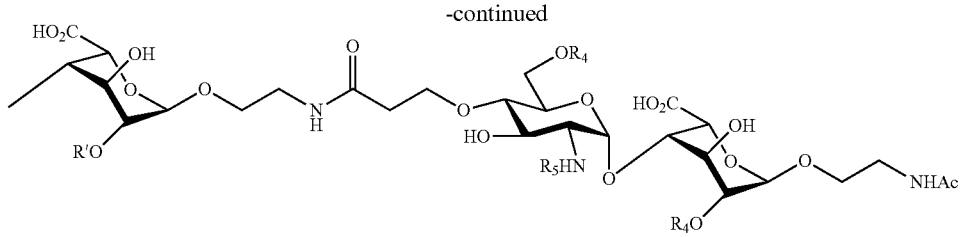

wherein, independently at each occurrence:
R is H, SO$_3$H, or SO$_3^-$;
R' is H, SO$_3$H, or SO$_3^-$;
R$^1$ is SO$_3$H, SO$_3^-$, or C(O)CH$_3$;
R$^3$ is SO$_3$H, SO$_3^-$, or C(O)CH$_3$;
the method comprising:
(viii) reacting a compound of formula (Id')

(Id')

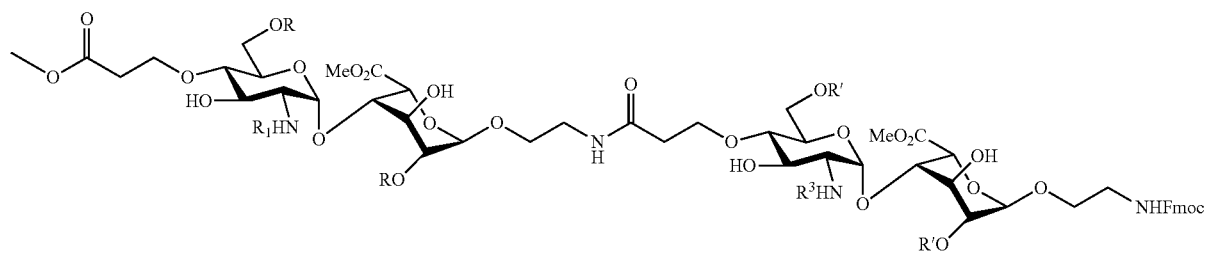

under deprotection conditions, to afford a sixteenth product mixture comprising a compound of formula (Ie)

(Ie)

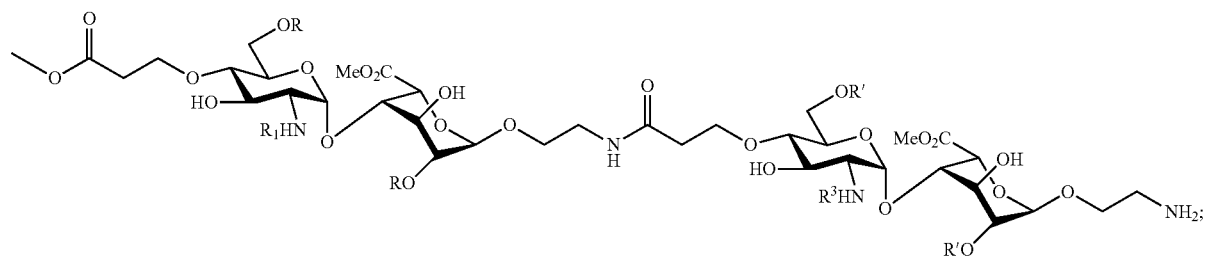

and
(ix) reacting the sixteenth product mixture with a compound of formula (Ic)

(Ic)

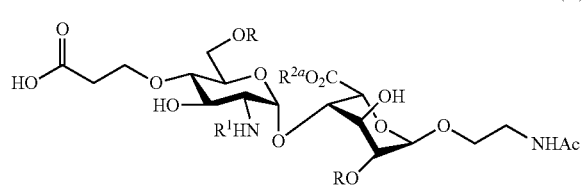

wherein R$^{2a}$ is Me,
under coupling conditions, to afford a seventeenth product mixture comprising the compound of formula (If).

In certain embodiments, deprotection conditions comprise DBU in a fifteenth solvent. In certain embodiments, the fifteenth solvent comprises DMF.

In certain embodiments, coupling conditions comprise HBTU and DIPEA in a sixteenth solvent. In certain embodiments, the sixteenth solvent comprises DMF.

In certain embodiments, the method further comprises:

(x) reacting the compound of formula (If) under saponification conditions, to provide an eighteenth product mixture comprising a compound of formula (Ig)

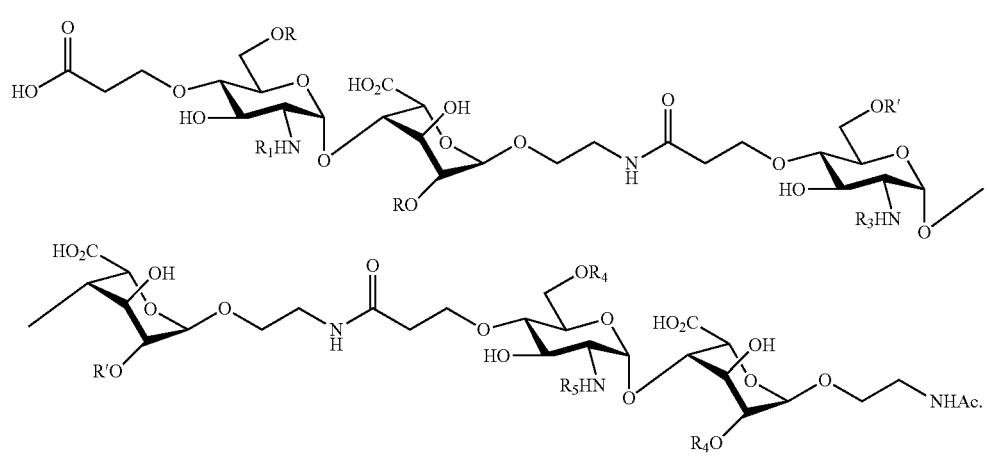

In certain embodiments, the method further comprises isolating the compound of formula (Ig) from the eighteenth product mixture, thereby obtaining substantially pure

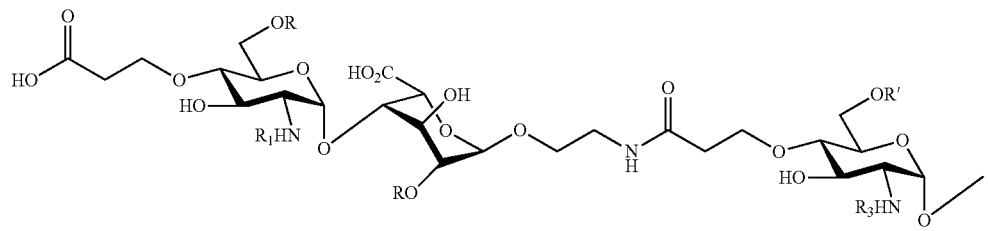

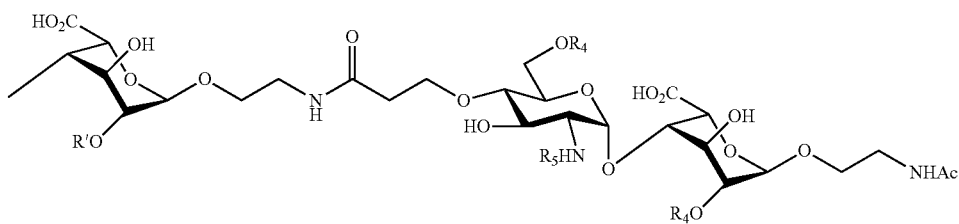

In certain embodiments, saponification conditions include lithium hydroxide.

In certain embodiments, the compound of formula (Ig) is selected from the group consisting of:

50 (R, $R_1$, R', $R_3$=$SO_3^-$; $R_4$, $R_5$=$SO_3^-$);
50a (R, $R_1$, R', $R_3$=$SO_3^-$; $R_4$=H; $R_5$=$SO_3^-$);
50b (R, $R_1$, R', $R_3$=$SO_3^-$; $R_4$=$SO_3^-$; $R_5$=Ac);
50c (R, $R_1$, $R_3$=$SO_3^-$; R'=H; $R_4$, $R_5$=$SO_3^-$);
50d (R, $R_1$, $R_3$=$SO_3^-$; R'=H; $R_4$=H; $R_5$=$SO_3^-$);
50e (R, $R_1$, $R_3$=$SO_3^-$; R'=H; $R_4$=$SO_3^-$; $R_5$=Ac);
50f (R, $R_1$, R'=$SO_3^-$; $R_3$=Ac, $R_4$, $R_5$=$SO_3^-$);
50g (R, $R_1$, R'=$SO_3^-$; $R_3$=Ac; $R_4$=H; $R_5$=$SO_3^-$);
50h (R, $R_1$, R'=$SO_3^-$; $R_3$=Ac; $R_4$=$SO_3^-$; $R_5$=Ac);
50i (R=H; $R_1$, R', $R_3$=$SO_3^-$; $R_4$, $R_5$=$SO_3^-$);
50j (R=H; $R_1$, R', $R_3$=$SO_3^-$; $R_4$=H; $R_5$=$SO_3^-$);
50k (R=H; $R_1$, R', $R_3$=$SO_3^-$; $R_4$=$SO_3^-$; $R_5$=Ac);
50l (R, R'=H; $R_1$, $R_3$=$SO_3^-$; $R_4$, $R_5$=$SO_3^-$);
50m (R, R'=H; $R_1$, $R_3$=$SO_3^-$; $R_4$=H; $R_5$=$SO_3^-$);
50n (R, R'=H; $R_1$, $R_3$=$SO_3^-$; $R_4$=$SO_3^-$; $R_5$=Ac);
50o (R=H; $R_1$, R'=$SO_3^-$; $R_3$=Ac; $R_4$, $R_5$=$SO_3^-$);
50p (R=H; $R_1$, R'=$SO_3^-$; $R_3$=Ac; $R_4$=H; $R_5$=$SO_3^-$);
50q (R=H; $R_1$, R'=$SO_3^-$; $R_3$=Ac; $R_4$=$SO_3^-$; $R_5$=Ac);
50r (R, R', $R_3$=$SO_3^-$; $R_1$=Ac; $R_4$, $R_5$=$SO_3^-$);
50s (R, R', $R_3$=$SO_3^-$; $R_1$=Ac; $R_4$=H; $R_5$=$SO_3^-$);
50t (R, R', $R_3$=$SO_3^-$; $R_1$=Ac; $R_4$=$SO_3^-$; $R_5$=Ac);
50u (R, $R_3$=$SO_3^-$; $R_1$=Ac; R'=H; $R_4$, $R_5$=$SO_3^-$);
50v (R, $R_3$=$SO_3^-$; $R_1$=Ac; R'=H; $R_4$=H; $R_5$=$SO_3^-$);
50w (R, $R_3$=$SO_3^-$; $R_1$=Ac; R'=H; $R_4$=$SO_3^-$; $R_5$=Ac);
50x (R, R'=$SO_3^-$; $R_1$, $R_3$=Ac; $R_4$, $R_5$=$SO_3^-$);
50y (R, R'=$SO_3^-$; $R_1$, $R_3$=Ac; $R_4$=H; $R_5$=$SO_3^-$);
50z (R, R'=$SO_3^-$; $R_1$, $R_3$=Ac; $R_4$=$SO_3^-$; $R_5$=Ac).

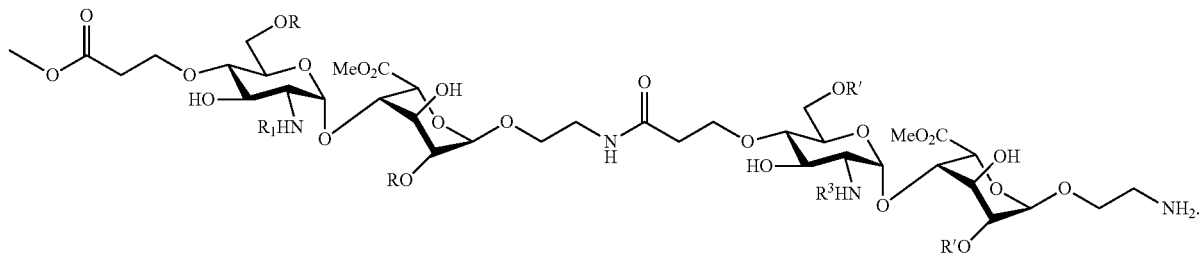

In certain embodiments, the method further comprises isolating the compound of formula (Ie) from the sixteenth product mixture, thereby obtaining substantially pure

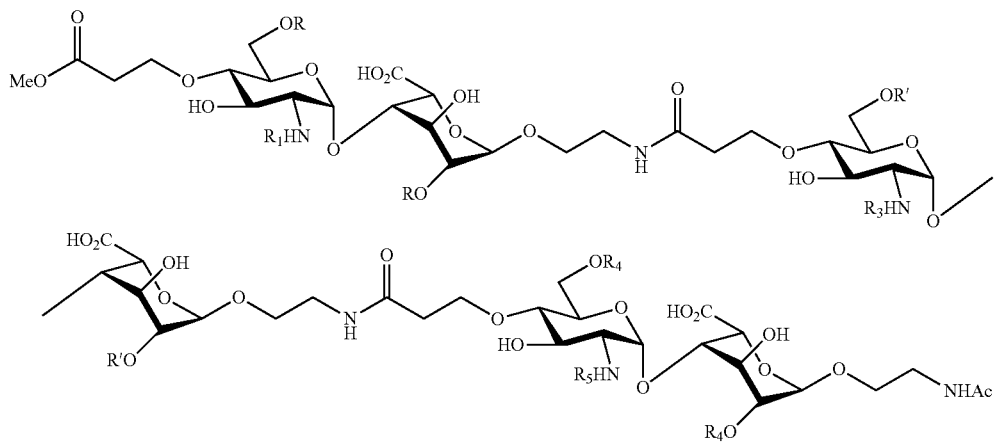

In still other aspects, the present invention is directed to a method of synthesizing a compound of formula (I)

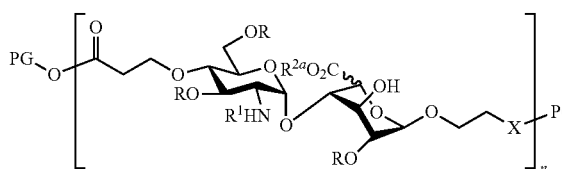

wherein, independently at each occurrence:

n is an integer from 1 to 40;

R is H, $SO_3H$, or $SO_3^-$;

$R_1$ is $SO_3H$, $SO_3^-$, or —C(O)CH$_3$;

$R^2$ is $C_{1-6}$ alkyl, H, or is a negative charge;

X is NH, S, or O;

$PG^1$ is H, Fmoc, —C(O)CH$_3$, —C(O)CF3, and Boc; and

PG is H, $C_{1-6}$ alkyl, allyl or benzyl;

the method comprising:

preparing a compound of formula (Id) as described herein, and repeating steps (vi) and (vii) at least once, to obtain a nineteenth product mixture comprising the compound of formula (I).

In certain embodiments, the method further comprises:

reacting the nineteenth product mixture under deprotection conditions to form a twentieth product mixture; and reacting the twentieth product mixture with a compound of formula (Ic)

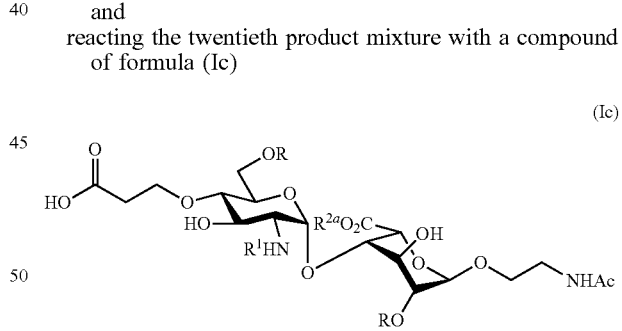

wherein $R^{2a}$ is $C_{1-6}$ alkyl, under coupling conditions to afford a 21$^{st}$ product mixture.

In certain embodiments, deprotection conditions comprise DBU in a thirteenth solvent. In certain such embodiments, the thirteenth solvent comprises DMF.

In certain embodiments, coupling conditions comprise HBTU and DIPEA in a fourteenth solvent. In certain such embodiments, the fourteenth solvent comprises DMF.

In certain embodiments, the method further comprises reacting the 21$^{st}$ product mixture under saponification conditions to provide a 22$^{nd}$ product mixture to provide a compound of formula (I) wherein PG is H and $R^2$ is H.

In still other aspects, the present invention is directed to a method of synthesizing a compound of formula 31

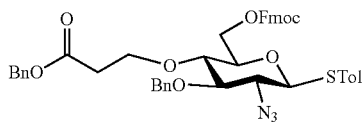

31 the method comprising:
(a) treating a compound of formula 29

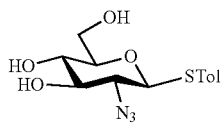

29 with anisaldehyde dimethyl acetal and CSA in acetonitrile, to afford a 23$^{rd}$ product mixture;
(b) treating the 23$^{rd}$ product mixture with sodium hydride and BnBr in DMF, to afford a 24$^{th}$ product mixture;
(c) treating the 24$^{th}$ product mixture with sodium cyanoborohydride and trifluoroacetic acid in DMF, to afford a 25$^{th}$ product mixture comprising a compound of formula 30

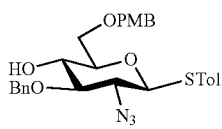

30

(d) treating the 25$^{th}$ product mixture with allyl bromide and sodium hydride, to afford a 26$^{th}$ product mixture;
(e) treating the 26$^{th}$ product mixture with 9-BBN, sodium hydroxide, and hydrogen peroxide, to afford a 27$^{th}$ product mixture;
(f) treating the 27$^{th}$ product mixture with TEMPO and BAIB in dichloromethane and water, to afford a 28$^{th}$ product mixture;
(g) treating the 28$^{th}$ product mixture with BnBr in DMF, to afford a 29$^{th}$ product mixture;
(h) treating the 29$^{th}$ product mixture with DDQ in dichloromethane and water to afford a 30$^{th}$ product mixture; and
(i) treating the 30$^{th}$ product mixture with FmocCl and pyridine in dichloromethane to afford a 31$^{st}$ product mixture comprising the compound of formula 31.

In certain embodiments, the method further comprises isolating the compound of formula 31 from the 31$^{st}$ product mixture, to afford substantially pure

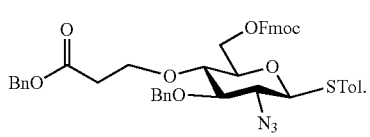

31

In still other aspects, the present invention is directed to a compound selected from:

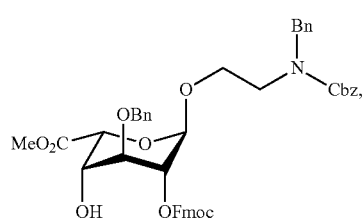

34

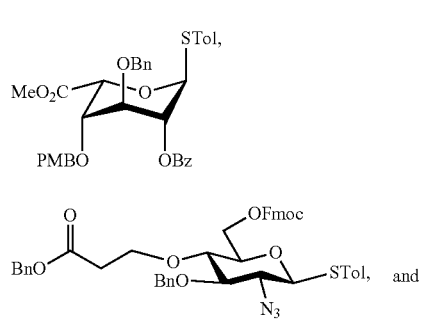

33

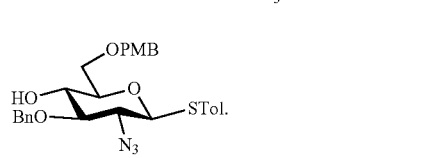

31

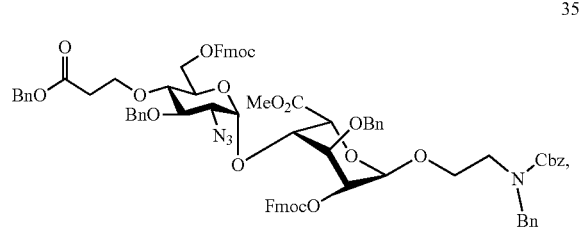

30

In still other aspects, the present invention is directed to a compound selected from:

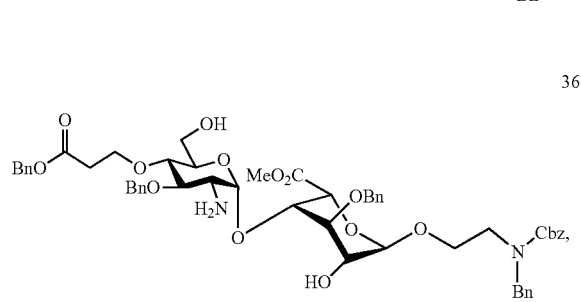

35

36

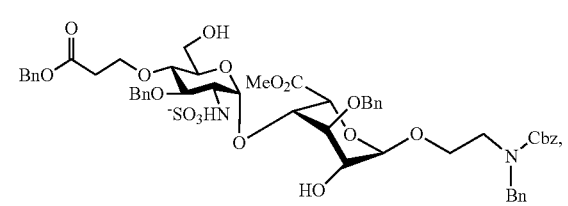

37

38
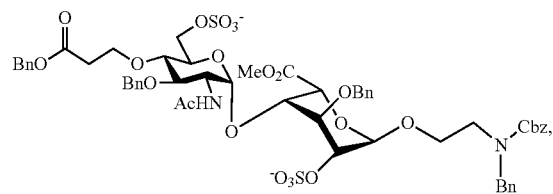
39
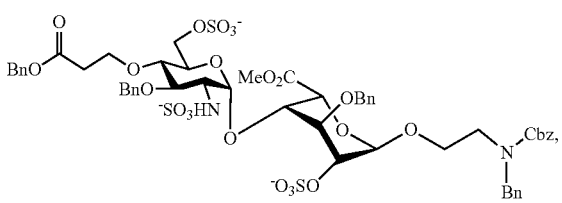
40
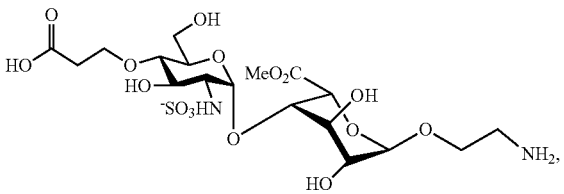
41
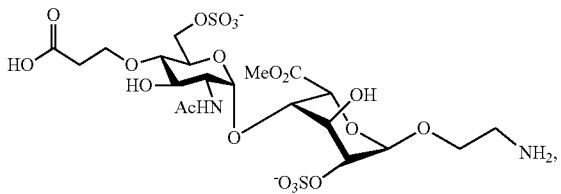
42
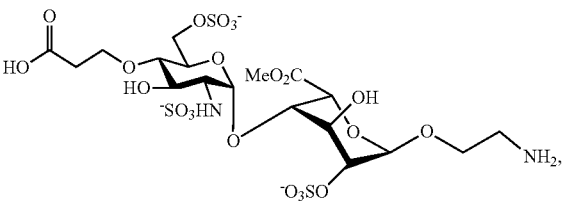
43
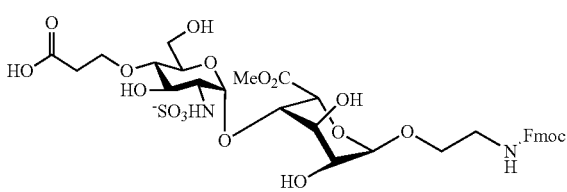
44
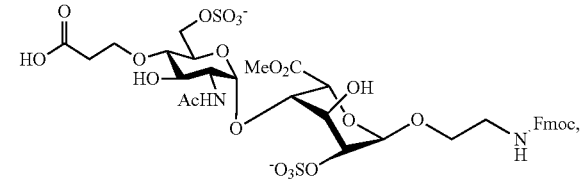
45
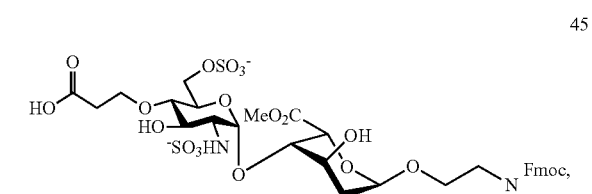
46
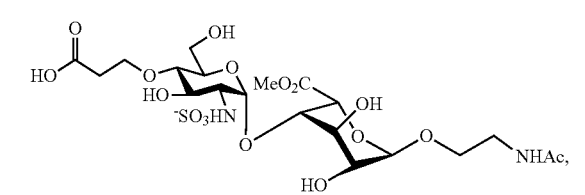
47
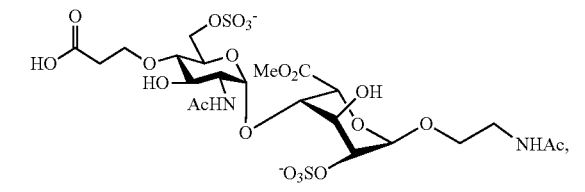
and
48
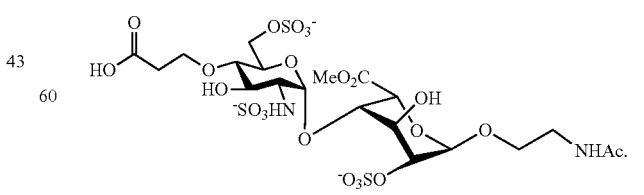
In still other aspects, the present invention is related to a compound of formula (Id')

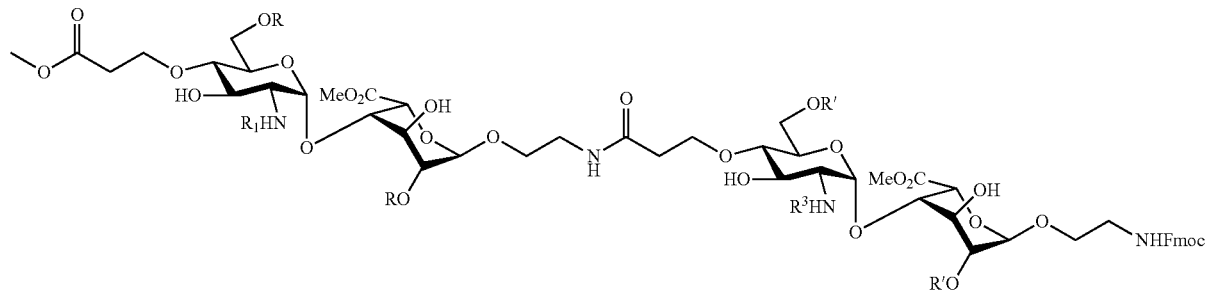

(Id)

selected from:
49a (R, R¹, R', R³=SO₃⁻);
49b (R, R¹, R³=SO₃⁻; R'=H);
49c (R, R¹, R'=SO₃⁻; R³=C(O)CH₃);
49d (R=H; R¹, R', R¹'=SO₃⁻);
49e (R, R'=H; R¹, R³=SO₃⁻);
49f (R=H; R¹, R'=SO₃⁻; R³=C(O)CH₃);
49g (R, R¹, R³=SO₃⁻; R'=C(O)CH₃);
49h (R, R³=SO₃⁻; R¹=C(O)CH₃; R'=H); and
49i (R, R'=SO₃⁻; R¹, R³=C(O)CH₃).

In still other aspects, the present invention is directed to a compound of formula (Ig)

50l (R, R'=H; R₁, R₃=SO₃⁻; R₄, R₅=SO₃⁻);
50m (R, R'=H; R₁, R₃=SO₃⁻; R₄=H; R₅=SO₃⁻);
50n (R, R'=H; R₁, R₃=SO₃⁻; R₄=SO₃⁻; R₅=Ac);
50o (R=H; R₁, R'=SO₃⁻; R₃=Ac; R₄, R₅=SO₃⁻);
50p (R=H; R₁, R'=SO₃⁻; R₃=Ac; R₄=H; R₅=SO₃⁻);
50q (R=H; R₁, R'=SO₃⁻; R₃=Ac; R₄=SO₃⁻; R₅=Ac);
50r (R, R', R₃=SO₃⁻; R₁=Ac; R₄, R₅=SO₃⁻);
50s (R, R', R₃=SO₃⁻; R₁=Ac; R₄=H; R₅=SO₃⁻);
50t (R, R', R₃=SO₃⁻; R₁=Ac; R₄=SO₃⁻; R₅=Ac);
50u (R, R₃=SO₃⁻; R₁=Ac; R'=H; R₄, R₅=SO₃⁻);
50v (R, R₃=SO₃⁻; R₁=Ac; R'=H; R₄=H; R₅=SO₃⁻);

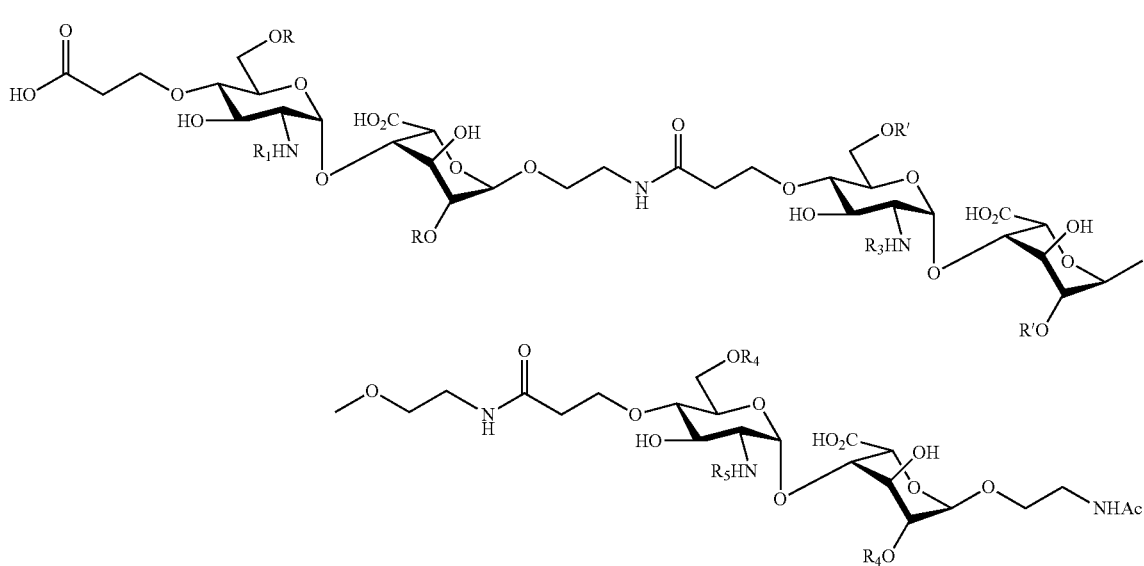

(Ig)

selected from:
50 (R, R₁, R', R₃=SO₃⁻; R₄, R₅=SO₃⁻);
50a (R, R₁, R', R₃=SO₃⁻; R₄=H; R₅=SO₃⁻);
50b (R, R₁, R', R₃=SO₃⁻; R₄=SO₃⁻; R₅=Ac);
50c (R, R₁, R₃=SO₃⁻; R'=H; R₄, R₅=SO₃⁻);
50d (R, R₁, R₃=SO₃⁻; R'=H; R₄=H; R₄=SO₃⁻);
50e (R, R₁, R₃=SO₃⁻; R'=H; R₄=SO₃⁻; R₅=Ac);
50f (R, R₁, R'=SO₃⁻; R₃=Ac; R₄, R₅=SO₃⁻);
50g (R, R₁, R'=SO₃⁻; R₃=Ac; R₄=H; R₅=SO₃⁻);
50h (R, R₁, R'=SO₃⁻; R₃=Ac; R₄=SO₃⁻; R₅=Ac);
50i (R=H; R₁, R', R₃=SO₃⁻; R₄, R₅=SO₃⁻);
50j (R=H; R₁, R', R₃=SO₃⁻; R₄=H; R₅=SO₃⁻);
50k (R=H; R₁, R', R₃=SO₃⁻; R₄=SO₃⁻; R₅=Ac);

50w (R, R₃=SO₃⁻; R₁=Ac; R'=H; R₄=SO₃⁻; R₅=Ac);
50x (R, R'=SO₃⁻; R₁, R₃=Ac; R₄, R₅=SO₃⁻);
50y (R, R'=SO₃⁻; R₁, R₃=Ac; R₄=H; R₅=SO₃⁻);
50z (R, R'=SO₃⁻; R₁, R₃=Ac; R₄=SO₃⁻; R₅=Ac).

As used herein, reactions that are run "at a temperature from −78° C. to 0° C." are initiated at −78° C. and allowed to warm up to 0° C. Such reactions may be set up by dissolving or stirring a reactant (e.g., a donor) in a solvent at room temperature before cooling to −78° C. Once at −78° C., another reactant is added (e.g., a promoter, itself optionally in a solvent, which may be different), such as to generate a reactive species, before yet another reactant (e.g., an acceptor) is added, which reacts with the reactive species; the reaction mixture is then allowed to warm up to 0° C. depending on the reactivity of one or more of the species involved (e.g., the donor and the acceptor).

Abbreviations

Ac$_2$O, acetic anhydride; AcOH, acetic acid; AF488, Alex Fluor 488; AgOTf, silver trifluoromethanesulfonate; APS, ammonium peroxodisulfate; ATM, Ataxia-telangiectasia-mutated kinase; AT-III, antithrombin III; BAIB, bis(acetoxy) iodobenzene; BF$_3$·Et$_2$O, boron trifluoride etherate; BLI, bio-layer interferometry; Bn, benzyl; BnBr, benzyl bromide; BSA, bovine serum albumin; Bz, benzoyl; Cbz, benzyloxy-carbonyl; CH$_3$CN acetonitrile; CSA, camphorsulfonic acid; CVDs, cardiovascular diseases; DBU, 1, 8-diazabicyclo [5.4.0]undec-7-ene; DCM, dichloromethane; DDQ, 2, 3-dichloro-5, 6-dicyanobenzoquinone; DIPEA, diisopropylethylamine; DMAP, 4-dimethylaminopyridine; DMF, dimethylformamide; DMSO, dimethyl sulfoxide; DTT dithiothreitol; ECM, extracellular matrix; EDC·HCl, 1-ethyl-3-(3-dimethylaminopropyl)carbodiimide hydrochloride; ELISA, enzyme-linked immunosorbent assay; ESI-MS, electrospray-ionization mass spectrometry; EtOAc, ethyl acetate; Et$_3$N, trimethylamine; FDA, Food and Drug Administration; FGFs, fibroblast growth factors; FGFRs, FGF receptors: Fmoc 9-fluorenylmethoxycarbonyl; FmocCl, Fmoc chloride; Fmoc-Osu, Fmoc N-hydroxysuccinimide ester; FXa, activated factor X; GAGS, glycosaminoglycans; GEMA, glucosyloxyethyl methacrylate; GlcA, glucuronic acid; GlcN, glucosamine; GlcNAc, 2-acetamido-2-deoxy-glucose; GlcNS, N-sulfated glucosamine; HCl, hydrochloric acid; HIT, heparin-induced thrombocytopenia; H$_2$O, water; H$_2$O$_2$, hydrogen peroxide; HMBC, heteronuclear multiple bond correlation; HOBT, hydroxybenzotriazole; HPLC, high performance liquid chromatography; HRMS, high resolution mass spectrometry; HS, heparan sulfate; HSPGs, heparan sulfate proteoglycans; HSQC, heteronuclear single quantum correlation; IdoA, iduronic acid; IV, intravenous; K$_2$CO$_3$, potassium carbonate; kDa, kilo-dalton; KPB, potassium phosphate buffer; LevOH, levulinic acid; LiAlHa, lithium aluminum hydride; LiGH, lithium hydroxide; LMWH, low-molecular-weight heparin; MALDI-TOF, matrix assisted laser desorption ionization-time of flight; MeI, methyl iodide; MeOH, methanol; mESCs, mouse embryonic stem cells; MS, mass spectrometry; NaBH$_4$, sodium borohydride; NaCNBH$_3$, sodium cyanoborohydride; NaH, sodium hydride; NaHCO$_3$, sodium bicarbonate; NaN$_3$, sodium azide; Na$_2$SO$_4$, sodium sulfate; neoPGs, neoproteo-glycans; NF-κB, nuclear factor kappa B; NH$_4$OH, ammonium hydroxide; NHS, N-hydroxysuccinimide; NIS, N-iodoxuccinimide; NMO, 4-methylmorpholine N-oxide; NMR, nuclear magnetic resonance spectroscopy; OD, Optical density; OsO$_4$, osmium tetraoxide; PBS, phosphate buffered saline; PBST, PBS/0.5% Tween-20; Pd(OH)$_2$, palladium hydroxide; PF4, platelet factor 4; PMB, p-methoxybenzyl; p-TolSCl, p-toluenesulfenyl chloride; p-TolSH, p-toluenethiol; Py/Pyr, pyridine; ROMP, ring-opening metathesis polymerization; SA, streptavidin; sat., saturated; SC, subcutaneous; SEC, size exclusion chromatography; SPR, surface plasmon resonance; TAMRA, tetramethylrhodamine; TBAI, tetrabutylammonium iodide; TBDPS, t-butyldiphe-nylsilyl; TBS, t-butyldimethylsilyl; t-Bu, t-butyl; TCT, tracheal cytotoxin; TEMPO, 2, 2, 6, 6-tetramethyl-1-piperidinyloxyl; TFA, trifluoroacetic acid; Tf$_2$O, trifluoromethanesulfonic anhydride; THF, tetrahydrofuran; TLC, thin layer chromatography; TR-FRET, Time-resolved fluorescence energy transfer; TrocCl, trichloroethyl chloroformate; TTBP, 2,4,6-tri-t-butylpyrimidine; UFH, unfractionated heparin; ULMW, ultralow molecular weight; VEGF, vascular endothelial growth factor; WHO, World Health Organization.

Definitions

For convenience, certain terms employed in the specification, examples, and appended claims are collected here.

The articles "a" and "an" are used herein to refer to one or to more than one (i.e., to at least one) of the grammatical object of the article.

As used herein, the term "administering" means providing an agent or composition to a subject, and includes, but is not limited to, administering by a medical professional and self-administering.

The term "agent" is used herein to denote a chemical compound, a small molecule, a mixture of chemical compounds and/or a biological macromolecule (such as a nucleic acid, an antibody, an antibody fragment, a protein or a peptide). The activity of such agents may render them suitable as a "therapeutic agent" which is a biologically, physiologically, or pharmacologically active substance (or substances) that acts locally or systemically in a subject.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the term "subject" means a human or non-human animal selected for treatment or therapy. In certain embodiments, of the methods and compositions described herein the subject is a human subject.

The terms "prevent," "preventing," "prevention." and the like refer to reducing the probability of developing a disease, disorder, or condition in a subject, who does not have, but is at risk of or susceptible to developing a disease, disorder, or condition.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) Science 282:63), and natural product extract libraries. In another embodiment, the compounds are small, organic non-peptidic compounds. In a further embodiment, a small molecule is not biosynthetic.

"Treating" a disease in a subject or "treating" a subject having a disease refers to subjecting the subject to a pharmaceutical treatment, e.g., the administration of a drug, such that at least one symptom of the disease is decreased or prevented from worsening.

As used herein, "mediating" a process such as cell proliferation, cell differentiation, amyloid plaque formation, anti-coagulation, or neuronal growth can refer to either inhibiting or enhancing the process. In some embodiments, mediating a process means inhibiting the process. In certain embodiments, the invention is directed to methods of inhibiting amyloid plaque formation or coagulation. In certain embodiments, the invention is directed to methods of enhancing cell proliferation, cell differentiation, anti-coagulation, or neuronal growth.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—. In certain preferred embodiments, acylamino is alkylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

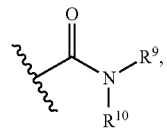

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

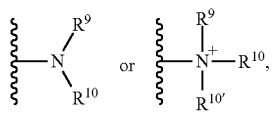

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

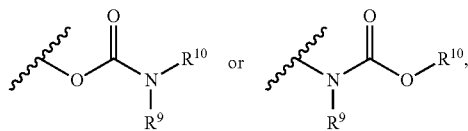

wherein $R^9$ and $R^{10}$ independently represent hydrogen or a hydrocarbyl group.

The term "carbocyclylalkyl", as used herein, refers to an alkyl group substituted with a carbocycle group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —$C(O)OR^9$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

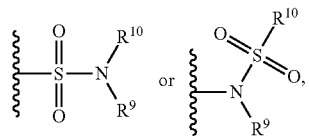

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$
wherein R$^9$ represents a hydrocarbyl.

The term "thioether", as used herein, is equivalent to an ether, wherein the oxygen is replaced with a sulfur.

The term "urea" is art-recognized and may be represented by the general formula

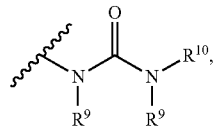

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

In certain embodiments, the compounds of the invention may be racemic. In certain embodiments, the compounds of the invention may be enriched in one enantiomer. For example, a compound of the invention may have greater than 30% ee, 40% ee, 50% ee, 60% ee, 70% ee, 80% ee, 90% ee, or even 95% or greater ee.

The compounds of the invention have more than one stereocenter. Accordingly, the compounds of the invention may be enriched in one or more diastereomers. For example, a compound of the invention may have greater than 30% de, 40% de, 50% de, 60% de, 70% de, 80% de, 90% de, or even 95% or greater de. In certain embodiments, the compounds of the invention have substantially one isomeric configuration at one or more stereogenic centers, and have multiple isomeric configurations at the remaining stereogenic centers.

In certain embodiments, the enantiomeric excess of the stereocenter is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound.

As used herein, hashed or bolded non-wedge bonds indicate relative, but not absolute, stereochemical configuration (e.g., do not distinguish between enantiomers of a given diastereomer).

As used herein, hashed or bolded wedge bonds indicate absolute stereochemical configuration.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "benzyl" as used herein refers to the group

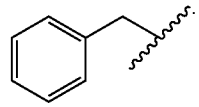

The term "allyl" as used herein refers to the group

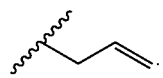 [SMILES: *CC=C]

Compositions

In some aspects, disclosed herein are compositions to mediating cell proliferation, cell differentiation, amyloid plaque formation, anti-coagulation, or neuronal growth in a subject in need thereof.

In certain embodiments, provided herein is a composition, e.g., a pharmaceutical composition, containing at least one compound described herein together with a pharmaceutically acceptable carrier. In one embodiment, the composition includes a combination of multiple (e.g., two or more) compounds described herein.

As described in detail below, the pharmaceutical compositions disclosed herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous, intrathecal, intracerebral or epidural injection as, for example, a sterile solution or suspension, or sustained-release formulation.

Methods of preparing these formulations or compositions include the step of bringing into association an agent described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions suitable for parenteral administration comprise one or more agents described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions include water, ethanol, dimethyl sulfoxide (DMSO), polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Regardless of the route of administration selected, the agents provided herein, which may be used in a suitable hydrated form, and/or the pharmaceutical compositions disclosed herein, are formulated into pharmaceutically-acceptable dosage forms by conventional methods known to those of skill in the art.

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

"Pharmaceutically acceptable salt" is used herein to refer to an acid addition salt or a basic addition salt which is suitable for or compatible with the treatment of patients.

The term "pharmaceutically acceptable acid addition salt" as used herein means any non-toxic organic or inorganic salt of the disclosed compounds. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, bitartaric, citric, ascorbic, maleic, benzoic, phenylacetic, cinnamic, salicylic, and sulfosalicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds disclosed herein are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds disclosed herein for laboratory use, or for subsequent conversion to a pharmaceutically acceptable acid addition salt.

The term "pharmaceutically acceptable basic addition salt" as used herein means any non-toxic organic or inorganic base addition salt of any acid compounds disclosed herein. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid: (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, intraocular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, about 0.1 to about 99.5% (more preferably, about 0.5 to about 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

As can be appreciated from the disclosure above, the present invention has a wide variety of applications. The invention is further illustrated by the following examples, which are only illustrative and are not intended to limit the definition and scope of the invention in any way.

EXEMPLIFICATION

Example 1: General Synthetic Procedures

Pre-activation Based Single-step Glycosylation. A solution of donor (1.0 equiv) and freshly activated molecular sieve MS 4 Å in DCM was stirred for 20 minutes under room temperature, and then cooled to −78° C. A solution of AgOTf (3.0 equiv) in anhydrous $Et_2O$/DCM (10/1, v/v) was added to reaction solution without touching the wall of the flask. After 5 minutes, orange colored p-TolSCl (1.0 equiv) was added to the solution through a micro syringe. p-TolSCl is supposed to be added directly to the reaction solution to prevent it from freezing on the flask wall and stir bar. The characteristic orange color became very faint in a few seconds indicating consumption of p-TolSCl promoter. TLC analysis could confirm the complete activation of donor in 5 minutes. A solution of acceptor (1.0 equiv) with TTBP (1.0 equiv) in DCM was added to reaction solution (0.3 M). The reaction mixture can be warmed up to 0° C. under stirring in 2 hours depending to the reactivity of both donor and acceptor. The reaction mixture was quenched by $Et_3N$ ($NaHCO_3$ saturated solution for Fmoc protected compounds) and filtered over Celite with DCM. DCM solution was washed by $NaHCO_3$ and NaCl saturated solutions. The organic layer was collected and dried over $Na_2SO_4$, concentrated and purified by silica gel flash chromatography.

Deprotection of PMB. The PMB-protected compound (1.0 equiv) was dissolved in DCM/H2O (0.1 M, 10:1, v/v). The mixture was cooled to 0° C., followed by addition DDQ (1.5 equiv). The mixture was stirred at room temperature for 1 hour. The residue was diluted with DCM and washed with saturated solutions of $NaHCO_3$ and NaCl, dried ($Na_2SO_4$), and filtered. The filtrate was concentrated in vacuo and the residue was purified by silica gel flash chromatography.

Protection of 6-OH with Lev. The compound containing 6-OH (1.0 equiv) was dissolved in DCM (0.3 M), followed by addition of EDC-HCl (3.0 equiv), levulinic acid (1.4 equiv) and DMAP (1.0 equiv). The mixture was stirred under room temperature for 1 hour. The residue was diluted with DCM and washed with 10% HCl, saturated solutions of $NaHCO_3$ and NaCl. The organic solution was dried over $Na_2SO_4$ and concentrated in vacuo, then purified by silica gel flash chromatography.

O-Acetylation. The compound containing —OH (1.0 equiv) was dissolved in pyridine (1.2 M), followed by addition of acetic anhydride (7.0 equiv for each hydroxyl group) at 0° C. The mixture was stirred at room temperature overnight and then washed with 3×1.0 M HCl and saturated solutions of $NaHCO_3$ and NaCl. The organic solution was dried over $Na_2SO_4$, filtered and concentrated in vacuo, then purified by silica gel flash chromatography to afford desired compounds.

N-Acetylation. The compound containing —$NH_2$ (1.0 equiv) was dissolved in MeOH (0.04 M), followed by addition of acetic anhydride (3.0 equiv) and $Et_3N$ (3.0 equiv). The mixture was stirred at room temperature for 1 h and then was passed through LH-20 gel column with MeOH to afford desired compounds.

Protection of OH with Fmoc. To a solution of starting material in DCM (0.3 M), FmocCl (3.0 equiv) and pyridine (4.0 equiv) was added. The reaction mixture was stirred at room temperature for 1 h and diluted with DCM. The organic mixture was washed with 3×1 M HCl, $NaHCO_3$ saturated solution and brine. The organic layer was dried over anhydrous $Na_2SO_4$ and filtered. The filtrate was concentrated by rotary evaporation and purified by silica gel column chromatography.

Protection of $NH_2$ with Fmoc. To a solution of starting material in $H_2O$/DMF (1/1, v/v, 0.3 M), Fmoc-OSu (3.0 equiv) and DIPEA (1.5 equiv) was added. The reaction mixture was stirred at room temperature for 2 h. The organic mixture was washed with 3×1 M HCl, $NaHCO_3$ saturated solution and brine. The organic layer was dried over anhydrous $Na_2SO_4$ and filtered. The filtrate was concentrated by rotary evaporation and purified by silica gel column chromatography. After reaction completed as indicated by TLC (EtOAc/MeOH/$H_2O$ 3/1/1), the reaction mixture was passed through LH-20 gel column with MeOH. A column of Dowex 50WX4 $Na^+$ resin was used for ion exchange to give sodium form product.

Preparation of methyl ester. $K_2CO_3$ (10.0 equiv) and $CH_3I$ (6.0 equiv) was added to a solution of starting material (1.0 equiv) in DMF (0.13M). The reaction mixture was stirred at room temperature for 4 h. After completion, the mixture was passed through LH-20 gel column to afford pure compounds.

NH-Fmoc Deprotection. A mixture of starting material (1.0 equiv) and DBU (5.0 equiv) in DMF (0.15 M) was stirred for 1 h at room temperature. After TLC (EtOAc/MeOH/$H_2O$, 3/1/1, v/v/v) indicated that the reaction was complete, the reaction mixture was passed through LH-20 gel column to give pure compounds.

Preparation of pseudo-Tetrasaccharides/Hexasaccharides. A solution of carboxyethyl disaccharides (1.0 equiv), HATU or HBTU (1.0 equiv) and DIPEA (2.0 equiv) in DMF was added to starting material (1.0 equiv) in DMF (0.013 M). After stirring 1 h at room temperature, TLC (EtOAc/MeOH/$H_2O$, 2.5/1/1, v/v/v) indicated completion of the reaction. Then the reaction mixture was passed through LH-20 gel column and the fractions containing product were collected and concentrated under reduced pressure. A column of Dowex 50WX4 $Na^+$ resin was used for ion exchange to give sodium form product.

Hydrogenolysis. A solution of the compound in mixed tBuOH and water [1/1 (v/v), 3 mL] in the presence of 10% $Pd(OH)_2$/C (80 mg) at room temperature was exposed to $H_2$ gas. After overnight, the suspension was filtered through Celite, and the filtrate was concentrated in vacuo. The residue was passed through LH-20 gel column using MeOH as eluent. The product fractions were concentrated under reduced pressure to give the target molecule.

Saponification of Methyl Esters. The starting material (1.0 equiv) was added to a LiOH (10.0 equiv per $CO_2Me$) solution (0.006 M) at 0° C. The reaction mixture was stirred at 0° C. for 8 h. After TLC (EtOAc/MeOH/H₂O, 1.5/1/1, v/v/v) indicated the reaction completed, Amberlite H⁺ resin was added until pH=7. The reaction mixture was passed through G-15 and Dowex 50W X4 Na⁺ gel columns give pure product as sodium salt.

Product Preparation and Characterization Data

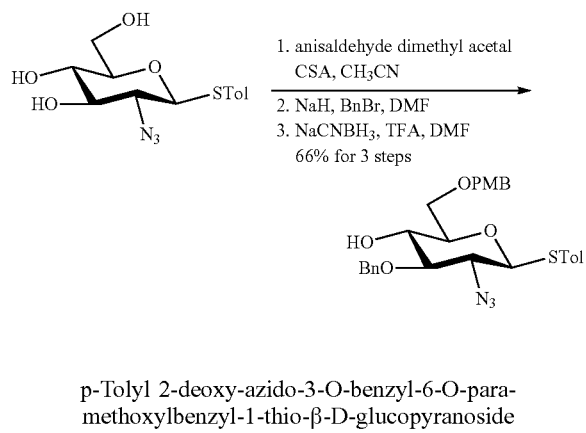

p-Tolyl 2-deoxy-azido-3-O-benzyl-6-O-para-methoxylbenzyl-1-thio-β-D-glucopyranoside The starting material (3.8 g, 12.2 mmol) was dissolved in CH₃CN (0.4 M, 32 ml) and anisaldehyde dimethyl acetal (4.1 ml, 24.4 mmol) and CSA (1.1 g, 4.9 mmol) were added. After stirring at room temperature for overnight, the reaction mixture was neutralized with Et₃N and concentrated under reduced pressure. The residue was diluted with DCM and washed with saturated NaHCO₃ solution and brine. The organic solution was dried over Na2SO4 and filtered. The filtrate was concentrated under reduced pressure and the residue was purified by silica gel column chromatography using a gradient of DCM and Methanol (from 20/1 to 12/1, v/v). A solution of the above compound (4.2 g, 9.85 mmol), NaH (0.6 g, 14.8 mmol) and BnBr (2.3 ml, 19.7 mmol) in DMF (15 ml, 0.65 M) was kept stirring at room temperature for 2 h. After the starting material was completely consumed, the reaction mixture was neutralized with NH₄Cl saturated solution and sequentially washed with NaHCO₃ saturated solution (3×70 ml) and brine (75 ml). The organic layer was dried over anhydrous Na₂SO₄ and concentrated in vacuo and the residue was purified by flash column chromatography to afford the compound. The above compound (4.9 g, 9.5 mmol) was dissolved in DMF (30 ml, 0.3 M), followed by addition of NaCNBH₃ (6.0 g, 95 mmol) and TFA (7.25 ml, 95 mmol) at 0° C. The reaction mixture was warmed to room temperature and stirred overnight, and then diluted with EtOAc. The organic mixture was washed with water (3×70 ml to get rid of DMF), NaHCO₃ saturated solution (3×70 ml) and brine (50 ml). The organic layer was concentrated under reduced pressure and the residue was purified by silica gel column chromatography using a gradient of hexanes and EtOAc (from 3/1 to 2/1, v/v) to give desired product (4.2 g, 66' for 3 steps). ¹H NMR (500 MHz, CDCl₃) δ 7.51-7.47 (m, 2H; ArCH₂), 7.43-7.31 (m, 5H; Ar—H), 7.29-7.25 (m, 2H; ArCH₂), 7.11 (d, J=8.0 Hz, 2H; ArCH₂), 6.95-6.88 (m, 2H; ArCH₂), 4.92-4.83 (m, 2H; BnCH₂), 4.57-4.48 (m, 2H; PMBCH₂), 4.39 (d, J=10.0 Hz, 1H; 1-H), 3.84 (s, 3H; OCH₃), 3.78 (dd, J=10.3, 4.9 Hz, 1H; 6-H), 3.73 (dd, J=10.4, 4.7 Hz, 1H; 6'-H), 3.65-3.59 (m, 1H; 4-H), 3.47-3.41 (m, 1H; 5-H), 3.38 (t, J=9.0 Hz, 1H; 3-H), 3.30 (t, J=9.7 Hz, 1H; 2-H), 2.85 (d, J=2.5 Hz, 1H; OH), 2.35 (s, 3H; STolCH₃). ¹³C NMR (125 MHz, CDCl3) δ 159.37, 138.75, 137.88, 134.20, 129.81, 129.74, 129.44, 128.63, 128.27, 128.12, 127.07, 113.88, 86.14, 84.57, 77.86, 75.50, 73.44, 72.24, 70.11, 64.30, 55.32, 21.22.

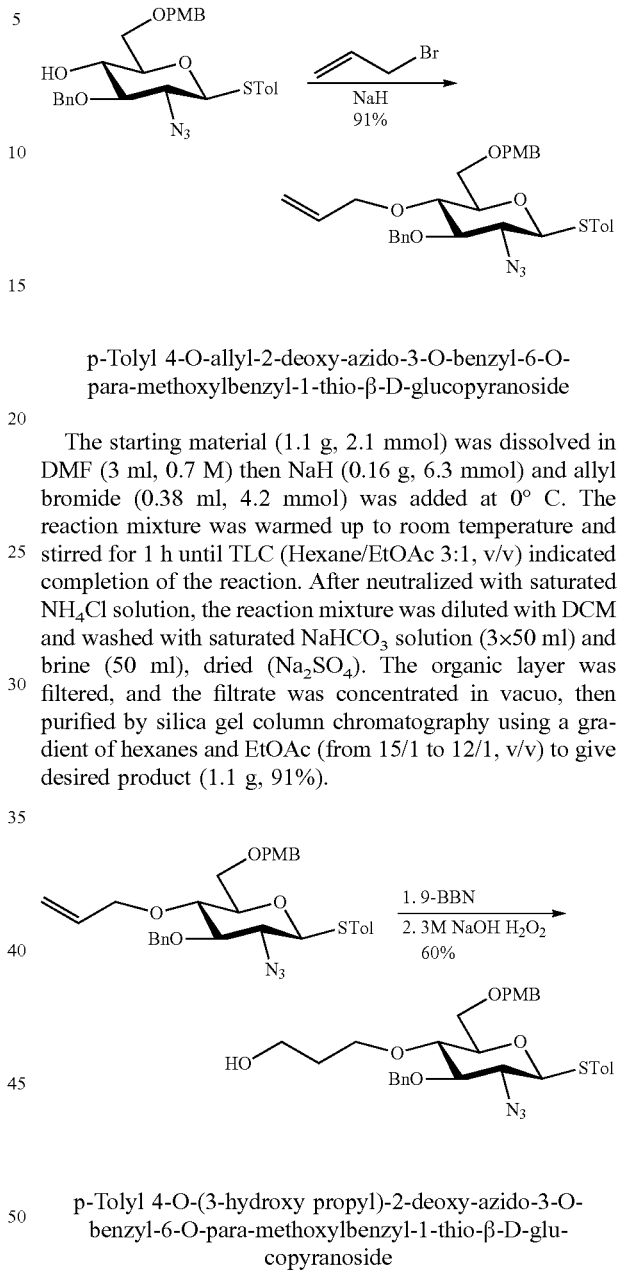

p-Tolyl 4-O-allyl-2-deoxy-azido-3-O-benzyl-6-O-para-methoxylbenzyl-1-thio-β-D-glucopyranoside The starting material (1.1 g, 2.1 mmol) was dissolved in DMF (3 ml, 0.7 M) then NaH (0.16 g, 6.3 mmol) and allyl bromide (0.38 ml, 4.2 mmol) was added at 0° C. The reaction mixture was warmed up to room temperature and stirred for 1 h until TLC (Hexane/EtOAc 3:1, v/v) indicated completion of the reaction. After neutralized with saturated NH₄Cl solution, the reaction mixture was diluted with DCM and washed with saturated NaHCO₃ solution (3×50 ml) and brine (50 ml), dried (Na₂SO₄). The organic layer was filtered, and the filtrate was concentrated in vacuo, then purified by silica gel column chromatography using a gradient of hexanes and EtOAc (from 15/1 to 12/1, v/v) to give desired product (1.1 g, 91%).

p-Tolyl 4-O-(3-hydroxy propyl)-2-deoxy-azido-3-O-benzyl-6-O-para-methoxylbenzyl-1-thio-β-D-glucopyranoside The starting material (10.8 g, 19 mmol) was dissolved in THF (85 ml, 0.2 M) and cooled to 0° C. A solution of 9-BBN in THF (0.5 M, 76 ml, 38 mmol) was added and the reaction mixture was warmed to room temperature and stirred overnight. After hydroboration was complete, ethanol (48 ml) was added slowly to reaction mixture at 0° C., followed by addition of NaOH (1.0 M aq, 96 ml) and H₂O₂ (30 wt % aq, 96 ml). The reaction mixture was warmed to 60° C. for 3 h, then quenched with saturated NH₄Cl solution and extracted into EtOAc (2×300 ml). The combined organic extracts were washed with NaHCO₃ saturated solution (3×150 ml) and brine (150 ml), dried over Na₂SO₄, and filtered. The filtrate was concentrated by rotary evaporation and the residue was purified by silica gel column chromatography from pure hexanes to hexanes/EtOAc (8/1 to 3.5/1) to give pure compound (6.7 g, 60% yield).

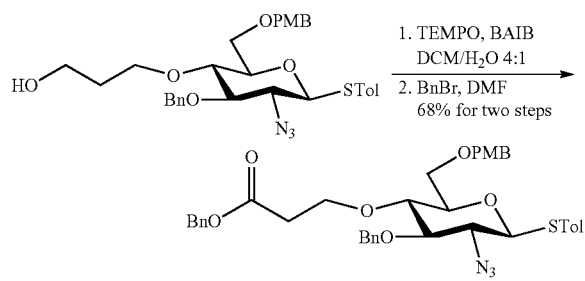

p-Tolyl 4-O-benzyl propionate-2-deoxy-azido-3-O-benzyl-6-O-para-methoxylbenzyl-1-thio-β-D-glucopyranoside A mixture of starting material (6.7 g, 11.6 mmol), BAIB (8.2 g, 25.5 mmol) and TEMPO (0.5 g, 3.5 mmol) was dissolved in DCM/H$_2$O (4/1, 1.2 M) solution. After stirring at room temperature for 2 h, the reaction mixture was diluted in DCM and washed with water (3×75 ml) and Na$_2$S$_2$O$_3$ (40 ml) solution. The organic solvent was evaporated under reduced pressure. The residue (6.8 g, 11.5 mmol) was dissolved in DMF (23 ml, 0.5 M), followed by addition of K$_2$CO$_3$ (9.5 g, 69 mmol) and BnBr (8.2 ml, 69 mmol). The reaction mixture was stirred at room temperature for 4 h and diluted with EtOAc and washed with 1M HCl (3×75 ml), NaHCO$_3$ saturated solution (3×75 ml) and brine (75 ml). The organic solution was dried over Na$_2$SO$_4$, and the filtrate was concentrated by rotary evaporation. The residue was purified by silica gel column chromatography from pure hexanes to hexanes/EtOAc (15/1 to 12/1) to yield pure compound (5.4 g, 68% yield).

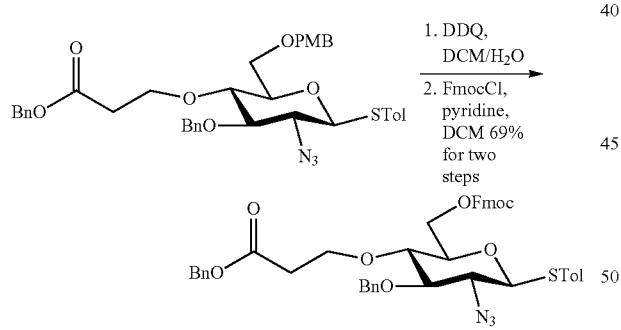

p-Tolyl 4-O-benzyl propionate-2-deoxy-azido-3-O-benzyl-6-O-fluorenylmethyloxycarbonyl-1-thio-1-D-glucopyranoside Compound (3.6 g, 5.3 mmol) was treated according to the general procedures of PMB deprotection and Fmoc protection to give compound (2.85 g, 69% for two steps). $^1$H NMR (500 MHz, CDCl$_3$) δ 7.82-7.76 (m, 2H; ArCH$_2$), 7.65 (ddd, J=7.6, 4.5, 1.0 Hz, 2H; ArCH$_2$), 7.52-7.22 (m, 15H; Ar—CH), 7.12-7.06 (m, 2H; ArCH$_2$), 5.14 (s, 2H; BnCH$_2$), 4.85-4.76 (m, 2H; BnCH$_2$), 4.54-4.41 (m, 3H), 4.36-4.26 (m, 3H), 4.14-4.04 (m, 1H), 3.88-3.81 (m, 1H), 3.47-3.39 (m, 2H), 3.34-3.21 (m, 2H), 2.64-2.51 (m, 2H), 2.30 (s, 3H).

$^{13}$C NMR (125 MHz, CDCl$_3$) δ 171.02, 154.96, 143.40, 143.33, 141.29, 138.88, 137.44, 135.72, 134.31, 129.79, 128.57, 128.54, 128.37, 128.31, 128.11, 127.91, 127.23, 127.21, 125.22, 120.07, 85.85, 84.74, 77.62, 76.93, 75.79, 70.04, 68.22, 66.50, 66.27, 64.70, 46.77, 35.36, 21.19.

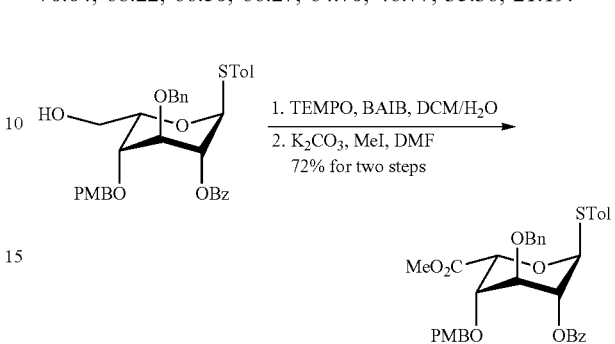

p-Tolyl 2-O-benzoyl-3-O-benzyl-4-O-para-methoxylbenzyl-6-O-methyl ester-1-thio-α-L-idopyranoside A mixture of starting material # (9.6 g, 16.0 mmol), BAIB (11.3 g, 35.2 mmol) and TEMPO (0.74 g, 4.8 mmol) was dissolved in DCM/H$_2$O (4/1, 0.64 M) solution. After stirring at room temperature for 4 h, the reaction mixture was diluted in DCM and washed with water (3×100 ml) and Na$_2$S$_2$O$_3$ (50 ml) solution. The organic solvent was evaporated under reduced pressure. The residue (9.8 g, 15.9 mmol) was dissolved in DMF (40 ml, 0.4 M), followed by addition of K$_2$CO$_3$ (13.2 g, 95.4 mmol) and CH$_3$I (6.0 ml, 95.4 mmol). The reaction mixture was stirred at room temperature for 4 h and diluted with EtOAc and washed with 1M HCl (3×100 ml), NaHCO$_3$ saturated solution (3×100 ml) and brine (100 ml). The organic solution was dried over Na$_2$SO$_4$, and the filtrate was concentrated by rotary evaporation. The residue was purified by silica gel column chromatography from pure hexanes to hexanes/EtOAc (9/1 to 8/1) to yield pure compound (7.2 g, 72% yield for two steps). $^1$H NMR (500 MHz, CDCl$_3$) δ 7.99 (dd, J=8.2, 1.5 Hz, 2H; ArCH$_2$), 7.55-7.19 (m, 9H; ArCH), 7.11 (d, J=7.9 Hz, 2H; ArCH$_2$), 7.07-7.00 (m, 2H; ArCH$_2$), 6.83-6.66 (m, 2H; ArCH$_2$), 5.77-5.65 (m, 1H), 5.44 (q, J=2.1, 1.2 Hz, 1H), 5.34-5.25 (m, 1H), 4.90 (d, J=11.9 Hz, 1H), 4.66 (d, J=11.7 Hz, 1H), 4.48-4.30 (m, 2H), 3.95 (dt, J=10.0, 3.3 Hz, 2H), 3.79 (d, J=5.1 Hz, 6H), 2.32 (s, 3H).

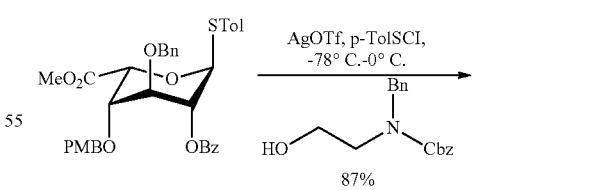

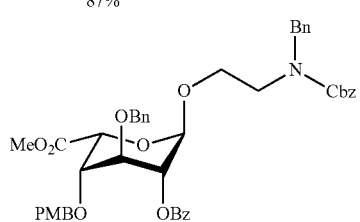

N-(Benzyl)-benzyloxycarbonyl-2-aminoethyl 2-O-benzoyl-3-O-benzyl-4-O-para-methoxylbenzyl-6-O-methyl ester-1-thio-α-L-idopyranoside Compound (2.0 g, 3.1 mmol) was treated according to the general procedures of pre-activation based single-step glycosylation with acceptor (1.5 equiv) to give compound (2.2 g, 89%). $^1$H NMR (500 MHz, CDCl$_3$) δ 8.02 (dd, J=8.2, 1.4 Hz, 2H; ArCH$_2$), 7.55 (d, J=6.5 Hz, 1H; ArCH), 7.41-7.21 (m, 16H; ArCH), 7.06 (td, J=8.9, 1.8 Hz, 3H; ArCH), 6.78-6.71 (m, 2H; ArCH$_2$), 5.23-5.09 (m, 4H), 4.83-4.77 (m, 2H), 4.66 (dd, J=11.7, 1.6 Hz, 1H), 4.60-4.50 (m, 2H), 4.46-4.27 (m, 4H), 3.91 (tt, J=6.2, 2.8 Hz, 2H), 3.78 (d, J=8.8 Hz, 6H), 3.47-3.37 (m, 2H). $^{13}$C NMR (125 MHz, CDCl$_3$) δ 169.08, 165.55, 159.26, 156.13, 137.86, 136.63, 135.76, 133.26, 130.03, 129.53, 129.47, 128.85, 128.46, 128.33, 128.19, 127.87, 127.83, 127.23, 113.61, 98.65, 73.99, 72.41, 72.31, 72.20, 68.56, 68.14, 67.58, 67.28, 61.77, 55.25, 52.34, 48.43, 46.66, 45.64, 43.95, 29.72. HRMS: m/z calc. for C$_{46}$H$_{47}$NO$_{11}$ [M+NH$_4$]$^+$: 807.3487; found: 807.3458.

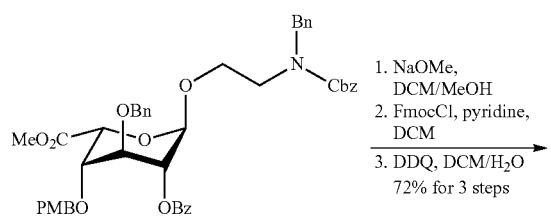

N-(Benzyl)-benzyloxycarbonyl-2-aminoethyl 2-O-fluorenylmethyloxycarbonyl-3-O-benzyl-4-O-para-methoxylbenzyl-6-O-methyl ester-1-thio-α-L-idopyranoside A mixture of starting material (2.66 g, 3.37 mmol) and NaOMe (25% in MeOH) (0.31 ml, 1.7 mmol) in DCM/MeOH (1/2, v/v, 0.2M) was stirred at room temperature for 1 h. Then the reaction mixture was neutralized with Amberlite-H$^+$ resin and filtered. The crude was evaporated under reduced pressure and subjected to 2-OH Fmoc protection and 4-OH PMB deprotection according to the general procedures to give compound (1.9 g, 72% yield for 3 steps). $^1$H NMR (500 MHz, CDCl$_3$) δ 7.77 (dt, J=7.6, 1.0 Hz, 2H; ArCH$_2$), 7.57 (ddd, J=7.7, 4.2, 1.1 Hz, 2H; ArCH$_2$), 7.41 (tt, J=7.5, 1.4 Hz, 2H; ArCH$_2$), 7.38-7.19 (m, 13H; ArCH), 7.16-6.99 (m, 2H; ArCH$_2$), 5.22-5.11 (m, 2H), 5.01-4.96 (m, 1H), 4.79 (dd, J=11.8, 3.0 Hz, 2H), 4.75-4.70 (m, 1H), 4.62 (dd, J=12.0, 7.4 Hz, 1H), 4.57-4.37 (m, 4H), 4.24 (t, J=7.4 Hz, 1H), 4.07 (s, 1H), 3.93 (m, 1H), 3.86-3.81 (m, 3H), 3.80 (td, J=3.0, 1.2 Hz, 1H), 3.74-3.51 (m, 2H), 3.41 (dt, J=22.2, 5.6 Hz, 2H), 2.78 (s, 1H). $^{13}$C NMR (125 MHz, CDCl$_3$) δ 169.68, 156.34, 153.75, 143.04, 141.33, 137.82, 137.23, 136.62, 129.06, 128.55, 128.53, 128.25, 128.08, 127.98, 127.87, 127.76, 127.32, 127.23, 125.33, 125.17, 125.13, 120.16, 98.49, 74.39, 72.32, 70.77, 70.60, 68.02, 67.74, 67.45, 52.46, 51.61, 46.69, 45.67. HRMS: m/z calc. for C$_{46}$H$_{45}$NO$_{11}$ [M+NH$_4$]$^+$: 805.3331; found: 805.3311.

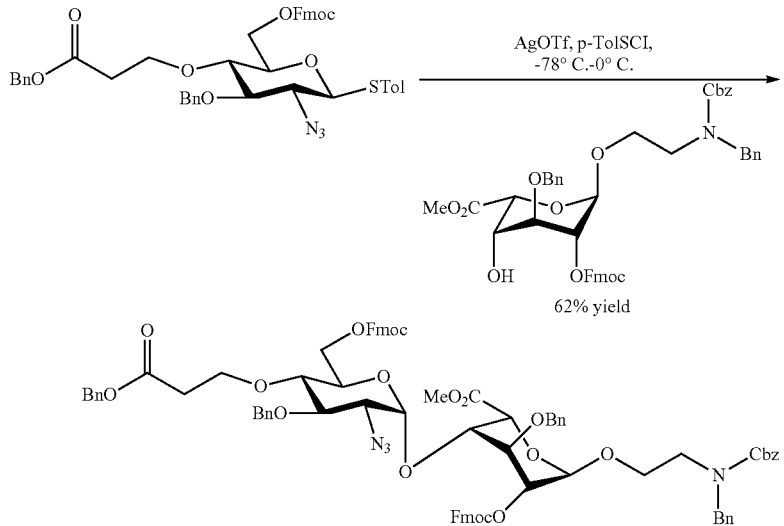

N-(Benzyl)-benzyloxycarbonyl-2-aminoethyl 3-O-benzyl-4-O-benzylpropionate-2-deoxy-azido-6-O-fluorenylmethyloxycarbonyl-1-thio-β-D-glucopyranoside-(1→4)-3-O-benzyl-2-O-fluorenylmethyloxycarbonyl-6-O-methyl ester-1-thio-α-L-idopyranoside Compound (1.8 g, 2.3 mmol) was treated according to the general procedures of pre-activation based single-step glycosylation to give compound (2.05 g, 62%, a/p, 3/1). 1H NMR (500 MHz, CDCl$_3$) δ 7.81-7.66 (m, 3H; Ar—H), -continued

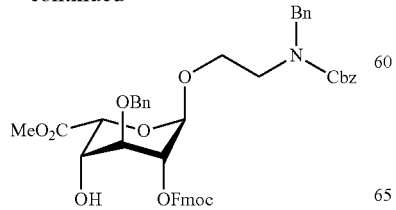

7.66-7.50 (m, 4H; Ar—H), 7.46-7.18 (m, 25H; Ar—H), 7.18-7.01 (m, 4H; Ar—H), 5.24-5.04 (m, 5H, 1-H), 4.93-4.86 (m, 1H, 1'-H), 4.86-4.69 (m, 5H), 4.63-4.44 (m, 4H), 4.43-4.29 (m, 4H), 4.27-4.01 (m, 5H), 4.01-3.81 (m, 4H), 3.76 (d, J=3.2 Hz, 3H), 3.68-3.59 (m, 1H), 3.57-3.35 (m, 3H), 3.29 (ddt, J=10.3, 6.9, 3.6 Hz, 1H), 2.54 (ddt, J=15.6, 11.2, 5.1 Hz, 2H), 2.33 (d, J=3.9 Hz, 3H). $^{13}$C NMR (125 MHz, CDCl$_3$) δ 171.00, 169.39, 156.18, 154.99, 154.58, 144.24, 143.35, 143.26, 141.27, 140.22, 137.75, 137.67, 137.34, 135.46, 131.39, 130.39, 130.20, 130.08, 128.77, 128.58, 128.47, 128.45, 128.35, 128.25, 128.00, 127.97, 127.91, 127.84, 127.80, 127.40, 127.29, 127.23, 127.19, 127.15, 125.36, 125.26, 125.15, 120.60, 120.09, 120.04, 98.50, 79.62, 76.78, 75.09, 73.89, 73.24, 70.42, 70.00, 69.61, 68.07, 67.70, 67.32, 66.44, 65.81, 63.30, 52.36, 51.59, 46.72, 46.56, 35.34.

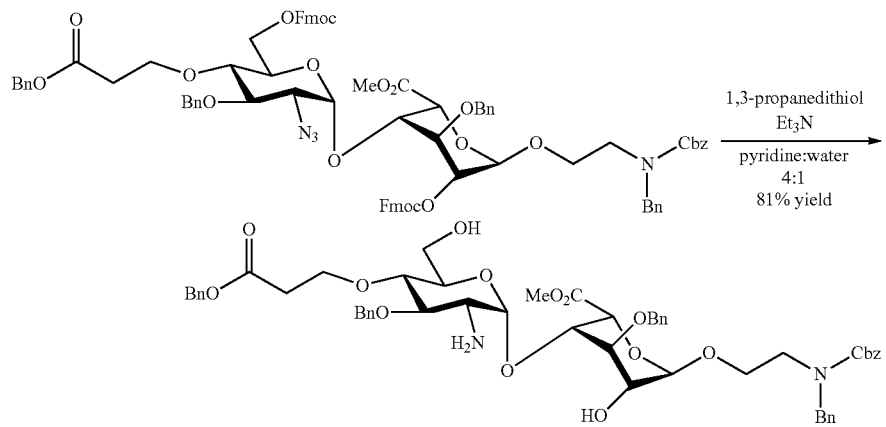

N-(Benzyl)-benzyloxycarbonyl-2-aminoethyl 3-O-benzyl-4-O-benzylpropionate-2-deoxy-amino-1-thio-β-D-glucopyranoside-(1→4)-3-O-benzyl-6-O-methyl ester-1-thio-α-L-idopyranoside At 50° C. under N$_2$ atmosphere, 1,3-propanedithiol (2.8 ml, 27.0 mmol) and Et$_3$N (3.7 ml, 27.0 mmol) was added to a solution of starting material (0.7 g, 0.48 mmol) in pyridine/H$_2$O (4/1, 0.04 M) for 2 h. The reaction mixture was concentrated by rotary evaporation and purified by silica gel column chromatography using a gradient of DCM and MeOH (from 50/1 to 40/1 to 20/1, v/v) to give desired product (0.38 g, 81%). $^1$H NMR (500 MHz, CDCl3) δ 7.45-6.95 (m, 19H; Ar—H), 7.12-7.04 (m, 2H; ArCH$_2$), 5.21-5.06 (m, 4H), 5.00-4.90 (m, 2H), 4.84 (m, 2H), 4.70 (d, J=11.9 Hz, 1H), 4.62-4.43 (m, 4H), 4.15 (s, 1H), 4.02 (dt, J=10.3, 5.4 Hz, 1H), 3.91 (dt, J=13.3, 4.5 Hz, 3H), 3.78-3.64 (m, 6H), 3.64-3.51 (m, 1H), 3.46-3.32 (m, 4H), 2.83 (dd, J=10.1, 3.7 Hz, 1H), 2.57 (m, 7H). $^{13}$C NMR (125 MHz, CDCl$_3$) δ 171.56, 138.09, 135.60, 128.60, 128.53, 128.49, 128.46, 128.42, 128.36, 128.32, 127.94, 127.82, 127.74, 127.66, 127.18, 101.88, 96.50, 82.19, 78.58, 76.77, 75.57, 72.23, 72.03, 7.87, 67.80, 67.36, 67.22, 66.54, 66.43, 61.22, 55.04, 52.37, 51.61, 46.68, 45.70, 35.41. HRMS: m/z calc. for C$_{54}$H$_{62}$N$_2$O$_{15}$ [M+H$^+$]$^+$: 978.4150; found: 978.4205.

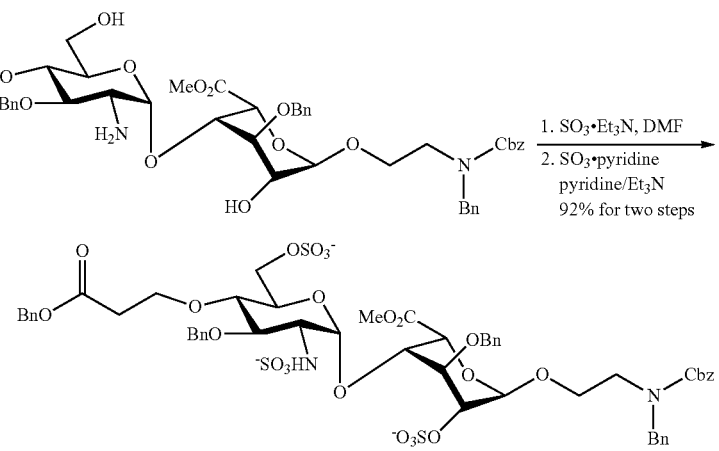

N-(Benzyl)-benzyloxycarbonyl-2-aminoethyl 3-O-benzyl-4-O-benzylpropionate-2-deoxy-sulfoamino-6-O-sulfoamino-1-thio-β-D-glucopyranoside-(1→4)-3-O-benzyl-6-O-methyl ester-2-O-sulfonato-1-thio-α-L-idopyranoside To a solution of starting material (0.3 g, 0.3 mmol) in DMF (2.0 ml, 0.15 M) was added sulfur trioxide triethylamine complex (1.12 g, 6.0 mmol) and resulting reaction mixture was stirred at 55° C. for 2 h. The reaction mixture was purified by a LH-20 gel column with CH$_3$OH. Fractions containing product were collected under reduced pressure and the crude was dissolved in pyridine/Et$_3$N (10/1, v/v, 0.15M). Sulfur trioxide pyridine complex (0.45 g, 3 mmol) was added to reaction mixture at 55° C. and stirred for 2 h. After reaction completed as indicated by TLC (EtOAc/MeOH/H$_2$O 6/1/1), the reaction mixture was passed through LH-20 gel column with CH$_3$OH. A column of Dowex 50WX4 Na$^+$ resin was used for ion exchange to give sodium form product. (0.34 g, 92% for two steps). $^1$H NMR (500 MHz, CD$_3$OD) δ 7.45 (d, J=7.5 Hz, 2H; ArCH$_2$), 7.41-7.09 (m, 17H; Ar—H), 6.98-6.85 (m, 2H; ArCH$_2$), 5.40 (d, J=3.4 Hz, 1H), 5.32-5.24 (m, 1H), 5.13-4.99 (m, 4H), 4.75 (dd, J=11.4, 7.1 Hz, 1H), 4.69-4.58 (m, 3H), 4.54 (s, 8H), 4.50 (s, 1H), 4.40-4.19 (m, 4H), 4.05-3.86 (m, 3H), 3.82-3.63 (m, 5H), 3.59-3.28 (m, 5H), 2.49 (t, J=6.4 Hz, 2H). $^{13}$C NMR (125 MHz, CD3OD) δ 172.29, 170.58, 156.68, 138.91, 137.97, 137.64, 137.43, 136.15, 128.34, 128.32, 128.24, 128.18, 128.11, 128.07, 128.00, 127.97, 127.89, 127.87, 127.61, 127.54, 127.46, 127.43, 127.32, 126.97, 99.33, 98.72, 79.70, 77.42, 75.01, 73.47, 73.06, 72.41, 70.87, 70.03, 67.90, 67.25, 66.75, 66.37, 66.13, 65.90, 58.15, 58.07, 52.18, 51.45, 51.38, 46.69, 45.72, 35.26. HRMS: m/z calc. for C$_{54}$H$_{59}$N$_2$O$_{24}$S$_3^{3-}$ [M+H$^+$]$^{2-}$: 608.1355; found: 608.1370.

N-(Benzyl)-benzyloxycarbonyl-2-aminoethyl 3-O-benzyl-4-O-benzylpropionate-2-deoxy-sulfoamino-1-thio-β-D-glucopyranoside-(1→4)-3-O-benzyl-6-O-methyl ester-1-thio-α-L-idopyranoside The starting material (90 mg, 0.09 mmol) was dissolved in H$_2$O/THF (1/1, v/v, 0.05 M) mixture, followed by addition of NaHCO$_3$ (115 mg, 1.37 mmol) and sulfur trioxide triethylamine complex (142 mg, 0.9 mmol). The reaction mixture was stirred at room temperature for 2 h and diluted with DCM. The organic mixture was washed with water and brine, and then filtered. The filtrate was concentrated under reduced pressure and the residue was purified by silica gel column chromatography using a mixture of DCM and Methanol (20/1, v/v). $^1$H NMR (500 MHz, CD$_3$OD) δ 7.45 (d, J=7.4 Hz, 2H; ArCH$_2$), 7.40-7.10 (m, 15H; Ar—H), 6.96 (dq, J=9.0, 4.7, 3.8 Hz, 2H; ArCH$_2$), 5.41 (d, J=3.4 Hz, 1H), 5.16-5.06 (m, 3H), 4.99 (d, J=10.8 Hz, 1H), 4.88 (s, 2H), 4.81 (d, J=9.5 Hz, 1H), 4.75-4.59 (m, 3H), 4.55 (d, J=15.5 Hz, 1H), 4.49-4.33 (m, 2H), 4.18 (s, 2H), 4.01 (dt, J=9.2, 5.6 Hz, 1H), 3.95-3.80 (m, 3H), 3.78-3.51 (m, 6H), 3.49-3.25 (m, 5H), 2.51 (td, J=6.2, 5.7, 3.4 Hz, 2H). $^{13}$C NMR (125 MHz, CD$_3$OD) δ 171.81, 170.46, 156.65, 139.00, 138.10, 137.68, 128.24, 128.13, 128.10, 128.06, 128.01, 127.86, 127.84, 127.79, 127.77, 127.56, 127.52, 127.47, 127.38, 127.34, 127.26, 127.02, 126.90, 126.87, 101.38, 96.25, 79.92, 77.36, 74.71, 73.59, 72.15, 71.56, 67.64, 67.42, 66.47, 65.88, 60.36, 58.11, 51.55, 51.28, 46.67, 45.78, 35.15. HRMS: m/z calc. for C$_{34}$H$_{61}$N$_2$O$_{18}$S$^-$ [M]$^-$: 1057.3646; found: 1057.3646.

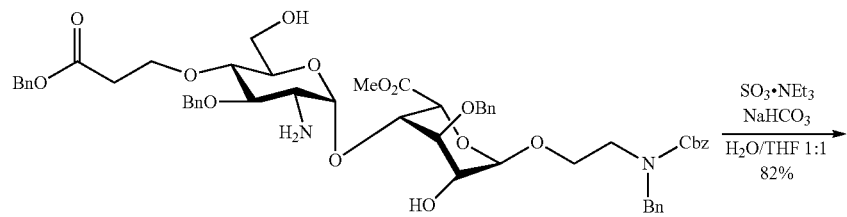

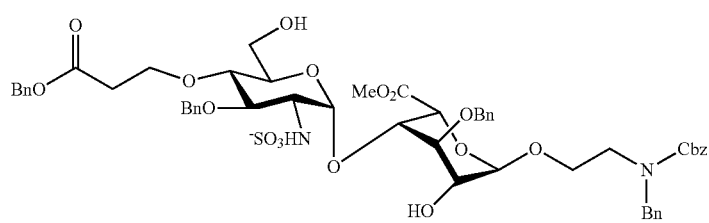

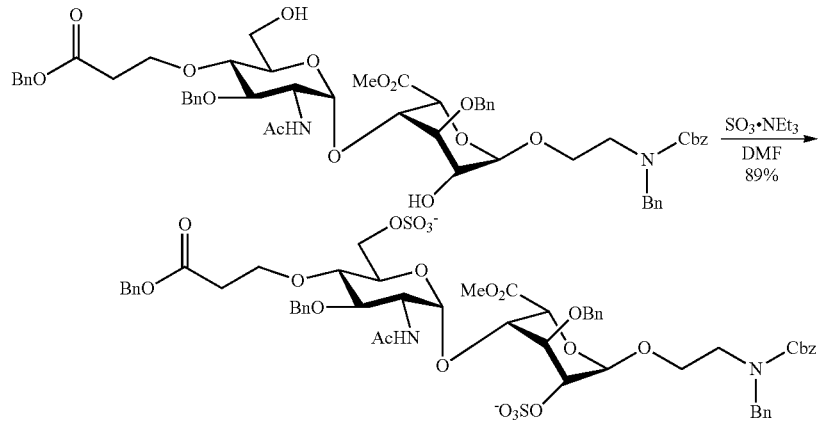

N-(Benzyl)-benzyloxycarbonyl-2-aminoethyl 3-O-benzyl-4-O-benzylpropionate-2-deoxy-acetamido-6-O-sulfonato-1-thio-β-D-glucopyranoside-(1→4)-3-O-benzyl-6-O-methyl ester 2-O-sulfonato-1-thio-α-L-idopyranoside To a solution of starting material (225 mg, 0.22 mmol) in DMF (0.08 M) was added sulfur trioxide triethylamine complex (800 mg, 4.4 mmol) and resulting reaction mixture was stirred at 55° C. for 2 h. The reaction mixture was purified by a LH-20 gel column with $CH_3OH$. Fractions containing product were collected under reduced pressure and the residue was passed through a column of Dowex 50WX4 $Na^+$ resin using $H_2O$ as eluent to give sodium form product (223 mg, 89%). $^1H$ NMR (500 MHz, CD3OD) δ 7.56 (dd, J=9.8, 4.7 Hz, 1H; Ar—H), 7.44-7.17 (m, 17H; Ar—H), 7.05 (m, 2H; ArCH$_2$), 5.22-5.09 (m, 4H), 4.83-4.73 (m, 3H), 4.73-4.57 (m, 4H), 4.56-4.41 (m, 3H), 4.29-4.13 (m, 3H), 4.12-4.03 (m, 3H), 4.00-3.85 (m, 2H), 3.76 (d, J=12.3 Hz, 3H), 3.70-3.61 (m, 3H), 3.51-3.36 (m, 3H), 3.35 (s, 3H), 2.64-2.52 (m, 2H), 1.97 (s, 3H). HRMS: m/z calc. for $C_{56}H_{62}N_2O_{22}S_2{}^{2-}$ $[M]^{2-}$: 589.1623; found: 589.1611.

Aminoethyl 4-O-carboxyethyl-2-deoxy-acetamido-6-O-sulfonato-1-thio-β-D-glucopyranoside-(1→4)-6-O-methyl ester-2-O-sulfonato-1-thio-α-L-idopyranoside Compound (350 mg, 0.29 mmol) was treated according to the general procedures of Hydrogenolysis to give compound (180 mg, 87%). $^1H$ NMR (500 MHz, $D_2O$) δ 5.19 (d, J=3.4 Hz, 1H, 1-H), 5.02 (d, J=2.0 Hz, 1H, 1'-H), 4.77 (d, J=2.1 Hz, 1H), 4.26 (t, J=4.0 Hz, 1H), 4.19-4.05 (m, 3H), 4.04-4.00 (m, 1H), 3.87 (ddd, J=11.2, 5.5, 3.5 Hz, 2H), 3.81-3.75 (m, 1H), 3.69 (s, 3H), 3.65-3.56 (m, 2H), 3.48 (t, J=9.8 Hz, 1H), 3.25 (t, J=9.5 Hz, 1H), 3.16-3.05 (m, 3H), 2.40 (d, J=6.4 Hz, 2H). $^{13}C$ NMR (125 MHz, $D_2O$) δ 170.99, 99.30, 98.96, 77.76, 76.90, 74.53, 70.46, 69.25, 69.07, 67.26, 67.11, 66.16, 64.60, 57.61, 53.01, 38.89. HRMS: m/z calc. for $C_{18}H_{29}N_2O_{22}S_3{}^{3-}$ $[M+H^+]^{2-}$: 361.0232; found: 361.0238.

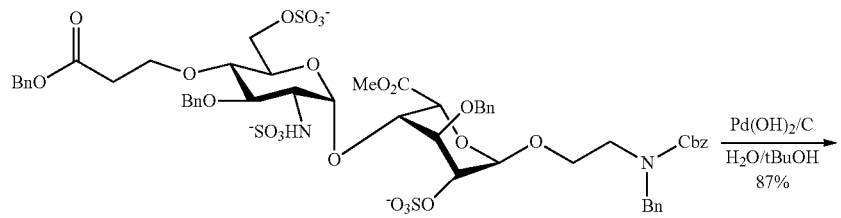

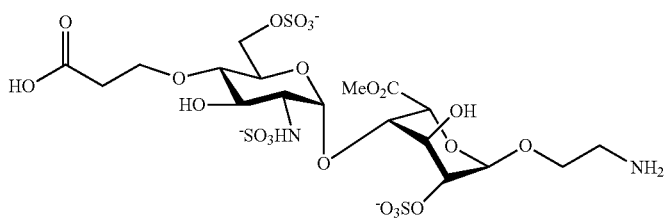

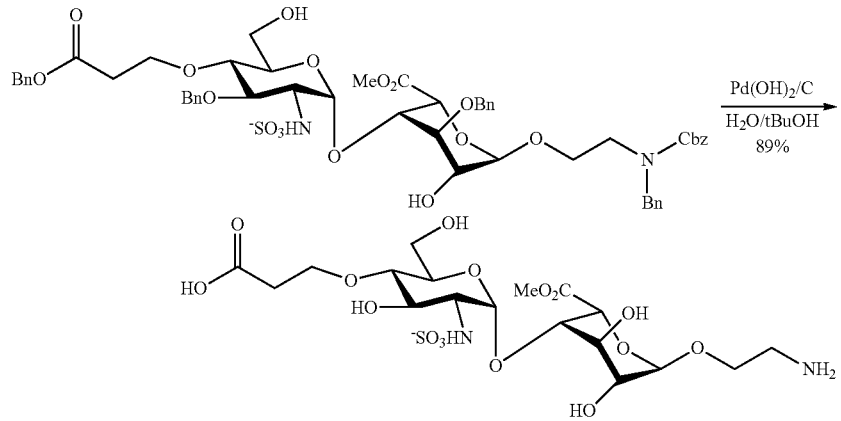

Aminoethyl 4-O-carboxyethyl-2-deoxy-sulfoamino-1-thio-β-D-glucopyranoside-(1→4)-6-O-methyl ester-1-thio-α-L-idopyranoside Compound (170 mg, 0.16 mmol) was treated according to the general procedures of Hydrogenolysis to give compound (80.5 mg, 87%). $^1$H NMR (500 MHz, CD$_3$OD) δ 5.36 (d, J=3.7 Hz, 1H, 1-H), 4.95 (d, J=3.0 Hz, 1H, 1'-H), 4.80 (d, J=3.2 Hz, 1H), 4.18 (t, J=4.3 Hz, 1H), 4.06-3.97 (m, 2H), 3.88 (tdd, J=11.1, 7.7, 4.7 Hz, 2H), 3.75 (s, 3H), 3.71 (td, J=12.0, 11.1, 3.0 Hz, 2H), 3.62 (ddt, J=18.5, 7.5, 3.7 Hz, 3H), 3.57-3.53 (m, 1H), 3.41 (dt, J=10.2, 2.8 Hz, 1H), 3.29-3.22 (m, 2H), 3.04 (dtt, J=9.5, 7.0, 3.4 Hz, 2H), 2.39 (t, J=5.9 Hz, 2H). $^{13}$C NMR (125 MHz, CD$_3$OD) δ 170.39, 101.45, 96.63, 78.53, 74.10, 71.71, 69.08, 68.65, 68.01, 67.12, 64.71, 60.57, 58.06, 51.62, 46.32, 42.68, 39.26, 36.85. HRMS: m/z calc. for $C_{18}H_{31}N_2O_{16}S^-$ [M]$^-$: 563.1400; found: 563.1401.

Aminoethyl 4-O-carboxyethyl-2-deoxy-acetamido-6-O-sulfonato-1-thio-β-D-glucopyranoside-(1→4)-6-O-methyl ester-2-O-sulfonato-1-thio-α-L-idopyranoside Compound (290 mg, 0.25 mmol) was treated according to the general procedures of hydrogenolysis to give compound (138 mg, 82%). $^1$H NMR (500 MHz, D$_2$O) δ 7.72 (d, J=9.6 Hz, 1H, NH), 5.02 (s, 1H, 1-H), 4.95 (d, J=3.4 Hz, 1H, 1'-H), 4.83 (d, J=1.9 Hz, 1H), 4.20 (d, J=3.0 Hz, 1H), 4.15-4.06 (m, 3H), 3.95 (d, J=2.6 Hz, 1H), 3.92-3.74 (m, 4H), 3.66 (s, 3H), 3.64-3.59 (m, 1H), 3.50-3.41 (m, 2H), 3.25-3.00 (m, 4H), 2.47 (t, J=5.9 Hz, 2H), 1.88 (s, 3H). $^{13}$C NMR (125 MHz, D$_2$O) δ 171.11, 98.96, 94.39, 77.66, 72.93, 71.10, 70.95, 69.64, 68.33, 66.58, 66.42, 64.67, 62.93, 52.96, 52.85, 38.83, 22.03. HRMS: m/z calc. for $C_{20}H_{32}N_2O_{20}S_2^{2-}$ [M+H$^+$]$^-$: 685.1074; found: 685.1086.

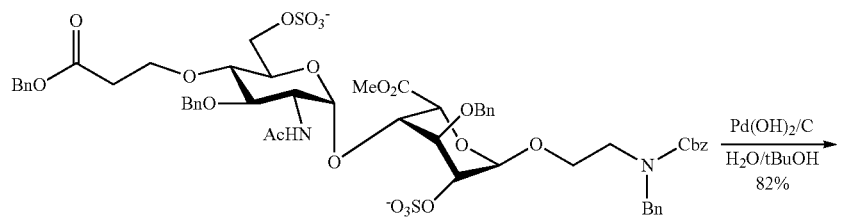

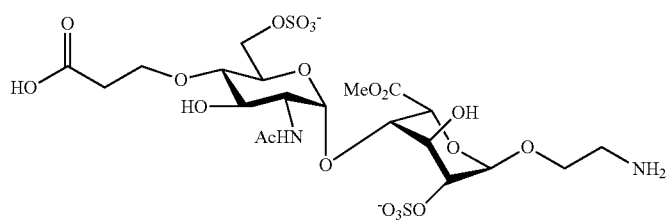

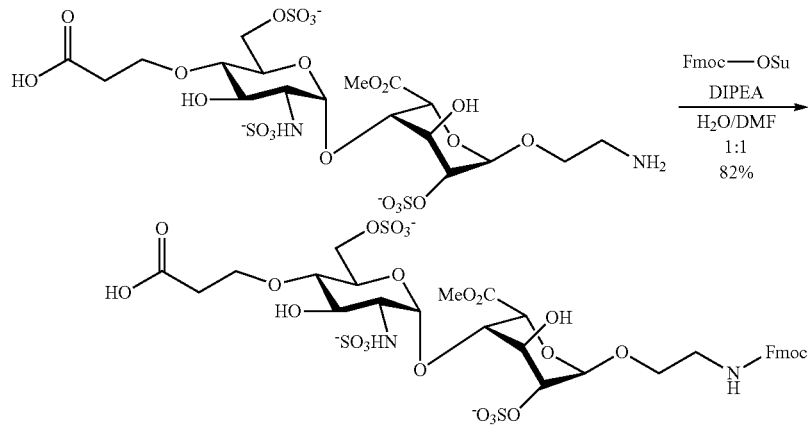

N-fluorenylmethyloxycarbonyl-2-aminoethyl 4-O-carboxyethyl-2-deoxy-acetamido-6-O-sulfonato-1-thio-β-D-glucopyranoside-(1→4)-6-O-methyl ester-2-O-sulfonato-1-thio-α-L-idopyranoside Compound (220 mg, 0.31 mmol) was treated according to the general procedures of protection of $NH_2$ with Fmoc to give compound (235 mg, 82%). $^1$H NMR (500 MHz, $CD_3OD$) δ 7.80 (d, J=7.6 Hz, 2H), 7.67 (d, J=7.5 Hz, 2H), 7.40 (td, J=7.8, 2.6 Hz, 2H), 7.33 (t, J=7.5 Hz, 2H), 5.26 (d, J=3.4 Hz, 1H, 1-H), 5.21 (s, 1H, 1'-H), 4.84 (d, J=2.2 Hz, 1H), 4.41 (d, J=3.3 Hz, 1H), 4.32 (dt, J=7.0, 3.3 Hz, 3H), 4.25-4.17 (m, 3H), 4.06 (dt, J=9.1, 6.1 Hz, 2H), 3.98 (td, J=6.7, 6.2, 3.2 Hz, 2H), 3.79 (dd, J=12.2, 7.0 Hz, 2H), 3.74 (s, 3H), 3.64 (dd, J=10.7, 8.9 Hz, 2H), 3.56 (dt, J=10.2, 5.1 Hz, 2H), 3.27 (dd, J=10.6, 3.5 Hz, 2H), 2.56 (q, J=5.7 Hz, 3H). $^{13}$C NMR (125 MHz, $CD_3OD$) δ 170.51, 143.88, 141.13, 127.39, 126.80, 124.88, 124.85, 119.48, 99.31, 98.68, 78.87, 75.80, 73.53, 71.03, 69.75, 67.70, 66.60, 66.54, 66.14, 65.95, 57.62, 51.88, 40.12, 37.32. HRMS: m/z calc. for $C_{33}H_{39}N_2O_{24}S_3{}^{3-}$ [M]$^{3-}$: 314.3690; found: 314.3696.

N-fluorenylmethyloxycarbonyl-2-aminoethyl 4-O-carboxyethyl-2-deoxy-sulfoamino-1-thio-β-D-glucopyranoside-(1→4)-6-O-methyl ester-1-thio-α-L-idopyranoside Compound (80 mg, 0.14 mmol) was treated according to the general procedures of protection of $NH_2$ with Fmoc to give compound (79 mg, 71%). $^1$H NMR (500 MHz, $CD_3OD$) δ 7.79 (d, J=7.5 Hz, 2H), 7.64 (d, J=7.5 Hz, 2H), 7.39 (t, J=7.4 Hz, 2H), 7.31 (td, J=7.5, 1.2 Hz, 2H), 5.35 (d, J=3.7 Hz, 1H), 4.79 (d, J=2.9 Hz, 1H), 4.32 (t, J=6.4 Hz, 2H), 4.22-4.13 (m, 2H), 4.04-3.95 (m, 2H), 3.87 (dd, J=9.5, 5.6 Hz, 1H), 3.78-3.70 (m, 3H), 3.68 (s, 3H), 3.61-3.47 (m, 3H), 3.38 (dt, J=10.1, 2.8 Hz, 1H), 3.28-3.21 (m, 2H), 2.40 (t, J=5.9 Hz, 2H). $^{13}$C NMR (125 MHz, $CD_3OD$) δ 178.87, 170.39, 157.50, 143.88, 141.15, 127.36, 126.77, 124.76, 119.48, 101.33, 96.54, 78.64, 74.02, 71.71, 71.48, 69.30, 69.10, 67.67, 67.59, 67.00, 66.37, 60.46, 57.79, 51.53, 51.51, 40.21, 37.97. HRMS: m/z calc. for $C_{33}H_{41}N_2O_{18}S^-$ [M]$^-$: 785.2081; found: 785.2103.

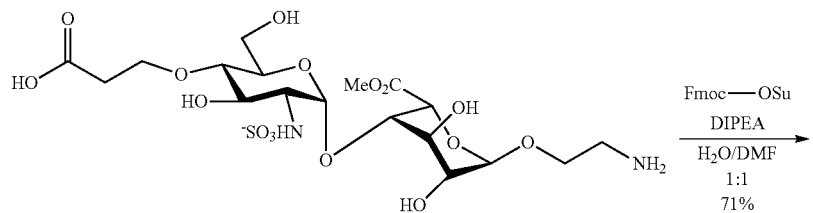

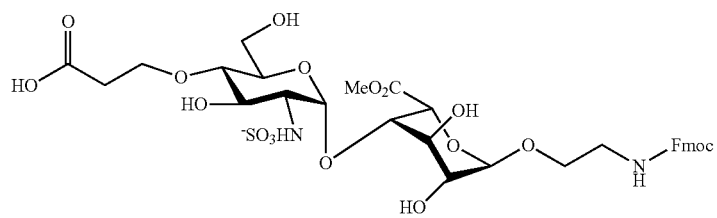

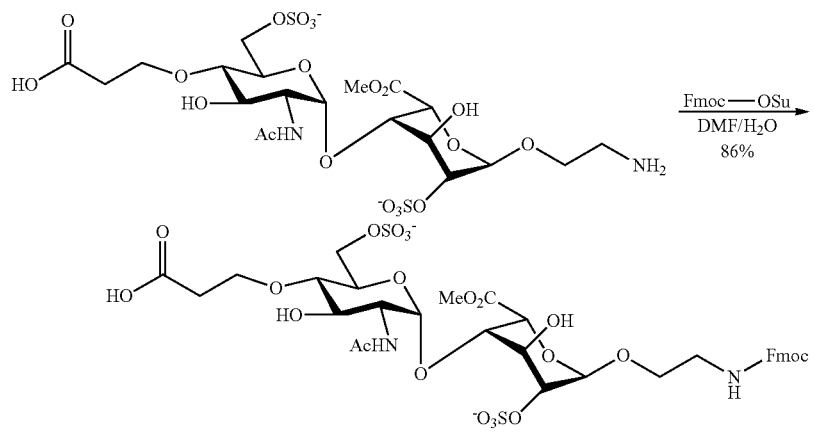

N-fluorenylmethyloxycarbonyl-2-aminoethyl 4-O-carboxyethyl-2-deoxy-acetamido-6-O-sulfonato-1-thio-β-D-glucopyranoside-(1→4)-6-O-methyl ester-2-O-sulfonato-1-thio-α-L-idopyranoside Compound (167 mg, 0.24 mmol) was treated according to the general procedures of protection of $NH_2$ with Fmoc to give compound (190 mg, 86%). $^1$H NMR (500 MHz, $CD_3OD$) δ 7.80 (d, J=7.5 Hz, 2H), 7.67 (d, J=7.5 Hz, 2H), 7.50 (d, J=9.2 Hz, 1H), 7.40 (tt, J=7.5, 1.7 Hz, 2H), 7.33 (tdd, J=7.5, 2.5, 1.2 Hz, 2H), 5.16 (s, 1H; 1-H), 5.03 (d, J=3.4 Hz, 1H; 1'-H), 4.86 (d, J=2.1 Hz, 1H), 4.31 (td, J=8.9, 8.2, 3.2 Hz, 4H), 4.25-4.17 (m, 4H), 4.07-3.91 (m, 5H), 3.84-3.75 (m, 2H), 3.73 (s, 3H), 3.68 (dd, J=10.8, 8.6 Hz, 1H), 3.64-3.55 (m, 2H), 3.27 (s, 1H), 2.44 (dd, J=6.8, 5.1 Hz, 3H), 2.07 (s, 3H). $^{13}$C NMR (125 MHz, $CD_3OD$) δ 178.30, 172.95, 170.30, 157.48, 143.88, 141.14, 127.37, 126.80, 124.86, 119.46, 99.57, 95.93, 78.75, 73.28, 72.93, 71.48, 69.91, 69.14, 67.55, 66.48, 66.36, 66.03, 64.34, 52.95, 51.75, 40.18, 37.44, 21.75. HRMS: m/z calc. for $C_{35}H_{42}N_2O_{22}S_2^{2-}$ [M]$^{2-}$: 453.0841; found: 453.0840.

N-Acetamidoethyl 4-O-carboxyethyl-2-deoxy-acetamido-6-O-sulfonato-1-thio-β-D-glucopyranoside-(1→4)-6-O-methyl ester-2-O-sulfonato-1-thio-α-L-idopyranoside Compound (20 mg, 0.03 mmol) was treated according to the general procedures of N-acetylation to give compound (13 mg, 62%). $^1$H NMR (500 MHz, $CD_3OD$) δ 5.32 (d, J=3.5 Hz, 1H, 1-H), 5.15 (d, J=2.7 Hz, 1H, 1'-H), 4.80 (d, J=2.9 Hz, 1H), 4.38-4.26 (m, 2H), 4.21 (d, J=2.8 Hz, 2H), 4.14-3.92 (m, 3H), 3.81 (s, 4H), 3.73-3.50 (m, 4H), 3.42 (ddd, J=14.5, 5.8, 3.4 Hz, 1H), 3.26 (dd, J=10.6, 3.5 Hz, 1H), 2.64-2.47 (m, 2H), 1.95 (s, 3H). $^{13}$C NMR (125 MHz, $CD_3OD$) δ 175.49, 171.98, 170.26, 99.76, 98.97, 78.53, 76.58, 75.02, 71.53, 69.71, 67.96, 67.85, 67.54, 67.41, 66.03, 58.04, 51.76, 38.81, 35.41, 21.13. HRMS: m/z calc. for $C_{20}H_{31}N_2O_{23}S_3^{3-}$ [M+Na$^+$]$^{2-}$: 393.0194; found: 393.0200.

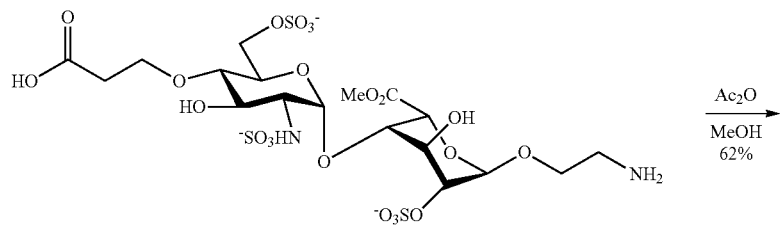

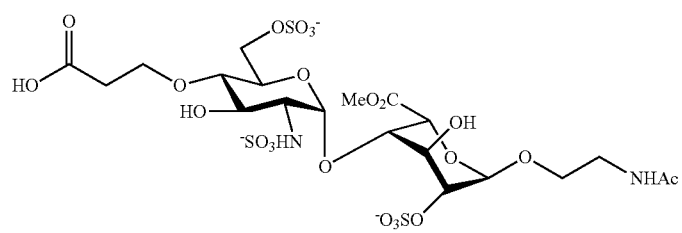

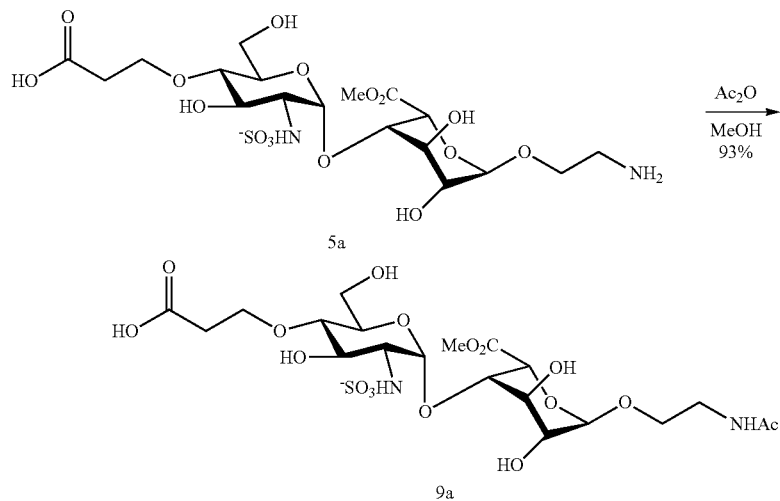

N-Acetamidoethyl 4-O-carboxyethyl-2-deoxy-sulfoamino-1-thio-β-D-glucopyranoside-(1→4)-6-O-methyl ester-1-thio-α-L-idopyranoside Compound (40 mg, 0.07 mmol) was treated according to the general procedures of Hydrogenolysis to give compound (40 mg, 93%). $^1$H NMR (500 MHz, CD$_3$OD) δ 5.36 (d, J=3.6 Hz, 1H, 1-H), 4.80 (d, J=3.0 Hz, 1H), 4.16 (t, J=4.3 Hz, 1H), 4.08-3.97 (m, 2H), 3.93-3.85 (m, 1H), 3.80-3.69 (m, 6H), 3.62-3.50 (m, 3H), 3.45-3.34 (m, 3H), 3.30-3.22 (m, 2H), 2.47 (ddd, J=6.5, 5.2, 3.5 Hz, 2H), 1.94 (s, 3H). $^{13}$C NMR (125 MHz, CD3OD) δ 177.09, 171.96, 170.45, 101.41, 96.58, 78.48, 74.12, 71.67, 71.62, 69.30, 68.55, 67.89, 67.27, 67.22, 60.53, 57.92, 51.55, 38.94, 36.65, 21.13. HRMS: m/z calc. for C$_{20}$H$_{33}$N$_2$O$_{17}$S$^-$ [M]$^-$: 605.1505; found: 605.1513.

N-Acetamidoethyl 4-O-carboxyethyl-2-deoxy-acetamido-6-O-sulfonato-1-thio-β-D-glucopyranoside-(1→4)-6-O-methyl ester-2-O-sulfonato-1-thio-α-L-idopyranoside Compound (19 mg, 0.03 mmol) was treated according to the general procedures of Hydrogenolysis to give compound (15 mg, 75%). $^1$H NMR (500 MHz, D$_2$O) δ 4.98 (s, 1H, 1-H), 4.96 (d, J=3.5 Hz, 1H, 1'-H), 4.81 (d, J=2.2 Hz, 1H), 4.18 (d, J=3.0 Hz, 1H), 4.14-4.10 (m, 3H), 3.93 (t, J=2.6 Hz, 1H), 3.91-3.82 (m, 2H), 3.79-3.72 (m, 1H), 3.71-3.63 (m, 4H), 3.58-3.46 (m, 3H), 3.26-3.19 (m, 3H), 3.18 (s, 1H), 2.37-2.31 (m, 2H), 1.89 (s, 3H), 1.82 (s, 3H). $^{13}$C NMR (125 MHz, D$_2$O) δ 174.64, 174.16, 171.21, 99.07, 94.35, 77.88, 73.08, 71.02, 69.63, 69.41, 67.33, 66.56, 66.32, 63.00, 53.07, 52.71, 48.75, 39.00, 37.35, 22.07, 21.68. HRMS: m/z calc. for C$_{22}$H$_{34}$N$_2$O$_{21}$S$_2$$^{2-}$ [M]$^{2-}$: 363.0553; found: 363.0555.

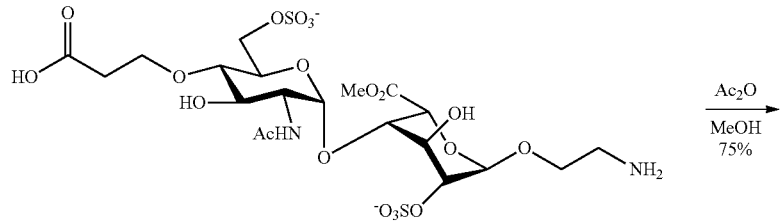

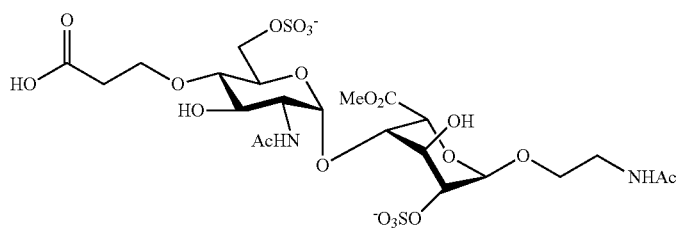

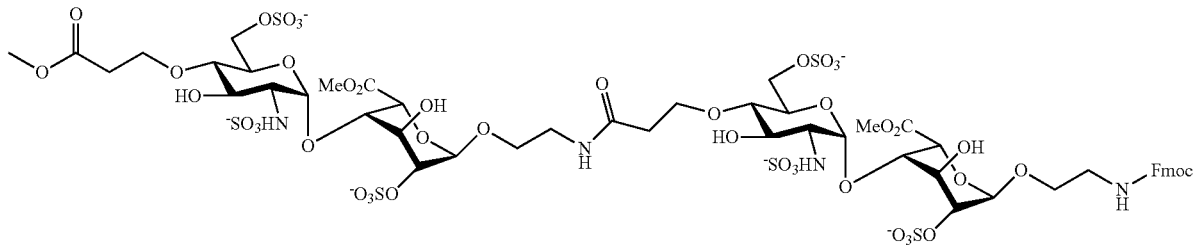

N-Fluorenylmethyloxycarbonyl-2-aminoethyl O-(4-O-methylpropionate-2-deoxy-sulfoamino-6-O-sulfoamino-1-thio-β-D-glucopyranoside)-(1→4)-O-(6-O-methyl ester-2-O-sulfonato-1-thio-α-L-idopyranoside)-(1→4)-O-(4-O-carboxyethyl-2-deoxy-sulfoamino-6-O-sulfonato-1-thio-β-D-glucopyranoside)-(1→4)—O-6-O-methyl ester-2-O-sulfonato-1-thio-α-L-idopyranoside Starting material (9 mg, 0.012 mmol) was treated according to the general procedures of pseudo-tetrasaccharides preparation with HBTU to give compound (15 mg, 76%). $^1$H NMR (500 MHz, D$_2$O) δ 7.79 (d, J=7.5 Hz, 2H), 7.56 (t, J=7.0 Hz, 2H), 7.40-7.33 (m, 2H), 7.32-7.23 (m, 2H), 5.14 (dd, J=22.2, 3.5 Hz, 2H), 4.94 (s, 1H), 4.89 (s, 1H), 4.54 (d, J=2.3 Hz, 1H), 4.39 (dd, J=10.7, 6.0 Hz, 1H), 4.28 (d, J=11.5 Hz, 2H), 4.22-4.00 (m, 7H), 3.95-3.79 (m, 5H), 3.75 (s, 1H), 3.64 (d, J=9.2 Hz, 3H), 3.55 (s, 3H), 3.52-3.38 (m, 6H), 3.25 (dd, J=20.8, 10.5 Hz, 2H), 3.19 (s, 3H), 3.07 (ddd, J=13.6, 11.1, 4.5 Hz, 3H), 2.52 (d, J=7.8 Hz, 2H), 2.34 (s, 2H). $^{13}$C NMR (125 MHz, D$_2$O) δ 174.62, 173.99, 171.17, 148.60, 143.64, 140.89, 128.16, 128.02, 127.44, 125.17, 124.96, 120.70, 120.10, 99.61, 99.20, 77.44, 77.36, 77.18, 73.69, 70.62, 70.27, 69.13, 69.05, 68.27, 67.48, 67.31, 67.03, 66.40, 66.26, 66.05, 65.86, 57.91, 52.90, 52.67, 52.18, 46.91, 40.09, 38.89, 36.46, 34.74.

N-Fluorenylmethyloxycarbonyl-2-aminoethyl O-(4-O-methylpropionate-2-deoxy-sulfoamino-6-O-sulfoamino-1-thio-β-D-glucopyranoside)-(1→4)-O-(6-O-methyl ester-2-O-sulfonato-1-thio-α-L-idopyranoside)-(1→4)-O-(4-O-carboxyethyl-2-deoxy-sulfoamino-1-thio-β-D-glucopyranoside)-(1→4)—O-6-O-methyl ester-1-thio-α-L-idopyranoside Starting material (13.5 mg, 0.018 mmol) was treated according to the general procedures of pseudo-tetrasaccharides preparation with HBTU to give compound (17 mg, 65%).

1H NMR (500 MHz, D$_2$O) δ 7.77 (d, J=7.6 Hz, 2H), 7.55 (t, J=6.9 Hz, 2H), 7.36 (t, J=7.5 Hz, 2H), 7.29-7.22 (m, 2H), 5.18 (d, J=3.5 Hz, 1H), 5.13 (d, J=3.5 Hz, 1H), 4.95 (s, 1H), 4.74-4.71 (m, 1H), 4.68-4.67 (m, 1H), 4.58 (d, J=2.6 Hz, 1H), 4.42-4.35 (m, 1H), 4.31-4.23 (m, 2H), 4.16-4.00 (m, 5H), 3.95 (t, J=2.6 Hz, 2H), 3.92-3.78 (m, 5H), 3.76-3.65 (m, 3H), 3.64 (s, 3H), 3.61-3.51 (m, 9H), 3.51-3.45 (m, 3H), 3.26 (td, J=10.3, 9.6, 5.7 Hz, 3H), 3.19 (d, J=1.9 Hz, 3H), 3.13-3.00 (m, 5H), 2.53-2.45 (m, 2H), 2.37-2.26 (m, 2H). $^{13}$C NMR (125 MHz, CD3OD) δ 173.05, 170.54, 170.44, 157.55, 143.90, 141.15, 127.38, 126.79, 124.84, 124.81, 119.50, 101.24, 99.58, 98.79, 96.69, 78.29, 78.16, 76.10, 74.19, 71.60, 71.30, 69.65, 69.00, 67.88, 67.66, 67.44, 67.08, 66.86, 66.42, 65.95, 60.37, 58.12, 51.84, 51.70, 50.85, 40.21, 38.75, 36.47, 34.77. HRMS: m/z calc. for $C_{37}H_{60}N_4O_{37}S_4^{4-}$ [M+H$^+$]$^{3-}$: 427.0638; found: 427.0630.

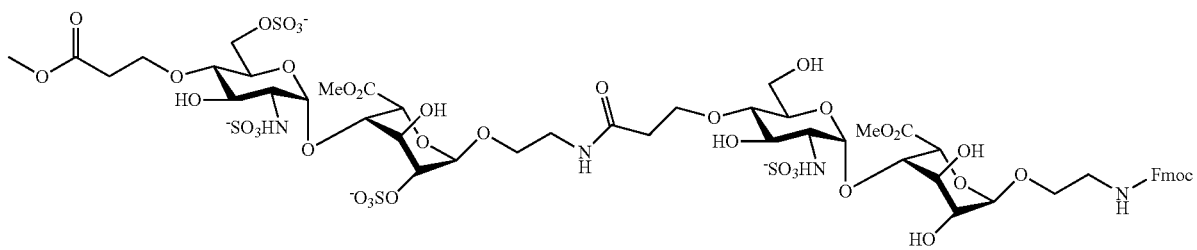

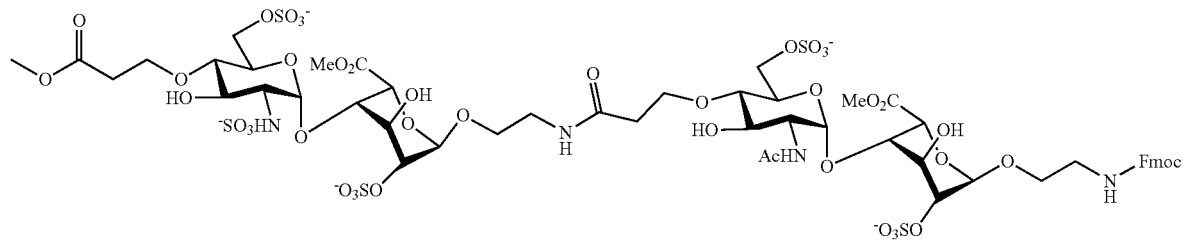

N-Fluorenylmethyloxycarbonyl-2-aminoethyl O-(4-O-methylpropionate-2-deoxy-sulfoamino-6-O-sulfonato-1-thio-β-D-glucopyranoside)-(1→4)-O-(6-O-methyl ester-2-O-sulfonato-1-thio-α-L-idopyranoside)-(1→4)-O-(4-O-carboxyethyl-2-deoxy-acetamido-6-O-sulfonato-1-thio-β-D-glucopyranoside)-(1→4)—O-6-O-methyl ester-2-O-sulfonato-1-thio-α-L-idopyranoside Starting material (18 mg, 0.024 mmol) was treated according to the general procedures of pseudo-tetrasaccharides preparation with HBTU to give compound (25 mg, 63%). $^1$H NMR (500 MHz, CD3OD) δ 7.80 (d, J=7.5 Hz, 2H), 7.67 (d, J=7.5 Hz, 2H), 7.40 (ddd, J=9.1, 5.2, 1.9 Hz, 2H), 7.35-7.29 (m, 2H), 5.28 (d, J=3.6 Hz, 1H), 5.18 (d, J=4.4 Hz, 2H), 5.00 (d, J=3.4 Hz, 1H), 4.86 (d, J=1.9 Hz, 1H), 4.84 (d, J=2.4 Hz, 1H), 4.40 (t, J=3.7 Hz, 1H), 4.31 (dh, J=6.7, 3.6 Hz, 5H), 4.25-4.15 (m, 5H), 4.13-4.05 (m, 2H), 3.99 (ddd, J=12.1, 6.1, 3.0 Hz, 5H), 3.84-3.76 (m, 5H), 3.72 (d, J=3.1 Hz, 2H), 3.69 (s, 3H), 3.66-3.54 (m, 5H), 3.48-3.34 (m, 5H), 3.26 (dd, J=10.6, 3.4 Hz, 1H), 2.60 (td, J=6.1, 3.5 Hz, 2H), 2.48 (t, J=5.9 Hz, 2H), 2.08 (s, 3H). $^{13}$C NMR (125 MHz, CD$_3$OD) δ 173.02, 170.48, 157.50, 143.89, 141.14, 127.39, 126.81, 124.89, 119.48, 99.55, 98.86, 96.42, 78.29, 76.15, 73.75, 73.44, 73.08, 71.53, 69.95, 69.64, 68.35, 67.56, 67.42, 67.37, 66.49, 66.21, 65.93, 64.31, 58.15, 53.35, 51.85, 50.84, 40.15, 38.62, 36.53, 34.76, 21.79. HRMS: m/z calc. for $C_{39}H_{61}N_4O_{41}S_5^{5-}$ $[M+H^+]^{4-}$: 350.5379; found: 350.5379.

N-Fluorenylmethyloxycarbonyl-2-aminoethyl O-(4-O-methylpropionate-2-deoxy-sulfoamino-1-thio-β-D-glucopyranoside)-(1→4)-O-(6-O-methyl ester-1-thio-α-L-idopyranoside)-(1→4)-O-(4-O-carboxyethyl-2-deoxy-sulfoamino-6-O-sulfonato-1-thio-β-D-glucopyranoside)-(1→4)—O-6-O-methyl ester-2-O-sulfonato-1-thio-α-L-idopyranoside Starting material (21 mg, 0.036 mmol) was treated according to the general procedures of pseudo-tetrasaccharides preparation with HATU to give compound (32 mg, 59%). $^1$H NMR (500 MHz, CD$_3$OD) δ 7.80 (d, J=7.5 Hz, 2H), 7.67 (d, J=7.4 Hz, 2H), 7.43-7.38 (m, 2H), 7.33 (td, J=7.5, 1.2 Hz, 2H), 5.41 (d, J=3.6 Hz, 1H), 5.28-5.19 (m, 2H), 4.97 (d, J=2.8 Hz, 1H), 4.84 (t, J=2.9 Hz, 2H), 4.43 (d, J=3.2 Hz, 1H), 4.31 (dq, J=10.5, 3.7, 3.3 Hz, 3H), 4.23-4.15 (m, 4H), 4.07 (dt, J=8.7, 5.5 Hz, 2H), 4.02-3.96 (m, 3H), 3.89 (ddd, J=9.5, 7.9, 5.0 Hz, 2H), 3.81-3.77 (m, 3H), 3.75 (d, J=6.6 Hz, 6H), 3.72 (dd, J=8.0, 3.2 Hz, 2H), 3.68 (s, 3H), 3.66-3.55 (m, 6H), 3.50-3.45 (m, 1H), 3.43-3.34 (m, 5H), 3.30-3.21 (m, 3H), 2.65-2.50 (m, 4H), 2.41 (dd, J=13.8, 7.4 Hz, 2H). $^{13}$C NMR (125 MHz, CD$_3$OD) δ 173.21, 172.85, 170.56, 157.50, 143.90, 141.13, 127.38, 126.82, 124.91, 124.87, 119.47, 101.44, 99.36, 99.17, 96.17, 78.16, 77.94, 76.57, 73.61, 73.43, 71.74, 71.48, 71.35, 69.59, 68.99, 67.99, 67.92, 67.57, 67.33, 66.75, 66.50, 66.36, 66.10, 65.65, 60.51, 58.27, 58.03, 51.83, 51.52, 50.72, 40.17, 38.86, 36.63, 34.74. HRMS: m/z calc. for $C_{37}H_{60}N_4O_{37}S_4^{4-}$ $[M]^{4-}$: 320.0460; found: 320.0446.

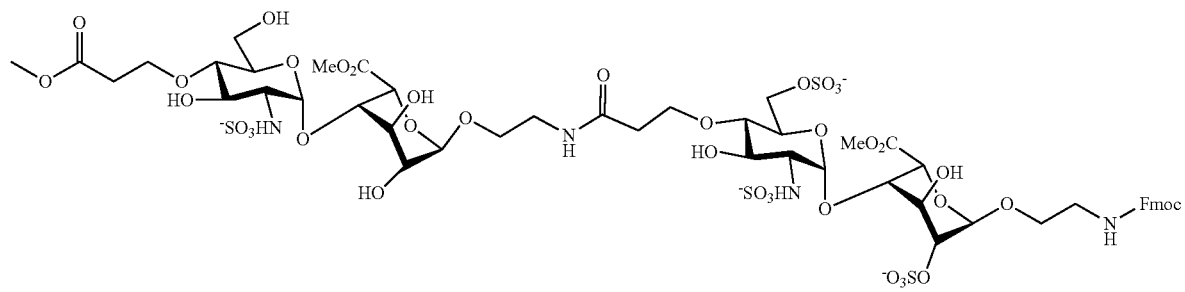

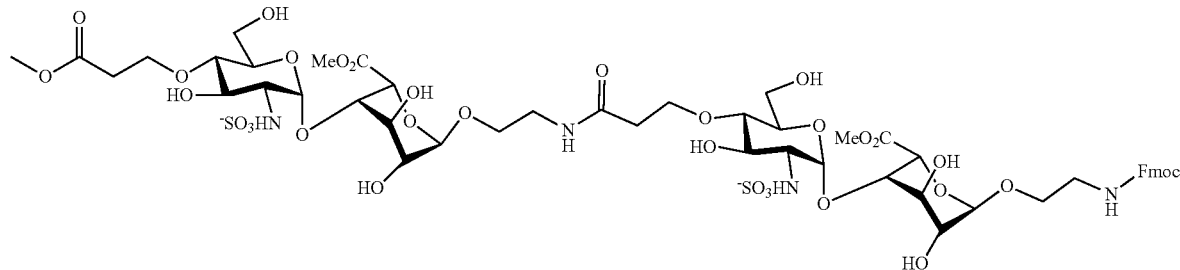

N-Fluorenylmethyloxycarbonyl-2-aminoethyl O-(4-O-methylpropionate-2-deoxy-sulfoamino-1-thio-β-D-glucopyranoside)-(1→4)-O-(6-O-methyl ester-1-thio-α-L-idopyranoside)-(1→4)-O-(4-O-carboxyethyl-2-deoxy-sulfoamino-1-thio-β-D-glucopyranoside)-(1→4)—O-6-O-methyl ester-1-thio-α-L-idopyranoside Starting material (12 mg, 0.020 mmol) was treated according to the general procedures of pseudo-tetrasaccharides preparation with HATU to give compound (20 mg, 70%). $^1$H NMR (500 MHz, CD$_3$OD) δ 7.81 (d, J=7.5 Hz, 2H), 7.66 (d, J=7.5 Hz, 2H), 7.40 (t, J=7.5 Hz, 2H), 7.33 (t, J=7.4 Hz, 2H), 5.35 (d, J=3.5 Hz, 1H), 5.32 (d, J=3.5 Hz, 1H), 4.97 (d, J=2.6 Hz, 1H), 4.81 (dd, J=6.5, 3.0 Hz, 2H), 4.32 (dd, J=7.0, 5.0 Hz, 2H), 4.19 (dd, J=11.8, 7.2 Hz, 3H), 4.10-3.95 (m, 5H), 3.92-3.85 (m, 3H), 3.75 (d, J=4.0 Hz, 5H), 3.73-3.68 (m, 8H), 3.67 (s, 3H), 3.63-3.59 (m, 4H), 3.58-3.53 (m, 4H), 3.42 (dt, J=9.8, 3.2 Hz, 3H), 3.31 (dq, J=3.6, 1.8 Hz, 6H), 2.62-2.47 (m, 5H), 2.37 (ddd, J=15.0, 6.7, 4.1 Hz, 2H). $^{13}$C NMR (125 MHz, CD$_3$OD) δ 173.03, 172.75, 170.43, 143.93, 141.17, 127.38, 126.80, 124.84, 119.50, 101.54, 101.37, 96.93, 96.39, 78.14, 78.08, 74.57, 74.04, 72.13, 71.63, 71.44, 69.30, 69.01, 67.92, 67.88, 67.46, 67.27, 67.21, 66.40, 60.62, 60.46, 58.45, 58.30, 54.42, 53.98, 51.50, 51.41, 50.66, 46.48, 42.39, 40.27, 38.88, 37.97, 36.57, 34.78. HRMS: m/z calc. for $C_{37}H_{62}N_4O_{31}S_2^{2-}$ [M]$^{2-}$: 561.1425; found: 561.1426.

N-Fluorenylmethyloxycarbonyl-2-aminoethyl O-(4-O-methylpropionate-2-deoxy-sulfoamino-1-thio-β-D-glucopyranoside)-(1→4)-O-(6-O-methyl ester-1-thio-α-L-idopyranoside)-(1→4)-O-(4-O-carboxyethyl-2-deoxy-acetamido-6-O-sulfonato-1-thio-β-D-glucopyranoside)-(1→4)—O-6-O-methyl ester-2-O-sulfonato-1-thio-α-L-idopyranoside Starting material (8 mg, 0.013 mmol) was treated according to the general procedures of pseudo-tetrasaccharides preparation with HATU to give compound (20 mg, 61%). $^1$H NMR (500 MHz, CD$_3$OD) δ 7.81 (d, J=7.5 Hz, 2H), 7.67 (d, J=7.6 Hz, 2H), 7.40 (tt, J=8.0, 1.6 Hz, 2H), 7.33 (tt, J=7.5, 1.4 Hz, 2H), 5.37 (d, J=3.6 Hz, 1H), 5.18 (s, 1H), 4.96 (d, J=3.4 Hz, 1H), 4.92 (d, J=2.9 Hz, 1H), 4.85 (d, J=2.0 Hz, 1H), 4.83 (d, J=3.0 Hz, 1H), 4.35-4.27 (m, 4H), 4.24-4.15 (m, 4H), 4.11-4.04 (m, 2H), 4.03-3.94 (m, 4H), 3.89 (ddd, J=9.4, 7.9, 5.1 Hz, 2H), 3.81-3.74 (m, 5H), 3.73-3.66 (m, 8H), 3.59 (ddt, J=21.0, 10.5, 2.4 Hz, 5H), 3.43-3.37 (m, 2H), 3.29-3.19 (m, 2H), 2.64-2.52 (m, 3H), 2.46 (dt, J=10.8, 5.3 Hz, 3H), 2.09 (s, 3H). $^{13}$C NMR (125 MHz, CD$_3$OD) δ 173.03, 172.97, 172.79, 170.47, 170.40, 143.90, 141.14, 127.37, 126.81, 124.90, 124.87, 119.47, 101.36, 99.53, 97.08, 96.29, 77.28, 78.12, 74.22, 73.87, 73.06, 71.87, 71.48, 71.42, 69.92, 69.17, 68.31, 67.87, 67.50, 67.29, 67.16, 66.48, 66.10, 65.84, 64.69, 60.55, 58.16, 53.60, 51.76, 51.51, 50.69, 40.18, 38.75, 36.62, 34.74, 21.75. HRMS: m/z calc. for $C_{39}H_{63}N_4O_{35}S_3^{3-}$ [M+H$^+$]$^{2-}$: 622.1262; found: 622.1260.

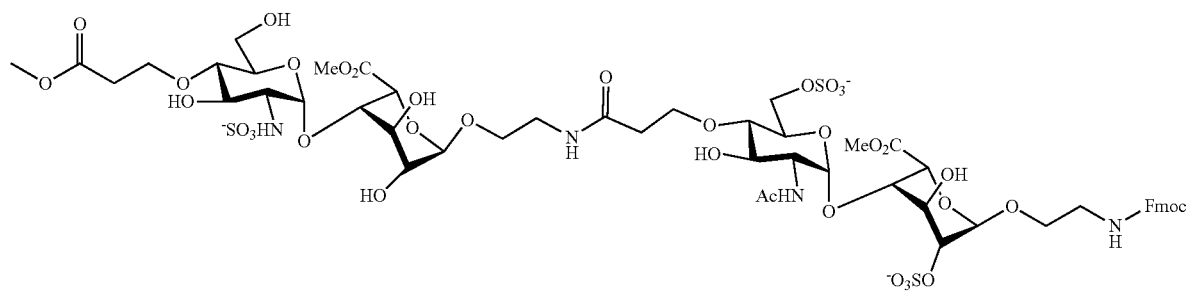

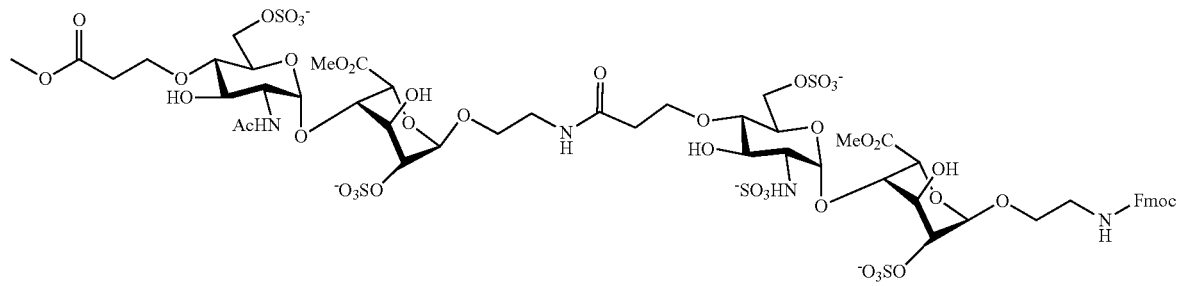

N-Fluorenylmethyloxycarbonyl-2-aminoethyl O-(4-O-methylpropionate-2-deoxy-acetamido-6-O-sulfonato-1-thio-β-D-glucopyranoside)-(1→4)-O-(6-O-methyl ester-2-O-sulfonato-1-thio-α-L-idopyranoside)-(1→4)-O-(4-O-carboxyethyl-2-deoxy-sulfoamino-6-O-sulfonato-1-thio-β-D-glucopyranoside)-(1→4)—O-6-O-methyl ester-2-O-sulfonato-1-thio-α-L-idopyranoside Starting material (22 mg, 0.03 mmol) was treated according to the general procedures of pseudo-tetrasaccharides preparation with HATU to give compound (26 mg, 62%). $^1$H NMR (500 MHz, CD$_3$OD) δ 8.00 (d, J=7.6 Hz, 2H), 7.78 (t, J=7.0 Hz, 2H), 7.58 (td, J=7.5, 3.6 Hz, 2H), 7.52-7.46 (m, 2H), 5.37 (d, J=3.6 Hz, 1H), 5.19 (s, 1H), 5.15-5.07 (m, 2H), 4.98 (s, 1H), 4.76 (d, J=2.2 Hz, 1H), 4.61 (d, J=5.9 Hz, 1H), 4.50 (s, 1H), 4.45-4.20 (m, 9H), 4.18-3.94 (m, 8H), 3.85 (d, J=7.8 Hz, 5H), 3.76 (s, 4H), 3.72-3.55 (m, 7H), 3.51-3.41 (m, 4H), 3.33-3.22 (m, 3H), 2.77-2.66 (m, 2H), 2.56 (t, J=5.9 Hz, 2H), 2.10 (s, 3H). $^{13}$C NMR (125 MHz, CD$_3$OD) δ 173.39, 173.31, 172.68, 169.77, 169.41, 142.34, 139.55, 126.65, 126.07, 123.81, 123.58, 118.73, 98.01, 97.65, 97.22, 93.48, 76.05, 75.93, 75.20, 73.28, 71.48, 70.13, 69.61, 69.24, 68.15, 67.75, 66.88, 66.52, 65.98, 65.82, 65.42, 64.86, 64.74, 64.66, 61.61, 56.36, 51.32, 51.62, 51.49, 50.81, 47.38, 45.57, 38.71, 37.54, 35.12, 33.52, 20.69. HRMS: m/z calc. for C$_{39}$H$_1$N$_4$O$_{41}$S$_5$$^{5-}$ [M]$^{5-}$: 280.2288; found: 280.2278.

N-Fluorenylmethyloxycarbonyl-2-aminoethyl O-(4-O-methylpropionate-2-deoxy-acetamido-6-O-sulfonato-1-thio-β-D-glucopyranoside)-(1→4)-O-(6-O-methyl ester-2-O-sulfonato-1-thio-α-L-idopyranoside)-(1→4)-O-(4-O-carboxyethyl-2-deoxy-sulfoamino-1-thio-β-D-glucopyranoside)-(1→4)—O-6-O-methyl ester-1-thio-α-L-idopyranoside Starting material (8.5 mg, 0.01 mmol) was treated according to the general procedures of pseudo-tetrasaccharides preparation with HATU to give compound (11.7 mg, 80%). $^1$H NMR (500 MHz, CD$_3$OD) δ 7.81 (d, J=7.5 Hz, 2H), 7.66 (d, J=7.5 Hz, 2H), 7.44-7.38 (m, 2H), 7.33 (td, J=7.5, 1.2 Hz, 2H), 5.35 (d, J=3.7 Hz, 1H), 5.16 (s, 1H), 4.99 (d, J=3.5 Hz, 1H), 4.92 (d, J=2.7 Hz, 1H), 4.87 (d, J=2.0 Hz, 1H), 4.80 (d, J=2.9 Hz, JH), 4.36-4.24 (m, 4H), 4.22-4.13 (m, 4H), 4.12-3.93 (m, 7H), 3.89 (ddd, J=9.7, 7.6, 4.4 Hz, 2H), 3.85-3.74 (m, 6H), 3.65-3.52 (m, 6H), 3.48-3.38 (m, 4H), 3.27-3.19 (m, 1H), 2.60 (tt, J=6.1, 2.8 Hz, 2H), 2.55-2.38 (m, 3H), 2.08 (s, 3H). $^{13}$C NMR (125 MHz, CD$_3$OD) δ 173.03, 172.96, 172.89, 170.43, 143.92, 141.18, 127.38, 126.79, 124.84, 119.50, 101.37, 99.69, 96.98, 96.69, 78.32, 78.27, 74.30, 74.12, 73.31, 71.59, 71.56, 71.50, 69.98, 69.13, 67.87, 67.78, 67.66, 67.60, 67.27, 66.39, 66.34, 65.93, 64.82, 60.48, 58.19, 53.59, 51.78, 51.60, 40.24, 38.79, 36.43, 34.86, 21.74. HRMS: m/z calc. for C$_{39}$H$_{63}$N$_4$O$_{35}$S$_3$$^{3-}$ [M+H$^+$]$^{2-}$: 622.1262; found: 622.1260.

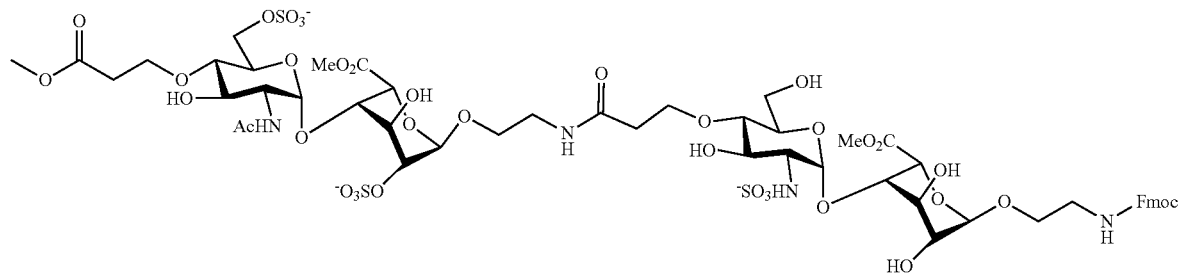

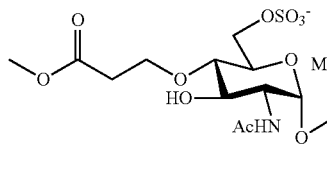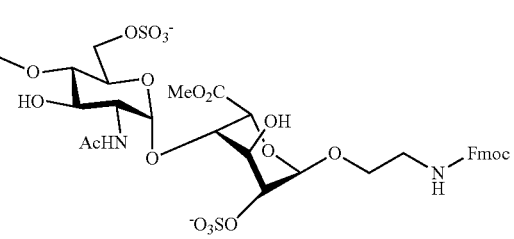

N-Fluorenylmethyloxycarbonyl-2-aminoethyl O-(4-O-methylpropionate-2-deoxy-acetamido-6-O-sulfonato-1-thio-β-D-glucopyranoside)-(1→4)-O-(6-O-methyl ester-2-O-sulfonato-1-thio-α-L-idopyranoside)-(1→4)-O-(4-O-carboxyethyl-2-deoxy-acetamido-6-O-sulfonato-1-thio-β-D-glucopyranoside)-(1→4)—O-6-O-methyl ester-2-O-sulfonato-1-thio-α-L-idopyranoside Starting material (8.0 mg, 0.01 mmol) was treated according to the general procedure of pseudo-tetrasaccharide preparation with HATU to give compound # (12.7 mg, 80%). $^1$H NMR (500 MHz, CD$_3$OD) δ 7.81 (d, J=7.5 Hz, 2H), 7.67 (d, J=7.5 Hz, 2H), 7.40 (tt, J=7.6, 1.6 Hz, 2H), 7.33 (tt, J=7.2, 1.5 Hz, 2H), 5.16 (d, J=4.8 Hz, 2H), 4.99 (d, J=3.5 Hz, 1H), 4.97 (d, J=3.4 Hz, 1H), 4.86 (dd, J=5.6, 1.9 Hz, 2H), 4.34-4.25 (m, 6H), 4.22-4.18 (m, 5H), 4.11-4.05 (m, 3H), 3.97 (ddt, J=10.7, 8.7, 5.1 Hz, 7H), 3.82 (s, 3H), 3.70 (d, J=15.6 Hz, 7H), 3.66-3.54 (m, 6H), 3.41 (q, J=5.5 Hz, 3H), 3.34 (t, J=3.9 Hz, 2H), 3.30 (d, J=2.7 Hz, 1H), 2.60 (td, J=6.2, 2.5 Hz, 2H), 2.49-2.43 (m, 2H), 2.07 (d, J=1.7 Hz, 6H). $^{13}$C NMR (125 MHz, CD$_3$OD) δ 172.96, 172.92, 170.49, 170.33, 157.48, 143.90, 141.14, 127.38, 126.81, 124.89, 119.48, 99.61, 99.56, 97.23, 96.43, 78.34, 78.26, 74.36, 73.47, 73.09, 71.52, 71.42, 69.99, 69.91, 68.22, 67.76, 67.55, 67.25, 66.49, 66.27, 66.22, 65.91, 64.79, 64.40, 53.60, 53.40, 51.83, 51.75, 50.82, 40.17, 38.67, 36.46, 34.85, 21.74. HRMS: m/z calc. for C$_{41}$H$_{64}$N$_4$O$_{39}$S$_4$$^{4-}$ [M+H$^+$]$^{3-}$: 455.0708; found: 455.0688.

N-acetamidoethyl O-(4-O-carboxyethyl-2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)

The starting material (5.8 mg, 0.004 mmol) was treated according to the general procedures of NH-Fmoc deprotection, pseudo-hexasaccharide preparation with HBTU and saponification of methyl esters give compound (3.8 mg, 51% for 3 steps).
$^1$H NMR (500 MHz, D$_2$O) δ 5.22 (d, J=3.6 Hz, 1H), 5.16 (t, J=4.2 Hz, 2H), 5.00 (d, J=3.6 Hz, 2H), 4.95 (d, J=2.8 Hz, 1H), 4.45 (dd, J=11.5, 2.3 Hz, 2H), 4.41 (d, J=2.8 Hz, 1H), 4.17 (dd, J=11.0, 2.1 Hz, 1H), 4.10 (dq, J=6.3, 3.0 Hz, 5H), 4.07-3.99 (m, 4H), 3.94-3.62 (m, 14H), 3.57-3.44 (m, 6H), 3.25 (dqd, J=15.5, 8.4, 7.4, 4.4 Hz, 8H), 3.09 (dt, J=10.5, 3.9 Hz, 3H), 2.53-2.34 (m, 6H), 1.82 (s, 3H). $^{13}$C NMR (125 MHz, D$_2$O) δ 173.83, 99.07, 98.72, 96.85, 77.81, 77.78, 77.59, 76.06, 75.94, 74.68, 74.55, 70.48, 70.43, 68.84, 68.82, 68.77, 68.62, 68.40, 68.29, 68.08, 67.61, 67.52, 67.30, 66.92, 66.81, 66.20, 66.12, 57.78, 57.77, 57.71, 39.04, 38.91, 36.22, 36.20, 35.30, 21.69.

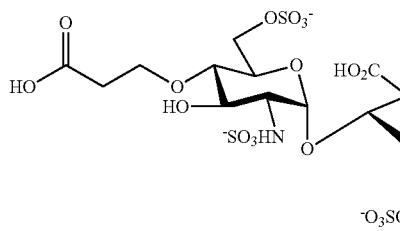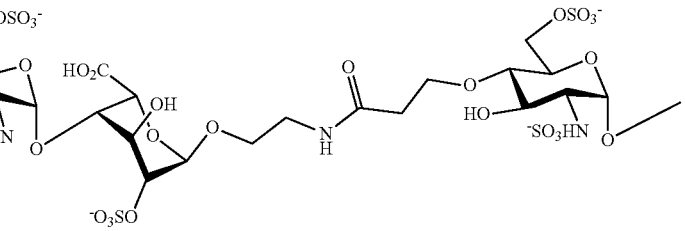

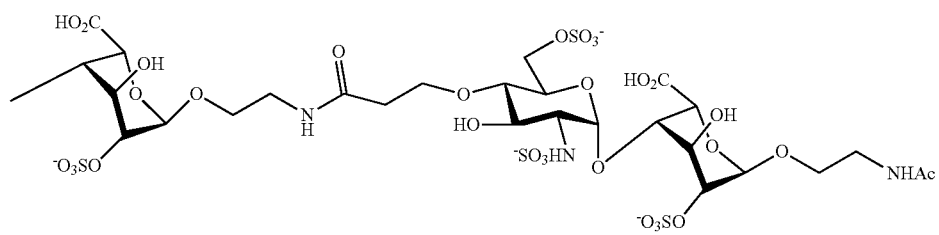

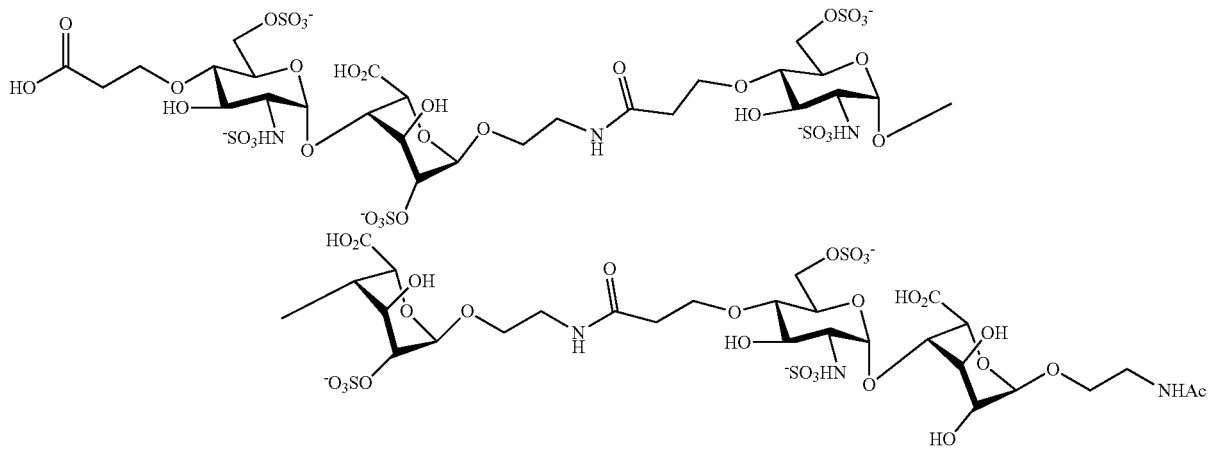

N-Acetamidoethyl O-(4-O-carboxyethyl-2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-6-O-sulfonato-1-thio-β-D-glucopyranoside)-(1→4)-O-(6—O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)

The starting material (6.5 mg, 0.004 mmol) was treated according to the general procedures of NH-Fmoc deprotection, pseudo-hexasaccharide preparation with HBTU and saponification of methyl Esters give compound (3.7 mg, 48% for 3 steps). $^1$H NMR (500 MHz, D$_2$O) δ 5.19 (d, J=3.6 Hz, 1H), 5.15 (dd, J=6.2, 3.6 Hz, 2H), 5.01-4.96 (m, 2H), 4.73-4.70 (m, 1H), 4.38 (dd, J=26.8, 2.4 Hz, 3H), 4.17 (dd, J=10.8, 2.0 Hz, 1H), 4.09 (dtt, J=13.6, 8.8, 4.2 Hz, 5H), 4.02 (dt, J=11.0, 2.1 Hz, 2H), 3.96 (t, J=3.8 Hz, 1H), 3.92-3.71 (m, 12H), 3.70-3.44 (m, 14H), 3.32-3.15 (m, 9H), 3.12-3.00 (m, 4H), 2.50-2.35 (m, 6H), 1.82 (s, 3H). 13C NMR (126 MHz, Deuterium Oxide) δ 173.84, 100.61, 98.90, 98.70, 97.47, 97.09, 95.60, 78.04, 77.82, 77.64, 75.98, 75.95, 75.38, 74.69, 74.43, 70.68, 70.54, 70.47, 68.79, 68.46, 68.27, 68.22, 68.18, 67.78, 67.66, 67.52, 66.77, 66.71, 66.16, 59.75, 57.77, 57.75, 57.72, 39.05, 38.97, 38.91, 36.19, 21.70.

N-Acetamidoethyl O-(4-O-carboxyethyl-2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (5.8 mg, 0.004 mmol) was treated according to the general procedures of NH-Fmoc deprotection, pseudo-hexasaccharides preparation with HBTU and saponification of methyl Esters give compound (1.4 mg, 19% for 3 steps). $^1$H NMR (500 MHz, D$_2$O) δ 5.17 (dd, J=8.9, 3.5 Hz, 2H), 4.98 (s, 2H), 4.94 (d, J=3.7 Hz, 1H), 4.91 (s, 1H), 4.43-4.34 (m, 4H), 4.19-3.99 (m, 13H), 3.94-3.72 (m, 14H), 3.71-3.43 (m, 13H), 3.25 (dq, J=18.0, 5.8, 5.0 Hz, 10H), 3.09 (dt, J=10.7, 3.0 Hz, 3H), 2.47-2.35 (m, 7H), 1.88 (s, 3H), 1.82 (s, 3H). $^{13}$C NMR (125 MHz, D$_2$O) δ 77.87, 75.88, 73.73, 70.49, 70.81, 68.86, 68.76, 68.61, 66.85, 66.91, 66.28, 66.16, 57.76, 39.01, 38.90, 36.18, 27.45, 22.07, 21.70.

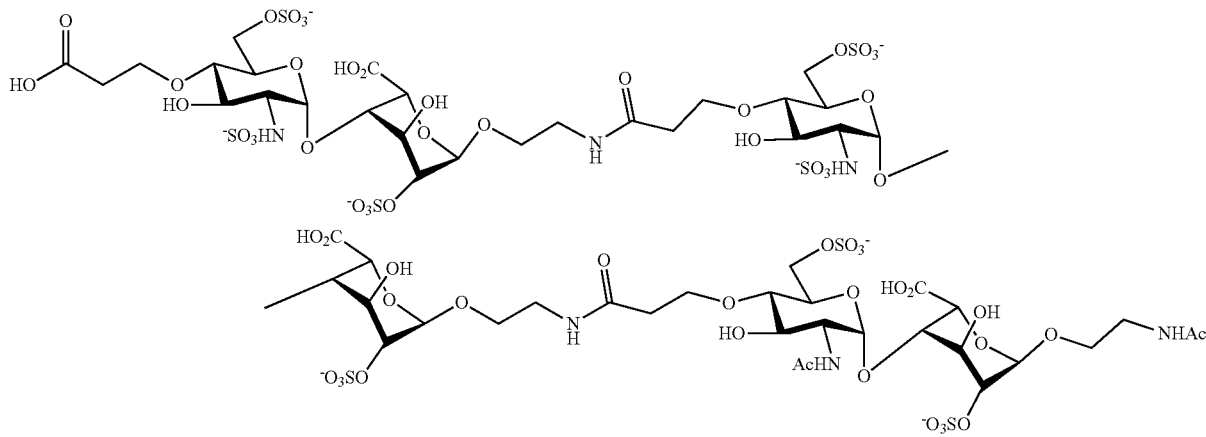

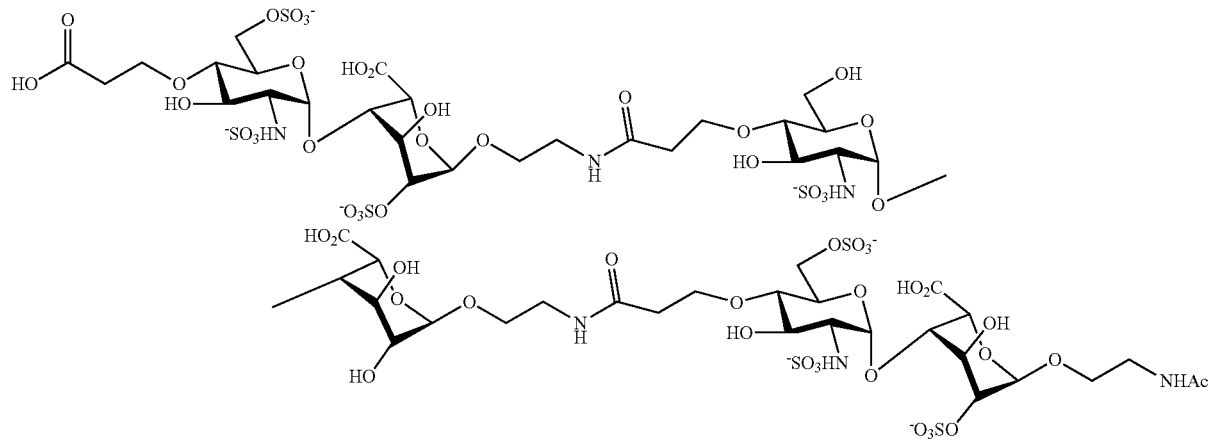

N-Acetamidoethyl O-(4-O-carboxyethyl-2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (4.5 mg, 0.003 mmol) was treated according to the general procedures of NH-Fmoc deprotection, pseudo-hexasaccharides preparation with HBTU and saponification of methyl Esters give compound (1.4 mg, 51% for 3 steps). $^1$H NMR (500 MHz, D$_2$O) δ 5.22 (d, J=3.5 Hz, 1H), 5.18 (d, J=3.6 Hz, 1H), 5.14 (d, J=3.9 Hz, 1H), 4.97 (d, J=2.4 Hz, 1H), 4.94 (d, J=2.9 Hz, 1H), 4.73 (d, J=2.7 Hz, 1H), 4.41-4.32 (m, 3H), 4.19-3.99 (m, 9H), 3.95 (d, J=3.8 Hz, 1H), 3.92-3.73 (m, 12H), 3.71-3.42 (m, 15H), 3.37-3.16 (m, 10H), 3.12-3.01 (m, 4H), 2.52-2.30 (m, 7H), 1.82 (s, 3H). $^{13}$C NMR (125 MHz, D$_2$O) δ 177.77, 173.87, 122.73, 119.89, 109.99, 100.57, 98.83, 97.48, 97.10, 96.74, 95.65, 78.05, 77.75, 77.69, 76.04, 75.93, 74.32, 70.73, 70.58, 70.49, 68.75, 68.70, 68.41, 68.34, 66.87, 66.75, 66.47, 66.20, 57.78, 57.73, 39.05, 38.98, 38.85, 36.35, 21.69.

N-Acetamidoethyl O-(4-O-carboxyethyl-2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)-(1→4)-O-(2-deoxy-sulfonato-1-thio-β-D-glucopyranoside)-(1→4)-O-(6-O-carboxyl-1-thio-α-L-idopyranoside)

The starting material (4.5 mg, 0.003 mmol) was treated according to the general procedures of NH-Fmoc deprotection, pseudo-hexasaccharides preparation with HBTU and saponification of methyl esters give compound (3.0 mg, 56% for 3 steps). $^1$H NMR (500 MHz, D$_2$O) δ 5.18 (d, J=3.7 Hz, 1H), 5.14 (dd, J=3.9, 1.4 Hz, 2H), 4.97 (d, J=2.5 Hz, 1H), 4.74-4.71 (m, 2H), 4.39-4.32 (m, 3H), 4.18-4.14 (m, 1H), 4.12-3.99 (m, 4H), 3.95 (q, J=4.3 Hz, 2H), 3.91-3.72 (m, 11H), 3.70-3.45 (m, 18H), 3.31-3.16 (m, 10H), 3.06 (ddd, J=23.6, 10.5, 3.5 Hz, 4H), 2.48-2.33 (m, 7H), 1.82 (s, 3H). $^{13}$C NMR (125 MHz, D$_2$O) δ 173.93, 173.85, 100.61, 98.85, 97.11, 95.65, 95.57, 78.12, 78.05, 77.97, 75.94, 74.45, 74.30, 70.71, 70.55, 70.50, 68.78, 68.39, 68.27, 68.12, 67.83, 67.58, 67.38, 66.75, 66.69, 66.49, 66.19, 59.76, 57.78, 57.74, 38.99, 39.06, 36.26, 36.15, 21.70.

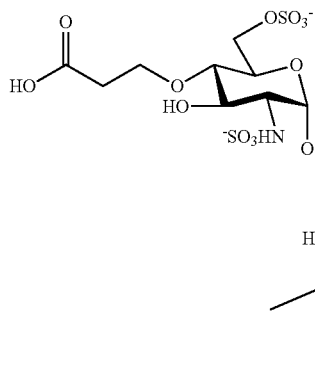

N-Acetamidoethyl O-(4-O-carboxyethyl-2-deoxy-sulfoamino-6-O-sulfonato-1-thio-β-D-glucopyrano-side)-(1→4)-O-(6-O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)-(1→4)-O-(2-deoxy-acetamido-1-thio-β-D-glucopyranoside)-(1→4)-O-(6-O-carboxyl-1-thio-α-L-idopyranoside)

The starting material (4.5 mg, 0.003 mmol) was treated according to the general procedures of NH-Fmoc deprotection, pseudo-hexasaccharides preparation with HBTU and saponification of methyl esters give compound (2.9 mg, 50% for 3 steps). $^1$H NMR (500 MHz, $D_2O$) δ 7.96 (d, J=9.8 Hz, 1H), 5.18 (d, J=3.7 Hz, 1H), 5.14 (d, J=3.7 Hz, 1H), 4.98-4.90 (m, 3H), 4.75-4.71 (m, 1H), 4.39 (d, J=2.3 Hz, 1H), 4.35 (dd, J=6.9, 2.4 Hz, 2H), 4.17-4.00 (m, 8H), 3.97-3.74 (m, 13H), 3.70-3.44 (m, 13H), 3.35-3.17 (m, 9H), 3.10-3.01 (m, 2H), 2.46-2.34 (m, 6H), 1.85 (d, J=30.7 Hz, 6H). $^{13}$C NMR (125 MHz, $D_2O$) δ 190.14, 109.99, 109.71, 99.00, 98.65, 98.64, 96.97, 95.61, 93.51, 78.11, 77.77, 75.88, 75.41, 74.39, 73.67, 70.85, 70.73, 70.81, 70.53, 68.83, 68.71, 68.59, 68.26, 68.10, 67.42, 66.85, 66.44, 66.18, 63.81, 57.70, 53.04, 39.00, 38.87, 36.28, 36.13, 22.07, 21.70. HRMS: m/z calc. for $C_{55}H_{84}N_6O_{57}S_6^{6-}$ [M+Na$^+$]$^{5-}$: 391.0422; found: 391.0433.

N-Acetamidoethyl O-(4-O-carboxyethyl-2-deoxy-sulfoamino-6-O-sulfonato-1-thio-β-D-glucopyrano-side)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfonato-6-O-sulfonato 1-thio-β-D-glucopyranoside)-(1→4)-O-(6-O-carboxyl-2-O-sulfonato-1-thio-α-L-idopyranoside)

The starting material (5.2 mg, 0.003 mmol) was treated according to the general procedures of NH-Fmoc deprotection, pseudo-hexasaccharides preparation with HBTU and saponification of methyl esters give compound (3.7 mg, 55% for 3 steps). $^1$H NMR (500 MHz, $D_2O$) δ 5.22 (d, J=3.5 Hz, 1H), 5.16 (d, J=3.5 Hz, 1H), 5.00-4.97 (m, 1H), 4.94 (q, J=3.7 Hz, 3H), 4.46-4.38 (m, 3H), 4.20-3.98 (m, 11H), 3.97-3.71 (m, 12H), 3.66 (p, J=4.8 Hz, 3H), 3.60-3.44 (m, 6H), 3.38-3.15 (m, 9H), 3.09 (dt, J=10.6, 3.4 Hz, 2H), 2.50-2.33 (m, 6H), 1.85 (d, J=32.5 Hz, 6H). $^{13}$C NMR (125 MHz, $D_2O$) δ 99.08, 98.74, 98.58, 97.49, 96.82, 93.69, 90.46, 77.83, 77.61, 76.03, 75.95, 73.19, 70.78, 70.51, 70.45, 68.80, 68.76, 68.67, 68.63, 68.41, 68.14, 67.70, 66.80, 66.91, 66.71, 66.20, 66.12, 57.79, 57.73, 53.01, 39.04, 38.93, 38.84, 36.24, 36.15, 22.11, 21.69. HRMS: m/z calc. for $C_{55}H_{82}N_6O_{63}S_8{}^{8-}$ [M+Na$^+$]$^{7-}$: 301.8728; found: 301.8744.

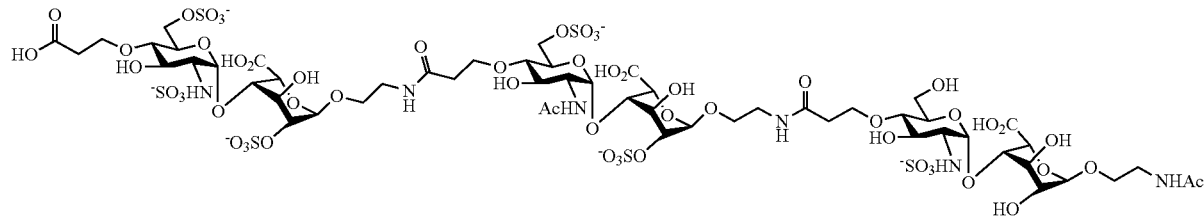

N-Acetamidoethyl O-(4-O-carboxyethyl-2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfonato-1-thio-β-D-glucopyranoside)-(1→4)-O-(6-O-carboxyl-1-thio-α-L-idopyranoside)

The starting material (4.8 mg, 0.003 mmol) was treated according to the general procedures of NH-Fmoc deprotection, pseudo-hexasaccharides preparation with HBTU and saponification of methyl esters give compound (2.5 mg, 44% for 3 steps). $^1$H NMR (500 MHz, D$_2$O) δ 5.17 (d, J=3.7 Hz, 1H), 5.14 (d, J=3.6 Hz, 1H), 4.99-4.97 (m, 1H), 4.93 (d, J=3.1 Hz, 2H), 4.73-4.69 (m, 1H), 4.39 (dd, J=13.7, 2.3 Hz, 2H), 4.33 (d, J=2.4 Hz, 1H), 4.18-3.99 (m, 8H), 3.95 (t, J=3.9 Hz, 2H), 3.92-3.72 (m, 11H), 3.70-3.42 (m, 13H), 3.36-3.17 (m, 9H), 3.06 (ddd, J=23.0, 10.5, 3.6 Hz, 3H), 2.51-2.32 (m, 6H), 1.88 (s, 3H), 1.81 (s, 3H). $^{13}$C NMR (125 MHz, D$_2$O) δ 174.21, 173.90, 109.99, 100.60, 97.21, 95.57, 93.54, 78.03, 77.85, 77.70, 75.91, 75.02, 74.45, 73.45, 70.69, 70.49, 68.75, 68.32, 68.17, 67.60, 66.69, 66.15, 63.59, 59.74, 57.74, 39.05, 38.93, 36.13, 22.09, 21.70. HRMS: m/z calc. for $C_{55}H_{84}N_6O_{57}S_6{}^{6-}$ [M+Na$^+$]$^{5-}$: 391.0422; found: 391.0435.

N-Acetamidoethyl O-(4-O-carboxyethyl-2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (5.2 mg, 0.003 mmol) was treated according to the general procedures of NH-Fmoc deprotection, pseudo-hexasaccharides preparation with HBTU and saponification of methyl esters give compound (2.8 mg, 42% for 3 steps). $^1$H NMR (500 MHz, D$_2$O) δ 5.16 (d, J=3.7 Hz, 1H), 4.98 (s, 1H), 4.93 (dd, J=7.2, 3.7 Hz, 4H), 4.42 (dd, J=11.1, 1.9 Hz, 3H), 4.22-3.99 (m, 12H), 3.94-3.71 (m, 14H), 3.65 (dp, J=16.1, 5.4, 4.7 Hz, 3H), 3.60-3.41 (m, 7H), 3.26 (ddt, J=18.5, 10.5, 4.5 Hz, 9H), 3.17 (s, 1H), 3.08 (dd, J=10.6, 3.5 Hz, 1H), 2.52-2.28 (m, 7H), 1.88 (d, J=1.5 Hz, 6H), 1.82 (s, 3H). $^{13}$C NMR (125 MHz, D$_2$O) δ 174.62, 174.15, 173.87, 98.73, 98.67, 98.58, 97.46, 93.65, 93.54, 77.82, 77.62, 76.01, 74.77, 73.65, 73.26, 70.83, 70.78, 70.45, 68.88, 68.79, 68.62, 68.58, 68.48, 68.15, 67.72, 66.87, 66.79, 66.70, 66.22, 66.10, 63.79, 57.77, 53.01, 39.00, 38.93, 38.86, 36.20, 36.15, 35.39, 22.09, 21.69. HRMS: m/z calc. for $C_{57}H_{85}N_6O_{61}S_7{}^{7-}$ [M+2Na$^+$]$^{5-}$: 419.8320; found: 419.8341.

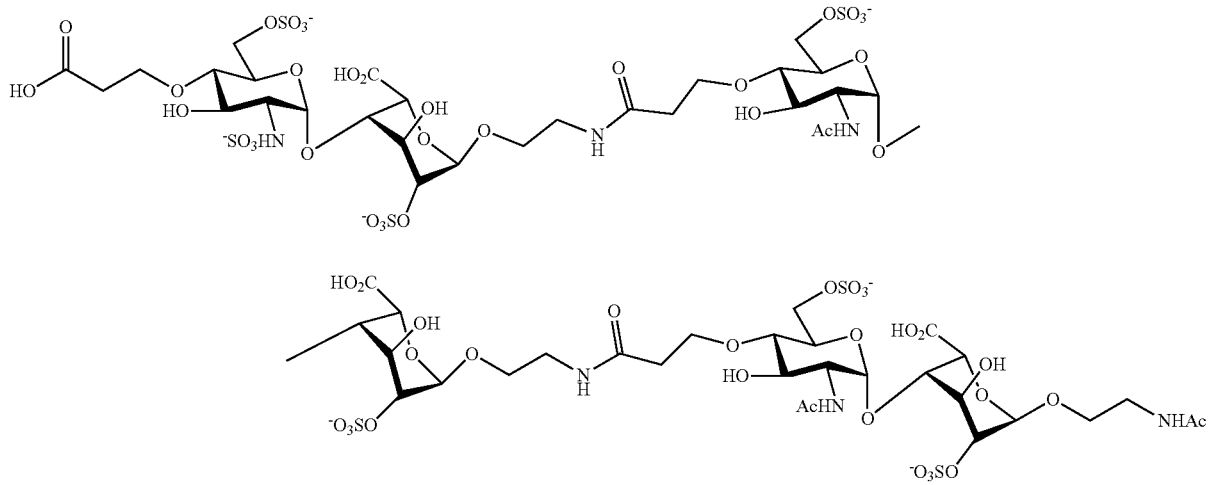

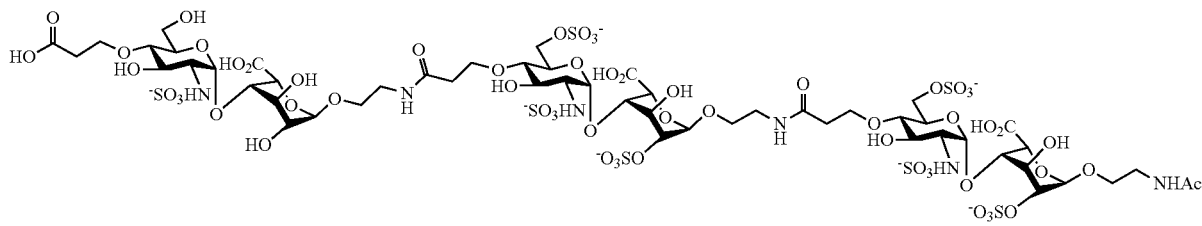

N-Acetamidoethyl O-(4-O-carboxyethyl-2-deoxy-
sulfoamino-1-thio-β-D-glucopyranoside)-(1→4)-O-
(6-O-carboxyl-1-thio-α-L-idopyranoside)-(1→4)-O-
(2-deoxy-sulfoamino-6-O-sulfonato-1-thio-β-D-
glucopyranoside)-(1→4)-O-(6-O-carboxyl-2-O-
sulfonato-1-thio-α-L-idopyranoside)-(1→4)-O-(2-
deoxy-sulfoamino-6-O-sulfonato-1-thio-β-D-
glucopyranoside)-(1→4)-O-(6-O-carboxyl-2-O-
sulfonato-1-thio-α-L-idopyranoside)

The starting material (4.6 mg, 0.003 mmol) was treated according to the general procedures of NH-Fmoc deprotection, pseudo-hexasaccharides preparation with HBTU and saponification of methyl esters give compound (1.2 mg, 20% for 3 steps). $^1$H NMR (500 MHz, D$_2$O) δ 5.24 (s, 1H), 5.15 (d, J=12.9 Hz, 2H), 4.99 (s, 1H), 4.93 (s, 2H), 4.38-4.31 (m, 3H), 4.14-3.99 (m, 8H), 3.96-3.71 (m, 13H), 3.69-3.42 (m, 14H), 3.24 (dq, J=19.4, 9.2, 8.7 Hz, 9H), 3.12-3.01 (m, 4H), 2.44-2.32 (m, 5H), 1.82 (d, J=1.8 Hz, 3H). HRMS: m/z calc. for C$_{53}$H$_{81}$N$_6$O$_{59}$S$_7$$^{7-}$ [M+2Na$^+$]$^{5-}$: 403.0278; found: 403.0296.

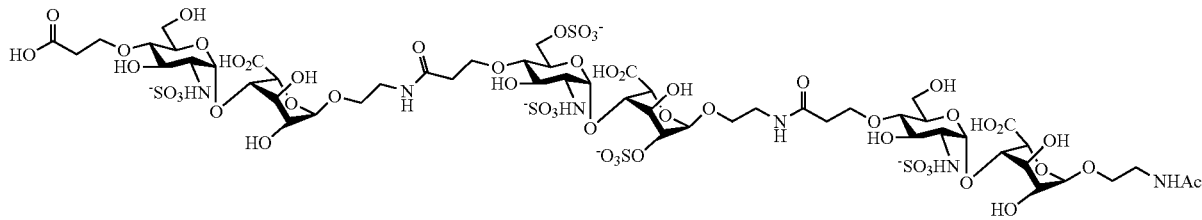

N-Acetamidoethyl O-(4-O-carboxyethyl-2-deoxy-
sulfoamino-1-thio-β-D-glucopyranoside)-(1→4)-O-
(6-O-carboxyl-1-thio-α-L-idopyranoside)-(1→4)-O-
(2-deoxy-sulfoamino-6-O-sulfonato-1-thio-β-D-
glucopyranoside)-(1→4)-O-(6-O-carboxyl-2-O-
sulfonato-1-thio-α-L-idopyranoside)-(1→4)-O-(2-
deoxy-sulfoamino-1-thio-β-D-glucopyranoside)-
(1→4)-O-(6-O-carboxyl-1-thio-α-L-idopyranoside)

The starting material (4.2 mg, 0.003 mmol) was treated according to the general procedures of NH-Fmoc deprotection, pseudo-hexasaccharides preparation with HBTU and saponification of methyl esters give compound (2.4 mg, 48% for 3 steps). $^1$H NMR (500 MHz, D$_2$O) δ 5.17 (d, J=2.9 Hz, 1H), 5.14 (t, J=2.5 Hz, 2H), 4.98 (s, 1H), 4.72 (dd, J=5.4, 2.5 Hz, 2H), 4.46-4.35 (m, 3H), 4.12-4.05 (m, 3H), 4.03-3.83 (m, 9H), 3.83-3.69 (m, 5H), 3.68-3.44 (m, 15H), 3.36-3.13 (m, 9H), 3.11-2.99 (m, 3H), 2.41 (dt, J=28.4, 6.4 Hz, 6H), 1.81 (d, J=1.9 Hz, 3H). $^{13}$C NMR (125 MHz, D$_2$O) δ 173.88, 170.07, 100.62, 100.60, 98.86, 97.38, 95.63, 77.98, 77.81, 77.66, 76.06, 75.08, 74.38, 74.22, 70.75, 70.66, 70.57, 70.51, 68.79, 68.19, 68.15, 68.09, 67.97, 67.91, 67.64, 67.41, 67.28, 66.82, 66.73, 66.54, 66.11, 59.73, 57.81, 57.70, 39.04, 38.98, 38.88, 36.33, 36.18, 35.58, 21.69. HRMS: m/z calc. for C$_{53}$H$_{83}$N$_6$O$_{53}$S$_5$$^{5-}$ [M+Na$^+$]$^{4-}$: 458.5627; found: 458.5641.

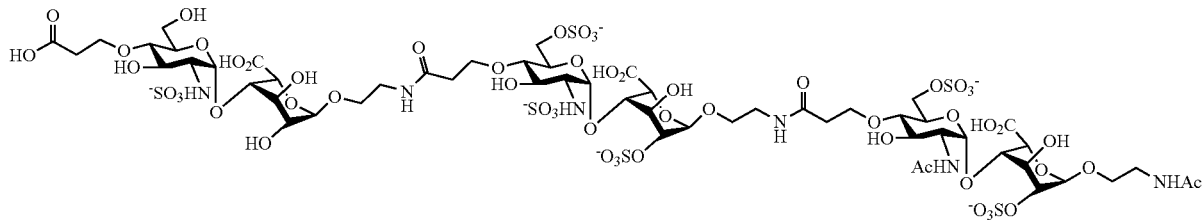

N-Acetamidoethyl O-(4-O-carboxyethyl-2-deoxy-sulfoamino-1-thio-β-D-glucopyranoside)-(1→4)-O-(6-O-carboxyl-1-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-1-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (6.6 mg, 0.004 mmol) was treated according to the general procedures of NH-Fmoc deprotection, pseudo-hexasaccharides preparation with HBTU and saponification of methyl esters give compound (5.0 mg, 59% for 3 steps). $^1$H NMR (500 MHz, D$_2$O) δ 5.15 (dd, J=11.0, 3.6 Hz, 2H), 4.99 (s, 1H), 4.94-4.90 (m, 2H), 4.72 (s, 1H), 4.45-4.36 (m, 3H), 4.13-3.99 (m, 8H), 3.95 (t, J=3.7 Hz, 1H), 3.91-3.70 (m, 12H), 3.70-3.60 (m, 5H), 3.60-3.43 (m, 8H), 3.36-3.17 (m, 9H), 3.06 (ddd, J=26.4, 10.5, 3.6 Hz, 3H), 2.41 (dt, J=16.7, 4.8 Hz, 6H), 1.88 (s, 3H), 1.82 (s, 3H). $^{13}$C NMR (125 MHz, D$_2$O) δ 174.62, 173.88, 100.60, 98.77, 98.68, 95.61, 93.54, 77.84, 77.68, 76.04, 74.81, 74.70, 74.23, 73.63, 70.82, 70.76, 70.56, 70.49, 68.88, 68.80, 68.58, 68.40, 68.20, 68.00, 67.72, 67.32, 66.88, 66.81, 66.53, 66.25, 66.14, 63.77, 59.70, 57.82, 57.69, 53.00, 39.00, 38.88, 36.33, 36.17, 22.07, 21.69. HRMS: m/z calc. for $C_{55}H_{84}N_6O_{57}S_6{}^{6-}$ [M+Na$^+$]$^{5-}$: 391.0422; found: 391.0430.

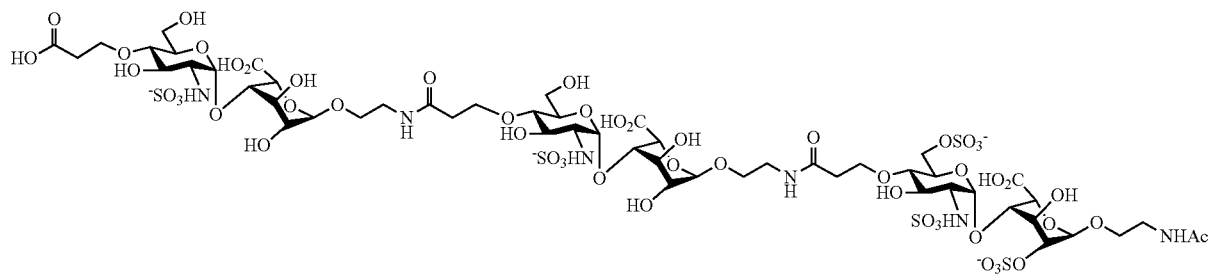

N-Acetamidoethyl O-(4-O-carboxyethyl-2-deoxy-sulfoamino-1-thio-β-D-glucopyranoside)-(1→4)-O-(6-O-carboxyl-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)

The starting material (2.5 mg, 0.002 mmol) was treated according to the general procedures of NH-Fmoc deprotection, pseudo-hexasaccharides preparation with HBTU and saponification of methyl esters give compound (1.4 mg, 42% for 3 steps). $^1$H NMR (500 MHz, D$_2$O) δ 5.22 (d, J=3.5 Hz, 1H), 5.14 (t, J=3.6 Hz, 2H), 4.94 (s, 1H), 4.77-4.71 (m, 2H), 4.38-4.30 (m, 3H), 4.13-4.07 (m, 2H), 4.05-3.99 (m, 2H), 3.95 (t, J=3.9 Hz, 2H), 3.93-3.83 (m, 6H), 3.78 (dq, J=16.0, 9.1, 7.6 Hz, 4H), 3.70-3.41 (m, 16H), 3.23 (ddd, J=24.8, 18.6, 9.3 Hz, 9H), 3.06 (ddd, J=24.3, 10.3, 3.4 Hz, 4H), 2.44-2.31 (m, 6H), 1.82 (s, 3H). HRMS: m/z calc. for $C_{53}H_{83}N_6O_{53}S_5{}^{5-}$ [M+Na$^+$]$^{4-}$: 458.5627; found: 458.5623.

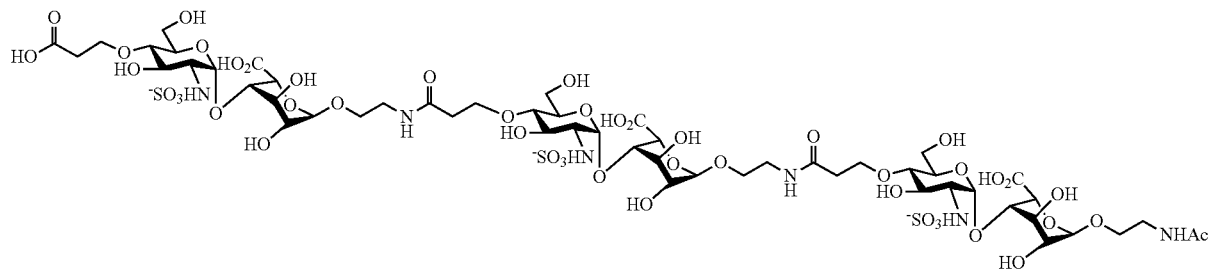

N-Acetamidoethyl O-(4-O-carboxyethyl-2-deoxy-sulfoamino-1-thio-β-D-glucopyranoside)-(1→4)-O-(6-O-carboxyl-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)

The starting material (3.0 mg, 0.002 mmol) was treated according to the general procedures of NH-Fmoc deprotection, pseudo-hexasaccharides preparation with HATU and saponification of methyl esters give compound (0.8 mg, 22% for 3 steps). $^1$H NMR (500 MHz, D$_2$O) δ 5.15 (d, J=3.6 Hz, 3H), 4.73 (d, J=4.1 Hz, 3H), 4.33 (d, J=4.0 Hz, 3H), 3.95 (d, J=4.6 Hz, 3H), 3.86 (d, J=3.7 Hz, 6H), 3.76 (d, J=6.7 Hz, 4H), 3.70-3.44 (m, 20H), 3.33-3.17 (m, 9H), 3.04 (dd, J=10.3, 3.5 Hz, 4H), 2.37 (q, J=6.2 Hz, 6H), 1.82 (s, 2H). HRMS: m/z calc. for $C_{53}H_{85}N_6O_{47}S_3^{3-}$ [M]$^{3-}$: 551.1208; found: 551.1201.

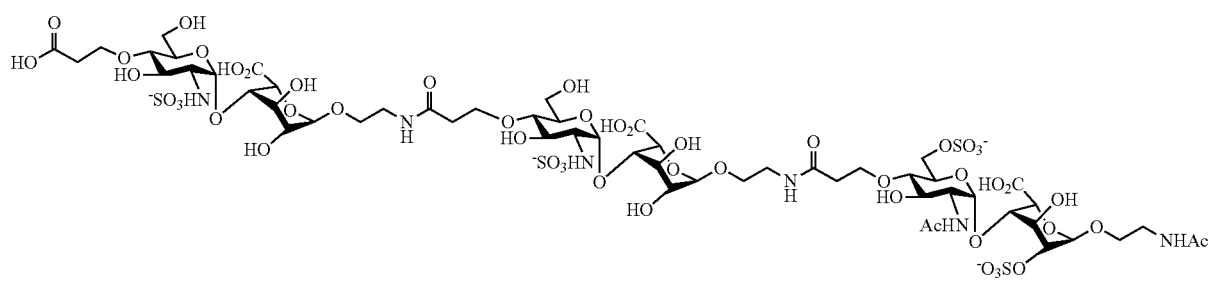

N-Acetamidoethyl O-(4-O-carboxyethyl-2-deoxy-sulfoamino-1-thio-β-D-glucopyranoside)-(1→4)-O-(6-O-carboxyl-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (3.8 mg, 0.003 mmol) was treated according to the general procedures of NH-Fmoc deprotection, pseudo-hexasaccharides preparation with HATU and saponification of methyl esters give compound (2.6 mg, 52% for 3 steps). $^1$H NMR (500 MHz, D$_2$O) δ 5.14 (t, J=3.2 Hz, 2H), 4.95-4.91 (m, 2H), 4.73 (dd, J=4.6, 2.1 Hz, 2H), 4.43-4.35 (m, 3H), 4.12-4.01 (m, 4H), 3.95 (d, J=4.0 Hz, 2H), 3.92-3.72 (m, 12H), 3.70-3.42 (m, 18H), 3.32-3.19 (m, 9H), 3.04 (dd, J=10.4, 3.6 Hz, 3H), 2.47-2.33 (m, 7H), 1.85 (d, J=31.3 Hz, 6H). $^{13}$C NMR (125 MHz, D$_2$O) δ 174.62, 173.88, 100.61, 98.65, 95.67, 95.59, 93.61, 77.90, 77.86, 77.75, 74.30, 74.27, 73.59, 70.85, 70.75, 70.71, 70.55, 68.87, 68.56, 68.18, 68.08, 67.37, 67.28, 66.88, 66.52, 63.77, 59.72, 57.77, 57.70, 53.04, 39.00, 38.89, 36.29, 36.23, 22.07, 21.70.

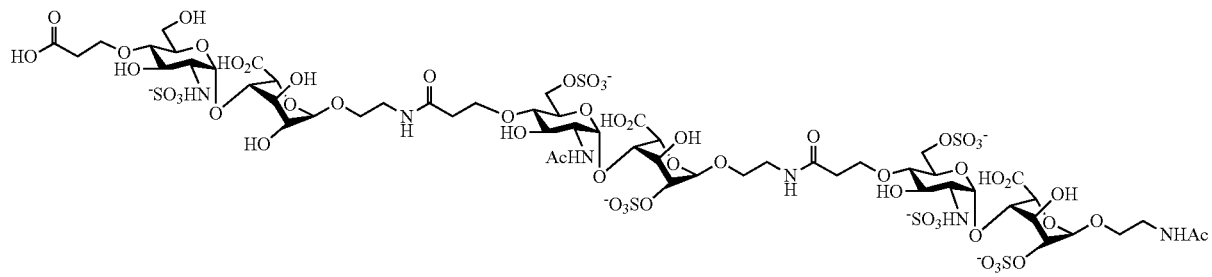

N-Acetamidoethyl O-(4-O-carboxyethyl-2-deoxy-sulfoamino-1-thio-β-D-glucopyranoside)-(1→4)-O-(6-O-carboxyl-1-thio-α-L-idopyranoside)-(1→4)-O-(2-deoxy-acetamido-1-thio-β-D-glucopyranoside)-(1→4)-O-(6-O-carboxyl-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato 1-thio-α-L-idopyranoside)

The starting material (3.9 mg, 0.003 mmol) was treated according to the general procedures of NH-Fmoc deprotection, pseudo-hexasaccharides preparation with HATU and saponification of methyl esters give compound (1.7 mg, 34% for 3 steps). $^1$H NMR (500 MHz, D$_2$O) δ 5.21 (d, J=3.7 Hz, 1H), 5.14 (d, J=3.7 Hz, 1H), 4.97-4.91 (m, 3H), 4.73 (s, 1H), 4.48-4.36 (m, 3H), 4.14-3.99 (m, 8H), 3.98-3.71 (m, 13H), 3.70-3.44 (m, 13H), 3.25 (dtd, J=23.9, 9.8, 9.2, 4.8 Hz, 9H), 3.06 (ddd, J=27.5, 10.4, 3.5 Hz, 3H), 2.47-2.33 (m, 6H), 1.88 (s, 3H), 1.82 (s, 3H). HRMS: m/z calc. for $C_5H_{84}N_6O_{57}S_6^{6-}$ [M+2Na$^+$]$^{4-}$: 494.5500; found: 494.5502.

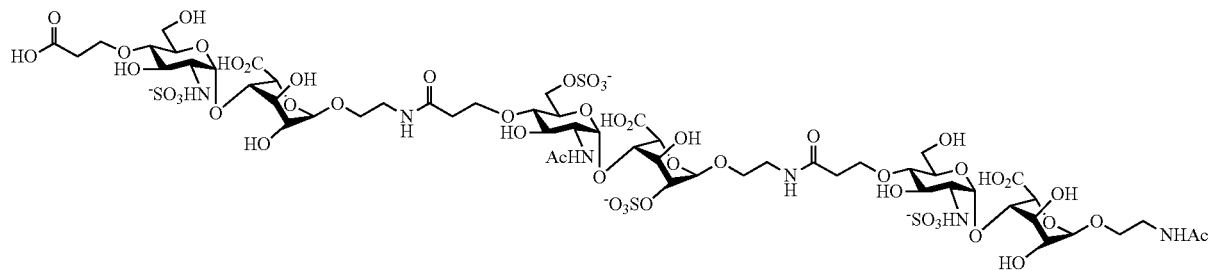

N-Acetamidoethyl O-(4-O-carboxyethyl-2-deoxy-sulfoamino-1-thio-β-D-glucopyranoside)-(1→4)-O-(6-O-carboxyl-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)

The starting material (7.1 mg, 0.005 mmol) was treated according to the general procedures of NH-Fmoc deprotection, pseudo-hexasaccharides preparation with HATU and saponification of methyl esters give compound (4.4 mg, 51% for 3 steps). $^1$H NMR (500 MHz, D$_2$O) δ 5.14 (d, J=3.7 Hz, 2H), 4.96-4.92 (m, 2H), 4.74-4.71 (m, 2H), 4.45 (d, J=2.1 Hz, 1H), 4.40 (dd, J=4.4, 2.5 Hz, 2H), 4.12-4.00 (m, 5H), 3.95 (d, J=4.3 Hz, 2H), 3.91-3.73 (m, 12H), 3.71-3.44 (m, 19H), 3.38-3.17 (m, 10H), 3.04 (ddd, J=10.2, 3.5, 2.0 Hz, 3H), 2.42 (ddd, J=34.4, 7.0, 4.6 Hz, 7H), 1.89 (s, 3H), 1.81 (s, 3H). $^{13}$C NMR (125 MHz, D$_2$O) δ 174.65, 174.47, 174.15, 173.94, 100.65, 98.65, 95.66, 93.79, 77.94, 77.78, 77.71, 74.37, 74.22, 73.35, 70.92, 70.82, 70.73, 70.67, 70.59, 68.92, 68.54, 68.17, 68.13, 67.98, 67.40, 67.27, 66.79, 66.75, 66.59, 66.19, 63.57, 59.73, 59.70, 57.72, 53.05, 39.04, 38.93, 36.28, 36.21, 35.40, 22.09, 21.69. HRMS: m/z calc. for $C_{55}H_{86}N_6O_{51}S_4^{4-}$ [M]$^{4-}$: 443.5806; found: 443.5805.

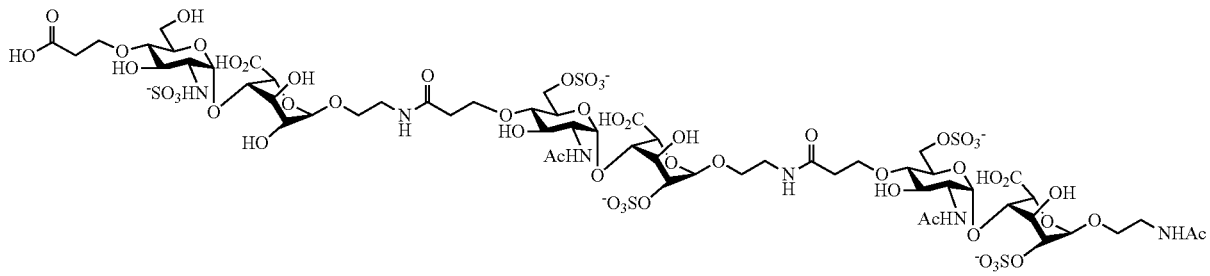

N-Acetamidoethyl O-(4-O-carboxyethyl-2-deoxy-sulfoamino-1-thio-β-D-glucopyranoside)-(1→4)-O-(6-O-carboxyl-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (6.9 mg, 0.005 mmol) was treated according to the general procedures of NH-Fmoc deprotection, pseudo-hexasaccharides preparation with HATU and saponification of methyl esters give compound (4.0 mg, 45% for 3 steps). $^1$H NMR (500 MHz, D$_2$O) δ 7.96 (dd, J=27.1, 9.8 Hz, 2H), 5.14 (d, J=3.6 Hz, 1H), 4.96-4.91 (m, 4H), 4.39 (d, J=2.4 Hz, 2H), 4.32 (s, 1H), 4.15-4.02 (m, 9H), 3.96-3.73 (m, 16H), 3.69-3.42 (m, 16H), 3.38-3.19 (m, 11H), 3.05 (dd, J=10.4, 3.5 Hz, 2H), 2.46-2.31 (m, 7H), 1.89 (d, J=1.7 Hz, 6H), 1.83 (s, 3H). $^{13}$C NMR (125 MHz, D$_2$O) δ 174.63, 98.68, 98.54, 95.59, 93.55, 93.50, 78.13, 77.86, 77.75, 74.38, 73.74, 73.33, 70.85, 70.72, 70.57, 69.28, 68.85, 68.63, 68.18, 67.52, 66.86, 66.65, 66.46, 66.27, 63.89, 63.47, 59.81, 59.70, 57.66, 53.05, 39.03, 38.89, 36.28, 36.21, 22.12, 22.09, 21.72. HRMS: m/z calc. for C$_{57}$H$_{87}$N$_6$O$_{55}$S$_5{}^{5-}$ [M+Li$^+$]$^{4-}$: 475.5745; found: 475.5755.

N-Acetamidoethyl O-(4-O-carboxyethyl-2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)

The starting material (5.5 mg, 0.003 mmol) was treated according to the general procedures of NH-Fmoc deprotection, pseudo-hexasaccharides preparation with HBTU and saponification of methyl esters give compound (2.4 mg, 34% for 3 steps). $^1$H NMR (500 MHz, D$_2$O) δ 5.22 (d, J=3.3 Hz, 1H), 5.16 (d, J=3.6 Hz, 1H), 5.00 (s, 2H), 4.94 (dd, J=9.3, 3.9 Hz, 3H), 4.48-4.39 (m, 3H), 4.08 (ddt, J=28.2, 18.3, 10.9 Hz, 10H), 3.93-3.45 (m, 20H), 3.34-3.04 (m, 11H), 2.52-2.33 (m, 6H), 1.86 (dd, J=33.2, 1.5 Hz, 5H). $^{13}$C NMR (125 MHz, D$_2$O) δ 173.79, 171.71, 109.99, 99.08, 98.56, 97.59, 93.80, 91.93, 91.61, 77.81, 77.76, 77.61, 76.07, 75.96, 74.67, 74.22, 73.18, 72.85, 70.86, 70.79, 70.49, 68.91, 68.78, 68.37, 67.62, 66.93, 66.13, 57.72, 53.00, 45.75, 38.87, 57.72, 39.05, 38.87, 36.23, 22.10, 21.70. HRMS: m/z calc. for C$_{55}$H$_{82}$N$_6$O$_{63}$S$_8{}^{8-}$ [M+3Na$^+$]$^{5-}$: 431.8177; found: 431.8196.

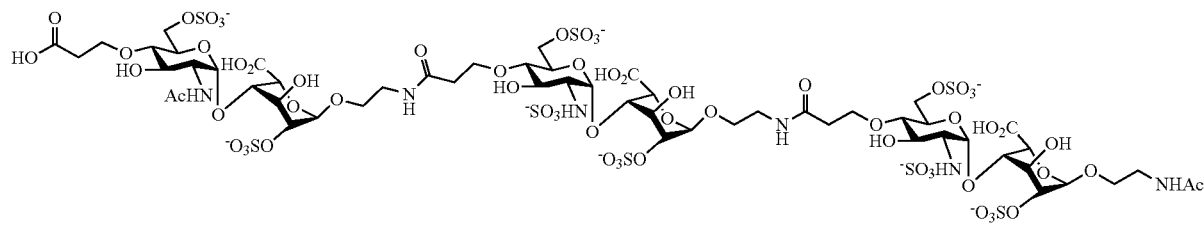

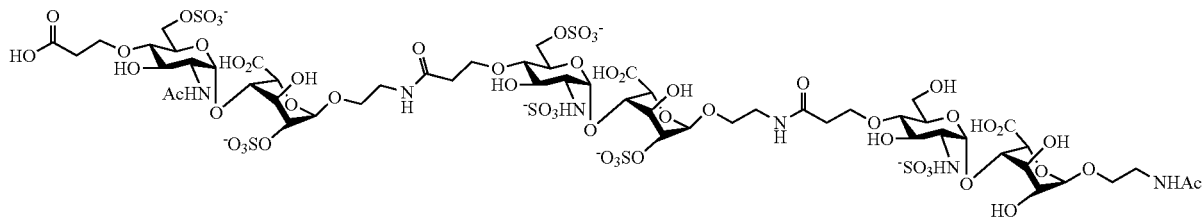

N-Acetamidoethyl O-(4-O-carboxyethyl-2-deoxy-acetamido-6-O-sulfonato-1-thio-β-D-glucopyrano-side)-(1→4)-O-(6-O-carboxyl-2-O-sulfonato-1-thio-α-L-idopyranoside) (1→4)-O-(2-deoxy-sulfoamino-6-O-sulfonato-1-thio-1-D-glucopyranoside)-(1→4)-O-(6-O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)

The starting material (8.2 mg, 0.005 mmol) was treated according to the general procedures of NH-Fmoc deprotection, pseudo-hexasaccharides preparation with HBTU and saponification of methyl esters give compound (5.0 mg, 51% for 3 steps). 1H NMR (500 MHz, D$_2$O) δ 5.19 (d, J=3.6 Hz, 1H), 5.14 (d, J=3.7 Hz, 1H), 4.98 (d, J=2.1 Hz, 1H), 4.96-4.91 (m, 2H), 4.73-4.70 (m, 1H), 4.43 (d, J=2.0 Hz, 2H), 4.37 (d, J=2.4 Hz, 1H), 4.19-3.99 (m, 9H), 3.96 (t, J=3.9 Hz, 2H), 3.92-3.44 (m, 29H), 3.35-3.16 (m, 10H), 3.07 (ddd, J=24.8, 10.4, 3.5 Hz, 3H), 2.50-2.33 (m, 7H), 1.89 (s, 3H), 1.81 (s, 3H). $^{13}$C NMR (125 MHz, D$_2$O) δ 174.66, 174.16, 173.87, 100.63, 98.91, 98.56, 97.22, 95.62, 93.76, 78.01, 77.77, 77.61, 76.01, 75.29, 74.41, 73.18, 70.83, 70.79, 70.67, 70.56, 68.90, 68.81, 68.41, 68.24, 68.17, 68.09, 67.72, 67.48, 66.81, 66.73, 66.16, 66.13, 63.42, 59.74, 57.77, 57.72, 52.99, 39.05, 38.97, 38.87, 36.25, 36.18, 35.51, 22.09, 21.70. HRMS: m/z calc. for $C_{55}H_{84}N_6O_{57}S_6^{6-}$ [M+2Na$^+$]$^{4-}$: 494.5500; found: 494.5519.

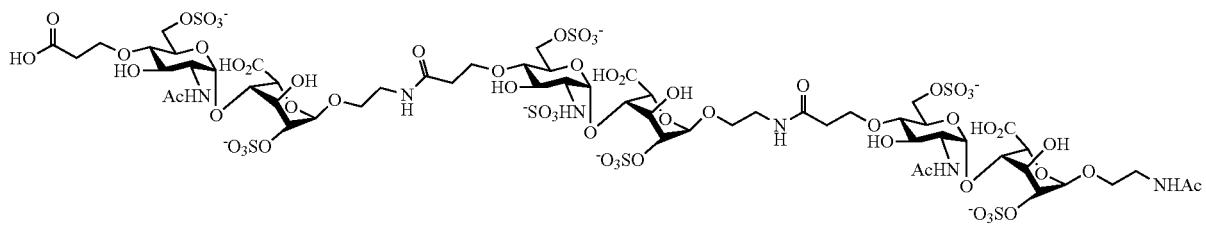

N-Acetamidoethyl O-(4-O-carboxyethyl-2-deoxy-acetamido-6-O-sulfonato-1-thio-β-D-glucopyrano-side)-(1→4)-O-(6-O-carboxyl-2-O-sulfonato-1-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (7.1 mg, 0.004 mmol) was treated according to the general procedures of NH-Fmoc deprotection, pseudo-hexasaccharides preparation with HBTU and saponification of methyl esters give compound (4.5 mg, 50% for 3 steps). $^1$H NMR (500 MHz, D$_2$O) δ 5.17 (d, J=3.5 Hz, 1H), 4.99 (s, 1H), 4.97-4.90 (m, 4H), 4.47-4.40 (m, 3H), 4.16 (dd, J=11.1, 2.7 Hz, 1H), 4.13-3.99 (m, 10H), 3.95-3.42 (m, 24H), 3.35-3.18 (m, 9H), 3.09 (dd, J=10.5, 3.5 Hz, 2H), 2.53-2.32 (m, 7H), 1.88 (d, J=2.0 Hz, 5H), 1.82 (s, 2H). $^{13}$C NMR (125 MHz, D$_2$O) δ 199.58, 177.66, 174.62, 174.16, 173.84, 98.77, 98.68, 98.56, 97.48, 93.80, 93.57, 77.84, 77.75, 77.61, 76.04, 74.83, 73.63, 73.17, 70.85, 70.78, 70.46, 68.90, 68.84, 68.58, 68.44, 68.36, 67.74, 66.89, 66.83, 66.75, 66.26, 66.13, 63.79, 63.43, 57.78, 53.00, 39.00, 38.93, 36.24, 36.18, 35.43, 22.09, 21.70. HRMS: m/z calc. for $C_{57}H_{85}N_6O_{61}S_7^{7-}$ [M+2Na$^+$]$^{5-}$: 419.8320; found: 419.8333.

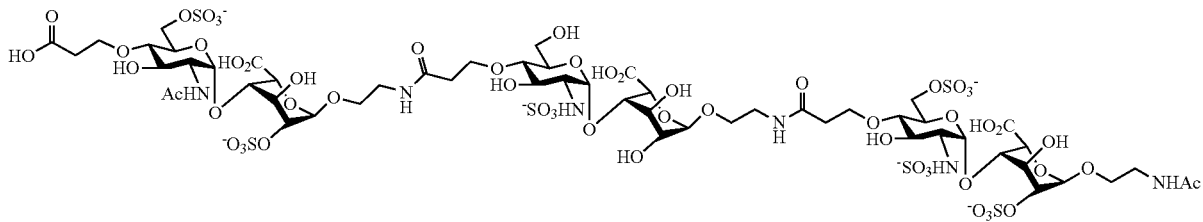

N-Acetamidoethyl O-(4-O-carboxyethyl-2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)

The starting material (6.8 mg, 0.005 mmol) was treated according to the general procedures of NH-Fmoc deprotection, pseudo-hexasaccharides preparation with HBTU and saponification of methyl esters give compound (4.0 mg, 45% for 3 steps). $^1$H NMR (500 MHz, D$_2$O) δ 5.21 (d, J=3.5 Hz, 1H), 5.14 (d, J=3.7 Hz, 1H), 4.96-4.91 (m, 3H), 4.75-4.71 (m, 1H), 4.39 (dd, J=13.1, 2.4 Hz, 3H), 4.20-3.99 (m, 9H), 3.96 (t, J=3.8 Hz, 1H), 3.93-3.73 (m, 13H), 3.70-3.43 (m, 15H), 3.39-3.16 (m, 11H), 3.06 (ddd, J=25.2, 10.4, 3.6 Hz, 3H), 2.49-2.33 (m, 7H), 1.89 (s, 3H), 1.82 (s, 3H). $^{13}$C NMR (125 MHz, D$_2$O) δ 174.64, 173.89, 99.03, 98.60, 96.80, 95.65, 93.68, 78.02, 77.74, 77.66, 75.95, 74.31, 73.36, 70.84, 70.57, 68.86, 68.72, 68.57, 68.41, 68.19, 66.89, 66.74, 66.48, 66.15, 63.58, 59.74, 57.78, 57.74, 52.97, 39.05, 36.35, 35.78, 22.09, 21.69. HRMS: m/z calc. for $C_{55}H_{84}N_6O_{57}S_6^{6-}$ [M+Na$^+$]$^{5-}$: 391.0422; found: 391.0437.

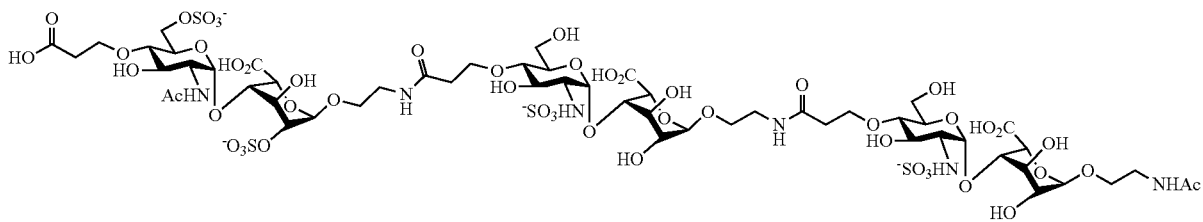

N-Acetamidoethyl O-(4-O-carboxyethyl-2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)

The starting material (7.3 mg, 0.005 mmol) was treated according to the general procedures of NH-Fmoc deprotection, pseudo-hexasaccharides preparation with HBTU and saponification of methyl esters give compound (4.1 mg, 46% for 3 steps). $^1$H NMR (500 MHz, D$_2$O) δ 5.14 (d, J=3.7 Hz, 2H), 4.93 (d, J=3.8 Hz, 2H), 4.75-4.70 (m, 2H), 4.43-4.30 (m, 4H), 4.20-4.02 (m, 5H), 3.95 (q, J=4.1 Hz, 2H), 3.91-3.71 (m, 12H), 3.69-3.42 (m, 18H), 3.33-3.13 (m, 10H), 3.04 (dd, J=10.5, 3.7 Hz, 3H), 2.48-2.30 (m, 7H), 1.85 (d, J=34.6 Hz, 6H). $^{13}$C NMR (125 MHz, D$_2$O) δ 174.63, 173.93, 100.60, 98.60, 95.63, 95.58, 93.67, 78.00, 77.94, 77.65, 74.42, 74.33, 73.36, 70.79, 70.69, 70.50, 68.86, 68.54, 68.23, 68.10, 67.52, 66.69, 66.51, 66.14, 63.57, 59.74, 57.77, 57.74, 52.96, 39.05, 38.95, 36.25, 36.17, 22.08, 21.70. HRMS: m/z calc. for $C_{55}H_{86}N_6O_{51}S_4^{4-}$ [M]$^{4-}$: 443.5806; found: 443.5793.

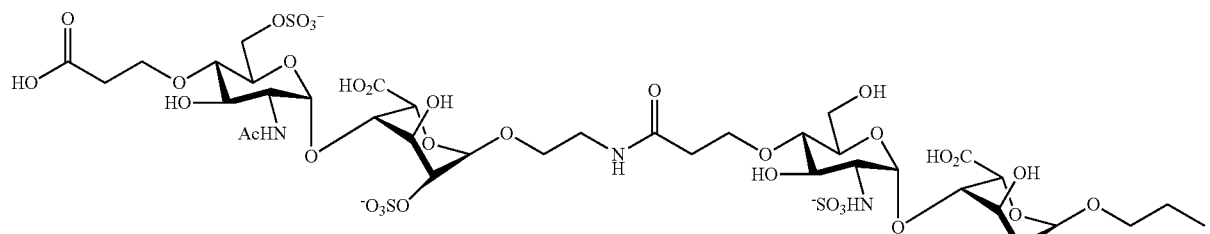

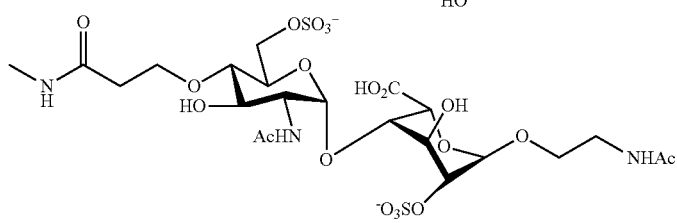

N-Acetamidoethyl O-(4-O-carboxyethyl-2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-sulfoamino-1-thio-β-D-glucopyranoside)-(1→4)-O-(6-O-carboxyl-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (7.0 mg, 0.005 mmol) was treated according to the general procedures of NH-Fmoc deprotection, pseudo-hexasaccharides preparation with HBTU and saponification of methyl esters give compound (4.5 mg, 50% for 3 steps). $^1$H NMR (500 MHz, D$_2$O) δ 5.14 (d, J=3.7 Hz, 1H), 4.95-4.90 (m, 4H), 4.75-4.71 (m, 1H), 4.39 (dd, J=14.1, 2.3 Hz, 3H), 4.18-4.01 (m, 8H), 3.96 (t, J=3.7 Hz, 1H), 3.92-3.73 (m, 13H), 3.70-3.44 (m, 14H), 3.25 (m, 10H), 3.04 (dd, J=10.4, 3.6 Hz, 1H), 2.51-2.30 (m, 7H), 1.93-1.75 (m, 9H). $^{13}$C NMR (125 MHz, D$_2$O) δ 174.63, 173.87, 100.56, 98.65, 98.60, 95.66, 93.68, 93.56, 78.00, 77.75, 77.65, 74.32, 73.61, 73.35, 70.84, 70.80, 70.72, 70.58, 68.85, 68.51, 68.16, 66.86, 66.74, 66.49, 66.14, 63.78, 63.57, 59.73, 57.74, 53.04, 52.97, 39.00, 36.29, 36.16, 35.67, 22.07, 21.70. HRMS: m/z calc. for $C_{57}H_{87}N_6O_{55}S_5^{5-}$ [M]$^{5-}$: 379.0565; found: 379.0584.

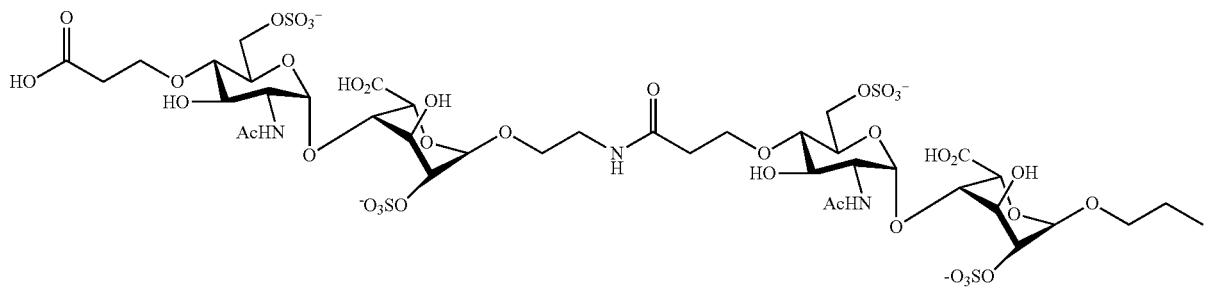

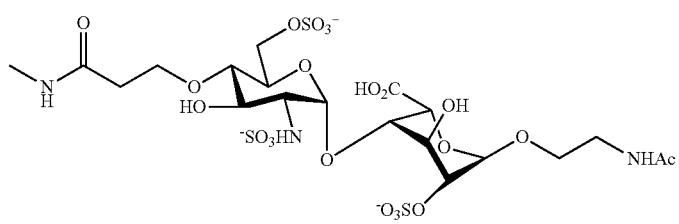

N-Acetamidoethyl O-(4-O-carboxyethyl-2-deoxy-acetamido-6-O-sulfonato-1-thio-β-D-glucopyrano-side)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-thio-α-L-idopyranoside)-(1→4)-O-(2-deoxy-sulfoamino-6-O-sulfonato-1-thio-β-D-glucopyranoside)-(1→4)-O-(6-O-carboxyl-2-O-sulfonato-1-thio-α-L-idopyranoside)

The starting material (5.3 mg, 0.003 mmol) was treated according to the general procedures of NH-Fmoc deprotection, pseudo-hexasaccharides preparation with HBTU and saponification of methyl esters give compound (1.0 mg, 15% for 3 steps). $^1$H NMR (500 MHz, D$_2$O) δ 5.24 (d, J=3.6 Hz, 1H), 4.92 (d, J=3.4 Hz, 4H), 4.40-4.32 (m, 3H), 4.16-3.97 (m, 10H), 3.95-3.73 (m, 12H), 3.70-3.43 (m, 11H), 3.39-3.13 (m, 11H), 2.38 (d, J=27.8 Hz, 7H), 1.85 (d, J=30.4 Hz, 7H). HRMS: m/z calc. for $C_{57}H_{85}N_6O_{61}S_7^{7-}$ $[M+3Na^+]^{4-}$: 530.5373; found: 530.5389.

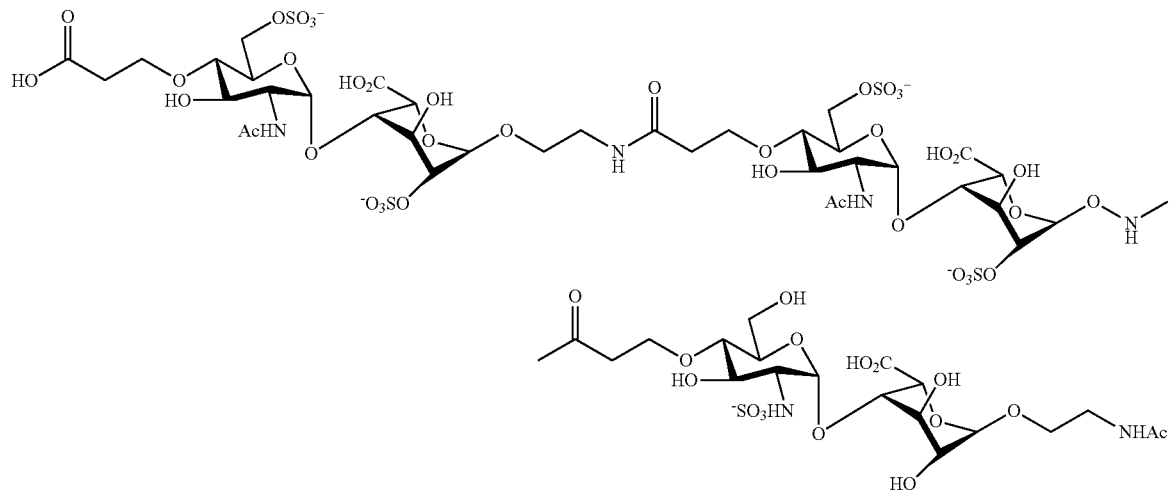

N-Acetamidoethyl O-(4-O-carboxyethyl-2-deoxy-acetamido-6-O-sulfonato-1-thio-β-D-glucopyrano-side)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-thio-α-L-idopyranoside)-(1→4)-O-(2-deoxy-sulfoamino-1-thio-β-D-glucopyranoside)-(1→4)-O-(6-O-carboxyl-1-thio-α-L-idopyranoside)

The starting material (6.7 mg, 0.004 mmol) was treated according to the general procedures of NH-Fmoc deprotection, pseudo-hexasaccharides preparation with HBTU and saponification of methyl esters give compound (4.4 mg, 55% for 3 steps). $^1$H NMR (500 MHz, D$_2$O) δ 5.13 (d, J=3.8 Hz, 1H), 4.92 (d, J=3.3 Hz, 3H), 4.73-4.69 (m, 1H), 4.46-4.32 (m, 3H), 4.17-3.99 (m, 7H), 3.94 (t, J=3.9 Hz, 1H), 3.91-3.70 (m, 11H), 3.69-3.43 (m, 11H), 3.34-3.14 (m, 8H), 3.03 (dd, J=10.5, 3.6 Hz, 1H), 2.50-2.31 (m, 6H), 1.87 (s, 4H), 1.80 (s, 2H). $^{13}$C NMR (125 MHz, D$_2$O) δ 174.64, 173.91, 100.61, 98.63, 98.55, 95.61, 93.74, 93.65, 77.96, 77.78, 77.59, 74.38, 73.37, 73.20, 70.81, 70.66, 70.54, 68.89, 68.33, 68.20, 67.45, 66.73, 66.11, 63.53, 63.42, 59.71, 57.71, 52.98, 39.03, 38.92, 36.19, 35.39, 22.07, 21.68. HRMS: m/z calc. for $C_{57}H_{87}N_6O_{55}S_5^{5-}$ $[M]^{5-}$: 379.0565; found: 379.0574.

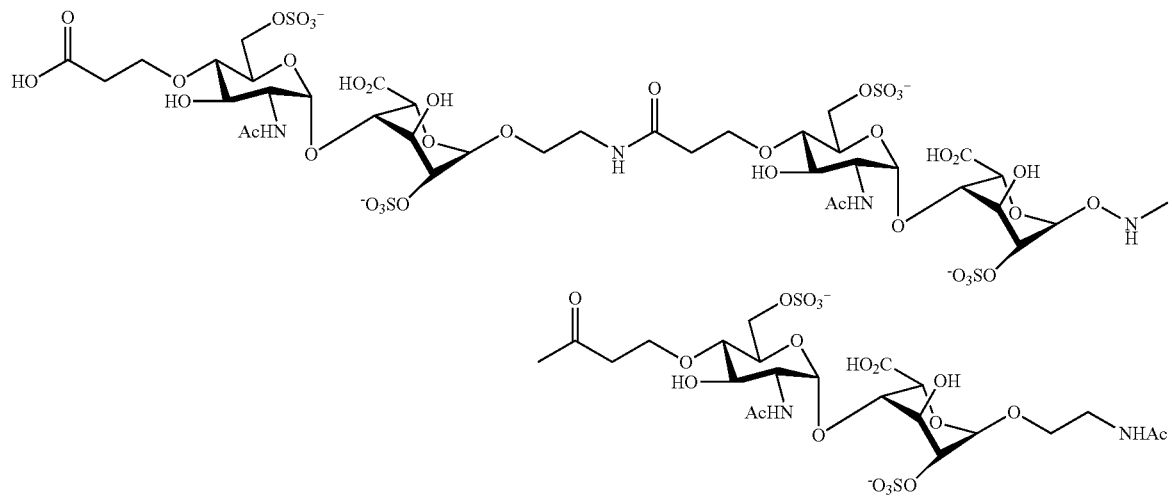

N-Acetamidoethyl O-(4-O-carboxyethyl-2-deoxy-acetamido-6-O-sulfonato-1-thio-β-D-glucopyranoside)-(1→4)-O-(6-O-carboxyl-2-O-sulfonato-1-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-thio-α-L-idopyranoside)-(1→4)-O-(2-deoxy-acetamido-6-O-sulfonato-1-thio-β-D-glucopyranoside)-(1→4)-O-(6-O-carboxyl-2-O-sulfonato-1-thio-α-L-idopyranoside)

The starting material (8.0 mg, 0.005 mmol) was treated according to the general procedures of NH-Fmoc deprotection, pseudo-hexasaccharides preparation with HBTU and saponification of methyl esters give compound (4.5 mg, 44% for 3 steps). $^1$H NMR (500 MHz, D$_2$O) δ 4.94 (q, J=6.0, 5.1 Hz, 6H), 4.42-4.35 (m, 3H), 4.17-4.01 (m, 12H), 3.93-3.74 (m, 15H), 3.70-3.45 (m, 11H), 3.26 (ddt, J=21.3, 7.6, 3.8 Hz, 10H), 2.41 (d, J=7.7 Hz, 6H), 1.89 (d, J=1.4 Hz, 8H), 1.83 (s, 3H). $^{13}$C NMR (125 MHz, D$_2$O) δ 174.67, 170.33, 109.99, 98.68, 98.57, 93.63, 77.86, 73.74, 73.35, 70.86, 69.21, 68.87, 68.67, 66.87, 66.65, 66.28, 63.90, 63.55, 53.05, 52.91, 39.03, 38.89, 36.22, 22.12, 22.09, 21.72. HRMS: m/z calc. for $C_{59}H_{88}N_6O_{19}S_6^{6-}$ [M]$^{6-}$: 336.0405; found: 336.0412.

Example 2

Monosaccharide Building Block Preparation

4-Methoxybenzylidene acetal was utilized to protect the 4-O and 6-O positions of compound 29, and the 3-O was protected by the Bn group. NaCNBH$_3$-mediated reductive 4-methoxybenzylidene 4-O-ring opening afforded compound 30. Allyl group was installed at 4-O position of 30 followed by a hydroboration-oxidation reaction to obtain the primary alcohol linker. The alcohol was then oxidized to a carboxylate group, which was subsequently protected as a benzyl ester. The 6-O-PMB protecting group was replaced with Fmoc as a potential O-sulfation site to form the GlcN donor 31 (Scheme 1).

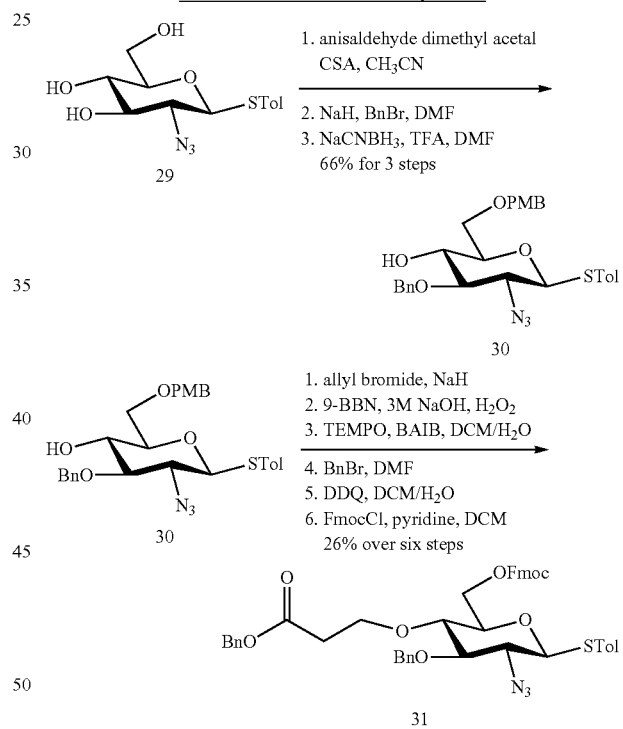

Scheme 1. Glucosamine donor synthesis.

6-OH on idopyranosyluronate 32 was oxidized by a catalytic amount of 2,2,6,6-tetramethyl-1-piperidinyloxy (TEMPO) with bis(acetoxy)iodobenzene (BAIB), followed by methyl ester formation to afford idopyranosyluronate 33. Glycosylation of 33 with N-Cbz and N-Bn protected ethanolamine linker provided a product in 87% yield. The stereochemistry was confirmed by one-bond coupling constants between the anomeric carbon and hydrogen atoms ($^1J_{CH}$=172 Hz). 2-O-Bz conferred better neighboring group assistance than 2-O-Fmoc, which only afforded a/s stereoselectivity in 3:1 ratio. 2-O-Bz was removed by NaOMe in DCM and MeOH cosolvent system followed by 2-O-Fmoc protection and 4-O-PMB deprotection to provide the idopyranosyluronate acceptor 34 (Scheme 2).

Scheme 2. Idopyranosyluronate acceptor 34 preparation.

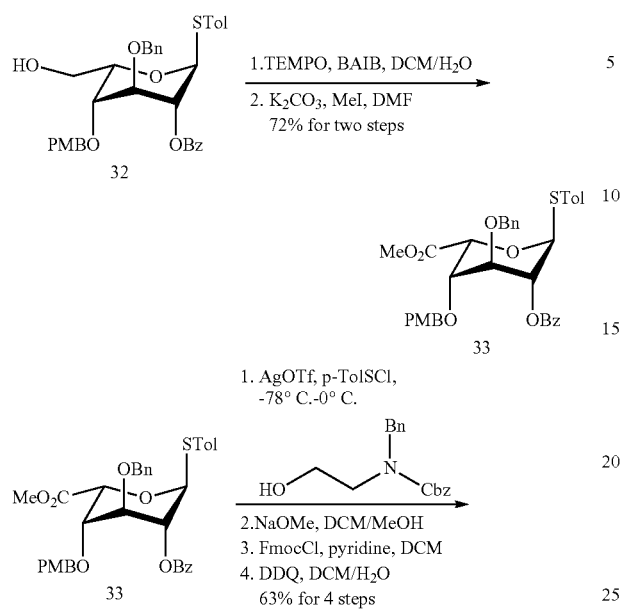

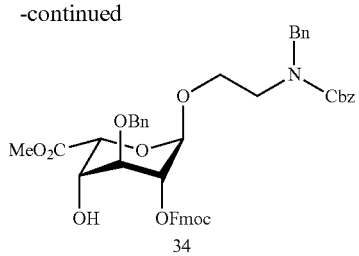

Synthesis of Disaccharide modules with Various Sulfation Patterns

The presence of non-participating azide group at C2 of glucosamine donor 31 assisted the formation of the desired 1,2-cis disaccharide 35 via promotion by p-TolSCl/AgOTf (Scheme 2). Disaccharide 36 was originally obtained by a two-step procedure of azide reduction with Zn/HOAc followed by Fmoc deprotection. Instead, treatment of 36 with 1,3-propanedithiol in $Et_3N$ furnished 36 in one step with an 81% yield (Scheme 3) (*J. Med. Chem.* 2006, 49 (14), 4333-4343).

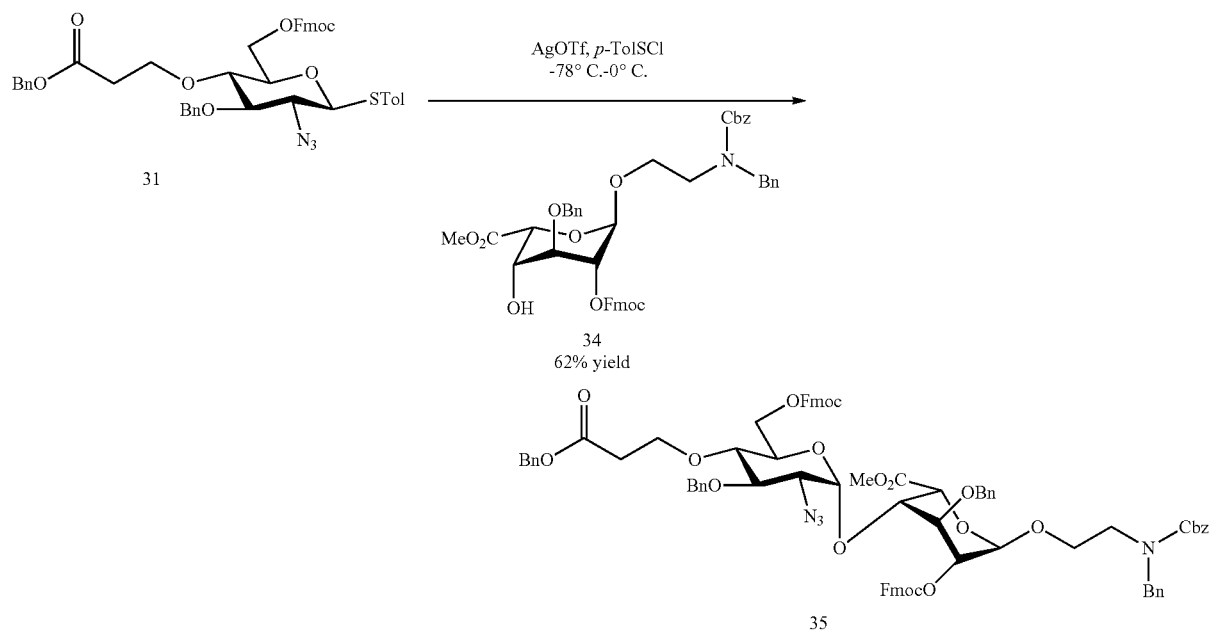

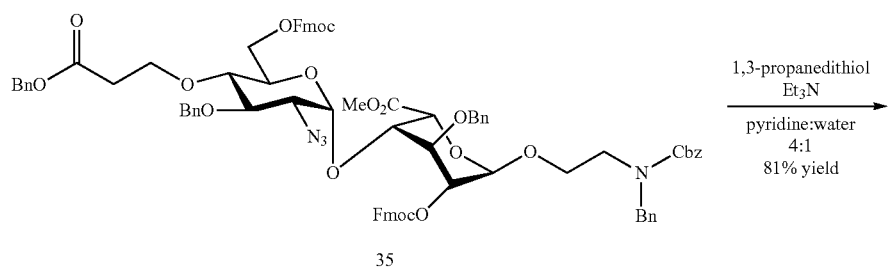

-continued

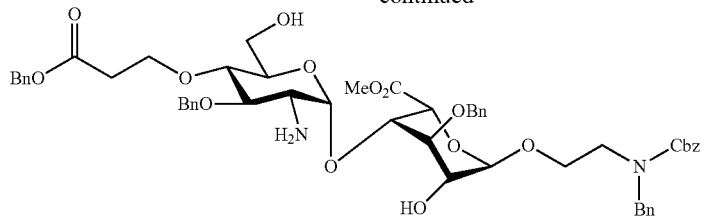

36

Next, we explored whether different sulfation pattern disaccharides could be generated from 36 under various sulfation conditions. N-sulfation of 37 was achieved by treatment with $SO_3 \cdot Et_3N$ in a $H_2O$ and THF cosolvent system. The amine of 36 was converted to acetamide followed by O-sulfation via $SO_3 \cdot Et_3N$ at 55° C. in DMF to obtain 0-sulfated disaccharide 38. $SO_3$ pyridine complex in pyridine solution was implemented for fully sulfated compound 39 preparation. However, incomplete sulfation byproduct was observed even with extended reaction time and an increased amount of sulfation reagents. Two-step sulfation was performed next with O-sulfation followed by N-sulfation to furnish 39 in 92% yield over two steps. The Bn and Cbz protecting groups were removed by hydrogenation with Pd/C to afford compounds 40-42. The elongation sequence disaccharides 43-45 were prepared by N-Fmoc protection of amines. FmocCl gave the Fmoc protected carboxylate byproduct, and Fmoc-OSu was used to afford selectively N-Fmoc protected 43-45 (Scheme 4) (*J. Pept. Sci.* 2008, 14 (6), 763-766).

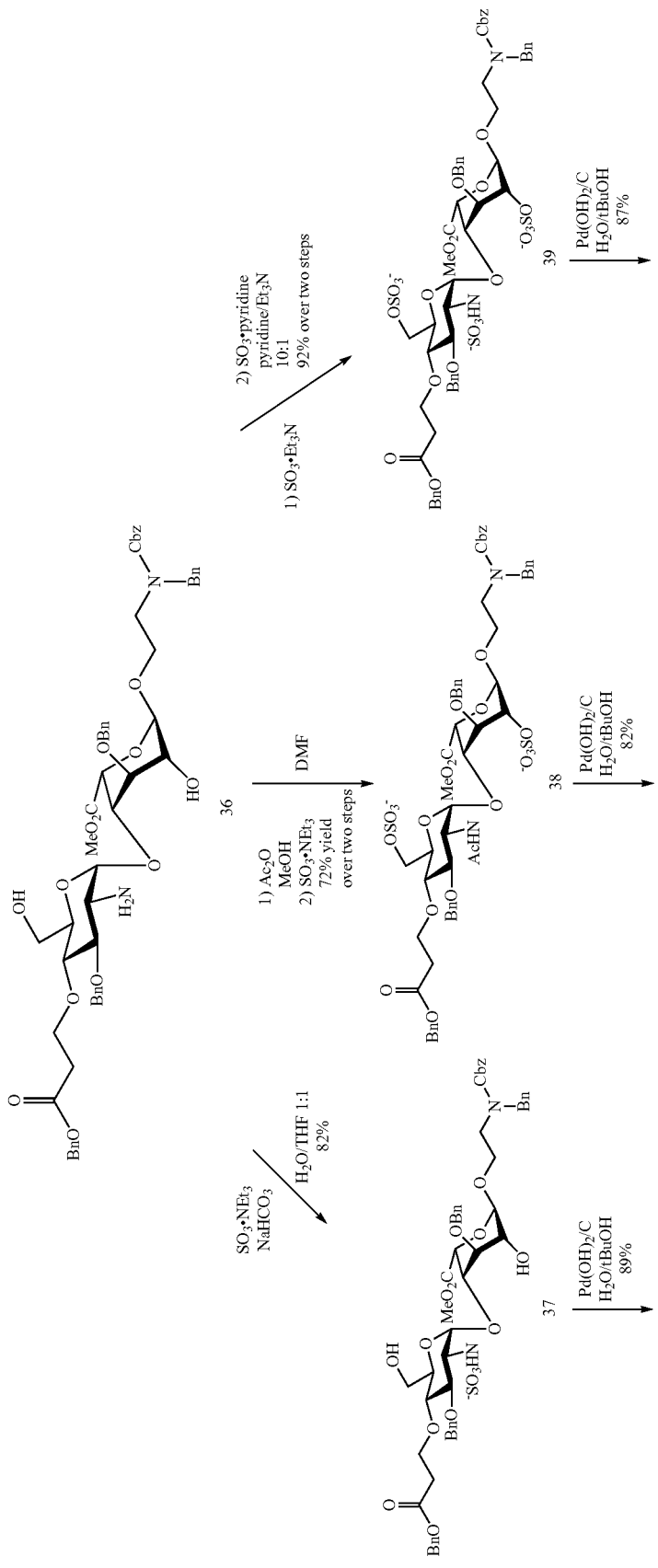

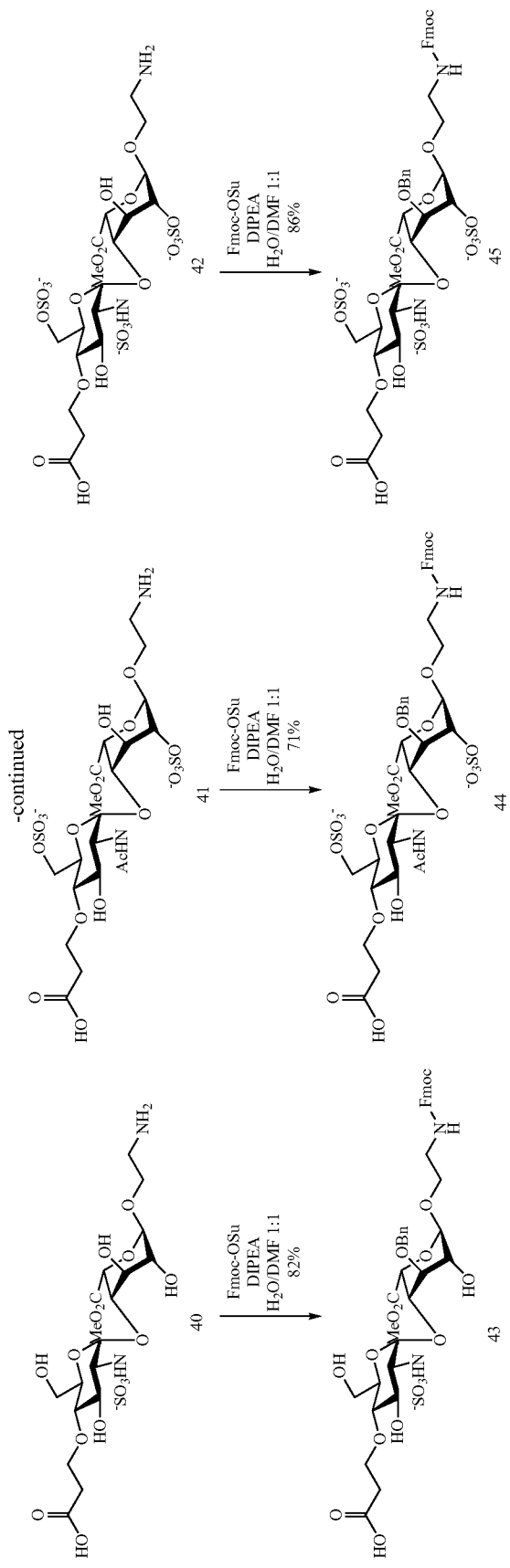

Next, the reducing end sequence disaccharides were designed with a masked amine as part of the aglycon linker. Treatment with acetic anhydride in MeOH enabled acetylation of amines to furnish desired disaccharides 46-48 (Scheme 5).

Synthesis of a Library of 27 Pseudo-hexasaccharide Heparin Mimetics

In order to build a pseudo tetrasaccharide library, the carboxylate groups of disaccharides 43-45 were blocked by methyl ester followed by N-Fmoc deprotection via DBU.

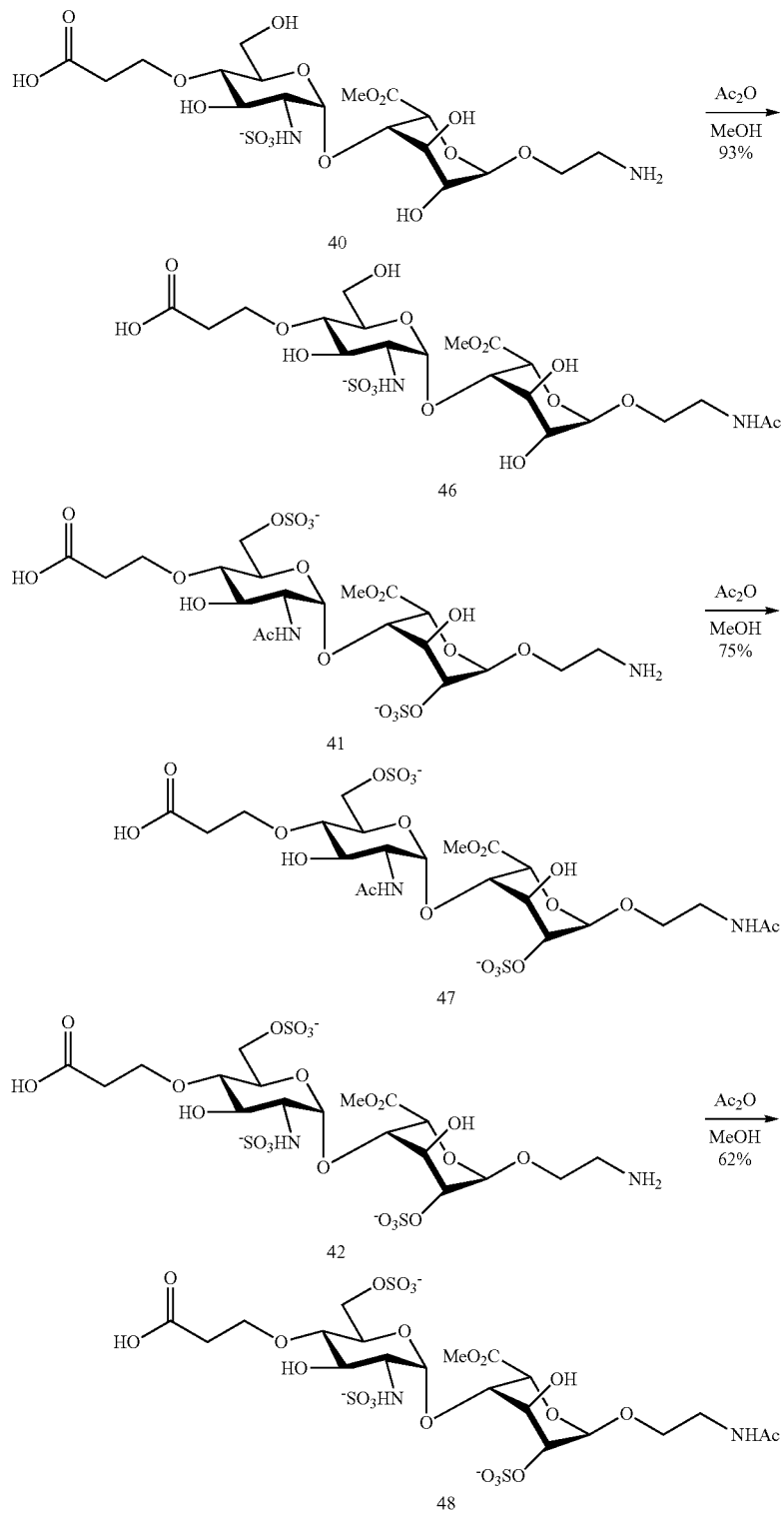

Scheme 5. Reducing end sequence disaccharides 46-48.

Nine pseudo-tetrasaccharides with different combinations of sulfation patterns on disaccharide modules were prepared by HATU or HBTU mediated coupling reactions. We observed seven-membered lactone byproduct (10-20%) produced with fully sulfated disaccharide 45. In this case, HBTU was used for amidation reactions (Scheme 6).

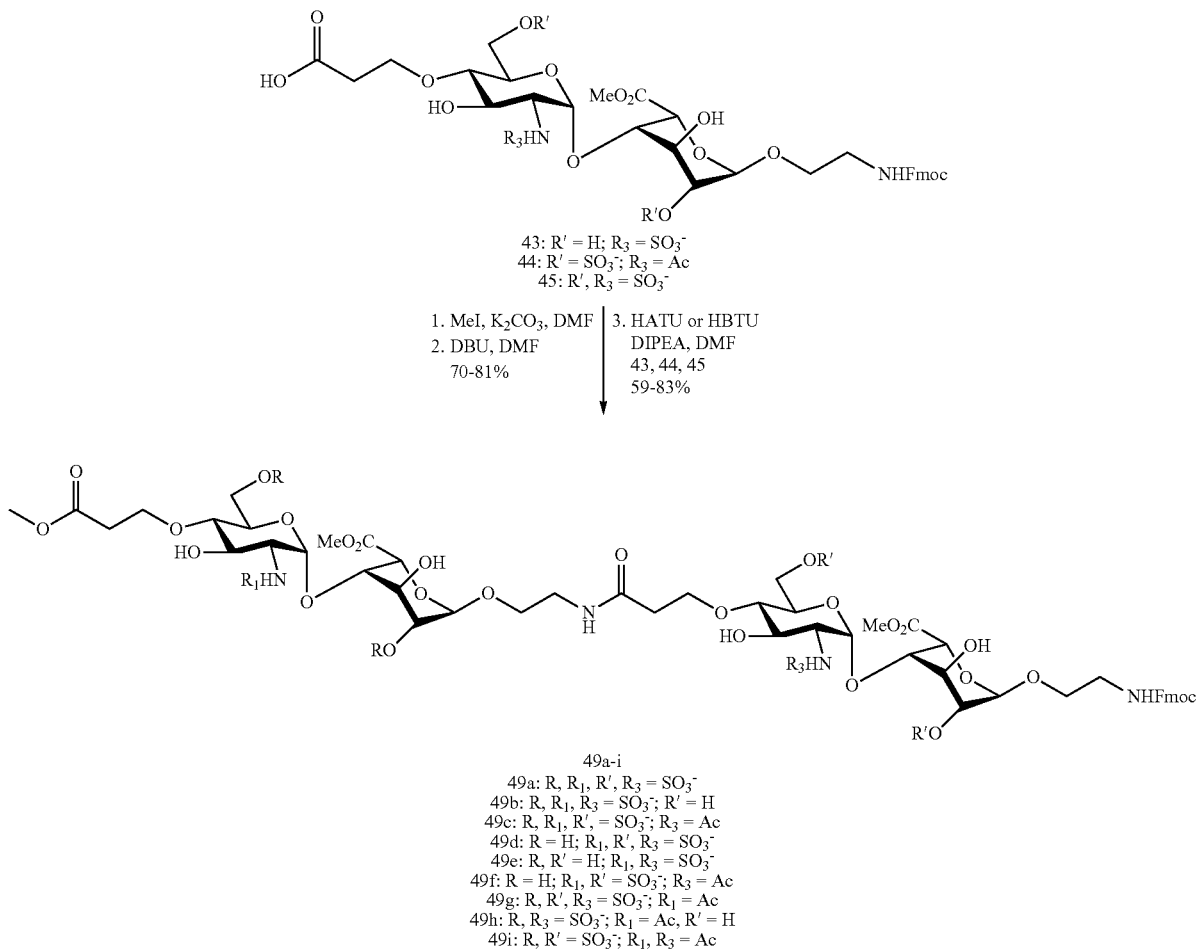

As each disaccharide module possesses three different sulfation patterns, 27 various pseudo hexasaccharide mimetics could be generated. Developing such a library is regarded as a potential tool to understand the heparin structure and its biological functions. The pseudo tetrasaccharides (49a-i) were treated with DBU to deprotect the N-Fmoc group followed by HATU or HBTU coupling reaction to furnish the desired pseudo hexasaccharides. Saponification of methyl esters afforded the fully deprotected 27 pseudo hexasaccharides (50, 50a-z) (Scheme 7).

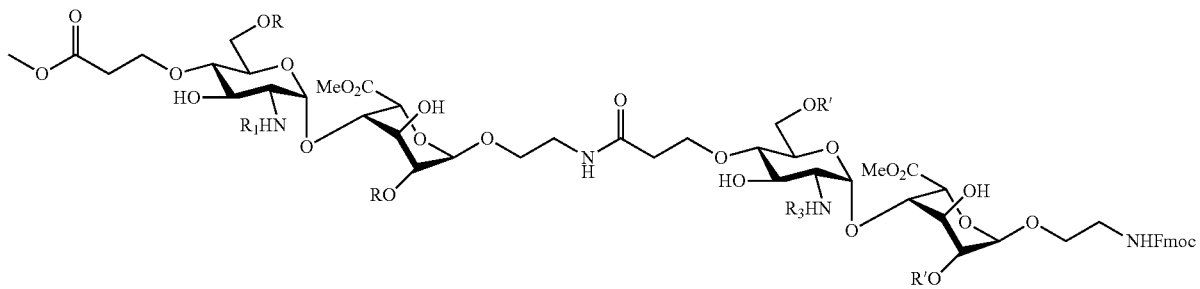

-continued 49a-i
49a: R, R₁, R', R₃ = SO₃⁻
49b: R, R₁, R₃ = SO₃⁻; R' = H
49c: R, R₁, R', = SO₃⁻; R₃ = Ac
49d: R = H; R₁, R', R₃ = SO₃⁻
49e: R, R' = H; R₁, R₃ = SO₃⁻
49f: R = H; R₁, R' = SO₃⁻; R₃ = Ac
49g: R, R', R₃ = SO₃⁻; R₁ = Ac
49h: R, R₃ = SO₃⁻; R₁ = Ac, R' = H
49i: R, R' = SO₃⁻; R₁, R₃ = Ac

1. DBU, DMF  86-95%
2. HATU, DIPEA  DMF

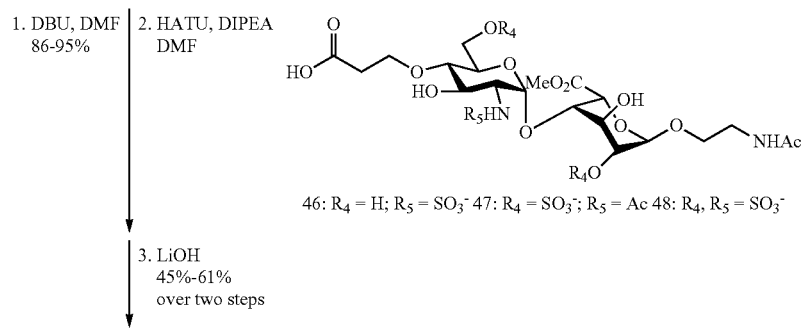

46: R₄ = H; R₅ = SO₃⁻   47: R₄ = SO₃⁻; R₅ = Ac   48: R₄, R₅ = SO₃⁻

3. LiOH
45%-61%
over two steps

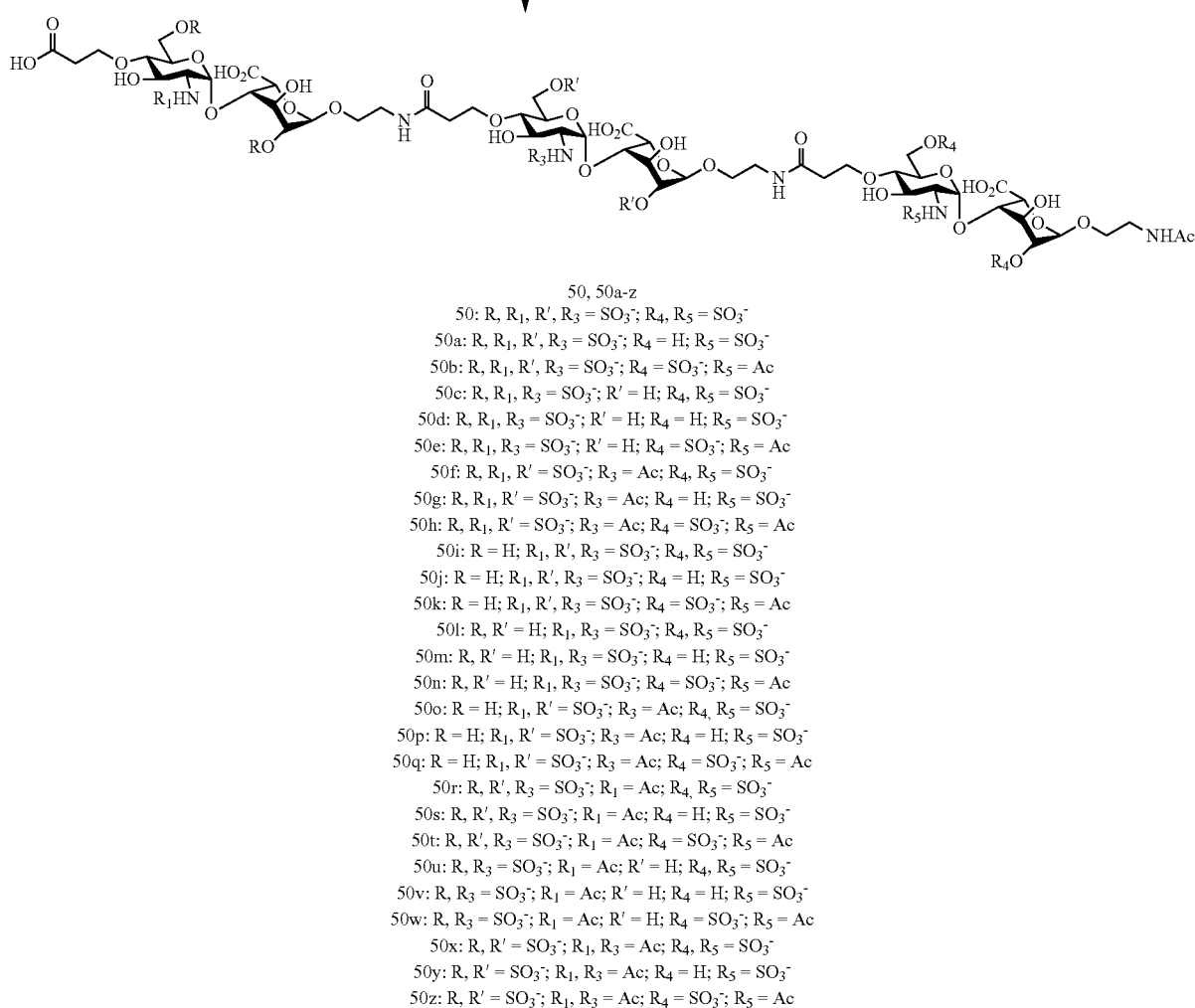

50, 50a-z
50: R, R₁, R', R₃ = SO₃⁻; R₄, R₅ = SO₃⁻
50a: R, R₁, R', R₃ = SO₃⁻; R₄ = H; R₅ = SO₃⁻
50b: R, R₁, R', R₃ = SO₃⁻; R₄ = SO₃⁻; R₅ = Ac
50c: R, R₁, R₃ = SO₃⁻; R' = H; R₄, R₅ = SO₃⁻
50d: R, R₁, R₃ = SO₃⁻; R' = H; R₄ = H; R₅ = SO₃⁻
50e: R, R₁, R₃ = SO₃⁻; R' = H; R₄ = SO₃⁻; R₅ = Ac
50f: R, R₁, R' = SO₃⁻; R₃ = Ac; R₄, R₅ = SO₃⁻
50g: R, R₁, R' = SO₃⁻; R₃ = Ac; R₄ = H; R₅ = SO₃⁻
50h: R, R₁, R' = SO₃⁻; R₃ = Ac; R₄ = SO₃⁻; R₅ = Ac
50i: R = H; R₁, R', R₃ = SO₃⁻; R₄, R₅ = SO₃⁻
50j: R = H; R₁, R', R₃ = SO₃⁻; R₄ = H; R₅ = SO₃⁻
50k: R = H; R₁, R', R₃ = SO₃⁻; R₄ = SO₃⁻; R₅ = Ac
50l: R, R' = H; R₁, R₃ = SO₃⁻; R₄, R₅ = SO₃⁻
50m: R, R' = H; R₁, R₃ = SO₃⁻; R₄ = H; R₅ = SO₃⁻
50n: R, R' = H; R₁, R₃ = SO₃⁻; R₄ = SO₃⁻; R₅ = Ac
50o: R = H; R₁, R' = SO₃⁻; R₃ = Ac; R₄, R₅ = SO₃⁻
50p: R = H; R₁, R' = SO₃⁻; R₃ = Ac; R₄ = H; R₅ = SO₃⁻
50q: R = H; R₁, R' = SO₃⁻; R₃ = Ac; R₄ = SO₃⁻; R₅ = Ac
50r: R, R', R₃ = SO₃⁻; R₁ = Ac; R₄, R₅ = SO₃⁻
50s: R, R', R₃ = SO₃⁻; R₁ = Ac; R₄ = H; R₅ = SO₃⁻
50t: R, R', R₃ = SO₃⁻; R₁ = Ac; R₄ = SO₃⁻; R₅ = Ac
50u: R, R₃ = SO₃⁻; R₁ = Ac; R' = H; R₄, R₅ = SO₃⁻
50v: R, R₃ = SO₃⁻; R₁ = Ac; R' = H; R₄ = H; R₅ = SO₃⁻
50w: R, R₃ = SO₃⁻; R₁ = Ac; R' = H; R₄ = SO₃⁻; R₅ = Ac
50x: R, R' = SO₃⁻; R₁, R₃ = Ac; R₄, R₅ = SO₃⁻
50y: R, R' = SO₃⁻; R₁, R₃ = Ac; R₄ = H; R₅ = SO₃⁻
50z: R, R' = SO₃⁻; R₁, R₃ = Ac; R₄ = SO₃⁻; R₅ = Ac

General Synthetic Procedures

All reactions were performed under a nitrogen atmosphere with anhydrous solvents. Solvents were dried using a solvent purification system. Glycosylation reactions were performed with 4 Å molecular sieves that were flamed dried under high vacuum. Chemicals used were reagent grade unless noted. Reactions were visualized by UV light (254 nm) and by staining with either $Ce(NH_4)_2(NO_3)_6$ (0.5 g) and $(NH_4)_6Mo_7O_{24} \cdot 4H_2O$ (24.0 g) in 6% $H_2SO_4$ (500 mL), 5% $H_2SO_4$ in EtOH. Flash chromatography was performed on silica gel 601 (230-400 Mesh). NMR spectra were referenced using residual $CHCl_3$, $CO_3OD$, and $D_2O$. Peak and coupling constants assignments are based on $^1$H-NMR, $^1$H-$^1$H gCOSY, $^1$H and $^1$H-$^1$H TOCSY, $^1$H-$^1$H NOESY, $^1$H-$^{13}$C gHSQC, $^1$H-$^{13}$C gHMBC.

General Procedure for Pre-Activation Based Single-Step Glycosylation.

A solution of the donor (1.0 equiv) and freshly activated molecular sieve MS 4 Å in DCM was stirred for 20 minutes under room temperature and then cooled to −78° C. A solution of AgOTf (3.0 equiv) in anhydrous Et$_2$O/DCM (10/1, v/v) was added to the reaction solution without touching the wall of the flask. After 5 minutes, orange-colored p-TolSCl (1.0 equiv) was added to the solution through a microsyringe. p-TolSCl should be added directly to the reaction solution to prevent it from freezing on the flask wall and stir bar. The characteristic orange color of p-TolSCl should dissipate within a few seconds indicating consumption of p-TolSCl promoter. TLC analysis could confirm the complete activation of the donor in 5 minutes. A solution of acceptor (1.0 equiv) with TTBP (1.0 equiv) in DCM was added to reaction solution (0.3 M). The reaction mixture can be warmed up to 0° C. under stirring in 2 hours, depending on the reactivity of both donor and acceptor. The reaction mixture was quenched by Et$_3$N (NaHCO$_3$ saturated solution for Fmoc protected compounds) and filtered over Celite with DCM. DCM solution was washed by NaHCO$_3$ and NaCl saturated solutions. The organic layer was collected and dried over Na$_2$SO$_4$, concentrated and purified by silica gel flash chromatography.

General Procedure for Deprotection of PMB.

The PMB-protected compound (1.0 equiv) was dissolved in DCM/H$_2$O (0.1 M, 10:1, v/v). The mixture was cooled to 0° C., followed by the addition of DDQ (1.5 equiv). The mixture was stirred at room temperature for 1 hour. The residue was diluted with DCM and washed with saturated solutions of NaHCO$_3$ and NaCl, dried (Na$_2$SO$_4$), and filtered. The filtrate was concentrated in vacuo, and the residue was purified by silica gel flash chromatography.

General Procedure for Protection of 6-OH with Lev.

The compound containing 6-OH (1.0 equiv) was dissolved in DCM (0.3 M), followed by the addition of EDC-HCl (3.0 equiv), levulinic acid (1.4 equiv) and DMAP (1.0 equiv). The mixture was stirred under room temperature for 1 hour. The residue was diluted with DCM and washed with 10% HCl, saturated solutions of NaHCO$_3$ and NaCl. The organic solution was dried over Na$_2$SO$_4$ and concentrated in vacuo, then purified by silica gel flash chromatography.

General Procedure for O-Acetylation.

The compound containing —OH (1.0 equiv) was dissolved in pyridine (1.2 M), followed by the addition of acetic anhydride (7.0 equiv for each hydroxyl group) at 0° C. The mixture was stirred at room temperature overnight and then washed with 3×1.0 M HCl and saturated solutions of NaHCO$_3$ and NaCl. The organic solution was dried over Na$_2$SO$_4$, filtered and concentrated in vacuo, then purified by silica gel flash chromatography to afford the desired compounds.

General Procedure for N-Acetylation.

The compound containing —NH$_2$ (1.0 equiv) was dissolved in MeOH (0.04 M), followed by the addition of acetic anhydride (3.0 equiv) and Et$_3$N (3.0 equiv). The mixture was stirred at room temperature for 1 h and then was passed through LH-20 gel column with MeOH to afford the desired compounds.

General Procedure for Protection of OH with Fmoc.

To a solution of starting material in DCM (0.3 M), FmocCl (3.0 equiv) and pyridine (4.0 equiv) were added. The reaction mixture was stirred at room temperature for 1 h and diluted with DCM. The organic mixture was washed with 3×1 M HCl, NaHCO$_3$ saturated solution, and brine. The organic layer was dried over anhydrous Na$_2$SO$_4$ and filtered. The filtrate was concentrated by rotary evaporation and the desired product was purified by silica gel column chromatography.

General Procedure for Protection of NH2 with Fmoc.

To a solution of starting material in H$_2$O/DMF (1/1, v/v, 0.3 M), Fmoc-OSu (3.0 equiv) and DIPEA (1.5 equiv) were added. The reaction mixture was stirred at room temperature for 2 h. The organic mixture was washed with 3×1 M HCl, NaHCO$_3$ saturated solution and brine. The organic layer was dried over anhydrous Na$_2$SO$_4$ and filtered. The filtrate was concentrated by rotary evaporation and the desired product was purified by silica gel column chromatography. For disaccharide Fmoc protection, after the reaction completed as indicated by TLC (EtOAc/MeOH/H$_2$O 3/1/1), the reaction mixture was passed through an LH-20 gel column with MeOH. A column of Dowex 50WX4 Na$^+$ resin was used for ion exchange for giving products as sodium salts.

General Procedure for Preparation of Methyl Ester.

K$_2$CO$_3$ (10.0 equiv) and CH$_3$I (6.0 equiv) was added to a solution of starting material (1.0 equiv) in DMF (0.13M). The reaction mixture was stirred at room temperature for 4 h. After completion, the mixture was passed through an LH-20 gel column to afford pure compounds.

General Procedure for NH-Fmoc Deprotection.

A mixture of starting material (1.0 equiv) and DBU (5.0 equiv) in DMF (0.15 M) was stirred for 1 h at room temperature. After TLC (EtOAc/MeOH/H$_2$O, 3/1/1, v/v/v) indicating that the reaction was complete, the reaction mixture was passed through an LH-20 gel column to give pure compounds.

General Procedure for Preparation of Pseudo-Tetrasaccharides/Hexasaccharides.

A solution of carboxyethyl disaccharides (1.0 equiv), HATU or HBTU (1.0 equiv) and DIPEA (2.0 equiv) in DMF was added to starting material (1.0 equiv) in DMF (0.013 M). After stirring 1 h at room temperature, TLC (EtOAc/MeOH/H$_2$O, 2.5/1/1, v/v/v) indicated completion of the reaction. Then the reaction mixture was passed through an LH-20 gel column, and the fractions containing product were collected and concentrated under reduced pressure. A column of Dowex 50WX4 Na$^+$ resin was used for ion exchange to give products as sodium salts.

General Procedure for Hydrogenolysis.

A solution of the compound in mixed tBuOH and water [1/1 (v/v), 3 mL] in the presence of 10% Pd(OH)$_2$/C (80 mg) at room temperature was exposed to H$_2$ gas. After overnight, the suspension was filtered through Celite, and the filtrate was concentrated in vacuo. The residue was passed through an LH-20 gel column using MeOH as eluent. The product fractions were concentrated under reduced pressure to give the target molecule.

General Procedure for Saponification of Methyl Esters.

The starting material (1.0 equiv) was added to a LiOH (10.0 equiv per CO$_2$Me) solution (0.006 M) at 0° C. The reaction mixture was stirred at 0° C. for 8 h. After TLC (EtOAc/MeOH/H$_2$O, 1.5/1/1, v/v/v) indicated the reaction completion, Amberlite H$^+$ resin was added until pH~7. The reaction mixture was passed through G-15, and Dowex 50WX4 Na$^+$ gel columns to give pure products as the sodium salts.

Product Preparation and Characterization Data

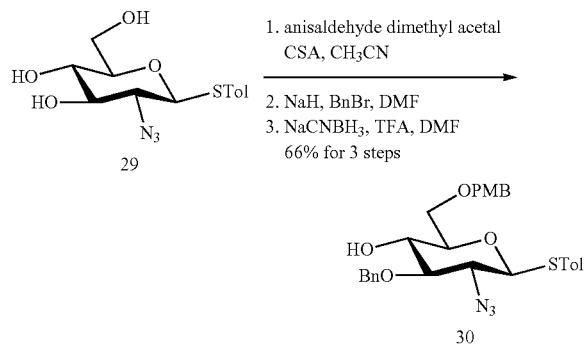

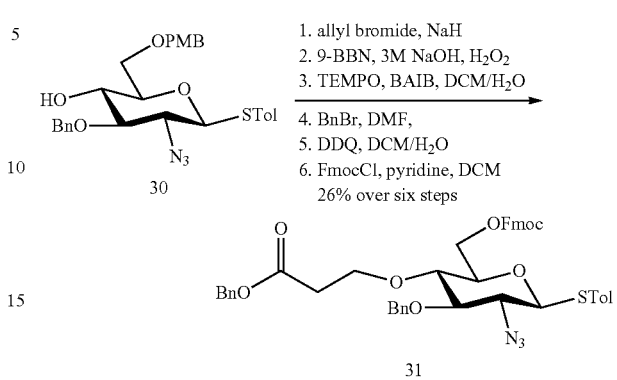

70.11, 64.30, 55.32, 21.22. HRMS: m/z calc. for $C_{28}H_{31}N_3O_5S$ [M+NH$_4^+$]$^+$: 539.2323; found: 539.2336.

p-Tolyl 2-azido-3-O-benzyl-2-deoxy-6-O-para-methoxylbenzyl-1-thio-β-D-glucopyranoside (30)

The starting material 29 (3.8 g, 12.2 mmol) was dissolved in CH$_3$CN (0.4 M, 32.0 ml), and anisaldehyde dimethyl acetal (4.1 ml, 24.4 mmol) and CSA (1.1 g, 4.9 mmol) were added. After stirring at room temperature overnight, the reaction mixture was neutralized with Et$_3$N and concentrated under reduced pressure. The residue was diluted with DCM and washed with saturated NaHCO$_3$ solution and brine. The organic solution was dried over Na$_2$SO$_4$ and filtered. The filtrate was concentrated under reduced pressure, and the residue was purified by silica gel column chromatography using a gradient of DCM and methanol (from 20/1 to 12/1, v/v). A solution of the above compound 30 (4.2 g, 9.9 mmol), NaH (0.6 g, 14.8 mmol) and BnBr (2.3 ml, 19.7 mmol) in DMF (15 ml, 0.7 M) was kept stirring at room temperature for 2 h. After the starting material was completely consumed, the reaction mixture was neutralized with NH$_4$Cl saturated solution and sequentially washed with NaHCO$_3$ saturated solution (3×70 ml) and brine (75 ml). The organic layer was dried over anhydrous Na$_2$SO$_4$ and concentrated in vacuo, and the residue was purified by flash column chromatography to afford the desired product. The above compound (4.9 g, 9.5 mmol) was dissolved in DMF (30 ml, 0.3 M), followed by the addition of NaCNBH$_3$ (6.0 g, 95 mmol) and TFA (7.3 ml, 95 mmol) at 0° C. The reaction mixture was warmed to room temperature and stirred overnight, and then diluted with EtOAc. The organic mixture was washed with water (3×70 ml) to get rid of DMF, NaHCO$_3$ saturated solution (3×70 ml) and brine (50 ml). The organic layer was concentrated under reduced pressure, and the residue was purified by silica gel column chromatography using a gradient of hexanes and EtOAc (from 3/1 to 2/1, v/v) to give the desired product (30) (4.2 g, 66% for 3 steps). $^1$H NMR (500 MHz, CDCl$_3$) δ 7.51-7.47 (m, 2H; ArCH$_2$—), 7.43-7.31 (m, 5H; Ar-H), 7.29-7.25 (m, 2H; ArCH$_2$—), 7.11 (d, J=8.0 Hz, 2H; ArCH$_2$—), 6.95-6.88 (m, 2H; ArCH$_2$—), 4.92-4.83 (m, 2H; BnCH$_2$), 4.57-4.48 (m, 2H; PMBCH$_2$), 4.39 (d, J=9.0 Hz, 1H; 1-H), 3.84 (s, 3H; OCH$_3$), 3.78 (dd, J=10.3, 4.9 Hz, 1H; 6-H), 3.73 (dd, J=10.3, 4.9 Hz, 1H; 6'-H), 3.65-3.59 (m, 1H; 4-H), 3.47-3.41 (m, 1H; 5-H), 3.38 (t, J=9.0 Hz, 1H; 3-H), 3.30 (t, J=9.0 Hz, 1H; 2-H), 2.85 (d, J=2.5 Hz, 1H; OH), 2.35 (s, 3H; STolCH$_3$). $^{13}$C NMR (125 MHz, CDCl$_3$) δ 159.37, 138.75, 137.88, 134.20, 129.81, 129.74, 129.44, 128.63, 128.27, 128.12, 127.07, 113.88, 86.14, 84.57, 77.86, 75.50, 73.44, 72.24, p-Tolyl 2-azido-3-O-benzyl-4-O-benzyl propionate-2-deoxy-6-O-fluorenylmethyloxycarbonyl-1-thio-β-D-glucopyranoside (31)

The starting material 30 (11 g, 21 mmol) was dissolved in DMF (30 ml, 0.7 M), then NaH (1.6 g, 63 mmol) and allyl bromide (3.8 ml, 42 mmol) were added at 0° C. The reaction mixture was warmed up to room temperature and stirred for 1 h until TLC (Hexanes/EtOAc 3:1, v/v) indicated completion of the reaction. After neutralization with saturated NH$_4$Cl solution, the reaction mixture was diluted with DCM and washed with saturated NaHCO$_3$ solution (3×200 ml) and brine (200 ml), dried (Na$_2$SO$_4$). The organic layer was filtered, and the filtrate was concentrated in vacuo, then purified by silica gel column chromatography using a gradient of hexanes and EtOAc (from 15/1 to 12/1, v/v). The above compound (11 g, 20 mmol) was dissolved in THF (87 ml, 0.2 M) and cooled to 0° C. A solution of 9-BBN in THF (0.5 M, 77 ml, 38 mmol) was added and the reaction mixture was warmed to room temperature and stirred overnight. After hydroboration was complete, ethanol (50 ml) was added slowly to the reaction mixture at 0° C., followed by the addition of NaOH (1.0 M aq, 98 ml) and H$_2$O$_2$ (30 wt % aq, 98 ml). The reaction mixture was warmed to 60° C. for 3 h, then quenched with saturated NH$_4$Cl solution and extracted into EtOAc (3×100 ml). The combined organic extracts were washed with NaHCO$_3$ saturated solution (3×100 ml) and brine (100 ml), dried over Na$_2$SO$_4$ and filtered. The filtrate was concentrated by rotary evaporation, and the residue was purified by silica gel column chromatography from pure hexanes to hexanes/EtOAc (10/1, v/v). The above compound (6.7 g, 11.6 mmol), BAIB (8.2 g, 25.5 mmol) and TEMPO (0.5 g, 3.5 mmol) were dissolved in DCM/H$_2$O (4/1, v/v, 1.2 M). After stirring at room temperature for 2 h, the reaction mixture was diluted in DCM and washed with water (3×75 ml) and Na$_2$S$_2$O$_3$ (40 ml) solution. The organic solvent was evaporated under reduced pressure. The residue (6.8 g, 11.5 mmol) was dissolved in DMF (23 ml, 0.5 M), followed by the addition of K$_2$CO$_3$ (9.5 g, 69 mmol) and BnBr (8.2 ml, 69 mmol). The reaction mixture was stirred at room temperature for 4 h and diluted with EtOAc and washed with 1M HCl (3×75 ml), NaHCO$_3$ saturated solution (3×75 ml) and brine (75 ml). The organic solution was dried over Na$_2$SO$_4$, and the filtrate was concentrated by rotary evaporation. The residue was purified by silica gel column chromatography from pure hexanes to hexanes/EtOAc (15/1 to 12/1, v/v). The above compound (5.4 g, 8.0 mmol) was treated according to the general procedures of PMB deprotection and Fmoc protection to give compound 31 (4.3 g, 26% for six steps). $^1$H NMR (500 MHz, CDCl$_3$) δ 7.82-7.76 (m, 2H; ArCH$_2$—), 7.65 (ddd, J=7.6, 4.5, 1.0 Hz, 2H; ArCH$_2$—), 7.52-7.22 (m, 15H; ArCH—), 7.12-7.06 (m, 2H; ArCH$_2$—), 5.14 (s, 2H; BnCH$_2$—), 4.85-4.76 (m, 2H; BnCH$_2$—), 4.54-4.41 (m, 3H; 6-H, FmocCH$_2$—), 4.36-4.26 (m, 3H; 1-H, 6'-H, FmocCH—), 4.14-4.04 (m, 1H; —OCH$_2$—), 3.88-3.81 (m, 1H; —OCH$_2$—), 3.47-3.39 (m, 2H; 4-H, 5-H), 3.34-3.21 (m, 2H; 2-H, 3-H), 2.64-2.51 (m, 2H; CO$_2$BnCH$_2$—), 2.30 (s, 3H; STolCH$_3$). $^{13}$C NMR (125 MHz, CDCl$_3$) δ 171.02, 154.96, 143.40, 143.33, 141.29, 138.88, 137.44, 135.72, 134.31, 129.79, 128.57, 128.54, 128.37, 128.31, 128.11, 127.91, 127.23, 127.21, 125.22, 120.07, 85.85, 84.74, 77.62, 76.93, 75.79, 70.04, 68.22, 66.50, 66.27, 64.70, 46.77, 35.36, 21.19. HRMS: m/z calc. for C$_{45}$H$_{43}$N$_3$O$_8$S [M+NH$_4^+$]$^+$: 803.3109; found: 803.3099.

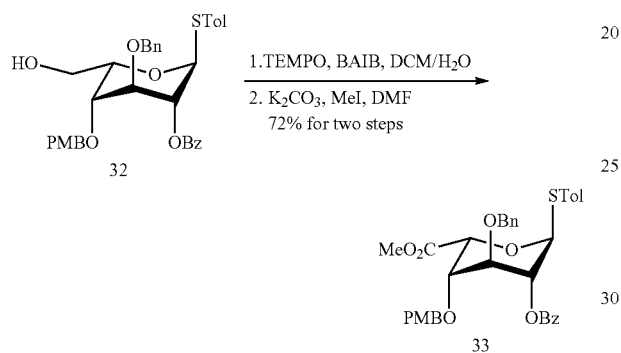

p-Tolyl methyl-2-O-benzoyl-3-O-benzyl-4-O-para-methoxylbenzyl-1-thio-α-L-idopyranosiduronate (33)

A mixture of starting material 32 (9.6 g, 16.0 mmol), BAIB (11.3 g, 35.2 mmol) and TEMPO (0.74 g, 4.8 mmol) was dissolved in DCM/H$_2$O (4/1, 0.64 M). After stirring at room temperature for 4 h, the reaction mixture was diluted in DCM and washed with water (3×100 ml) and Na$_2$S$_2$O$_3$ (50 ml) solution. The organic solvent was evaporated under reduced pressure. The residue (9.8 g, 15.9 mmol) was dissolved in DMF (40 ml, 0.4 M), followed by the addition of K$_2$CO$_3$ (13.2 g, 95.4 mmol) and CH$_3$I (6.0 ml, 95.4 mmol). The reaction mixture was stirred at room temperature for 4 h and diluted with EtOAc and washed with 1M HCl (3×100 ml), NaHCO$_3$ saturated solution (3×100 ml) and brine (100 ml). The organic solution was dried over Na$_2$SO$_4$, and the filtrate was concentrated by rotary evaporation. The residue was purified by silica gel column chromatography from pure hexanes to hexanes/EtOAc (9/1 to 8/1) to yield pure compound 33 (7.2 g, 72% yield for two steps). $^1$H NMR (500 MHz, CDCl$_3$) δ 7.99 (dd, J=8.2, 1.5 Hz, 2H; ArCH$_2$—), 7.55-7.19 (m, 9H; ArCH—), 7.11 (d, J=7.9 Hz, 2H; ArCH$_2$—), 7.07-7.00 (m, 2H; ArCH$_2$—), 6.83-6.66 (m, 2H; ArCH$_2$—), 5.77-5.65 (m, 1H; 1-H), 5.45-5.43 (m, 1H; 2-H), 5.34-5.25 (m, 1H; 5-H), 4.90 (d, J=11.9 Hz, 1H; BnCH$_2$—), 4.66 (d, J=11.9 Hz, 1H; BnCH$_2$—), 4.48-4.30 (m, 2H; PMBCH$_2$—), 3.99-3.92 (m, 3H; 3-H, 4-H, 5-H), 3.84-3.76 (m, 6H), 2.32 (s, 3H; SPhCH$_3$).

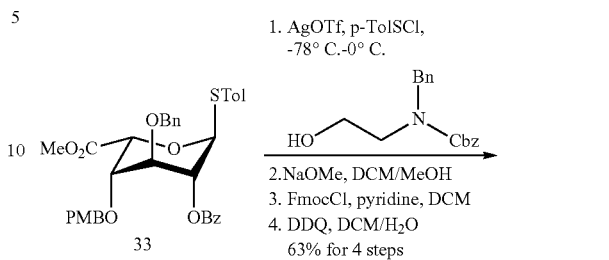

N-(Benzyl)-benzyloxycarbonyl-2-aminoethyl methyl-2-O-fluorenylmethyloxycarbonyl-3-O-benzyl-4-O-para-methoxylbenzyl-1-thio-α-L-idopyranosiduronate (34)

Compound 33 (2.4 g, 3.7 mmol) was treated according to the general procedures of pre-activation based single-step glycosylation with the acceptor (1.5 equiv) to give the desired compound. A mixture of the above compound (2.66 g, 3.37 mmol) and NaOMe (25% in MeOH) (0.31 ml, 1.7 mmol) in DCM/MeOH (1/2, v/v, 0.2M) was stirred at room temperature for 1 h. Then the reaction mixture was neutralized with Amberlite-H$^+$ resin and filtered. The crude was evaporated under reduced pressure and subjected to 2-OH Fmoc protection and 4-OH PMB deprotection according to the general procedures to give compound 34 (1.9 g, 72% yield for 3 steps). $^1$H NMR (500 MHz, CDCl$_3$) δ 7.77 (dt, J=7.6, 1.0 Hz, 2H; ArCH$_2$—), 7.57 (ddd, J=7.7, 4.2, 1.0 Hz, 2H; ArCH$_2$—), 7.41 (tt, J=7.6, 1.4 Hz, 2H; ArCH$_2$—), 7.38-7.19 (m, 13H; ArCH—), 7.16-6.99 (m, 2H; ArCH-2-), 5.22-5.11 (m, 2H; 2-H, CbzCH$_2$—), 5.03-4.95 (m, 1H; 1-H), 4.83-4.76 (m, 2H; 5-H, CbzCH$_2$—), 4.75-4.70 (m, 1H; OBnCH$_2$—), 4.66-4.59 (m, 1H; OBnCH$_2$—), 4.57-4.37 (m, 4H; FmocCH—, NBnCH$_2$—), 4.24 (t, J=7.4 Hz, 1H; FmocCH—), 4.07 (br, 1H; 3-H), 3.99-3.87 (m, 1H; —OCH$_2$—), 3.86-3.81 (m, 3H), 3.74-3.51 (m, 2H; —CH$_2$NBnCbz, —OCH$_2$—), 3.46-3.35 (m, 2H; 4-H, —CH$_2$NBnCbz), 2.78 (s, 1H). $^{13}$C NMR (125 MHz, CDCl$_3$) δ 169.68, 156.34, 153.75, 143.04, 141.33, 137.82, 137.23, 136.62, 129.06, 128.55, 128.53, 128.25, 128.08, 127.98, 127.87, 127.76, 127.32, 127.23, 125.33, 125.17, 125.13, 120.16, 98.49, 74.39, 72.32, 70.77, 70.60, 68.02, 67.74, 67.45, 52.46, 51.61, 46.69, 45.67. HRMS: m/z calc. for C$_{46}$H$_{43}$NO$_{11}$ [M+NH$_4^+$]$^+$: 805.3331; found: 805.3311.

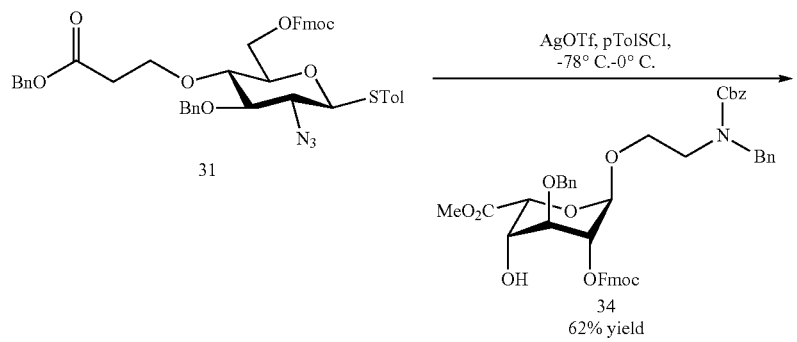

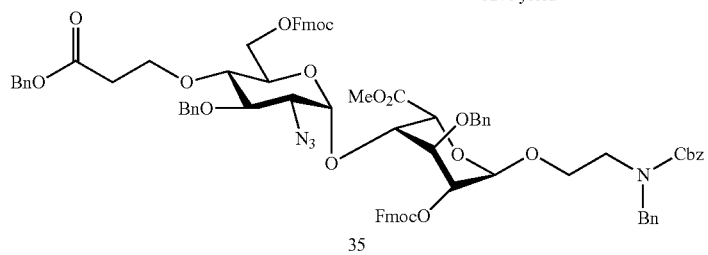

N-(Benzyl)-benzyloxycarbonyl-2-aminoethyl 3-O-benzyl-4-O-benzylpropionate-2-azido-2-deoxy-6-O-fluorenylmethyloxycarbonyl-1-thio-α-D-glucopyranoside-(1→4)-methyl-3-O-benzyl-2-O-fluorenylmethyloxycarbonyl-1-thio-α-L-idopyranosiduronate (35)

Compound 31 (1.8 g, 2.3 mmol) and 34 were treated according to the general procedures of pre-activation based single-step glycosylation to give compound 35 (2.05 g, 62%, a/P, 3/1). 1H NMR (500 MHz, CDCl$_3$) δ 7.81-7.66 (m, 3H; Ar-H), 7.66-7.50 (m, 4H; Ar-H), 7.46-7.18 (m, 25H; Ar-H), 7.18-7.01 (m, 4H; Ar-H), 5.24-5.04 (m, 5H, 1-H, 5-H, CbzCH$_2$—), 4.93-4.86 (m, 1H, 1'-H), 4.86-4.69 (m, 5H), 4.63-4.44 (m, 4H; 2-H), 4.43-4.29 (m, 4H), 4.27-4.01 (m, 5H), 4.01-3.81 (m, 4H; anomeric linker-OCH$_2$—), 3.78-3.71 (m, 3H; —CO$_2$CH$_3$), 3.68-3.59 (m, 1H), 3.57-3.35 (m, 4H; 2'-H, 3'-H, 4-H, 5'-H), 3.34-3.21 (m, 1H), 2.60-2.49 (m, 2H; BnCO$_2$CH$_2$—), $^{13}$C NMR (125 MHz, CDCl$_3$) δ 171.00, 169.39, 156.18, 154.99, 154.58, 144.24, 143.35, 143.26, 141.27, 140.22, 137.75, 137.67, 137.34, 135.46, 131.39, 130.39, 130.20, 130.08, 128.77, 128.58, 128.47, 128.45, 128.35, 128.25, 128.00, 127.97, 127.91, 127.84, 127.80, 127.40, 127.29, 127.23, 127.19, 127.15, 125.36, 125.26, 125.15, 120.60, 120.09, 120.04, 98.50, 79.62, 76.78, 75.09, 73.89, 73.24, 70.42, 70.00, 69.61, 68.07, 67.70, 67.32, 66.44, 65.81, 63.30, 52.36, 51.59, 46.72, 46.56, 35.34.

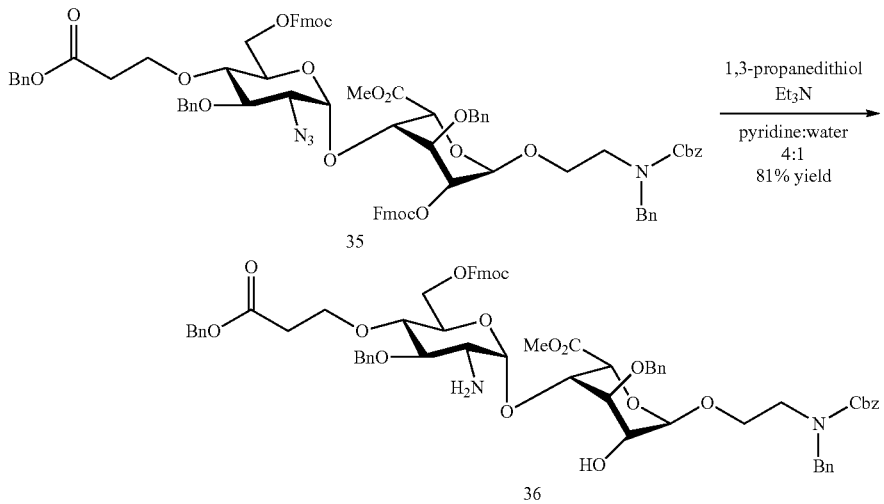

N-(Benzyl)-benzyloxycarbonyl-2-aminoethyl 2-amino-3-O-benzyl-4-O-benzylpropionate-2-deoxy-1-thio-α-D-glucopyranoside-(1→4)-methyl-3-O-benzyl-1-thio-α-L-idopyranosiduronate (36)

At 50° C. under N$_2$ atmosphere, 1,3-propanedithiol (2.8 ml, 27.0 mmol) and Et$_3$N (3.7 ml, 27.0 mmol) were added to a solution of starting material 35 (0.7 g, 0.48 mmol) in pyridine/H$_2$O (4/1, 0.04 M) and the reaction mixture was stirred for 2 h. The reaction mixture was concentrated by rotary evaporation and purified by silica gel column chromatography using a gradient of DCM and MeOH (from 50/1 to 40/1 to 20/1, v/v) to give the desired product 36 (0.38 g, 81%). $^1$H NMR (500 MHz, CDCl3) δ 7.45-6.95 (m, 19H; Ar-H), 7.12-7.04 (m, 2H; ArCH$_2$—), 5.21-5.06 (m, 4H; 1-H, 1'-H), 5.00-4.90 (m, 2H), 4.88-4.80 (m, 2H; BnCH—), 4.70 (d, J=11.9 Hz, 1H; BnCH—), 4.62-4.43 (m, 4H), 4.15 (s, 1H), 4.05-3.98 (m, 1H), 3.96-3.84 (m, 3H), 3.78-3.64 (m, 6H; —CO$_2$CH$_3$, —NCH$_2$—), 3.64-3.51 (m, 1H), 3.46-3.32 (m, 4H), 2.83 (dd, J=10.1, 3.7 Hz, 1H), 2.63-2.52 (m, 2H; BnCO$_2$CH$_2$—). $^{13}$C NMR (125 MHz, CDCl$_3$) δ 171.56, 138.09, 135.60, 128.60, 128.53, 128.49, 128.46, 128.42, 128.36, 128.32, 127.94, 127.82, 127.74, 127.66, 127.18, 101.88, 96.50, 82.19, 78.58, 76.77, 75.57, 72.23, 72.03, 7.87, 67.80, 67.36, 67.22, 66.54, 66.43, 61.22, 55.04, 52.37, 51.61, 46.68, 45.70, 35.41. HRMS: m/z calc. for C$_{54}$H$_{62}$N$_2$O$_{15}$ [M+H$^+$]$^+$: 978.4150; found: 978.4205.

ide triethylamine complex (142 mg, 0.9 mmol). The reaction mixture was stirred at room temperature for 2 h and diluted with DCM. The organic mixture was washed with water and brine, and then filtered. The filtrate was concentrated under reduced pressure and the residue was purified by silica gel column chromatography using a mixture of DCM and methanol to give desired product 37 (20/1, v/v). $^1$H NMR (500 MHz, CD$_3$OD) δ 7.45 (d, J=7.4 Hz, 2H; ArCH$_2$—), 7.40-7.10 (m, 16H; Ar-H), 7.01-6.91 (m, 2H; ArCH$_2$—), 5.41 (d, J=3.4 Hz, 1H; 1'-H), 5.16-5.06 (m, 3H; CO$_2$BnCH$_2$—, CbzCH—), 4.99 (d, J=10.8 Hz, 1H; CbzCH—), 4.88 (s, 2H; 1-H, 5-H), 4.81 (d, J=9.5 Hz, 1H; OBnCH—), 4.75-4.59 (m, 3H; OBnCH$_2$—), 4.58-4.33 (m, 2H; NBnCH$_2$—), 4.18 (s, 2H; 2-H, 4-H), 4.05-3.97 (m, 1H; 4'-linker-OCH—), 3.95-3.80 (m, 3H; 4'-linker-OCH—, 6'-H), 3.78-3.51 (m, 5H; 5'-H, 3-H, 4'-H, anomeric linker-OCH$_2$—), 3.49-3.25 (m, 5H; NCH$_2$-2'-H, 3'-H), 2.54-2.48 (m, 2H; BnCO$_2$CH$_2$—). $^{13}$C NMR (125 MHz, CD$_3$OD) δ

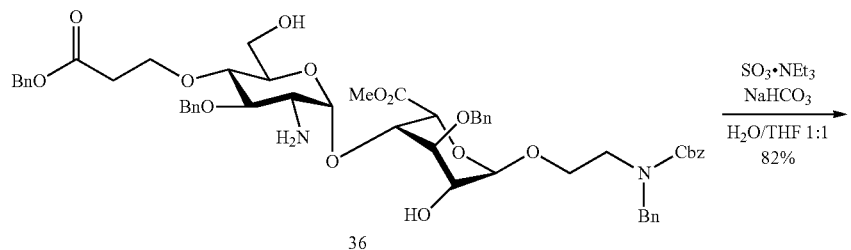

36

N-(Benzyl)-benzyloxycarbonyl-2-aminoethyl 3-O-benzyl-4-O-benzylpropionate-2-deoxy-2-sulfoamino-1-thio-α-D-glucopyranoside-(1→4)-methyl-3-O-benzyl-1-thio-α-L-idopyranosiduronate (37)

The starting material 36 (90 mg, 0.09 mmol) was dissolved in H$_2$O/THF (1/1, v/v, 0.05 M) mixture, followed by addition of NaHCO$_3$ (115 mg, 1.37 mmol) and sulfur triox-

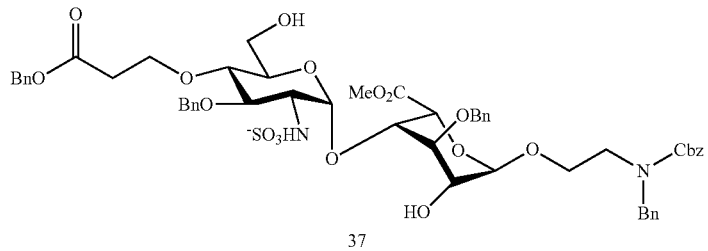

37

171.81, 170.46, 156.65, 139.00, 138.10, 137.68, 128.24, 128.13, 128.10, 128.06, 128.01, 127.86, 127.84, 127.79, 127.77, 127.56, 127.52, 127.47, 127.38, 127.34, 127.26, 127.02, 126.90, 126.87, 101.38, 96.25, 79.92, 77.36, 74.71, 73.59, 72.15, 71.56, 67.64, 67.42, 66.47, 65.88, 60.36, 58.11, 51.55, 51.28, 46.67, 45.78, 35.15. HRMS: m/z calc. for C$_{54}$H$_{61}$N$_2$O$_{18}$S$^-$ [M]$^-$: 1057.3646; found: 1057.3646.

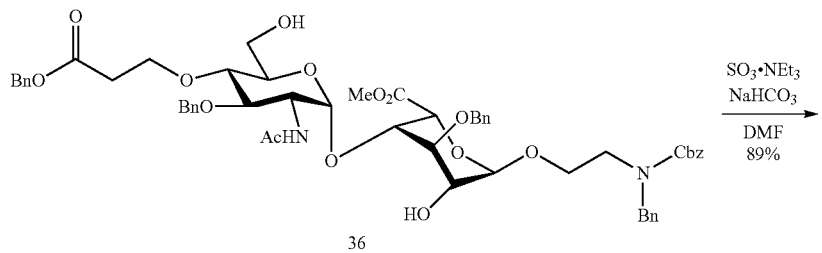

36

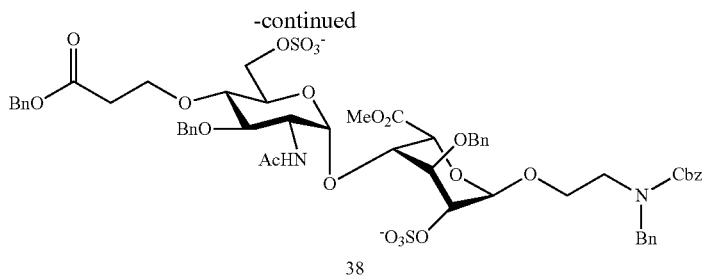

38

N-(Benzyl)-benzyloxycarbonyl-2-aminoethyl 2-acetamido-3-O-benzyl-4-O-benzylpropionate-2-deoxy-6-O-sulfonato-1-thio-α-D-glucopyranoside-(1→4)-methyl-3-O-benzyl-2-O-sulfonato-1-thio-α-L-idopyranosiduronate (38)

To a solution of starting material 36 (225 mg, 0.22 mmol) in DMF (0.08 M) was added sulfur trioxide triethylamine complex (800 mg, 4.4 mmol) and the resulting reaction mixture was stirred at 55° C. for 2 h. The reaction mixture was purified by a LH-20 gel column with CH$_3$OH. Fractions containing the product were collected under reduced pressure and the residue was passed through a column of Dowex 50WX4 Na$^+$ resin using H$_2$O as the eluent to give sodium form product 38 (223 mg, 89%). $^1$H NMR (500 MHz, CD3OD) δ 7.49-7.60 (m, 1H; Ar-H), 7.41-7.14 (m, 16H; Ar-H), 7.12-6.96 (m, 2H; ArCH$_2$—), 5.22-5.09 (m, 4H; CO$_2$BnCH$_2$-, 1-H, 1'-H), 4.83-4.73 (m, 3H; 5-H, CbzCH$_2$—), 4.73-4.57 (m, 4H; OBnCH$_2$—, OBnCH$_2$—), 4.56-4.41 (m, 2H; NBnCH$_2$—), 4.29-4.13 (m, 3H; 2-H, 6'-H), 4.12-4.03 (m, 3H; 4-H, 7-H), 4.00-3.85 (m, 2H; NCH$_2$—), 3.80-3.74 (m, 3H, CO$_2$CH$_3$), 3.70-3.61 (m, 3H; 5'-H, 3-H, 4'-H), 3.45-3.36 (m, 2H; 2'-H, 3'-H), 2.64-2.52 (m, 2H; BnCO$_2$CH$_2$—). HRMS: m/z calc. for C$_{56}$H$_{62}$N$_2$O$_{22}$S$_2^{2-}$ [M]$^{2-}$: 589.1623; found: 589.1611.

N-(Benzyl)-benzyloxycarbonyl-2-aminoethyl 3-O-benzyl-4-O-benzylpropionate-2-deoxy-2-sulfoamino-6-O-sulfonato-α-D-glucopyranoside-(1→4)-methyl-3-O-benzyl-2-O-sulfonato-1-thio-α-L-idopyranosiduronate (39)

To a solution of starting material 36 (0.3 g, 0.3 mmol) in DMF (2.0 ml, 0.15 M) was added sulfur trioxide triethylamine complex (1.12 g, 6.0 mmol) and the resulting reaction mixture was stirred at 55° C. for 2 h. The reaction mixture was purified by a LH-20 gel column with CH$_3$OH. Fractions containing product were collected under reduced pressure and the crude was dissolved in pyridine/Et$_3$N (10/1, v/v, 0.15M). Sulfur trioxide pyridine complex (0.45 g, 3 mmol) was added to the reaction mixture at 55° C. and stirred for 2 h. After reaction completion as indicated by TLC (EtOAc/MeOH/H$_2$O 6/1/1), the reaction mixture was passed through LH-20 gel column with CH$_3$OH. A column of Dowex 50WX4 Na$^+$ resin was used for ion exchange to give sodium form product 39 (0.34 g, 92% for two steps). $^1$H NMR (500 MHz, CD$_3$OD) δ 7.42-7.48 (d, J=7.5 Hz, 2H; ArCH$_2$—), 7.41-7.27 (m, 8H; Ar-H), 7.25-7.07 (m, 8H; Ar-H), 6.98-6.85 (m, 2H; ArCH$_2$—), 5.40 (d, J=3.4 Hz, 1H; 1'-H), 5.21-5.16 (m, 1H), 5.13-5.07 (m, 4H; 1-H), 5.05-5.01 (m, 1H), 4.81-4.71 (m, 3H; 5-H), 4.66 (d, J=11.4, 1H), 4.50-4.37 (m, 1H; 6'-H), 4.34-4.19 (m, 4H; 2-H, 6'-H), 4.07-4.01 (m, 1H), 3.95-3.85 (m, 2H), 3.82-3.71 (m, 4H; 4'-linker-OCH$_2$—), 3.70-3.56 (m, 2H), 3.46-3.38 (m, 3H; 2'-H), 2.51 (t, J=6.4 Hz, 2H). $^{13}$C NMR (125 MHz, CD$_3$OD) δ 172.29, 170.58, 156.68, 138.91, 137.97, 137.64, 137.43, 136.15,

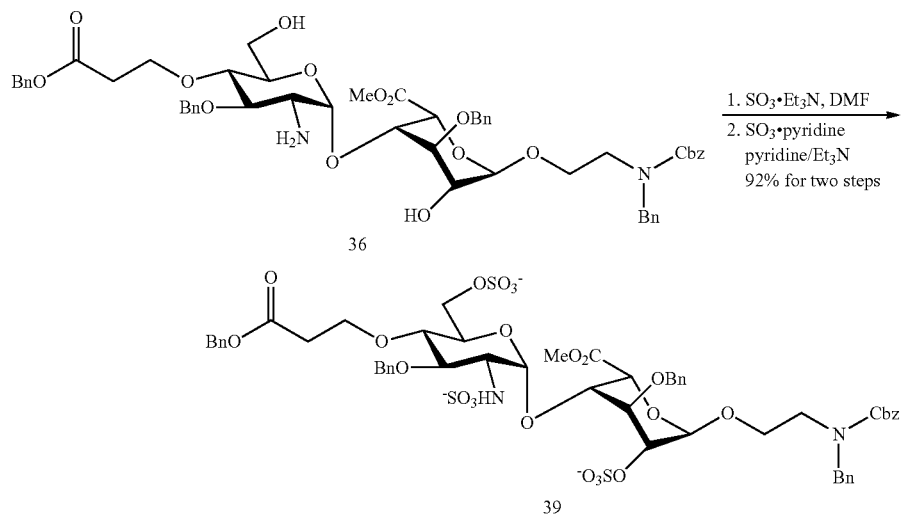

128.34, 128.32, 128.24, 128.18, 128.11, 128.07, 128.00, 127.97, 127.89, 127.87, 127.61, 127.54, 127.46, 127.43, 127.32, 126.97, 99.33, 98.72, 79.70, 77.42, 75.01, 73.47, 73.06, 72.41, 70.87, 70.03, 67.90, 67.25, 66.75, 66.37, 66.13, 65.90, 58.15, 58.07, 52.18, 51.45, 51.38, 46.69, 45.72, 35.26. HRMS: m/z calc. for $C_{54}H_{59}N_2O_{24}S_3^{3-}$ $[M+H^+]^{2-}$: 608.1355; found: 608.1370.

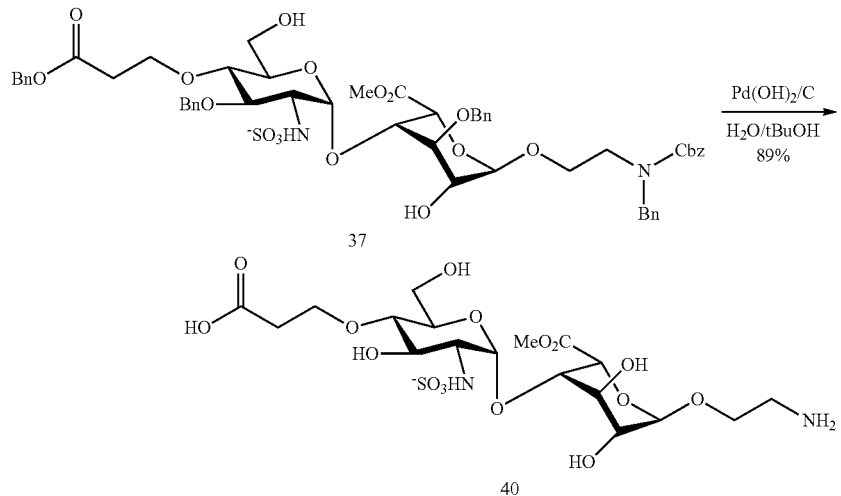

Aminoethyl 4-O-carboxyethyl-2-deoxy-2-sulfoamino-1-thio-α-D-glucopyranoside-(1→4)-methyl-1-thio-α-L-idopyranosiduronate (40)

Compound 37 (170 mg, 0.16 mmol) was treated according to the general procedures of hydrogenolysis to give compound 40 (80.5 mg, 87%). $^1$H NMR (500 MHz, CD$_3$OD) δ 5.36 (d, J=3.7 Hz, 1H; 1'-H), 4.95 (d, J=3.0 Hz, 1H; 1-H), 4.80 (d, J=3.2 Hz, 1H; 5-H), 4.18 (t, J=4.3 Hz, 1H; 3-H), 4.06-3.97 (m, 2H; 2-H, 4-H), 3.92-3.84 (m, 2H; 6'-CH$_2$—), 3.75 (s, 3H; —CO$_2$CH$_3$), 3.73-3.68 (m, 2H; 5'-H, 4'-linker-OCH$_2$—), 3.67-3.58 (m, 3H; 4'-linker-OCH$_2$—, anomeric linker-OCH$_2$—), 3.57-3.53 (m, 1H; 4'-H), 3.44-3.38 (m, 1H, 3'-H), 3.27-3.22 (m, 1H; 2'-H), 3.07-2.99 (m, 2H; NH$_2$CH$_2$—), 2.39 (t, J=5.9 Hz, 2H; CO$_2$HCH$_2$—). $^{13}$C NMR (125 MHz, CD$_3$OD) δ 170.39, 101.45, 96.63, 78.53, 74.10, 71.71, 69.08, 68.65, 68.01, 67.12, 64.71, 60.57, 58.06, 51.62, 46.32, 42.68, 39.26, 36.85. HRMS: m/z calc. for $C_{18}H_{31}N_2O_{16}S^-$ [M]$^-$: 563.1400; found: 563.1401.

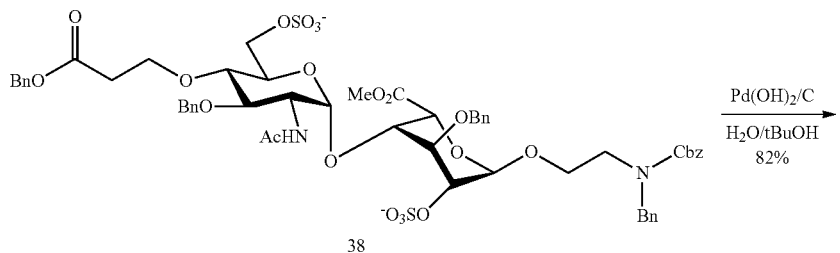

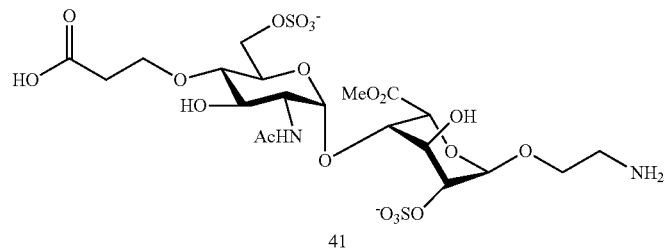

Aminoethyl 2-acetamido-4-O-carboxyethyl-2-deoxy-6-O-sulfonato-α-D-glucopyranoside-(1→4)-methyl-2-O-sulfonato-α-L-idopyranosiduronate (41)

Compound 38 (290 mg, 0.25 mmol) was treated according to the general procedures of hydrogenolysis to give compound 41 (138 mg, 82%). $^1$H NMR (500 MHz, D$_2$O) δ 7.72 (d, J=9.6 Hz, 1H; NHAc), 5.02 (s, 1H; 1'-H), 4.95 (d, J=3.4 Hz, 1H, 1-H), 4.83 (d, J=1.9 Hz, 1H; 5-H), 4.20 (d, J=3.0 Hz, 1H; 3-H), 4.15-4.06 (m, 3H; 2-H, 6'-CH$_2$—), 3.99-3.94 (m, 1H; 4-H), 3.92-3.82 (m, 3H; 5'-H, 4'-linker-OCH$_2$—), 3.80-3.74 (m, 1H; anomeric linker-OCH$_2$—), 3.66 (s, 3H; —CO$_2$CH$_3$), 3.64-3.59 (m, 1H; anomeric linker-OCH$_2$—), 3.50-3.41 (m, 2H; 3'-H, 4'-H), 3.25-3.16 (m, 1H; 2'-H), 3.25-3.00 (m, 2H; NH$_2$CH$_2$—), 2.47 (t, J=5.9 Hz, 2H; CO$_2$HCH$_2$—), 1.88 (s, 3H; —NHCOCH$_3$). $^{13}$C NMR (125 MHz, D$_2$O) δ 171.11, 98.96, 94.39, 77.66, 72.93, 71.10, 70.95, 69.64, 68.33, 66.58, 66.42, 64.67, 62.93, 52.96, 52.85, 38.83, 22.03. HRMS: m/z calc. for C$_{20}$H$_{32}$N$_2$O$_{20}$S$_2^{2-}$ [M+H$^+$]$^-$: 685.1074; found: 685.1086.

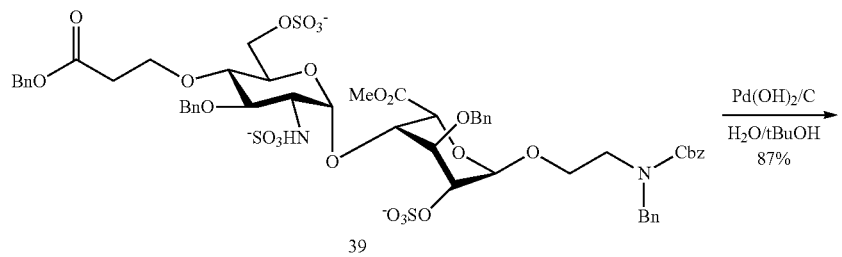

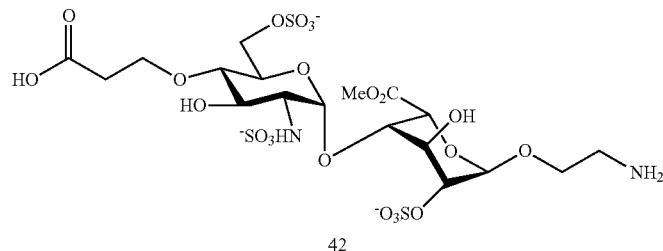

Aminoethyl 2-acetamido-4-O-carboxyethyl-2-deoxy-6-O-sulfonato-1-thio-α-D-glucopyranoside-(1→4)-methyl-2-O-sulfonato-1-thio-α-L-idopyranosiduronate (42)

Compound 39 (350 mg, 0.29 mmol) was treated according to the general procedures of Hydrogenolysis to give compound 42 (180 mg, 87%). $^1$H NMR (500 MHz, D$_2$O) δ 5.19 (d, J=3.4 Hz, 1H, 1'-H), 5.02 (d, J=2.0 Hz, 1H, 1-H), 4.77 (d, J=2.1 Hz, 1H; 5-H), 4.26 (t, J=4.0 Hz, 1H; 3-H), 4.19-4.05 (m, 3H; 2-H, 6'-CH$_2$—), 4.04-4.00 (m, 1H; 4-H), 3.90-3.83 (m, 2H; 5'-H, 4'-linker-OCH$_2$—), 3.81-3.75 (m, 1H; 4'-linker-OCH$_2$—), 3.69 (s, 3H; —CO$_2$CH$_3$), 3.65-3.56 (m, 2H; anomeric linker-OCH$_2$—), 3.48 (t, J=9.8 Hz, 1H, 4'-H), 3.25 (t, J=9.8 Hz, 1H, 3'-H), 3.16-3.05 (m, 3H; 2'-H, NH$_2$CH$_2$—), 2.43-2.29 (m, 2H; CO$_2$HCH$_2$—). $^{13}$C NMR (125 MHz, D$_2$O) δ 170.99, 99.30, 98.96, 77.76, 76.90, 74.53, 70.46, 69.25, 69.07, 67.26, 67.11, 66.16, 64.60, 57.61, 53.01, 38.89. HRMS: m/z calc. for C$_{18}$H$_{29}$N$_2$O$_{22}$S$_3^{3-}$ [M+H$^+$]$^{2-}$: 361.0232; found: 361.0238.

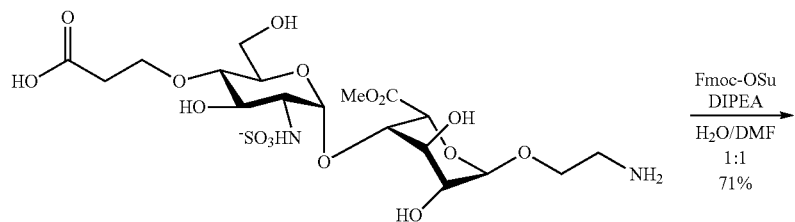

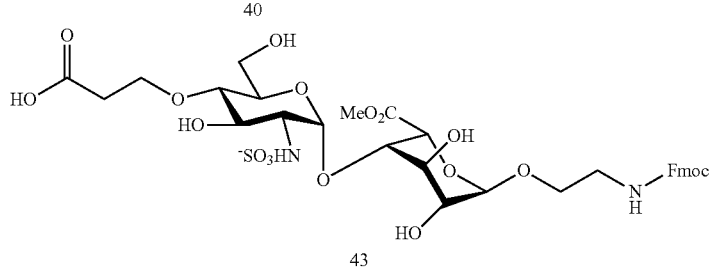

N-Fluorenylmethyloxycarbonyl-2-aminoethyl 4-O-carboxyethyl-2-deoxy-2-sulfoamino-1-thio-α-D-glucopyranoside-(1→4)-methyl-1-thio-α-L-idopyranosiduronate (43)

Compound 40 (80 mg, 0.14 mmol) was treated according to the general procedures of protection of NH$_2$ with Fmoc to give compound 43 (79 mg, 71%) $^1$H NMR (500 MHz, CD$_3$OD) δ 7.79 (d, J=7.5 Hz, 2H, Ar—H), 7.64 (d, J=7.5 Hz, 2H, Ar—H), 7.39 (dt, J=7.5 Hz, 1.2 Hz, 2H, Ar—H), 7.31 (td, J=7.5, 1.2 Hz, 2H, Ar—H), 5.35 (d, J=3.7 Hz, 1H; 1'-H), 4.91-4.89 (m, 1H; 1-H), 4.79 (d, J=2.9 Hz, 1H; 5-H), 4.37-4.28 (m, 2H; FmocCH$_2$—), 4.22-4.13 (m, 2H; FmocCH—, 3-H), 4.04-3.95 (m, 2H; 2-H, 6'-CH$_2$—), 3.90-3.82 (m, 1H; 6'-CH$_2$—), 3.78-3.70 (m, 3H; 5'-H, 4'-linker-OCH$_2$—), 3.68 (s, 3H; —CO$_2$CH$_3$), 3.61-3.47 (m, 3H; 4'-H, anomeric linker-OCH$_2$—), 3.43-3.35 (m, 1H; 3'-H), 3.35-3.32 (m, 1H; —CH$_2$NHFmoc), 3.28-3.21 (m, 2H; 2'-H, —CH$_2$NHFmoc), 2.40 (t, J=5.9 Hz, 2H; CO$_2$HCH$_2$—). $^{13}$C NMR (125 MHz, CD$_3$OD) δ 178.87, 170.39, 157.50, 143.88, 141.15, 127.36, 126.77, 124.76, 119.48, 101.33, 96.54, 78.64, 74.02, 71.71, 71.48, 69.30, 69.10, 67.67, 67.59, 67.00, 66.37, 60.46, 57.79, 51.53, 51.51, 40.21, 37.97. HRMS: m/z calc. for C$_{33}$H$_{41}$N$_2$O$_{18}$S$^-$ [M]$^-$: 785.2081; found: 785.2103.

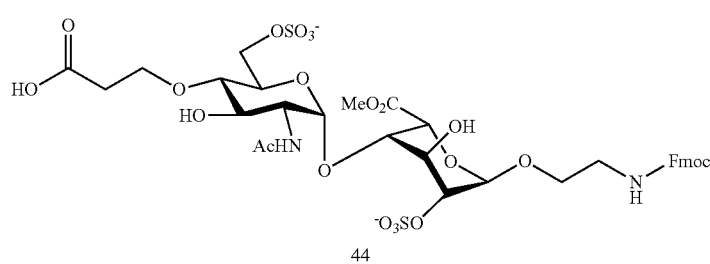

N-Fluorenylmethyloxycarbonyl-2-aminoethyl 2-acetamido-4-O-carboxyethyl-2-deoxy-6-O-sulfonato-1-thio-α-D-glucopyranoside-(1→4)-methyl-2-O-sulfonato-1-thio-α-L-idopyranosiduronate (44)

Compound 41 (167 mg, 0.24 mmol) was treated according to the general procedures of protection of $NH_2$ with Fmoc to give compound 44 (190 mg, 86%). $^1$H NMR (500 MHz, $CD_3OD$) δ 7.80 (d, J=7.5 Hz, 2H; Ar-CH), 7.67 (d, J=7.5 Hz, 2H; Ar-CH), 7.50 (d, J=9.2 Hz, 1H; NHAc), 7.40 (dt, J=7.5, 1.7 Hz, 2H; Ar-CH), 7.33 (dt, J=7.5, 1.7 Hz, 2H; Ar-CH), 5.16 (s, 1H; 1'-H), 5.03 (d, J=3.4 Hz, 1H; 1-H), 4.86 (d, J=2.1 Hz, 1H; 5-H), 4.34-4.28 (m, 4H; 3-H, 2-H, FmocCH$_2$—), 4.25-4.17 (m, 3H; 6'-CH$_2$—, FmocCH—), 4.07-3.91 (m, 5H; 4-H, 5'-H, 4'-linker-OCH$_2$—, anomeric linker-OCH$_2$—), 3.84-3.75 (m, 2H; anomeric linker-OCH$_2$—, —CH$_2$NHFmoc), 3.73 (s, 3H; CO$_2$CH$_3$), 3.69-3.65 (m, 1H; 3'-H), 3.64-3.55 (m, 2H; 4'-H, —CH$_2$NHFmoc), 3.28-3.24 (m, 1H, 2'-H), 2.44 (dd, J=6.8, 5.1 Hz, 2H; CO$_2$HCH$_2$—), 2.07 (s, 3H, NHCOCH$_3$). $^{13}$C NMR (125 MHz, $CD_3OD$) δ 178.30, 172.95, 170.30, 157.48, 143.88, 141.14, 127.37, 126.80, 124.86, 119.46, 99.57, 95.93, 78.75, 73.28, 72.93, 71.48, 69.91, 69.14, 67.55, 66.48, 66.36, 66.03, 64.34, 52.95, 51.75, 40.18, 37.44, 21.75. HRMS: m/z calc. for $C_{35}H_{42}N_2O_{22}S_2^{2-}$ [M]$^{2-}$: 453.0841; found: 453.0840.

N-Fluorenylmethyloxycarbonyl-2-aminoethyl 2-acetamido-4-O-carboxyethyl-2-deoxy-6-O-sulfonato-1-thio-α-D-glucopyranoside-(1→4)-methyl-2-O-sulfonato-1-thio-α-L-idopyranosiduronate (45)

Compound 42 (220 mg, 0.31 mmol) was treated according to the general procedures of protection of $NH_2$ with Fmoc to give compound 45 (235 mg, 82%). $^1$H NMR (500 MHz, $CD_3OD$) δ 7.80 (d, J=7.8 Hz, 2H; ArCH—), 7.67 (d, J=7.5 Hz, 2H; ArCH—), 7.40 (dt, J=7.8, 2.6 Hz, 2H; ArCH—), 7.33 (td, J=7.5 Hz, 2.6 Hz, 2H; ArCH—), 5.26 (d, J=3.4 Hz, 1H; 1'-H), 5.21 (s, 1H, 1-H), 4.84 (d, J=2.2 Hz, 1H; 5-H), 4.43-4.39 (m, 1H; 3-H), 4.34-4.28 (m, 3H; 2-H, FmocCH$_2$—), 4.25-4.17 (m, 3H; 6'-CH$_2$—, FmocCH—), 4.10-4.04 (m, 1H, 4-H), 4.01-3.94 (m, 2H, 5'-H, 4'-linker-OCH$_2$—), 3.82-3.76 (m, 1H, 4'-linker-OCH$_2$—), 3.74 (s, 3H, —CO$_2$CH$_3$), 3.68-3.61 (m, 2H; anomeric linker-OCH$_2$—), 3.60-3.53 (m, 1H; 4'-H), 3.37-3.34 (m, 2H; —CH$_2$NHFmoc), 3.30-3.25 (m, 1H; 2'-H), 2.61-2.50 (m, 2H; CO$_2$HCH$_2$—). $^{13}$C NMR (125 MHz, $CD_3OD$) δ 170.51, 143.88, 141.13, 127.39, 126.80, 124.88, 124.85, 119.48, 99.31, 98.68, 78.87, 75.80, 73.53, 71.03, 69.75, 67.70, 66.60, 66.54, 66.14, 65.95, 57.62, 51.88, 40.12, 37.32. HRMS: m/z calc. for $C_{33}H_{39}N_2O_{24}S_3^{3-}$ [M]$^{3-}$: 314.3690; found: 314.3696.

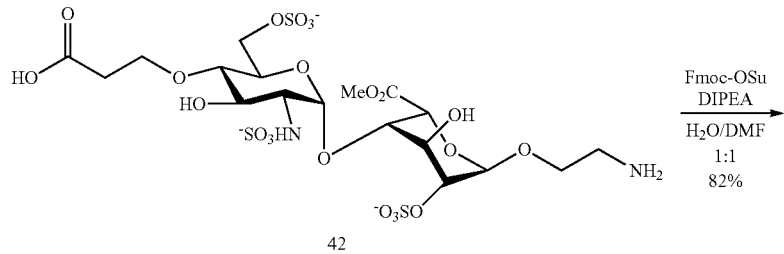

42

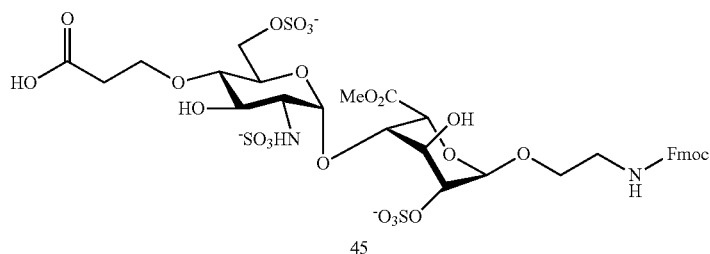

45

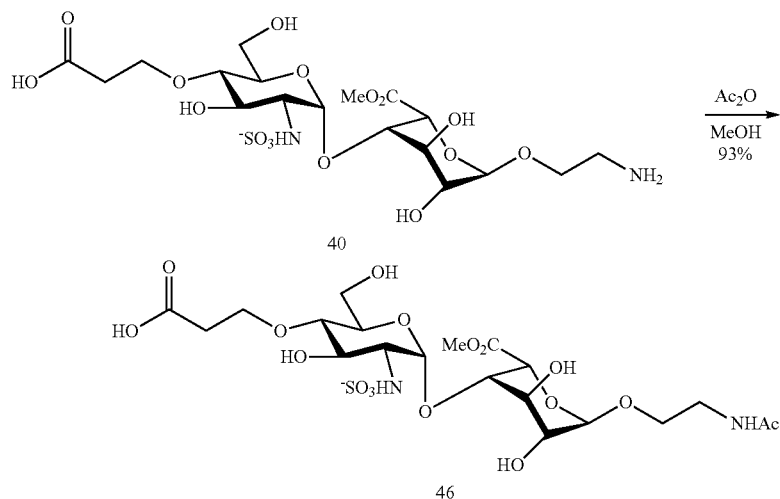

Acetamidoethyl 4-O-carboxyethyl-2-deoxy-2-sulfoamino-1-thio-α-D-glucopyranoside-(1→4)-methyl-1-thio-α-L-idopyranosiduronate (46)

Compound 40 (40 mg, 0.07 mmol) was treated according to the general procedures of hydrogenolysis to give compound 46 (40 mg, 93%). $^1$H NMR (500 MHz, CD$_3$OD) δ 5.36 (d, J=3.6 Hz, 1H, 1'-H), 4.89 (s, 1H, 1-H), 4.80 (d, J=3.0 Hz, 1H; 5-H), 4.16 (t, J=4.3 Hz, 1H; 3-H), 4.08-3.97 (m, 2H; 2-H, 4-H), 3.93-3.85 (m, 1H; 6'-CH$_2$—), 3.80-3.69 (m, 6H; —CO$_2$CH$_3$, 5'-H, 6'-CH$_2$—, 4'-linker-OCH$_2$—), 3.62-3.50 (m, 3H; 4'-linker-OCH$_2$—4'-H, anomeric linker-OCH$_2$—), 3.45-3.34 (m, 3H; anomeric linker-OCH$_2$—, 3'-H, —CH$_2$NHAc), 3.30-3.22 (m, 2H; 2'-H, —CH$_2$NHAc), 2.49-2.42 (m, 2H; CO$_2$HCH$_2$—), 1.94 (s, 3H; —NHCOCH$_3$). $^{13}$C NMR (125 MHz, CD$_3$OD) δ 177.09, 171.96, 170.45, 101.41, 96.58, 78.48, 74.12, 71.67, 71.62, 69.30, 68.55, 67.89, 67.27, 67.22, 60.53, 57.92, 51.55, 38.94, 36.65, 21.13. HRMS: m/z calc. for C$_{20}$H$_{33}$N$_2$O$_{17}$S$^-$ [M]$^-$: 605.1505; found: 605.1513.

Acetamidoethyl 2-acetamido-4-O-carboxyethyl-2-deoxy-6-O-sulfonato-1-thio-α-D-glucopyranoside-(1→4)-methyl-2-O-sulfonato-1-thio-α-L-idopyranosiduronate (47)

Compound 41 (19 mg, 0.03 mmol) was treated according to the general procedures of Hydrogenolysis to give compound 47 (15 mg, 75%). $^1$H NMR (500 MHz, D$_2$O) δ 4.98 (s, 1H, 1'-H), 4.96 (d, J=3.5 Hz, 1H, 1-H), 4.81 (d, J=2.2 Hz, 1H; 5-H), 4.18 (d, J=3.0 Hz, 1H, 3-H), 4.14-4.10 (m, 3H; 2-H, 6'-CH$_2$—), 3.93 (m, 1H; 4-H), 3.91-3.82 (m, 2H; 4'-linker-OCH$_2$—), 3.79-3.72 (m, 1H; anomeric linker-OCH$_2$—), 3.71-3.63 (m, 4H; —CO$_2$CH$_3$, 5'-H), 3.58-3.46 (m, 3H; 3'-H, 4'-H, anomeric linker-OCH$_2$—), 3.26-3.19 (m, 3H; 2'-H, —CH$_2$NHAc), 2.37-2.31 (m, 2H; CO$_2$HCH$_2$—), 1.89 (s, 3H; NHAc on linker), 1.82 (s, 3H; NHAc). $^{13}$C NMR (125 MHz, D$_2$O) δ 174.64, 174.16, 171.21, 99.07, 94.35, 77.88, 73.08, 71.02, 69.63, 69.41, 67.33, 66.56, 66.32, 63.00, 53.07, 52.71, 48.75, 39.00, 37.35, 22.07, 21.68. HRMS: m/z calc. for C$_{22}$H$_{34}$N$_2$O$_{21}$S$_2^{2-}$ [M]$^{2-}$: 363.0553; found: 363.0555.

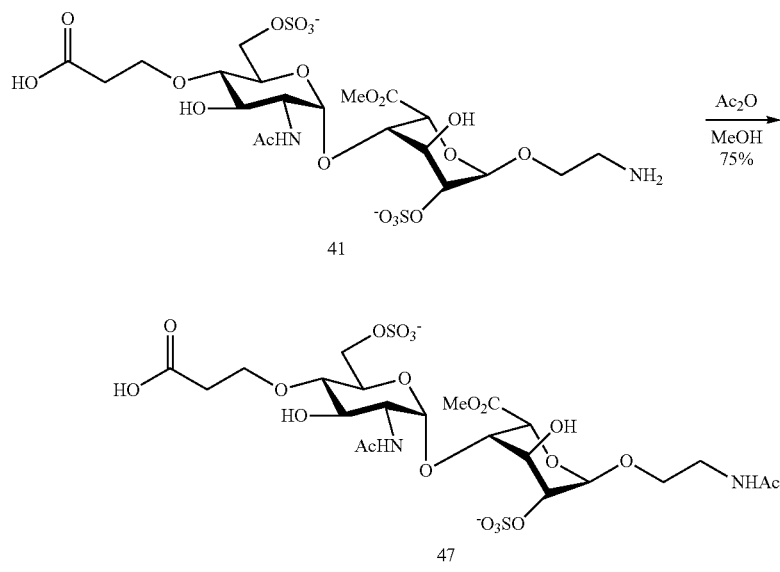

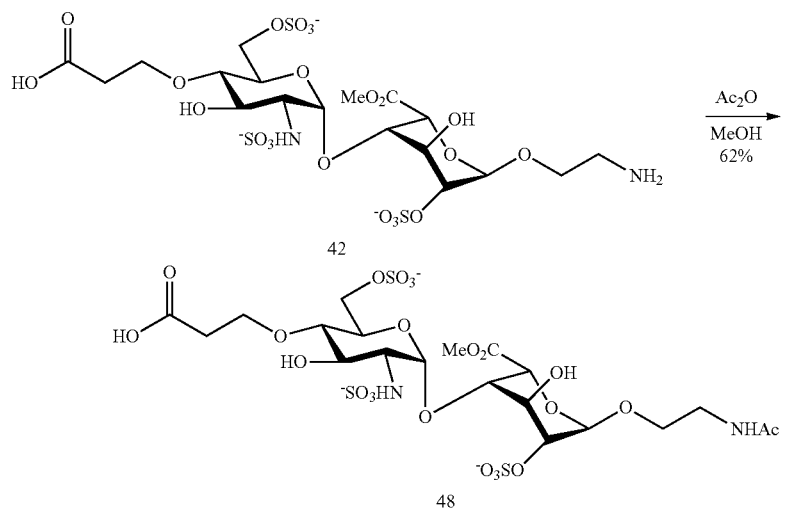

Acetamidoethyl 2-acetamido-4-O-carboxyethyl-2-deoxy-6-O-sulfonato-1-thio-α-D-glucopyranoside-(1→4)-methyl-2-O-sulfonato-1-thio-α-L-idopyranosiduronate (48)

Compound 42 (20 mg, 0.03 mmol) was treated according to the general procedures of N-acetylation to give compound 48 (13 mg, 62%). $^1$H NMR (500 MHz, CD$_3$OD) δ 5.32 (d, J=3.5 Hz, 1H, 1'-H), 5.15 (d, J=2.7 Hz, 1H, 1-H), 4.80 (d, J=2.9 Hz, 1H; 5-H), 4.36-4.32 (m, 1H; 3-H), 4.30-4.26 (m, 1H; 2-H), 4.21 (d, J=2.8 Hz, 2H; 6'-CH$_2$—), 4.14-3.92 (m, 3H; 4-H, 4'-linker-OCH$_2$—), 3.81 (s, 4H; CO$_2$CH$_3$, anomeric linker-OCH$_2$—), 3.72-3.67 (m, 1H; 5'-H), 3.64-3.59 (m, 1H; 4'-H), 3.58-3.56-3.49 (m, 1H; anomeric linker-OCH$_2$—), 3.47-3.38 (m, 1H; 3'-H), 3.37-3.30 (m, 2H; —CH$_2$NHAc), 3.28-3.23 (m, 1H, 2'-H) 2.64-2.47 (m, 2H, CO$_2$HCH$_2$—), 1.95 (s, 3H; —NHCOCH$_3$). $^{13}$C NMR (125 MHz, CD$_3$OD) δ 175.49, 171.98, 170.26, 99.76, 98.97, 78.53, 76.58, 75.02, 71.53, 69.71, 67.96, 67.85, 67.54, 67.41, 66.03, 58.04, 51.76, 38.81, 35.41, 21.13. HRMS: m/z calc. for C$_{20}$H$_{31}$N$_2$O$_{23}$S$_3^{3-}$ [M+Na$^+$]$^{2-}$: 393.0194; found: 393.0200.

N-Fluorenylmethyloxycarbonyl-2-aminoethyl O-(4-O-methylpropionate-2-deoxy-2-sulfoamino-6-O-sulfoamino-1-thio-α-D-glucopyranoside)-(1→4)—O-(methyl-2-O-sulfonato-1-thio-α-L-idopyranosiduronate)-(1→4)-O-(4-O-carboxyethyl-2-deoxy-2-sulfoamino-6-O-sulfonato-1-thio-α-D-glucopyranoside)-(1→4)—O-methyl-2-O-sulfonato-1-thio-α-L-idopyranosiduronate (49a)

Starting material (9 mg, 0.012 mmol) was treated according to the general procedures of pseudo-tetrasaccharide preparation with HBTU to give compound 49a (15 mg, 76%). $^1$H NMR (500 MHz, D$_2$O) δ 7.79 (d, J=7.5 Hz, 2H), 7.56 (t, J=7.5 Hz, 2H), 7.40-7.33 (m, 2H), 7.32-7.23 (m, 2H), 5.17-5.08 (m, 2H; A-1, C-1), 4.94 (s, 1H; B-1), 4.89 (s, 1H; D-1), 4.54 (s, 1H), 4.42-4.34 (m, 1H), 4.31-4.24 (m, 2H), 4.22-4.00 (m, 7H), 3.95-3.79 (m, 5H), 3.75 (s, 1H), 3.67-3.61 (m, 3H), 3.55 (s, 3H), 3.52-3.38 (m, 6H), 3.28-3.22 (m, 2H), 3.19 (s, 3H), 3.12-3.03 (m, 3H), 2.55-2.47 (m, 2H), 2.39-2.29 (m, 2H). $^{13}$C NMR (125 MHz, D$_2$O) δ 174.62, 173.99, 171.17, 148.60, 143.64, 140.89, 128.16, 128.02, 127.44, 125.17, 124.96, 120.70, 120.10, 99.61, 99.20, 77.44, 77.36, 77.18, 73.69, 70.62, 70.27, 69.13, 69.05, 68.27, 67.48, 67.31, 67.03, 66.40, 66.26, 66.05, 65.86, 57.91, 52.90, 52.67, 52.18, 46.91, 40.09, 38.89, 36.46, 34.74.

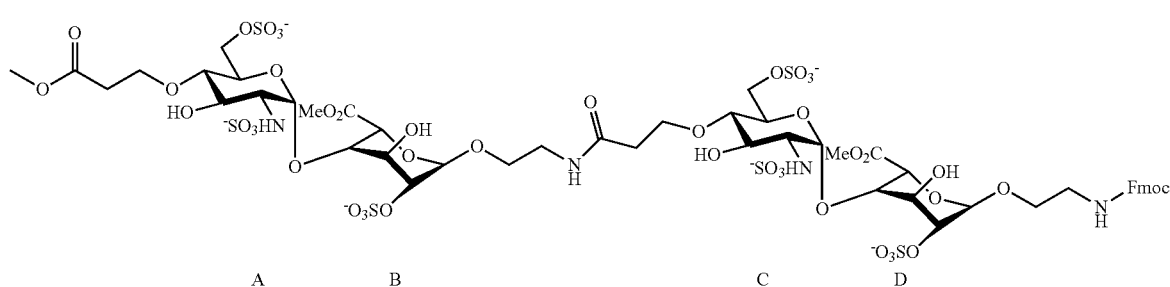

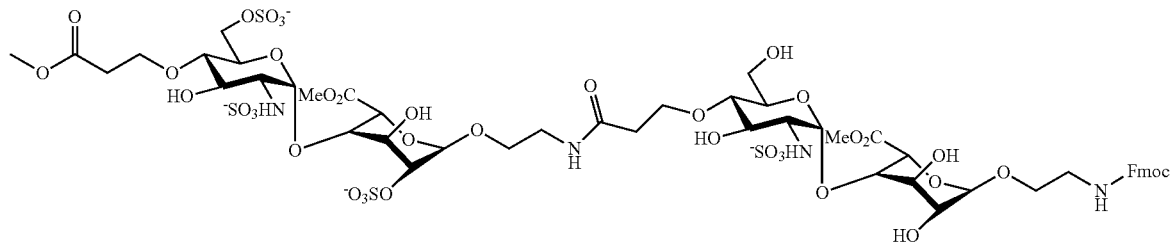

49b

N-Fluorenylmethyloxycarbonyl-2-aminoethyl O-(2-deoxy-4-O-methylpropionate-2-sulfoamino-6-O-sulfoamino-1-thio-α-D-glucopyranoside)-(1→4)—O-(methyl-2-O-sulfonato-1-thio-α-L-idopyranosiduronate)-(1→4)-O-(4-O-carboxyethyl-2-deoxy-2-sulfoamino-1-thio-α-D-glucopyranoside)-(1→4)—O-methyl-1-thio-α-L-idopyranosiduronate (49b)

Starting material (13.5 mg, 0.018 mmol) was treated according to the general procedures of pseudo-tetrasaccharide preparation with HBTU to give compound 49b (17 mg, 65%). $^1$H NMR (500 MHz, D$_2$O) δ 7.77 (d, J=7.5 Hz, 2H), 7.55 (t, J=6.9 Hz, 2H), 7.36 (t, J=7.5 Hz, 2H), 7.29-7.22 (m, 2H), 5.18 (d, J=3.5 Hz, 1H; A-1), 5.13 (d, J=3.5 Hz, 1H; C-1), 4.95 (s, 1H; B-1), 4.74-4.71 (m, 1H; D-1), 4.68-4.67 (m, 1H), 4.58 (d, J=2.6 Hz, 1H), 4.42-4.35 (m, 1H), 4.31-4.23 (m, 2H), 4.16-4.00 (m, 5H), 3.95 (t, J=2.6 Hz, 2H), 3.92-3.78 (m, 5H), 3.76-3.65 (m, 3H), 3.64 (s, 3H), 3.61-3.51 (m, 9H), 3.51-3.45 (m, 3H), 3.31-3.22 (m, 3H), 3.21-3.15 (m, 3H), 3.13-3.00 (m, 5H), 2.53-2.45 (m, 2H), 2.37-2.26 (m, 2H). $^{13}$C NMR (125 MHz, CD3OD) δ 173.05, 170.54, 170.44, 157.55, 143.90, 141.15, 127.38, 126.79, 124.84, 124.81, 119.50, 101.24, 99.58, 98.79, 96.69, 78.29, 78.16, 76.10, 74.19, 71.60, 71.30, 69.65, 69.00, 67.88, 67.66, 67.44, 67.08, 66.86, 66.42, 65.95, 60.37, 58.12, 51.84, 51.70, 50.85, 40.21, 38.75, 36.47, 34.77. HRMS: m/z calc. for $C_{37}H_{60}N_4O_{37}S_4^{4-}$ [M+H$^+$]$^{3-}$: 427.0638; found: 427.0630.

N-Fluorenylmethyloxycarbonyl-2-aminoethyl O-(4-O-methylpropionate-2-deoxy-2-sulfoamino-6-O-sulfonato-1-thio-α-D-glucopyranoside)-(1→4)—O-(methyl-2-O-sulfonato-1-thio-α-L-idopyranosiduronate)-(1→4)-O-(4-O-carboxyethyl-2-deoxy-2-acetamido-6-O-sulfonato-1-thio-α-D-glucopyranoside)-(1→4)—O-methyl-2-O-sulfonato-1-thio-α-L-idopyranosiduronate (49c)

Starting material (18 mg, 0.024 mmol) was treated according to the general procedures of pseudo-tetrasaccharide preparation with HBTU to give compound 49c (25 mg, 63/). $^1$H NMR (500 MHz, CD3OD) δ 7.80 (d, J=7.5 Hz, 2H), 7.67 (d, J=7.5 Hz, 2H), 7.44-7.37 (m, 2H), 7.35-7.29 (m, 2H), 5.28 (d, J=3.6 Hz, 1H; A-1), 5.18 (d, J=4.4 Hz, 2H; C-1, B-1), 5.00 (d, J=3.4 Hz, 1H; D-1), 4.86 (d, J=1.9 Hz, 1H), 4.84 (d, J=2.4 Hz, 1H), 4.40 (t, J=3.7 Hz, 1H), 4.35-4.27 (m, 5H), 4.25-4.15 (m, 5H), 4.13-4.05 (m, 2H), 4.03-3.94 (m, 5H), 3.84-3.76 (m, 5H), 3.74-3.71 (m, 2H), 3.69 (s, 3H), 3.66-3.54 (m, 5H), 3.48-3.34 (m, 5H), 3.26 (dd, J=10.6, 3.4 Hz, 1H), 2.66-2.56 (m, 2H), 2.48 (t, J=5.9 Hz, 2H), 2.08 (s, 3H). $^{13}$C NMR (125 MHz, CD$_3$OD) δ 173.02, 170.48, 157.50, 143.89, 141.14, 127.39, 126.81, 124.89, 119.48, 99.55, 98.86, 96.42, 78.29, 76.15, 73.75, 73.44, 73.08, 71.53, 69.95, 69.64, 68.35, 67.56, 67.42, 67.37, 66.49, 66.21, 65.93, 64.31, 58.15, 53.35, 51.85, 50.84, 40.15, 38.62, 36.53, 34.76, 21.79. HRMS: m/z calc. for $C_{39}H_{61}N_4O_{41}S_5^{5-}$ [M+H$^+$]$^{4-}$: 350.5379; found: 350.5379.

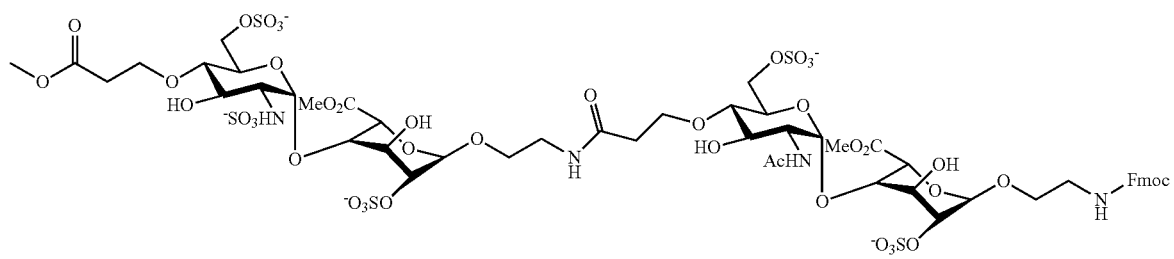

49c

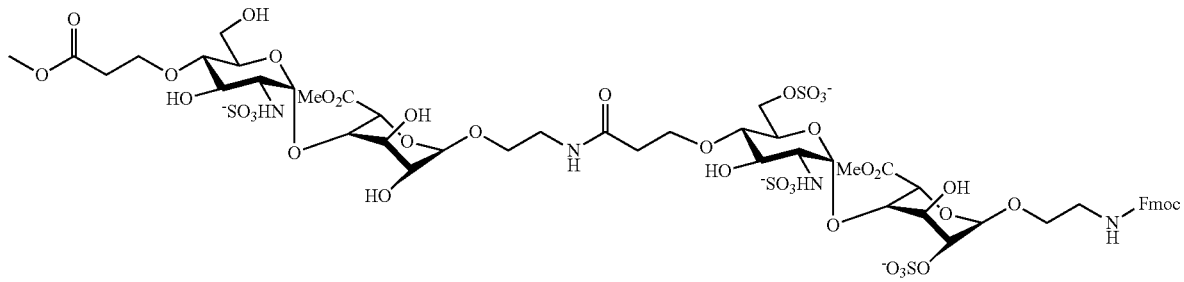

49d

N-Fluorenylmethyloxycarbonyl-2-aminoethyl-O-(2-deoxy-4-O-methylpropionate-2-sulfoamino-1-thio-α-D-glucopyranoside)-(1→4)—O-(methyl-1-thio-α-L-idopyranosiduronate)-(1→4)-O-(4-O-carboxyethyl-2-deoxy-2-sulfoamino-6-O-sulfonato-1-thio-α-D-glucopyranoside)-(1→4)—O-methyl-2-O-sulfonato-1-thio-α-L-idopyranosiduronate (49d)

Starting material (21 mg, 0.036 mmol) was treated according to the general procedures of pseudo-tetrasaccharide preparation with HATU to give compound 49d (32 mg, 59%). $^1$H NMR (500 MHz, CD$_3$OD) δ 7.80 (d, J=7.5 Hz, 2H), 7.67 (d, J=7.4 Hz, 2H), 7.43-7.38 (m, 2H), 7.33 (td, J=7.5, 1.2 Hz, 2H), 5.41 (d, J=3.6 Hz, 1H; A-1), 5.28-5.19 (m, 2H; C-1, B-1), 4.97 (d, J=2.8 Hz, 1H; D-1), 4.84 (t, J=2.9 Hz, 2H), 4.43 (d, J=3.2 Hz, 1H), 4.35-4.28 (m, 3H), 4.23-4.15 (m, 4H), 4.10-4.03 (m, 2H), 4.02-3.96 (m, 3H), 3.93-3.86 (m, 2H), 3.81-3.77 (m, 3H), 3.76-3.73 (m, 6H), 3.73-3.70 (m, 2H), 3.68 (s, 3H), 3.66-3.55 (m, 6H), 3.50-3.45 (m, 1H), 3.43-3.34 (m, 5H), 3.30-3.21 (m, 3H), 2.65-2.50 (m, 4H), 2.46-2.36 (m, 2H). $^{13}$C NMR (125 MHz, CD$_3$OD) δ 173.21, 172.85, 170.56, 157.50, 143.90, 141.13, 127.38, 126.82, 124.91, 124.87, 119.47, 101.44, 99.36, 99.17, 96.17, 78.16, 77.94, 76.57, 73.61, 73.43, 71.74, 71.48, 71.35, 69.59, 68.99, 67.99, 67.92, 67.57, 67.33, 66.75, 66.50, 66.36, 66.10, 65.65, 60.51, 58.27, 58.03, 51.83, 51.52, 50.72, 40.17, 38.86, 36.63, 34.74. HRMS: m/z calc. for $C_{37}H_{60}N_4O_{37}S_4^{4-}$ [M]$^{4-}$: 320.0460; found: 320.0446.

N-Fluorenylmethyloxycarbonyl-2-aminoethyl 4-O-methylpropionate-2-deoxy-2-sulfoamino-1-thio-α-D-glucopyranoside)-(1→4)-(methyl-1-thio-α-L-idopyranosiduronate-(1→4)-4-O-carboxyethyl-2-deoxy-2-sulfoamino-1-thio-α-D-glucopyranoside)-(1→4)-methyl-1-thio-α-L-idopyranosiduronate (49e)

Starting material (12 mg, 0.020 mmol) was treated according to the general procedures of pseudo-tetrasaccharide preparation with HATU to give compound 49e (20 mg, 70%). $^1$H NMR (500 MHz, CD$_3$OD) δ 7.81 (d, J=7.5 Hz, 2H), 7.66 (d, J=7.5 Hz, 2H), 7.40 (t, J=7.5 Hz, 2H), 7.33 (t, J=7.5 Hz, 2H), 5.35 (d, J=3.5 Hz, 1H; A-1), 5.32 (d, J=3.5 Hz, 1H; C-1), 4.97 (d, J=2.6 Hz, 1H; B-1), 4.82-4.77 (m, 2H; D-1), 4.37-4.27 (m, 2H), 4.22-4.16 (m, 3H), 4.10-3.95 (m, 5H), 3.92-3.85 (m, 3H), 3.76-3.72 (m, 5H), 3.73-3.68 (m, 8H), 3.67 (s, 3H), 3.63-3.59 (m, 4H), 3.58-3.53 (m, 4H), 3.43-3.48 (m, 3H), 3.32-3.29 (m, 6H), 2.62-2.47 (m, 5H), 2.41-2.32 (m, 2H). $^{13}$C NMR (125 MHz, CD$_3$OD) δ 173.03, 172.75, 170.43, 143.93, 141.17, 127.38, 126.80, 124.84, 119.50, 101.54, 101.37, 96.93, 96.39, 78.14, 78.08, 74.57, 74.04, 72.13, 71.63, 71.44, 69.30, 69.01, 67.92, 67.88, 67.46, 67.27, 67.21, 66.40, 60.62, 60.46, 58.45, 58.30, 54.42, 53.98, 51.50, 51.41, 50.66, 46.48, 42.39, 40.27, 38.88, 37.97, 36.57, 34.78. HRMS: m/z calc. for $C_{37}H_{62}N_4O_{31}S_2^{2-}$ [M]$^{2-}$: 561.1425. found: 561.1426.

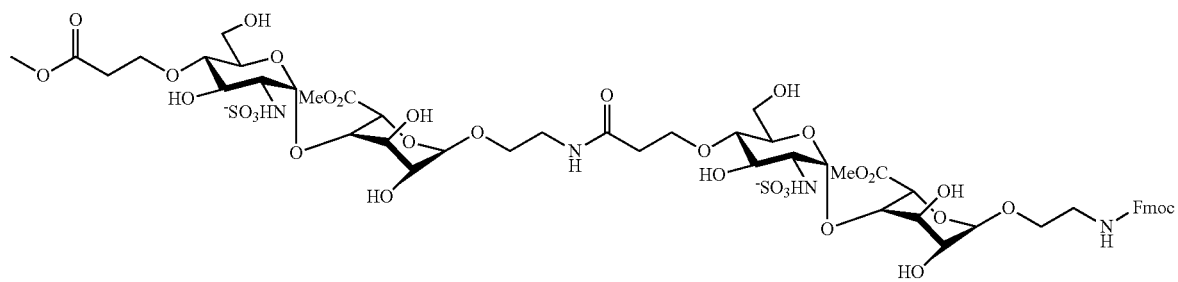

49e

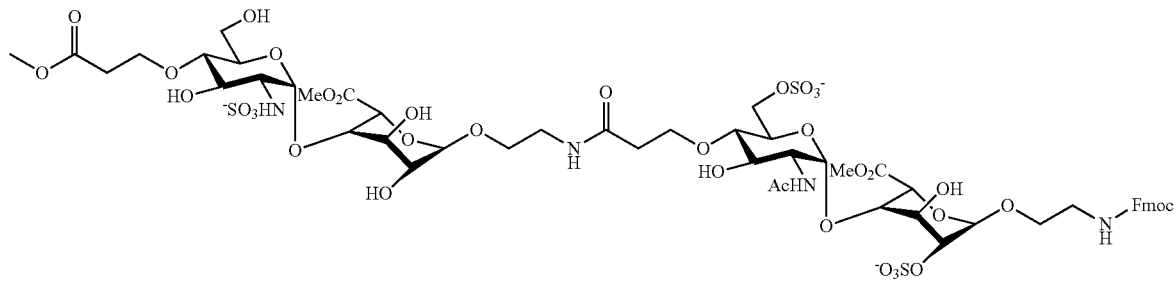

49f

N-Fluorenylmethyloxycarbonyl-2-aminoethyl O-(4-O-methylpropionate-2-deoxy-2-sulfoamino-1-thio-α-D-glucopyranoside)-(1→4)—O-(methyl-1-thio-α-L-idopyranosiduronate)-(1→4)-O-(2-acetamido-4-O-carboxyethyl-2-deoxy-6-O-sulfonato-1-thio-α-D-glucopyranoside)-(1→4)—O-methyl-2-O-sulfonato-1-thio-α-L-idopyranosiduronate (49f)

Starting material (8 mg, 0.013 mmol) was treated according to the general procedures of pseudo-tetrasaccharide preparation with HATU to give compound 49f (20 mg, 61%). $^1$H NMR (500 MHz, CD$_3$OD) δ 7.81 (d, J=7.5 Hz, 2H), 7.67 (d, J=7.6 Hz, 2H), 7.40 (tt, J=7.6, 1.6 Hz, 2H), 7.33 (tt, J=7.5, 1.4 Hz, 2H), 5.37 (d, J=3.6 Hz, 1H; A-1), 5.18 (s, 1H; C-1), 4.96 (d, J=3.4 Hz, 1H; B-1), 4.92 (d, J=2.9 Hz, 1H; D-1), 4.85 (d, J=2.0 Hz, 1H), 4.83 (d, J=3.0 Hz, 1H), 4.35-4.27 (m, 4H), 4.24-4.15 (m, 4H), 4.11-4.04 (m, 2H), 4.03-3.94 (m, 4H), 3.82-3.85 (m, 2H), 3.81-3.74 (m, 5H), 3.73-3.66 (m, 8H), 3.64-3.52 (m, 5H), 3.43-3.37 (m, 2H), 3.29-3.19 (m, 2H), 2.64-2.52 (m, 3H), 2.49-2.39 (m, 3H), 2.09 (s, 3H). $^{13}$C NMR (125 MHz, CD$_3$OD) δ 173.03, 172.97, 172.79, 170.47, 170.40, 143.90, 141.14, 127.37, 126.81, 124.90, 124.87, 119.47, 101.36, 99.53, 97.08, 96.29, 77.28, 78.12, 74.22, 73.87, 73.06, 71.87, 71.48, 71.42, 69.92, 69.17, 68.31, 67.87, 67.50, 67.29, 67.16, 66.48, 66.10, 65.84, 64.69, 60.55, 58.16, 53.60, 51.76, 51.51, 50.69, 40.18, 38.75, 36.62, 34.74, 21.75. HRMS: m/z calc. for C$_{39}$H$_{63}$N$_4$O$_{33}$S$_3$$^{3-}$ [M+H$^+$]$^{2-}$: 622.1262; found: 622.1260.

N-Fluorenylmethyloxycarbonyl-2-aminoethyl O-(2-acetamido-2-deoxy-4-O-methylpropionate-6-O-sulfonato-1-thio-α-D-glucopyranoside)-(1→4)—O-(methyl-2-O-sulfonato-1-thio-α-L-idopyranosiduronate)-(1→4)-O-(4-O-carboxyethyl-2-deoxy-2-sulfoamino-6-O-sulfonato-1-thio-α-D-glucopyranoside)-(1→4)—O-methyl-2-O-sulfonato-1-thio-α-L-idopyranosiduronate (49g)

Starting material (22 mg, 0.03 mmol) was treated according to the general procedures of pseudo-tetrasaccharide preparation with HATU to give compound 49g (26 mg, 62%). $^1$H NMR (500 MHz, CD$_3$OD) δ 8.00 (d, J=7.6 Hz, 2H), 7.78 (t, J=7.0 Hz, 2H), 7.58 (td, J=7.6, 3.6 Hz, 2H), 7.52-7.46 (m, 2H), 5.37 (d, J=3.6 Hz, 1H; A-1), 5.19 (s, 1H; C-1), 5.15-5.07 (m, 2H; B-1, D-1), 4.98 (s, 1H), 4.76 (d, J=2.2 Hz, 1H), 4.64-4.59 (m, 1H), 4.52-4.47 (m, 1H), 4.45-4.20 (m, 9H), 4.18-3.94 (m, 8H), 3.89-4.81 (m, 5H), 3.76 (s, 4H), 3.72-3.55 (m, 7H), 3.51-3.41 (m, 4H), 3.33-3.22 (m, 3H), 2.77-2.66 (m, 2H), 2.56 (t, J=5.9 Hz, 2H), 2.10 (s, 3H). $^{13}$C NMR (125 MHz, CD$_3$OD) δ 173.39, 173.31, 172.68, 169.77, 169.41, 142.34, 139.55, 126.65, 126.07, 123.81, 123.58, 118.73, 98.01, 97.65, 97.22, 93.48, 76.05, 75.93, 75.20, 73.28, 71.48, 70.13, 69.61, 69.24, 68.15, 67.75, 66.88, 66.52, 65.98, 65.82, 65.42, 64.86, 64.74, 64.66, 61.61, 56.36, 51.32, 51.62, 51.49, 50.81, 47.38, 45.57, 38.71, 37.54, 35.12, 33.52, 20.69. HRMS: m/z calc. for C$_{39}$H$_{61}$N$_4$O$_{41}$S$_5$$^{5-}$ [M]$^{5-}$: 280.2288. found: 280.2278.

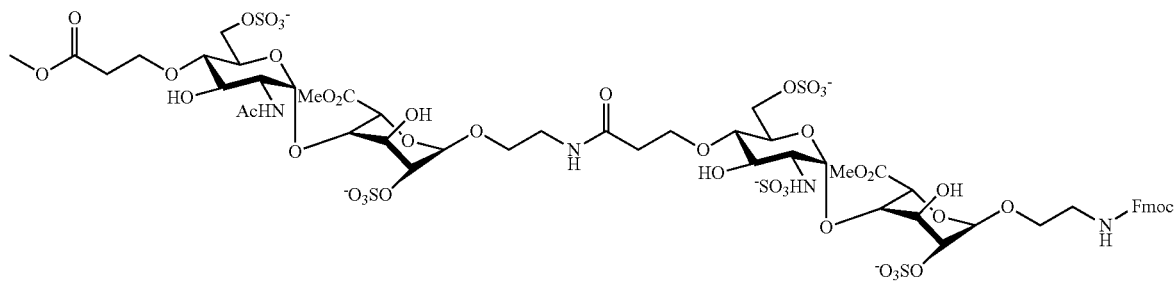

49g

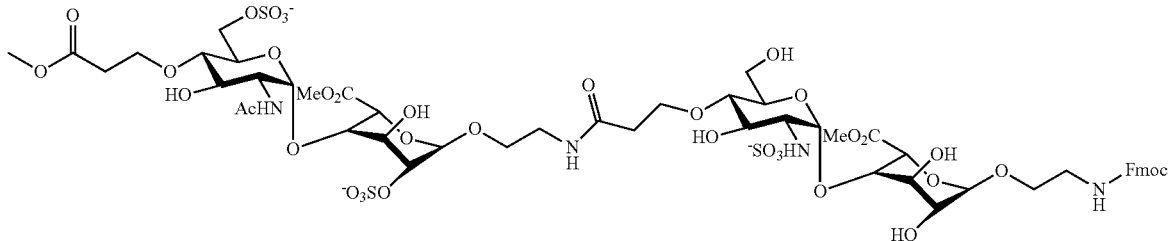

49h

N-Fluorenylmethyloxycarbonyl-2-aminoethyl O-(2-acetamido-2-deoxy-4-O-methylpropionate-6-O-sulfonato-1-thio-α-D-glucopyranoside)-(1→4)—O-(methyl-2-O-sulfonato-1-thio-α-L-idopyranosiduronate)-(1→4)-O-(4-O-carboxyethyl-2-deoxy-2-sulfoamino-1-thio-α-D-glucopyranoside)-(1→4)—O-methyl-1-thio-α-L-idopyranosiduronate (49h)

Starting material (8.5 mg, 0.01 mmol) was treated according to the general procedures of pseudo-tetrasaccharide preparation with HATU to give compound 49h (11.7 mg, 80%). $^1$H NMR (500 MHz, CD$_3$OD) δ 7.81 (d, J=7.5 Hz, 2H), 7.66 (d, J=7.5 Hz, 2H), 7.44-7.38 (m, 2H), 7.33 (td, J=7.5, 1.2 Hz, 2H), 5.35 (d, J=3.7 Hz, 1H; A-1), 5.16 (s, 1H; C-1), 4.99 (d, J=3.5 Hz, 1H; B-1), 4.92 (d, J=2.7 Hz, 1H; D-1), 4.87 (d, J=2.0 Hz, 1H), 4.80 (d, J=2.9 Hz, 1H), 4.36-4.24 (m, 4H), 4.22-4.13 (m, 4H), 4.12-3.93 (m, 7H), 3.93-3.85 (m, 2H), 3.85-3.74 (m, 6H), 3.65-3.52 (m, 6H), 3.48-3.38 (m, 4H), 3.27-3.19 (m, 1H), 2.63-2.56 (m, 2H), 2.55-2.38 (m, 3H), 2.08 (s, 3H). $^{13}$C NMR (125 MHz, CD$_3$OD) δ 173.03, 172.96, 172.89, 170.43, 143.92, 141.18, 127.38, 126.79, 124.84, 119.50, 101.37, 99.69, 96.98, 96.69, 78.32, 78.27, 74.30, 74.12, 73.31, 71.59, 71.56, 71.50, 69.98, 69.13, 67.87, 67.78, 67.66, 67.60, 67.27, 66.39, 66.34, 65.93, 64.82, 60.48, 58.19, 53.59, 51.78, 51.60, 40.24, 38.79, 36.43, 34.86, 21.74. HRMS: m/z calc. for $C_{39}H_{63}N_4O_{35}S_3^{3-}$ $[M+H^+]^{2-}$: 622.1262; found: 622.1260.

N-Fluorenylmethyloxycarbonyl-2-aminoethyl O-(2-acetamido-2-deoxy-4-O-methylpropionate-6-O-sulfonato-1-thio-α-D-glucopyranoside)-(1→4)—O-(methyl-2-O-sulfonato-1-thio-α-L-idopyranosiduronate)-(1→4)-O-(2-acetamido-4-O-carboxyethyl-2-deoxy-6-O-sulfonato-1-thio-α-D-glucopyranoside)-(1→4)—O-methyl-2-O-sulfonato-1-thio-α-L-idopyranosiduronate (49i)

Starting material (8.0 mg, 0.01 mmol) was treated according to the general procedures of pseudo-tetrasaccharide preparation with HATU to give compound 49i (12.7 mg, 80%). $^1$H NMR (500 MHz, CD$_3$OD) δ 7.81 (d, J=7.5 Hz, 2H), 7.67 (d, J=7.5 Hz, 2H), 7.40 (tt, J=7.5, 1.5 Hz, 2H), 7.33 (tt, J=7.5, 1.5 Hz, 2H), 5.16 (d, J=4.8 Hz, 2H; A-1, C-1), 4.99 (d, J=3.5 Hz, 1H; B-1), 4.97 (d, J=3.4 Hz, 1H; D-1), 4.86 (dd, J=5.6, 1.9 Hz, 2H), 4.34-4.25 (m, 6H), 4.22-4.18 (m, 5H), 4.11-4.05 (m, 3H), 4.02-3.93 (m, 7H), 3.82 (s, 3H), 3.74-3.66 (m, 7H), 3.66-3.54 (m, 6H), 3.43-3.37 (m, 3H), 3.33-3.35 (m, 2H), 3.30 (d, J=2.7 Hz, 1H), 2.62-2.56 (m, 2H), 2.49-2.43 (m, 2H), 2.07 (d, J=1.7 Hz, 6H). $^{13}$C NMR (125 MHz, CD$_3$OD) δ 172.96, 172.92, 170.49, 170.33, 157.48, 143.90, 141.14, 127.38, 126.81, 124.89, 119.48, 99.61, 99.56, 97.23, 96.43, 78.34, 78.26, 74.36, 73.47, 73.09, 71.52, 71.42, 69.99, 69.91, 68.22, 67.76, 67.55, 67.25, 66.49, 66.27, 66.22, 65.91, 64.79, 64.40, 53.60, 53.40, 51.83, 51.75, 50.82, 40.17, 38.67, 36.46, 34.85, 21.74. HRMS: m/z calc. for $C_{41}H_{64}N_4O_{39}S_4^{4-}$ $[M+H^+]^{3-}$: 455.0708; found: 455.0688.

49i

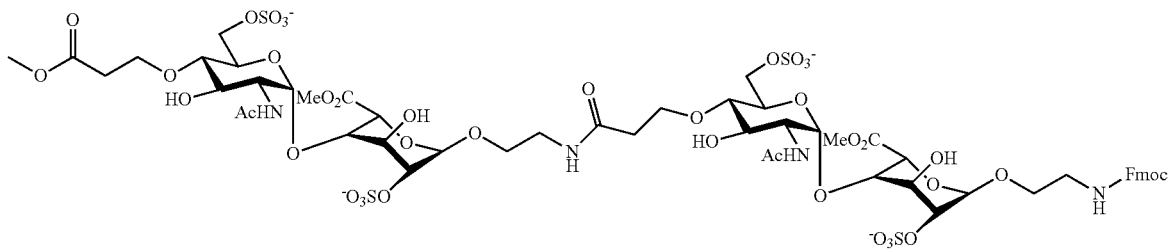

50

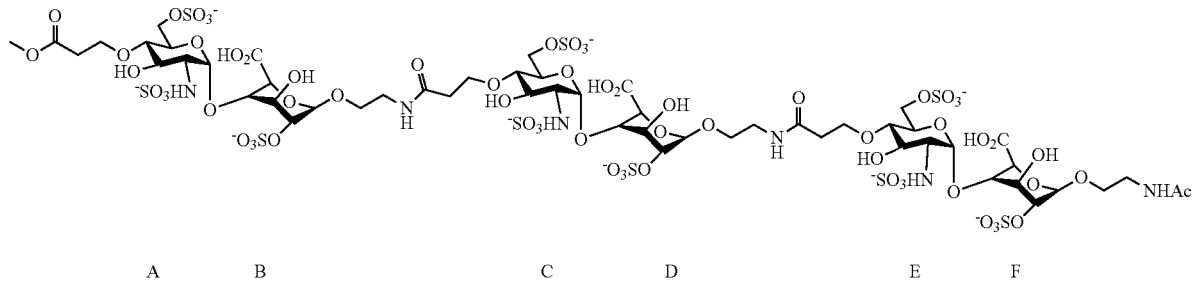

A B C D E F

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate) (50)

The starting material (5.8 mg, 0.004 mmol) was treated according to the general procedures of NH-Fmoc deprotection, pseudo-hexasaccharide preparation with HBTU and saponification of methyl esters to give compound 50 (3.8 mg, 51% for 3 steps). $^1$H NMR (500 MHz, D$_2$O) δ 5.22 (d, J=3.6 Hz, 1H; A-1), 5.16 (t, J=4.2 Hz, 2H; C-1, F-1), 5.00 (d, J=3.6 Hz, 2H; B-1, D-1), 4.95 (d, J=2.8 Hz, 1H; E-1), 4.45 (dd, J=11.5, 2.3 Hz, 2H), 4.41 (d, J=2.8 Hz, 1H), 4.17 (dd, J=11.0, 2.1 Hz, 1H), 4.13-4.08 (m, 5H), 4.07-3.99 (m, 4H), 3.94-3.62 (m, 14H), 3.57-3.44 (m, 6H), 3.32-3.16 (m, 8H), 3.13-3.05 (m, 3H), 2.53-2.34 (m, 6H), 1.82 (s, 3H). 13C NMR (125 MHz, D$_2$O) δ 173.83, 99.07, 98.72, 96.85, 77.81, 77.78, 77.59, 76.06, 75.94, 74.68, 74.55, 70.48, 70.43, 68.84, 68.82, 68.77, 68.62, 68.40, 68.29, 68.08, 67.61, 67.52, 67.30, 66.92, 66.81, 66.20, 66.12, 57.78, 57.77, 57.71, 39.04, 38.91, 36.22, 36.20, 35.30, 21.69. HRMS: m/z calc. for $C_{53}H_{79}N_6O_{65}S_9^{9-}$ [M+4Na$^+$]$^{5-}$: 443.8033; found: 443.8041.

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate) (50a)

The starting material (6.5 mg, 0.004 mmol) was treated according to the general procedures of NH-Fmoc deprotection, pseudo-hexasaccharide preparation with HBTU and saponification of methyl esters to give compound 50a (3.7 mg, 48% for 3 steps). 1H NMR (500 MHz, D$_2$O) δ 5.19 (d, J=3.6 Hz, 1H; A-1), 5.15 (dd, J=6.2, 3.6 Hz, 2H; C-1, F-1), 5.01-4.96 (m, 2H; B-1, D-1), 4.73-4.70 (m, 1H; E-1), 4.44-4.33 (m, 3H), 4.18-4.13 (m, 1H), 4.12-4.05 (m, 5H), 4.04-3.99 (m, 2H), 3.98-3.93 (m, 1H), 3.92-3.71 (m, 12H), 3.70-3.44 (m, 14H), 3.32-3.15 (m, 9H), 3.12-3.00 (m, 4H), 2.50-2.35 (m, 6H), 1.82 (s, 3H). $^{13}$C NMR (125 MHz, Deuterium Oxide) δ 173.84, 100.61, 98.90, 98.70, 97.47, 97.09, 95.60, 78.04, 77.82, 77.64, 75.98, 75.95, 75.38, 74.69, 74.43, 70.68, 70.54, 70.47, 68.79, 68.46, 68.27, 68.22, 68.18, 67.78, 67.66, 67.52, 66.77, 66.71, 66.16, 59.75, 57.77, 57.75, 57.72, 39.05, 38.97, 38.91, 36.19, 21.70. HRMS: m/z calc. for $C_{53}H_{81}N_6O_{59}S_7^{7-}$ [M+2Na$^+$]$^{5-}$: 403.0278; found: 403.0291.

50a

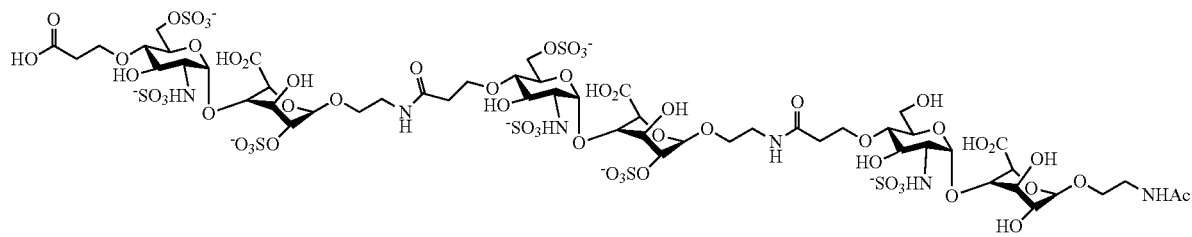

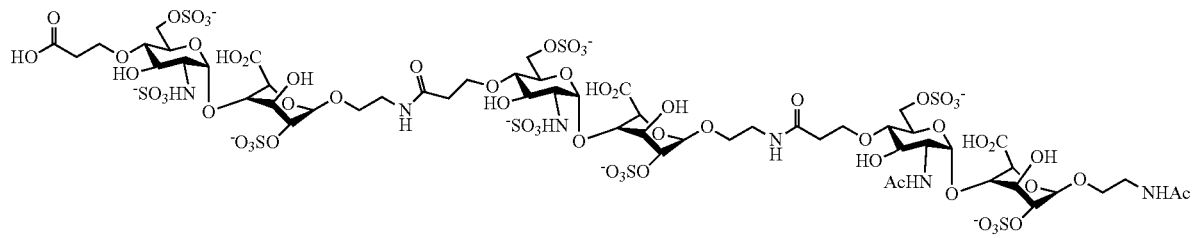

50b

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate) (50b)

The starting material (5.8 mg, 0.004 mmol) was treated according to the general procedures of NH-Fmoc deprotection, pseudo-hexasaccharide preparation with HBTU and saponification of methyl esters to give compound 50b (1.4 mg, 19% for 3 steps). $^1$H NMR (500 MHz, D$_2$O) δ 5.17 (dd, J=8.9, 3.5 Hz, 2H; A-1, C-1), 4.98 (s, 2H; F-1, B-1), 4.94 (d, J=3.7 Hz, 1H; D-1), 4.91 (s, 1H; E-1), 4.43-4.34 (m, 4H), 4.19-3.99 (m, 13H), 3.94-3.72 (m, 14H), 3.71-3.43 (m, 13H), 3.35-3.16 (m, 10H), 3.13-3.03 (m, 3H), 2.47-2.35 (m, 7H), 1.88 (s, 3H), 1.82 (s, 3H). $^{13}$C NMR (125 MHz, D$_2$O) δ 77.87, 75.88, 73.73, 70.49, 70.81, 68.86, 68.76, 68.61, 66.85, 66.91, 66.28, 66.16, 57.76, 39.01, 38.90, 36.18, 27.45, 22.07, 21.70. HRMS: m/z calc. for $C_{55}H_{52}N_6O_{63}S_8{}^{8-}$ [M+3Na$^+$]$^{5-}$: 431.8177; found: 431.8189.

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate) (50c)

The starting material (4.5 mg, 0.003 mmol) was treated according to the general procedures of NH-Fmoc deprotection, pseudo-hexasaccharide preparation with HBTU and saponification of methyl esters to give compound 50c (1.4 mg, 51% for 3 steps). $^1$H NMR (500 MHz, D$_2$O) δ 5.22 (d, J=3.5 Hz, 1H; A-1), 5.18 (d, J=3.6 Hz, 1H; C-1), 5.14 (d, J=3.9 Hz, 1H; E-1), 4.97 (d, J=2.4 Hz, 1H; B-1), 4.94 (d, J=2.9 Hz, 1H; D-1), 4.73 (d, J=2.7 Hz, 1H; F-1), 4.41-4.32 (m, 3H), 4.19-3.99 (m, 9H), 3.97-3.92 (m, 1H), 3.92-3.73 (m, 12H), 3.71-3.42 (m, 15H), 3.37-3.16 (m, 10H), 3.12-3.01 (m, 4H), 2.52-2.30 (m, 7H), 1.82 (s, 3H). $^{13}$C NMR (125 MHz, D$_2$O) δ 177.77, 173.87, 122.73, 119.89, 109.99, 100.57, 98.83, 97.48, 97.10, 96.74, 95.65, 78.05, 77.75, 77.69, 76.04, 75.93, 74.32, 70.73, 70.58, 70.49, 68.75, 68.70, 68.41, 68.34, 66.87, 66.75, 66.47, 66.20, 57.78, 57.73, 39.05, 38.98, 38.85, 36.35, 21.69. HRMS: m/z calc. for $C_{53}H_{81}N_6O_{59}S_7{}^{7-}$ [M+2Na$^+$]$^{5-}$: 403.0278; found: 403.0296.

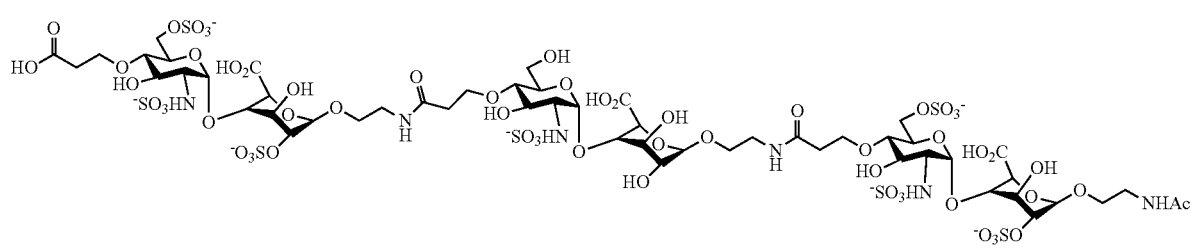

50c

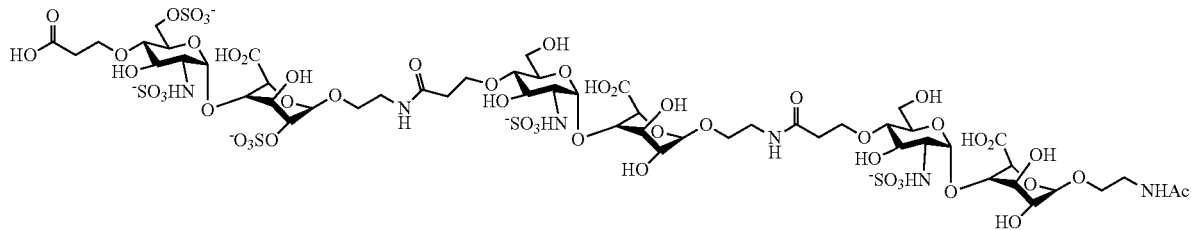

50d

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfonato-1-thio-α-D-glucopyranoside)-(1→4)-O-(6-O-carboxyl-1-thio-α-L-idopyranosiduronate) (50d)

The starting material (4.5 mg, 0.003 mmol) was treated according to the general procedures of NH-Fmoc deprotection, pseudo-hexasaccharide preparation with HBTU and saponification of methyl esters to give compound 50d (3.0 mg, 56% for 3 steps). $^1$H NMR (500 MHz, D$_2$O) δ 5.18 (d, J=3.7 Hz, 1H; A-1), 5.14 (dd, J=3.9, 1.4 Hz, 2H; C-1, E-1), 4.97 (d, J=2.5 Hz, 1H; B-1), 4.74-4.71 (m, 2H; D-1, F-1), 4.39-4.32 (m, 3H), 4.18-4.14 (m, 1H), 4.12-3.99 (m, 4H), 3.97-3.92 (m, 2H), 3.91-3.72 (m, 11H), 3.70-3.45 (m, 18H), 3.31-3.16 (m, 10H), 3.10-2.98 (m, 4H), 2.48-2.33 (m, 7H), 1.82 (s, 3H). $^{13}$C NMR (125 MHz, D$_2$O) δ 173.93, 173.85, 100.61, 98.85, 97.11, 95.65, 95.57, 78.12, 78.05, 77.97, 75.94, 74.45, 74.30, 70.71, 70.55, 70.50, 68.78, 68.39, 68.27, 68.12, 67.83, 67.58, 67.38, 66.75, 66.69, 66.49, 66.19, 59.76, 57.78, 57.74, 38.99, 39.06, 36.26, 36.15, 21.70. HRMS: m/z calc. for $C_{53}H_{83}N_6O_{53}S_5^{5-}$ [M+Na$^+$]$^{4-}$: 458.5627; found: 458.5641.

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate)-(1→4)-O-(2-acetamido-2-deoxy-1-thio-α-D-glucopyranoside)-(1→4)-O-(6-O-carboxyl-1-thio-α-L-idopyranosiduronate) (50e)

The starting material (4.5 mg, 0.003 mmol) was treated according to the general procedures of NH-Fmoc deprotection, pseudo-hexasaccharide preparation with HBTU and saponification of methyl esters to give compound 50e (2.9 mg, 50% for 3 steps). $^1$H NMR (500 MHz, D$_2$O) δ 7.96 (d, J=9.8 Hz, 1H; NHAc), 5.18 (d, J=3.7 Hz, 1H; A-1), 5.14 (d, J=3.7 Hz, 1H; C-1), 4.98-4.90 (m, 3H; D-1, B-1, E-1), 4.75-4.71 (m, 1H; F-1), 4.39 (d, J=2.3 Hz, 1H), 4.35 (dd, J=6.9, 2.4 Hz, 2H), 4.17-4.00 (m, 8H), 3.97-3.74 (m, 13H), 3.70-3.44 (m, 13H), 3.35-3.17 (m, 9H), 3.10-3.01 (m, 2H), 2.46-2.34 (m, 6H), 1.88 (s, 3H), 1.83 (s, 3H). $^{13}$C NMR (125 MHz, D$_2$O) δ 190.14, 109.99, 109.71, 99.00, 98.65, 98.64, 96.97, 95.61, 93.51, 78.11, 77.77, 75.88, 75.41, 74.39, 73.67, 70.85, 70.73, 70.81, 70.53, 68.83, 68.71, 68.59, 68.26, 68.10, 67.42, 66.85, 66.44, 66.18, 63.81, 57.70, 53.04, 39.00, 38.87, 36.28, 36.13, 22.07, 21.70. HRMS: m/z calc. for $C_{55}H_{84}N_6O_{57}S_6^{6-}$ [M+Na$^+$]$^{5-}$: 391.0422; found: 391.0433.

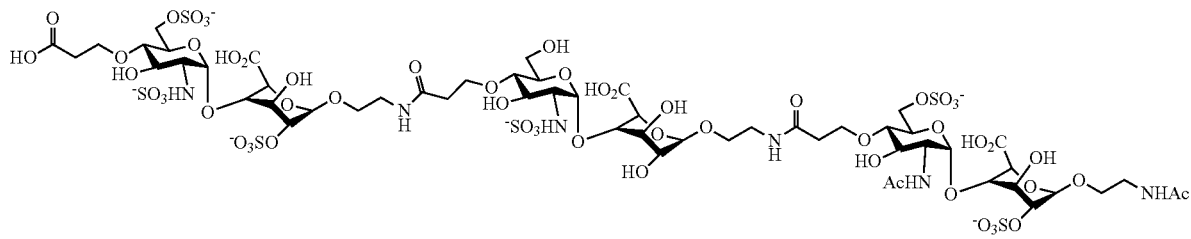

50e

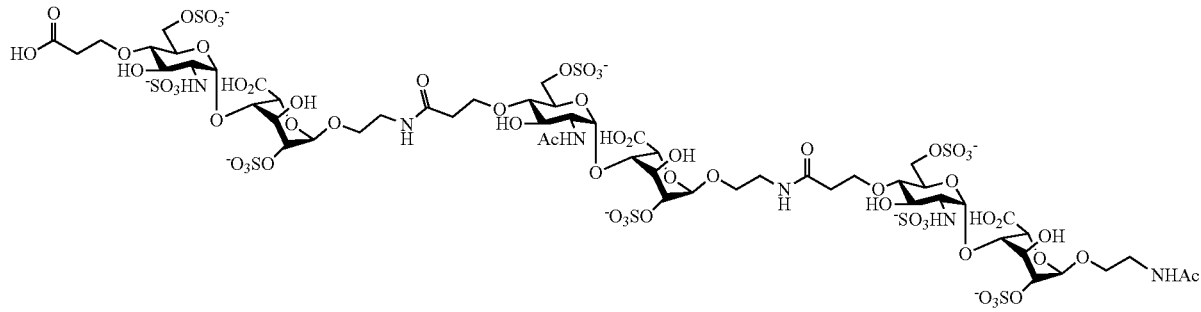

50f

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfonato-6-O-sulfonato-1-thio-α-D-glucopyranoside)-(1→4)-O-(6-O-carboxyl-2-O-sulfonato-1-thio-α-L-idopyranosiduronate) (50f)

The starting material (5.2 mg, 0.003 mmol) was treated according to the general procedures of NH-Fmoc deprotection, pseudo-hexasaccharide preparation with HBTU and saponification of methyl esters to give compound 50f (3.7 mg, 55% for 3 steps). $^1$H NMR (500 MHz, D$_2$O) δ 5.22 (d, J=3.5 Hz, 1H; A-1), 5.16 (d, J=3.5 Hz, 1H; C-1), 5.00-4.97 (m, 1H; E-1), 4.94 (m, 3H; B-1, D-1, F-1), 4.46-4.38 (m, 3H), 4.20-3.98 (m, 11H), 3.97-3.71 (m, 12H), 3.66 (m, 3H), 3.60-3.44 (m, 6H), 3.38-3.15 (m, 9H), 3.09 (m, 2H), 2.54-2.45 (m, 2H), 2.44-2.35 (m, 4H), 1.88 (s, 3H), 1.82 (s, 3H). $^{13}$C NMR (125 MHz, D$_2$O) δ 99.08, 98.74, 98.58, 97.49, 96.82, 93.69, 90.46, 77.83, 77.61, 76.03, 75.95, 73.19, 70.78, 70.51, 70.45, 68.80, 68.76, 68.67, 68.63, 68.41, 68.14, 67.70, 66.80, 66.91, 66.71, 66.20, 66.12, 57.79, 57.73, 53.01, 39.04, 38.93, 38.84, 36.24, 36.15, 22.11, 21.69. HRMS: m/z calc. for C$_5$H$_{82}$N$_6$O$_{63}$S$_8{}^{8-}$ [M+Na+]$^{7-}$: 301.8728; found: 301.8744.

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfonato-1-thio-α-D-glucopyranoside)-(1→4)-O-(6-O-carboxyl-1-thio-α-L-idopyranosiduronate) (50g)

The starting material (4.8 mg, 0.003 mmol) was treated according to the general procedures of NH-Fmoc deprotection, pseudo-hexasaccharide preparation with HBTU and saponification of methyl esters to give compound 50g (2.5 mg, 44% for 3 steps). $^1$H NMR (500 MHz, D$_2$O) δ 5.17 (d, J=3.7 Hz, 1H; A-1), 5.14 (d, J=3.6 Hz, 1H; C-1), 4.99-4.97 (in, 1H; E-1), 4.93 (d, J=3.1 Hz, 2H; B-1, D-1), 4.73-4.69 (in, 1H; F-1), 4.39 (dd, J=13.7, 2.3 Hz, 2H), 4.33 (d, J=2.4 Hz, 1H), 4.18-3.99 (m, 8H), 3.95 (t, J=3.9 Hz, 2H), 3.92-3.72 (in, 11H), 3.70-3.42 (m, 13H), 3.36-3.17 (m, 9H), 3.13-3.01 (m, 3H), 2.51-2.32 (m, 6H), 1.88 (s, 3H), 1.81 (s, 3H). $^{13}$C NMR (125 MHz, D$_2$O) δ 74.21, 173.90, 109.99, 100.60, 97.21, 95.57, 93.54, 78.03, 77.85, 77.70, 75.91, 75.02, 74.45, 73.45, 70.69, 70.49, 68.75, 68.32, 68.17, 67.60, 66.69, 66.15, 63.59, 59.74, 57.74, 39.05, 38.93, 36.13, 22.09, 21.70. HRMS: m/z calc. for C$_{55}$H$_{84}$N$_6$O$_{57}$S$_6{}^{6-}$ [M+Na$^+$]$^{5-}$: 391.0422; found: 391.0435.

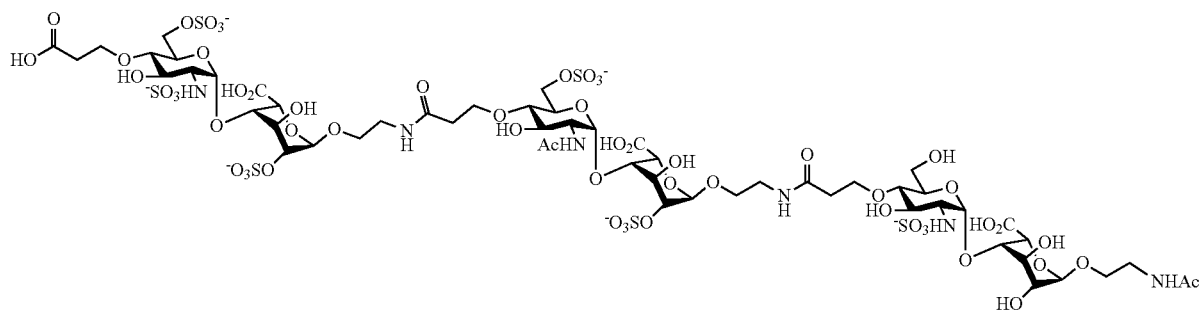

50g

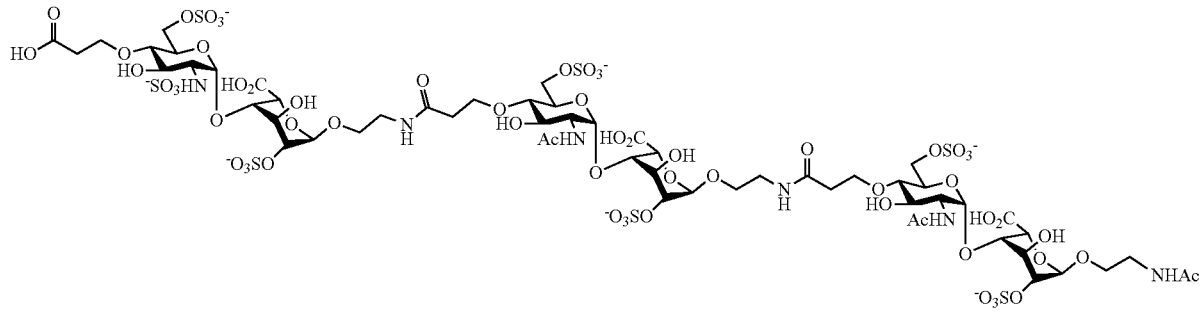

50h

N-Acetamidoethyl O-(4-O-carboxyethyl-2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate) (50h)

The starting material (5.2 mg, 0.003 mmol) was treated according to the general procedures of NH-Fmoc deprotection, pseudo-hexasaccharide preparation with HBTU and saponification of methyl esters to give compound 50h (2.8 mg, 42% for 3 steps). $^1$H NMR (500 MHz, D$_2$O) δ 5.16 (d, J=3.7 Hz, 1H; A-1), 4.98 (s, 1H; C-1), 4.93 (m, 4H; B-1, D-1, E-1, F-1), 4.46-4.38 (m, 3H), 4.22-3.99 (m, 12H), 3.94-3.71 (m, 14H), 3.69-3.62 (m, 3H), 3.60-3.41 (m, 7H), 3.35-3.19 (m, 9H), 3.17 (s, 1H), 3.08 (dd, J=10.6, 3.5 Hz, 1H), 2.52-2.28 (m, 7H), 1.88 (s, 6H), 1.82 (s, 3H). $^{13}$C NMR (125 MHz, D$_2$O) δ 174.62, 174.15, 173.87, 98.73, 98.67, 98.58, 97.46, 93.65, 93.54, 77.82, 77.62, 76.01, 74.77, 73.65, 73.26, 70.83, 70.78, 70.45, 68.88, 68.79, 68.62, 68.58, 68.48, 68.15, 67.72, 66.87, 66.79, 66.70, 66.22, 66.10, 63.79, 57.77, 53.01, 39.00, 38.93, 38.86, 36.20, 36.15, 35.39, 22.09, 21.69. HRMS: m/z calc. for C$_{57}$H$_{85}$N$_6$O$_{61}$S$_7$$^{7-}$ [M+2Na$^+$]$^{5-}$: 419.8320; found: 419.8341.

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate) (50i)

The starting material (4.6 mg, 0.003 mmol) was treated according to the general procedures of NH-Fmoc deprotection, pseudo-hexasaccharide preparation with HBTU and saponification of methyl esters to give compound 50i (1.2 mg, 20% for 3 steps). $^1$H NMR (500 MHz, D$_2$O) δ 5.24 (s, 1H; A-1), 5.15 (d, J=12.9 Hz, 2H; C-1, E-1), 4.99 (s, 1H; B-1), 4.93 (s, 2H; D-1, F-1), 4.38-4.31 (m, 3H), 4.14-3.99 (m, 8H), 3.96-3.71 (m, 13H), 3.69-3.42 (m, 14H), 3.36-3.15 (m, 9H), 3.12-3.01 (m, 4H), 2.44-2.32 (m, 6H), 1.82 (d, J=1.8 Hz, 3H). HRMS: m/z calc. for C$_{53}$H$_{81}$N$_6$O$_{59}$S$_7$$^{7-}$ [M+2Na$^+$]$^{5-}$: 403.0278; found: 403.0296.

50i

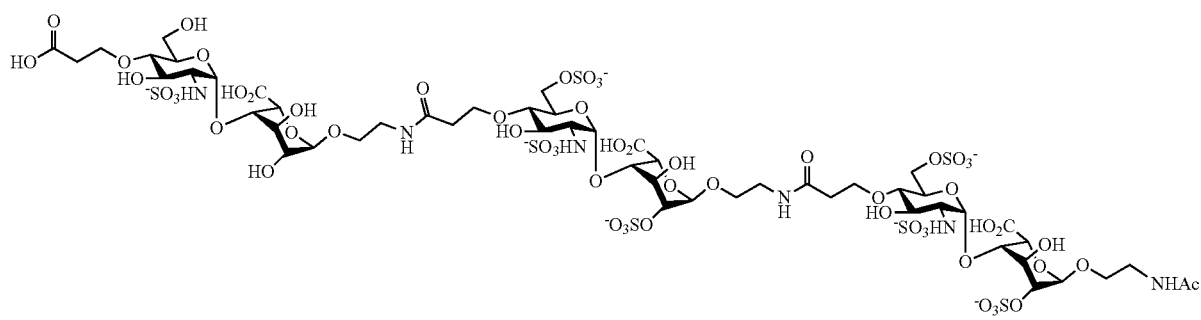

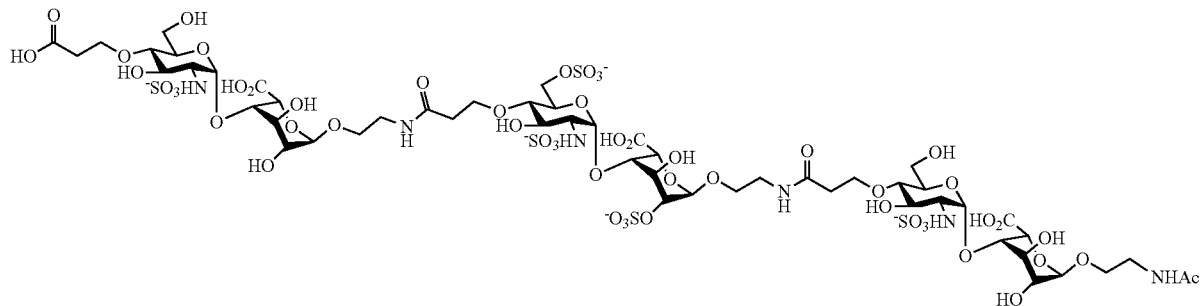

50j

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate) (50j)

The starting material (4.2 mg, 0.003 mmol) was treated according to the general procedures of NH-Fmoc deprotection, pseudo-hexasaccharide preparation with HBTU and saponification of methyl esters to give compound 50j (2.4 mg, 48% for 3 steps). $^1$H NMR (500 MHz, D$_2$O) δ 5.17 (d, J=2.9 Hz, 1H; A-1), 5.14 (t, J=2.5 Hz, 2H; C-1, E-1), 4.98 (s, 1H; B-1), 4.72 (dd, J=5.4, 2.5 Hz, 2H; D-1, F-1), 4.46-4.35 (m, 3H), 4.12-4.05 (m, 3H), 4.03-3.83 (m, 9H), 3.83-3.69 (m, 5H), 3.68-3.44 (m, 15H), 3.36-3.13 (m, 9H), 3.11-2.99 (m, 3H), 2.46-2.34 (m, 6H), 1.81 (d, J=1.9 Hz, 3H). $^{13}$C NMR (125 MHz, D$_2$O) δ 173.88, 170.07, 100.62, 100.60, 98.86, 97.38, 95.63, 77.98, 77.81, 77.66, 76.06, 75.08, 74.38, 74.22, 70.75, 70.66, 70.57, 70.51, 68.79, 68.19, 68.15, 68.09, 67.97, 67.91, 67.64, 67.41, 67.28, 66.82, 66.73, 66.54, 66.11, 59.73, 57.81, 57.70, 39.04, 38.98, 38.88, 36.33, 36.18, 35.58, 21.69. HRMS: m/z calc. for C$_{53}$H$_{83}$N$_6$O$_{53}$S$_5{}^{5-}$ [M+Na$^+$]$^{4-}$: 458.5627; found: 458.5641.

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate) (50k)

The starting material (6.6 mg, 0.004 mmol) was treated according to the general procedures of NH-Fmoc deprotection, pseudo-hexasaccharide preparation with HBTU and saponification of methyl esters to give compound 50k (5.0 mg, 59% for 3 steps). $^1$H NMR (500 MHz, D$_2$O) δ 5.15 (m, 2H; A-1, C-1), 4.99 (s, 1H; E-1), 4.94-4.90 (m, 2H; D-1, B-1), 4.72 (s, 1H; F-1), 4.45-4.36 (m, 3H), 4.13-3.99 (m, 8H), 3.95 (t, J=3.7 Hz, 1H), 3.91-3.70 (m, 12H), 3.70-3.60 (m, 5H), 3.60-3.43 (m, 8H), 3.36-3.17 (m, 9H), 3.12-2.96 (m, 3H), 2.44-2.34 (m, 6H), 1.88 (s, 3H), 1.82 (s, 3H). $^{13}$C NMR (125 MHz, D$_2$O) δ 174.62, 173.88, 100.60, 98.77, 98.68, 95.61, 93.54, 77.84, 77.68, 76.04, 74.81, 74.70, 74.23, 73.63, 70.82, 70.76, 70.56, 70.49, 68.88, 68.80, 68.58, 68.40, 68.20, 68.00, 67.72, 67.32, 66.88, 66.81, 66.53, 66.25, 66.14, 63.77, 59.70, 57.82, 57.69, 53.00, 39.00, 38.88, 36.33, 36.17, 22.07, 21.69. HRMS: m/z calc. for C$_{55}$H$_{54}$N$_6$O$_{57}$S$_6{}^{6-}$ [M+Na$^+$]$^{5-}$: 391.0422; found: 391.0430.

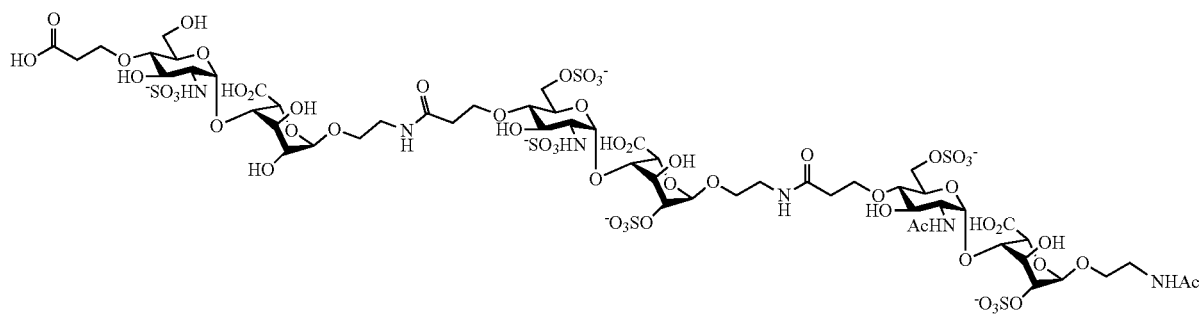

50k

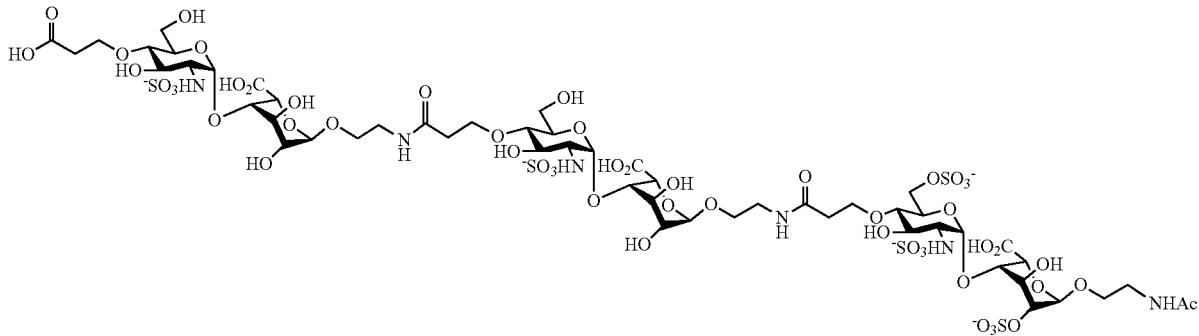

50l

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate) (50l)

The starting material (2.5 mg, 0.002 mmol) was treated according to the general procedures of NH-Fmoc deprotection, pseudo-hexasaccharide preparation with HBTU and saponification of methyl esters to give compound 50l (1.4 mg, 42% for 3 steps). $^1$H NMR (500 MHz, D$_2$O) δ 5.22 (d, J=3.5 Hz, 1H; A-1), 5.19-5.06 (m, 2H; C-1, E-1), 4.94 (s, 1H; B-1), 4.77-4.71 (m, 2H; D-1, F-1), 4.38-4.30 (m, 3H), 4.13-4.07 (m, 2H), 4.05-3.99 (m, 2H), 3.95 (t, J=3.9 Hz, 2H), 3.93-3.83 (m, 6H), 3.82-3.71 (m, 4H), 3.70-3.41 (m, 16H), 3.34-3.15 (m, 9H), 3.11-3.01 (m, 4H), 2.44-2.31 (m, 6H), 1.82 (s, 3H). HRMS: m/z calc. for $C_{53}H_{83}N_6O_{53}S_5{}^{5-}$ [M+Na$^+$]$^{4-}$: 458.5627; found: 458.5623.

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate) (50m)

The starting material (3.0 mg, 0.002 mmol) was treated according to the general procedures of NH-Fmoc deprotection, pseudo-hexasaccharides preparation with HATU and saponification of methyl esters to give compound 50m (0.8 mg, 22% for 3 steps). $^1$H NMR (500 MHz, D$_2$O) δ 5.15 (d, J=3.6 Hz, 3H; A-1, C-1, E-1), 4.73 (d, J=4.1 Hz, 3H; B-1, D-1, F-1), 4.38-4.28 (m, 3H), 3.93-3.99 (m, 3H), 3.91-3.82 (m, 6H), 3.80-3.73 (m, 4H), 3.70-3.44 (m, 20H), 3.33-3.17 (m, 9H), 3.11-2.99 (m, 4H), 2.46-2.33 (m, 6H), 1.82 (s, 2H). HRMS: m/z calc. for $C_{53}H_{85}N_6O_{47}S_3{}^{3-}$ [M]$^{3-}$: 551.1208; found: 551.1201.

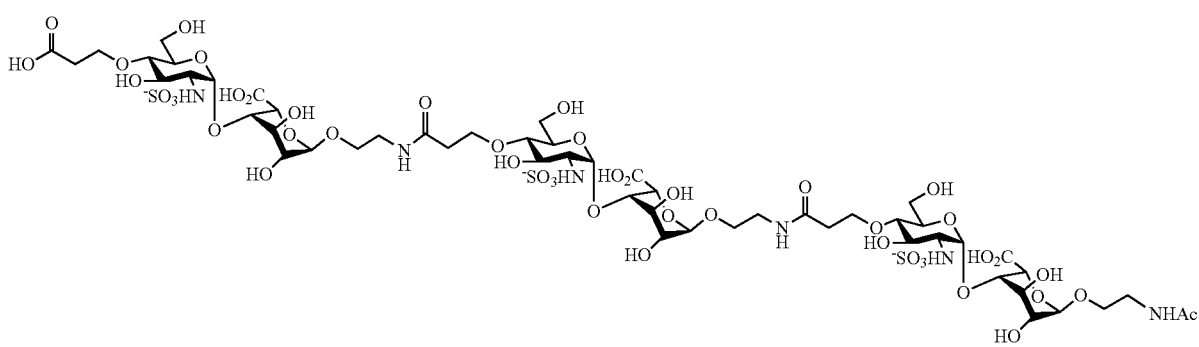

50m

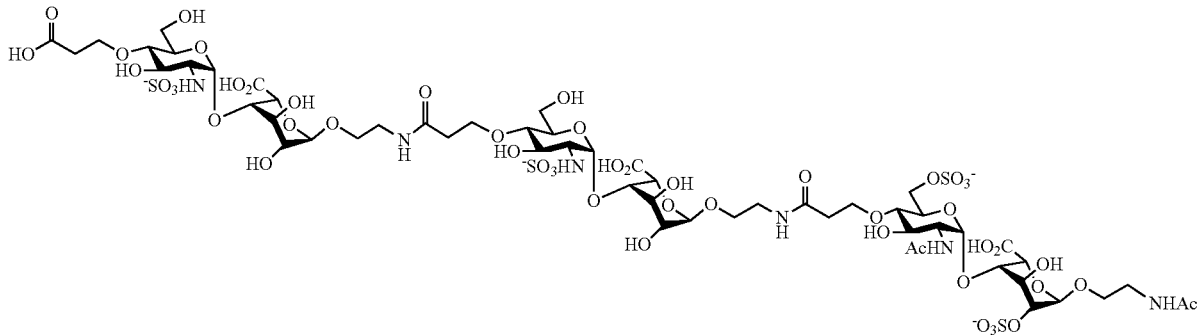

50n

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate) (50n)

The starting material (3.8 mg, 0.003 mmol) was treated according to the general procedures of NH-Fmoc deprotection, pseudo-hexasaccharide preparation with HATU and saponification of methyl esters to give compound 50n (2.6 mg, 52% for 3 steps). $^1$H NMR (500 MHz, D$_2$O) δ 5.19-5.05 (m, 2H; A-1, C-1), 4.95-4.91 (m, 2H; E-1, B-1), 4.73 (m, 2H; D-1, F-1), 4.43-4.35 (m, 3H), 4.12-4.01 (m, 4H), 3.95 (d, J=4.0 Hz, 2H), 3.92-3.72 (m, 12H), 3.70-3.42 (m, 18H), 3.32-3.19 (m, 9H), 3.08-2.98 (m, 3H), 2.47-2.33 (m, 7H), 1.88 (s, 3H), 1.81 (s, 3H). $^{13}$C NMR (125 MHz, D$_2$O) δ 174.62, 173.88, 100.61, 98.65, 95.67, 95.59, 93.61, 77.90, 77.86, 77.75, 74.30, 74.27, 73.59, 70.85, 70.75, 70.71, 70.55, 68.87, 68.56, 68.18, 68.08, 67.37, 67.28, 66.88, 66.52, 63.77, 59.72, 57.77, 57.70, 53.04, 39.00, 38.89, 36.29, 36.23, 22.07, 21.70. HRMS: m/z calc. for $C_{55}H_{56}N_6O_{51}S_4^{4-}$ [M]$^{4-}$: 443.5806; found: 443.5810.

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-acetamido-2-deoxy-1-thio-α-D-glucopyranoside)-(1→4)-O-(6-O-carboxyl-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato 1-thio-α-L-idopyranosiduronate) (50o)

The starting material (3.9 mg, 0.003 mmol) was treated according to the general procedures of NH-Fmoc deprotection, pseudo-hexasaccharide preparation with HATU and saponification of methyl esters to give compound 50o (1.7 mg, 34% for 3 steps). $^1$H NMR (500 MHz, D$_2$O) δ 5.21 (d, J=3.7 Hz, 1H; A-1), 5.14 (d, J=3.7 Hz, 1H; C-1), 4.97-4.91 (m, 3H; B-1, D-1, E-1), 4.73 (s, 1H; F-1), 4.48-4.36 (m, 3H), 4.14-3.99 (m, 8H), 3.98-3.71 (m, 13H), 3.70-3.44 (m, 13H), 3.36-3.15 (m, 9H), 3.14-3.00 (m, 3H), 2.47-2.33 (m, 6H), 1.88 (s, 3H), 1.82 (s, 3H). HRMS: m/z calc. for $C_{55}H_{84}N_6O_{57}S_6^{6-}$ [M+2Na$^+$]$^{4-}$: 494.5500; found: 494.5502.

50o

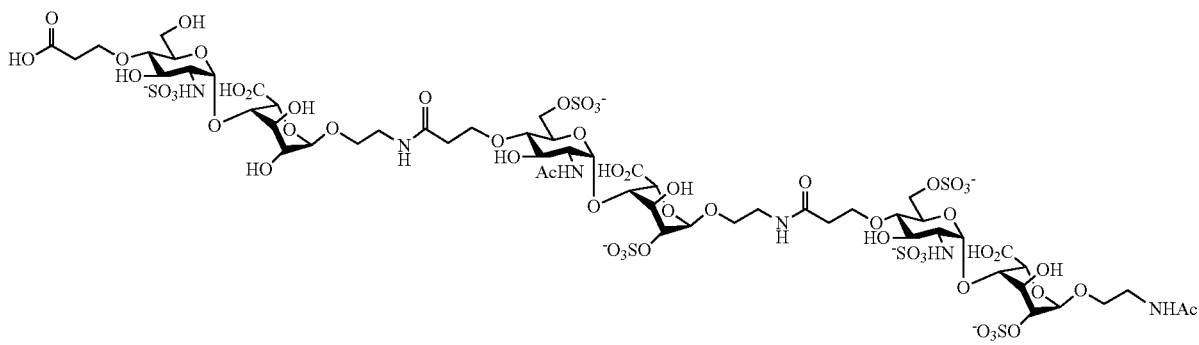

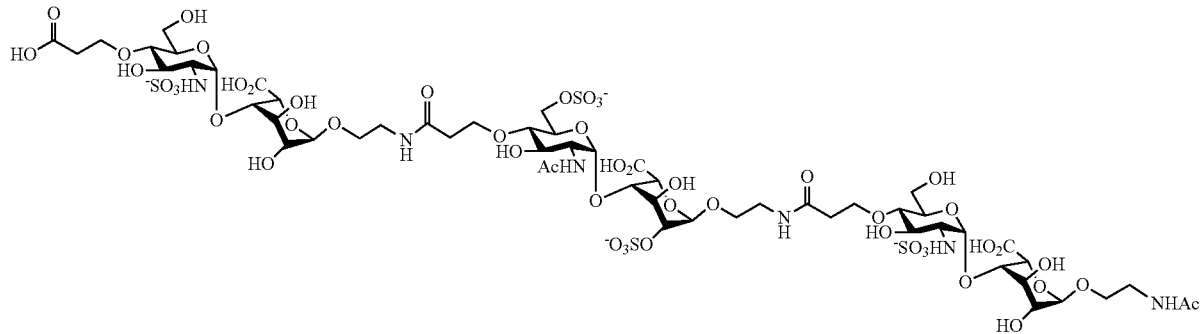

50p

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-acetamido-2-deoxy-6-O-sulfonato-1-thio-α-D-glucopyranoside)-(I-4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate) (50p)

The starting material (7.1 mg, 0.005 mmol) was treated according to the general procedures of NH-Fmoc deprotection, pseudo-hexasaccharide preparation with HATU and saponification of methyl esters to give compound 50p (4.4 mg, 51% for 3 steps). $^1$H NMR (500 MHz, D$_2$O) δ 5.19-5.04 (m, 2H; A-1, C-1), 4.96-4.92 (m, 2H; B-1, E-1), 4.74-4.71 (m, 2H; D-1, F-1), 4.45 (d, J=2.1 Hz, 1H), 4.40 (dd, J=4.4, 2.5 Hz, 2H), 4.12-4.00 (m, 5H), 3.95 (d, J=4.3 Hz, 2H), 3.91-3.73 (m, 12H), 3.71-3.44 (m, 19H), 3.38-3.17 (m, 10H), 3.07-3.01 (m, 3H), 2.47-2.36 (m, 6H), 1.89 (s, 3H), 1.81 (s, 3H). $^{13}$C NMR (125 MHz, D$_2$O) δ 174.65, 174.47, 174.15, 173.94, 100.65, 98.65, 95.66, 93.79, 77.94, 77.78, 77.71, 74.37, 74.22, 73.35, 70.92, 70.82, 70.73, 70.67, 70.59, 68.92, 68.54, 68.17, 68.13, 67.98, 67.40, 67.27, 66.79, 66.75, 66.59, 66.19, 63.57, 59.73, 59.70, 57.72, 53.05, 39.04, 38.93, 36.28, 36.21, 35.40, 22.09, 21.69. HRMS: m/z calc. for C$_{55}$H$_{86}$N$_6$O$_{51}$S$_4^{4-}$ [M]$^{4-}$: 443.5806; found: 443.5805.

N-Acetamidoethyl O-(4-O-carboxyethyl-2-deoxy-2-sulfoamino-1-thio-α-D-glucopyranoside)-(1→4)-O-(6-O-carboxyl-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate) (50q)

The starting material (6.9 mg, 0.005 mmol) was treated according to the general procedures of NH-Fmoc deprotection, pseudo-hexasaccharide preparation with HATU and saponification of methyl esters to give compound 50q (4.0 mg, 45% for 3 steps). $^1$H NMR (500 MHz, D$_2$O) δ 7.99-7.88 (m, 3H, NHAc), 5.14 (d, J=3.6 Hz, 1H; A-1), 4.96-4.91 (m, 4H; B-1, C-1, D-1, E-1), 4.39 (d, J=2.4 Hz, 2H; F-1), 4.32 (s, 1H), 4.15-4.02 (m, 9H), 3.96-3.73 (m, 16H), 3.69-3.42 (m, 16H), 3.38-3.19 (m, 11H), 3.05 (dd, J=10.4, 3.5 Hz, 2H), 2.46-2.31 (m, 6H), 1.89 (s, 6H), 1.83 (s, 3H). $^{13}$C NMR (125 MHz, D$_2$O) δ 174.63, 98.68, 98.54, 95.59, 93.55, 93.50, 78.13, 77.86, 77.75, 74.38, 73.74, 73.33, 70.85, 70.72, 70.57, 69.28, 68.85, 68.63, 68.18, 67.52, 66.86, 66.65, 66.46, 66.27, 63.89, 63.47, 59.81, 59.70, 57.66, 53.05, 39.03, 38.89, 36.28, 36.21, 22.12, 22.09, 21.72. HRMS: m/z calc. for C$_{57}$H$_{87}$N$_6$O$_{55}$S$_5^{5-}$ [M+Li$^+$]$^{4-}$: 475.5745; found: 475.5755.

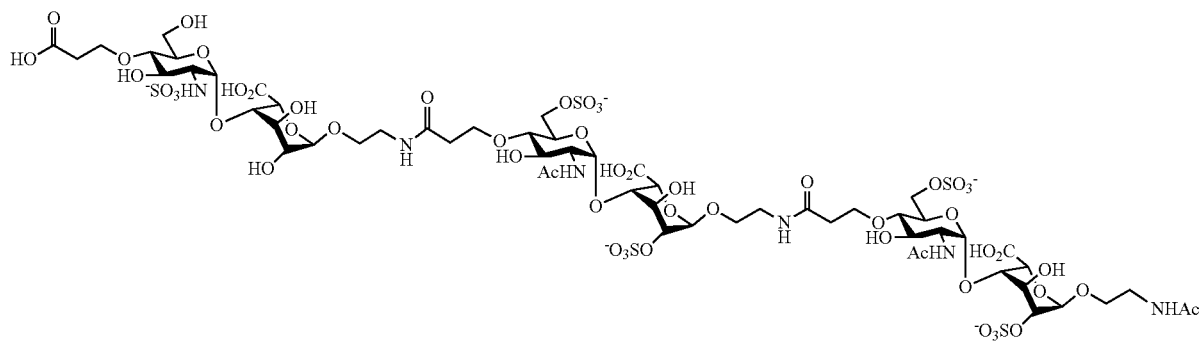

50q

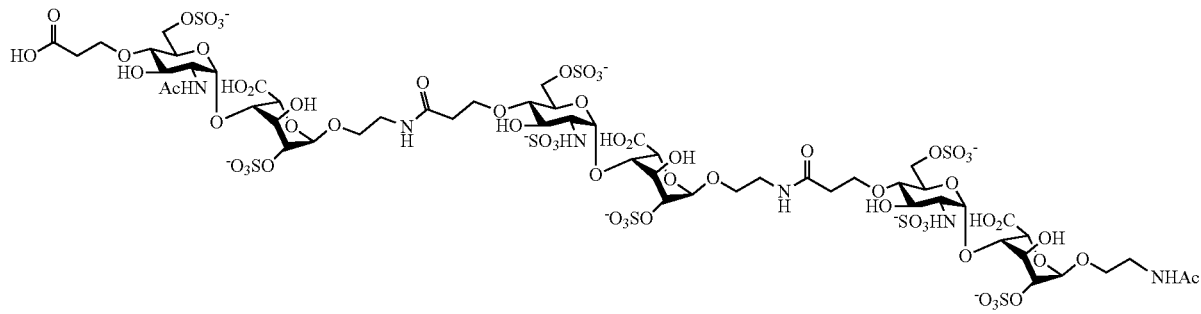

50r

N-Acetamidoethyl O-(2-acetamido-4-O-carboxyethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate) (50r)

The starting material (5.5 mg, 0.003 mmol) was treated according to the general procedures of NH-Fmoc deprotection, pseudo-hexasaccharide preparation with HBTU and saponification of methyl esters to give compound 50r (2.4 mg, 34% for 3 steps). $^1$H NMR (500 MHz, D$_2$O) δ 5.22 (d, J=3.3 Hz, 1H; A-1), 5.16 (d, J=3.6 Hz, 1H; C-1), 5.00 (s, 2H; E-1), 4.96-4.89 (m, 3H; B-1, D-1, F-1), 4.48-4.39 (m, 3H), 4.19-3.98 (m, 10H), 3.93-3.45 (m, 20H), 3.34-3.04 (m, 11H), 2.52-2.33 (m, 6H), 1.89 (s, 3H), 1.82 (s, 3H). $^{13}$C NMR (125 MHz, D$_2$O) δ 173.79, 171.71, 109.99, 99.08, 98.56, 97.59, 93.80, 91.93, 91.61, 77.81, 77.76, 77.61, 76.07, 75.96, 74.67, 74.22, 73.18, 72.85, 70.86, 70.79, 70.49, 68.91, 68.78, 68.37, 67.62, 66.93, 66.13, 57.72, 53.00, 45.75, 38.87, 57.72, 39.05, 38.87, 36.23, 22.10, 21.70. HRMS: m/z calc. for $C_{55}H_{82}N_6O_{63}S_8{}^{8-}$ [M+3Na$^+$]$^{5-}$: 431.8177; found: 431.8196.

N-Acetamidoethyl O-(2-acetamido-4-O-carboxyethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate) (50s)

The starting material (8.2 mg, 0.005 mmol) was treated according to the general procedures of NH-Fmoc deprotection, pseudo-hexasaccharide preparation with HBTU and saponification of methyl esters to give compound 50s (5.0 mg, 51% for 3 steps). $^1$H NMR (500 MHz, D$_2$O) δ 5.19 (d, J=3.6 Hz, 1H; A-1), 5.14 (d, J=3.7 Hz, 1H; C-1), 4.98 (d, J=2.1 Hz, 1H; E-1), 4.96-4.91 (m, 2H; B-1, D-1), 4.73-4.70 (m, 1H; F-1), 4.43 (d, J=2.0 Hz, 2H), 4.37 (d, J=2.4 Hz, 1H), 4.19-3.99 (m, 9H), 3.96 (t, J=3.9 Hz, 2H), 3.92-3.44 (m, 29H), 3.35-3.16 (m, 10H), 3.12-3.02 (m, 3H), 2.50-2.33 (m, 6H), 1.89 (s, 3H), 1.81 (s, 3H). $^{13}$C NMR (125 MHz, D$_2$O) δ 174.66, 174.16, 173.87, 100.63, 98.91, 98.56, 97.22, 95.62, 93.76, 78.01, 77.77, 77.61, 76.01, 75.29, 74.41, 73.18, 70.83, 70.79, 70.67, 70.56, 68.90, 68.81, 68.41, 68.24, 68.17, 68.09, 67.72, 67.48, 66.81, 66.73, 66.16, 66.13, 63.42, 59.74, 57.77, 57.72, 52.99, 39.05, 38.97, 38.87, 36.25, 36.18, 35.51, 22.09, 21.70. HRMS: m/z calc. for $C_{55}H_{84}N_6O_{57}S_6{}^{6-}$ [M+2Na$^+$]$^{4-}$: 494.5500; found: 494.5519.

50s

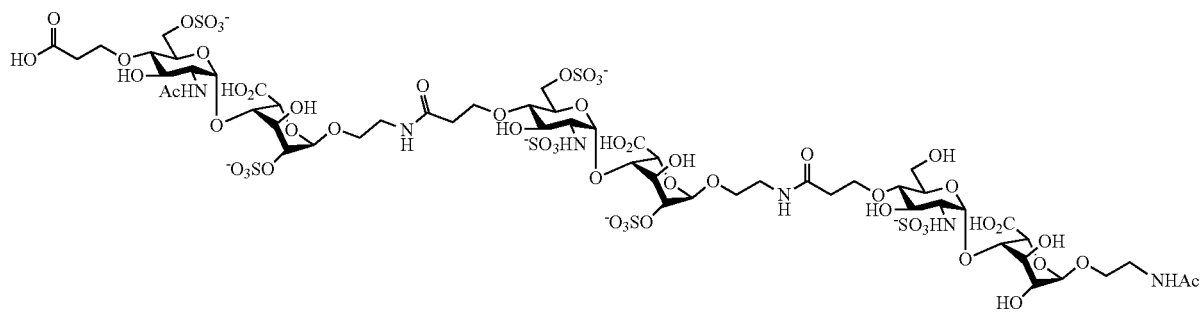

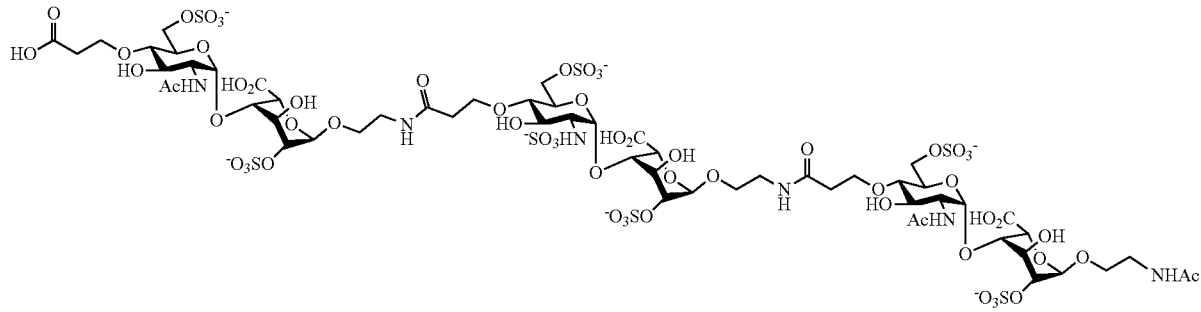

50t

N-Acetamidoethyl O-(2-acetamido-4-O-carboxy-ethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate) (50t)

The starting material (7.1 mg, 0.004 mmol) was treated according to the general procedures of NH-Fmoc deprotection, pseudo-hexasaccharide preparation with HBTU and saponification of methyl esters to give compound 50t (4.5 mg, 50% for 3 steps). $^1$H NMR (500 MHz, D$_2$O) δ 5.17 (d, J=3.5 Hz, 1H; A-1), 4.99 (s, 1H; C-1), 4.97-4.90 (m, 4H; B-1, D-1, E-1, F-1), 4.47-4.40 (m, 3H), 4.16 (dd, J=11.1, 2.7 Hz, 1H), 4.13-3.99 (m, 10H), 3.95-3.42 (m, 24H), 3.35-3.18 (m, 9H), 3.09 (dd, J=10.5, 3.5 Hz, 2H), 2.53-2.32 (m, 6H), 1.88 (s, 6H), 1.82 (s, 3H). $^{13}$C NMR (125 MHz, D$_2$O) δ 199.58, 177.66, 174.62, 174.16, 173.84, 98.77, 98.68, 98.56, 97.48, 93.80, 93.57, 77.84, 77.75, 77.61, 76.04, 74.83, 73.63, 73.17, 70.85, 70.78, 70.46, 68.90, 68.84, 68.58, 68.44, 68.36, 67.74, 66.89, 66.83, 66.75, 66.26, 66.13, 63.79, 63.43, 57.78, 53.00, 39.00, 38.93, 36.24, 36.18, 35.43, 22.09, 21.70. HRMS: m/z calc. for $C_{57}H_{85}N_6O_{61}S_7^{7-}$ [M+2Na$^+$]$^{5+}$: 419.8320; found: 419.8333.

N-Acetamidoethyl O-(2-acetamido-4-O-carboxy-ethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate) (50u)

The starting material (6.8 mg, 0.005 mmol) was treated according to the general procedures of NH-Fmoc deprotection, pseudo-hexasaccharide preparation with HBTU and saponification of methyl esters to give compound 50u (4.0 mg, 45% for 3 steps). $^1$H NMR (500 MHz, D$_2$O) δ 5.21 (d, J=3.5 Hz, 1H; A-1), 5.14 (d, J=3.7 Hz, 1H; C-1), 4.96-4.91 (m, 3H; E-1, B-1, D-1), 4.75-4.71 (m, 1H; F-1), 4.39 (dd, J=13.1, 2.4 Hz, 3H), 4.20-3.99 (m, 9H), 3.96 (t, J=3.8 Hz, 1H), 3.93-3.73 (m, 13H), 3.70-3.43 (m, 15H), 3.39-3.16 (m, 11H), 3.06 (m, 3H), 2.49-2.33 (m, 6H), 1.89 (s, 3H), 1.82 (s, 3H). $^{13}$C NMR (125 MHz, D$_2$O) δ 174.64, 173.89, 99.03, 98.60, 96.80, 95.65, 93.68, 78.02, 77.74, 77.66, 75.95, 74.31, 73.36, 70.84, 70.57, 68.86, 68.72, 68.57, 68.41, 68.19, 66.89, 66.74, 66.48, 66.15, 63.58, 59.74, 57.78, 57.74, 52.97, 39.05, 36.35, 35.78, 22.09, 21.69. HRMS: m/z calc. for $C_{55}H_{84}N_6O_{57}S_6^{6-}$ [M+Na$^+$]$^{5-}$: 391.0422; found: 391.0437.

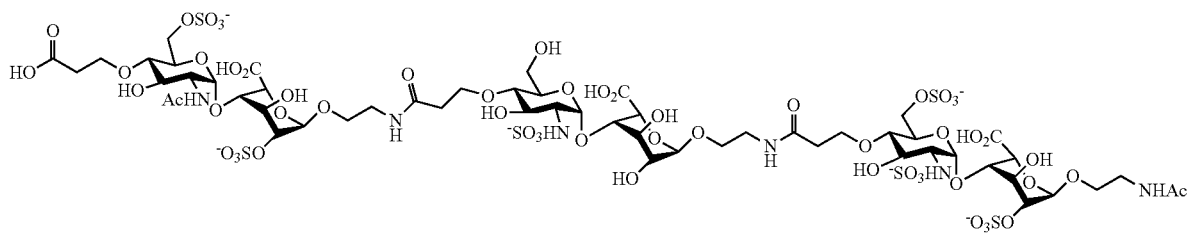

50u

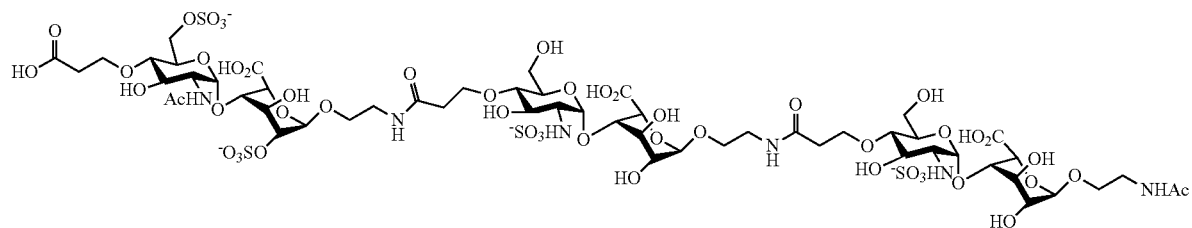

50v

N-Acetamidoethyl O-(2-acetamido-4-O-carboxyethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate) (50v)

The starting material (7.3 mg, 0.005 mmol) was treated according to the general procedures of NH-Fmoc deprotection, pseudo-hexasaccharide preparation with HBTU and saponification of methyl esters to give compound 50v (4.1 mg, 46% for 3 steps). $^1$H NMR (500 MHz, D$_2$O) δ 5.14 (s, 2H; A-1, C-1), 4.93 (s, 2H; B-1, E-1), 4.75-4.70 (m, 2H; D-1, F-1), 4.43-4.30 (m, 4H), 4.20-4.02 (m, 5H), 3.95 (q, J=4.1 Hz, 2H), 3.91-3.71 (m, 12H), 3.69-3.42 (m, 18H), 3.33-3.13 (m, 10H), 3.04 (dd, J=10.5, 3.7 Hz, 3H), 2.48-2.30 (m, 6H), 1.88 (s, 3H), 1.81 (s, 3H). $^{13}$C NMR (125 MHz, D$_2$O) δ 174.63, 173.93, 100.60, 98.60, 95.63, 95.58, 93.67, 78.00, 77.94, 77.65, 74.42, 74.33, 73.36, 70.79, 70.69, 70.50, 68.86, 68.54, 68.23, 68.10, 67.52, 66.69, 66.51, 66.14, 63.57, 59.74, 57.77, 57.74, 52.96, 39.05, 38.95, 36.25, 36.17, 22.08, 21.70. HRMS: m/z calc. for $C_{55}H_{86}N_6O_{51}S_4^{4-}$ [M]$^{4-}$: 443.5806; found: 443.5793.

N-Acetamidoethyl O-(2-acetamido-4-O-carboxyethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-deoxy-2-sulfoamino-1-thio-α-D-glucopyranoside)-(1→4)-O-(6-O-carboxyl-thio-α-L-idopyranosiduronate)-1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranoosiduronate) (50w)

The starting material (7.0 mg, 0.005 mmol) was treated according to the general procedures of NH-Fmoc deprotection, pseudo-hexasaccharide preparation with HBTU and saponification of methyl esters to give compound 50w (4.5 mg, 50% for 3 steps). $^1$H NMR (500 MHz, D$_2$O) δ 5.14 (d, J=3.7 Hz, 1H; A-1), 4.95-4.90 (m, 4H; B-1, C-1, D-1, E-1), 4.75-4.71 (m, 1H; F-1), 4.42-4.35 (m, 3H), 4.18-4.01 (m, 8H), 3.96 (t, J=3.7 Hz, 1H), 3.92-3.73 (m, 13H), 3.70-3.44 (m, 14H), 3.37-3.16 (m, 10H), 3.04 (dd, J=10.4, 3.6 Hz, 1H), 2.51-2.30 (m, 6H), 1.88 (s, 6H), 1.82 (s, 3H). $^{13}$C NMR (125 MHz, D$_2$O) δ 174.63, 173.87, 100.56, 98.65, 98.60, 95.66, 93.68, 93.56, 78.00, 77.75, 77.65, 74.32, 73.61, 73.35, 70.84, 70.80, 70.72, 70.58, 68.85, 68.51, 68.16, 66.86, 66.74, 66.49, 66.14, 63.78, 63.57, 59.73, 57.74, 53.04, 52.97, 39.00, 36.29, 36.16, 35.67, 22.07, 21.70. HRMS: m/z calc. for $C_{57}H_{87}N_6O_{55}S_5^{5-}$ [M]$^{5-}$: 379.0565; found: 379.0584.

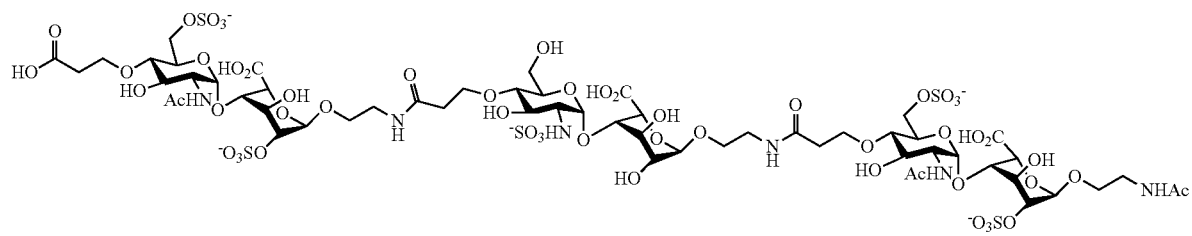

50w

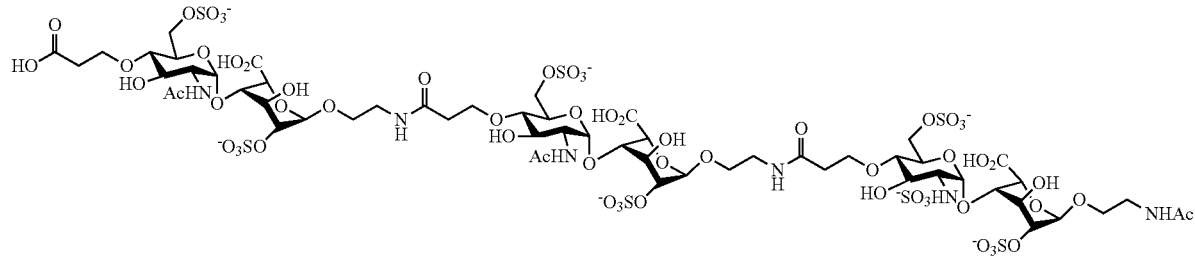

50x

N-Acetamidoethyl O-(2-acetamido-4-O-carboxyethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-thio-α-L-idopyranosiduronate)-(1→4)-O-(2-deoxy-2-sulfoamino-6-O-sulfonato-1-thio-α-D-glucopyranoside)-(1→4)-O-(6-O-carboxyl-2-O-sulfonato-1-thio-α-L-idopyranosiduronate) (50x)

The starting material (5.3 mg, 0.003 mmol) was treated according to the general procedures of NH-Fmoc deprotection, pseudo-hexasaccharide preparation with HBTU and saponification of methyl esters to give compound 50x (1.0 mg, 15% for 3 steps). $^1$H NMR (500 MHz, D$_2$O) δ 5.24 (d, J=3.6 Hz, 1H; A-1), 4.92 (d, J=3.4 Hz, 4H; C-1, B-1, D-1, E-1), 4.40-4.32 (m, 3H), 4.16-3.97 (m, 10H), 3.95-3.73 (m, 12H), 3.70-3.43 (m, 11H), 3.39-3.13 (m, 11H), 2.42-2.31 (m, 6H), 1.85 (s, 7H). HRMS: m/z calc. for C$_{57}$H$_{85}$N$_6$O$_{61}$S$_7^{7-}$ [M+3Na$^+$]$^{4-}$: 530.5373; found: 530.5389.

N-Acetamidoethyl O-(2-acetamido-4-O-carboxyethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-thio-α-L-idopyranosiduronate)-(1→4)-O-(2-deoxy-2-sulfoamino-1-thio-α-D-glucopyranoside)-(1→4)-O-(6-O-carboxyl-1-thio-α-L-idopyranosiduronate) (50y)

The starting material (6.7 mg, 0.004 mmol) was treated according to the general procedures of NH-Fmoc deprotection, pseudo-hexasaccharide preparation with HBTU and saponification of methyl esters to give compound 50y (4.4 mg, 55% for 3 steps). $^1$H NMR (500 MHz, D$_2$O) δ 5.13 (d, J=3.8 Hz, 1H; A-1), 4.92 (s, 3H; B-1, C-1, E-1), 4.73-4.69 (m, 1H, D-1), 4.46-4.32 (m, 3H), 4.17-3.99 (m, 7H), 3.94 (t, J=3.9 Hz, 1H), 3.91-3.70 (m, 11H), 3.69-3.43 (m, 11H), 3.34-3.14 (m, 8H), 3.03 (dd, J=10.5, 3.6 Hz, 1H), 2.50-2.31 (m, 6H), 1.87 (s, 4H), 1.80 (s, 3H). $^{13}$C NMR (125 MHz, D$_2$O) δ 174.64, 173.91, 100.61, 98.63, 98.55, 95.61, 93.74, 93.65, 77.96, 77.78, 77.59, 74.38, 73.37, 73.20, 70.81, 70.66, 70.54, 68.89, 68.33, 68.20, 67.45, 66.73, 66.11, 63.53, 63.42, 59.71, 57.71, 52.98, 39.03, 38.92, 36.19, 35.39, 22.07, 21.68. HRMS: m/z calc. for C$_{57}$H$_{87}$N$_6$O$_{55}$S$_5^{5-}$ [M]$^{5-}$: 379.0565; found: 379.0574.

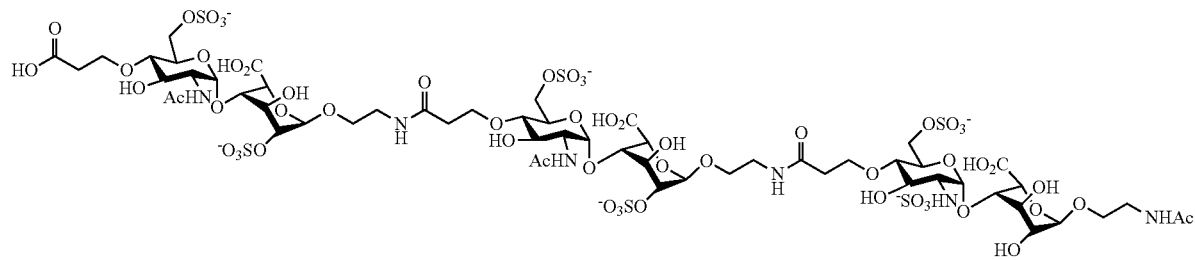

50y

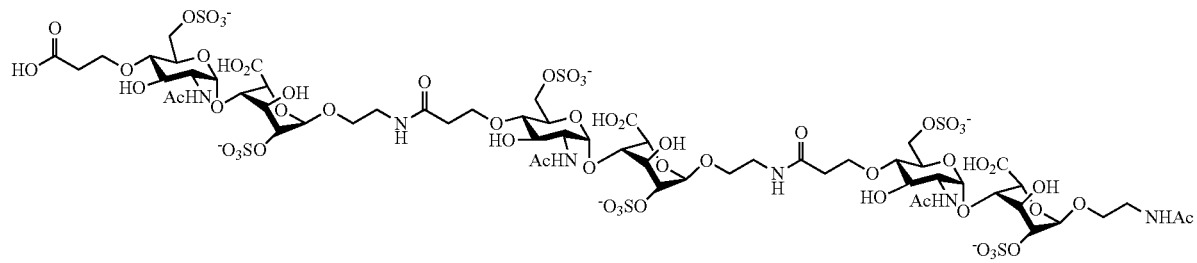

50z

N-Acetamidoethyl O-(2-acetamido-4-O-carboxyethyl-2-deoxy-6-O-sulfonato-1-thio-α-D-glucopyranoside)-(1→4)-O-(6-O-carboxyl-2-O-sulfonato-1-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-thio-α-L-idopyranosiduronate)-(1→4)-O-(2-acetamido-2-deoxy-6-O-sulfonato-1-thio-α-D-glucopyranoside)-(1→4)-O-(6-O-carboxyl-2-O-sulfonato-1-thio-α-L-idopyranosiduronate) (50z)

The starting material (8.0 mg, 0.005 mmol) was treated according to the general procedures of NH-Fmoc deprotection, pseudo-hexasaccharide preparation with HBTU and saponification of methyl esters to give compound 50z (4.5 mg, 44% for 3 steps). $^1$H NMR (500 MHz, $D_2O$) δ 4.98-4.90 (m, 6H; A-1, B-1, C-1, D-1, E-1, F-1), 4.42-4.35 (m, 3H), 4.17-4.01 (m, 12H), 3.93-3.74 (m, 15H), 3.70-3.45 (m, 11H), 3.36-3.21 (m, 10H), 2.44-2.31 (m, 6H), 1.89 (s, 8H), 1.83 (s, 3H). $^{13}$C NMR (125 MHz, $D_2O$) δ 174.67, 170.33, 109.99, 98.68, 98.57, 93.63, 77.86, 73.74, 73.35, 70.86, 69.21, 68.87, 68.67, 66.87, 66.65, 66.28, 63.90, 63.55, 53.05, 52.91, 39.03, 38.89, 36.22, 22.12, 22.09, 21.72. HRMS: m/z calc. for $C_{59}H_{88}N_6O_{59}S_6^{6-}$ [M]$^{6-}$: 336.0405; found: 336.0412.

Example 3: Biological Studies of Pseudo-hexasaccharide Heparin Mimetics

Bio-Layer Interferometry (BLI) Competition Assay on FGF-2-heparin interaction With the successful preparation of the library of heparin mimetics, we explored whether the library of pseudo-hexasaccharides could mimic the natural heparin oligosaccharides. We examined the binding with FGF-2 that is essential for normal and cancer biology (*Oncotarget* 2016, 7, 44735-44762). FGF-2 is one of the most extensively studied heparin-binding proteins, which can mediate cell growth, differentiation, survival, and patterning (*Nat. Rev. Drug Discovery* 2009, 8, 235-253). FGF-2 has low and high molecular weight isoforms, and low molecular weight FGF-2 binds with both FGFR and HSPGs on cell surface (*Proc. Natl. Acad. Sci. U.S.A* 1989, 86, 3978-3981). The formation of the FGF-2-FGFR-HSPGs ternary structure activates the downstream signaling pathways (Biochemistry 2004, 43, 4724-4730). FGF-2-FGFR1 complexes are also found in the nuclear matrix, promoting cell proliferation (*Mol. Biol. Cell* 2009, 20, 2401-2412). Dysregulation of FGF-2 signaling is associated with aggressive cancer phenotypes, enhanced chemotherapy resistance, and many acquired forms of cancers (*Curr. Cancer Drug Targets* 2009, 9, 639-651; Wiley Interdiscip. Rev.: *Dev. Biol.* 2015, 4, 215-266; *Endocr.-Relat. Cancer* 2000, 7, 165-97).

The binding studies were performed by competition bio-layer interferometry (BLI). Before testing the pseudo-hexasaccharides, heparin-FGF-2 interaction was studied. Biotinylated heparin (27.5 nM) was immobilized on streptavidin (SA) biosensors, and various concentrations of FGF-2 were prepared as analytes. The titration curves fitted well to a 1:1 binding mode, and strong binding was observed as expected with $K_D$ values of 2.7 nM (FIG. 1).

Figure 2A:
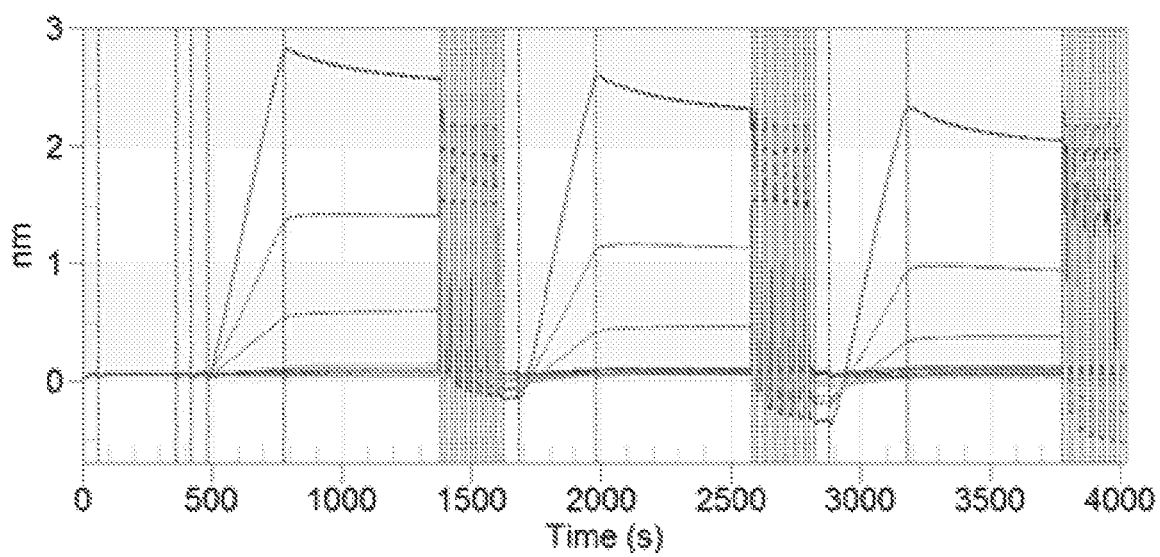
FIGS. 2A-2C show sensorgrams of competition Bio-Layer Interferometry (BLI) as described in Example 3.
Figure 2B:
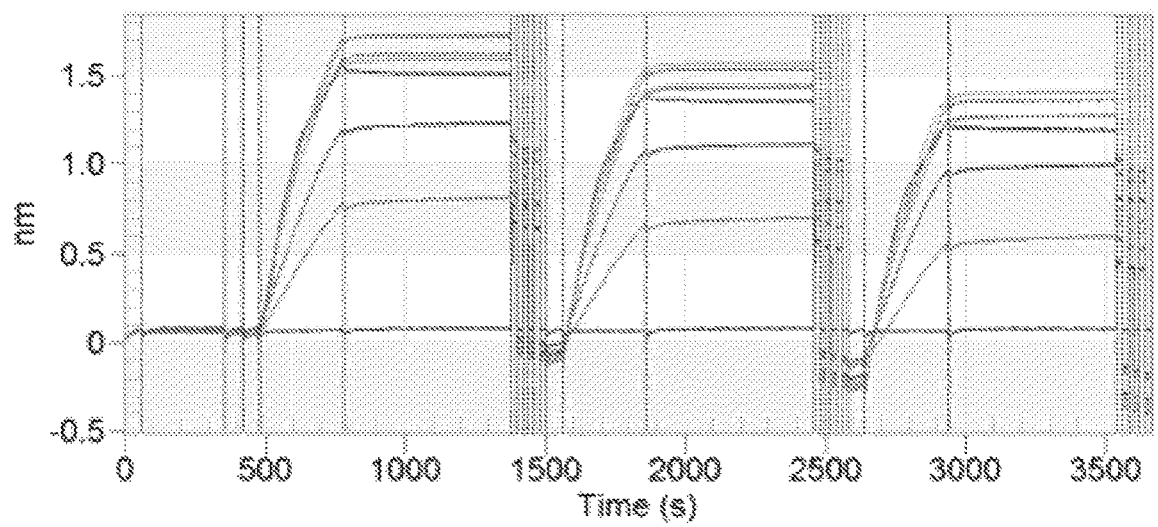
Figure 2C:
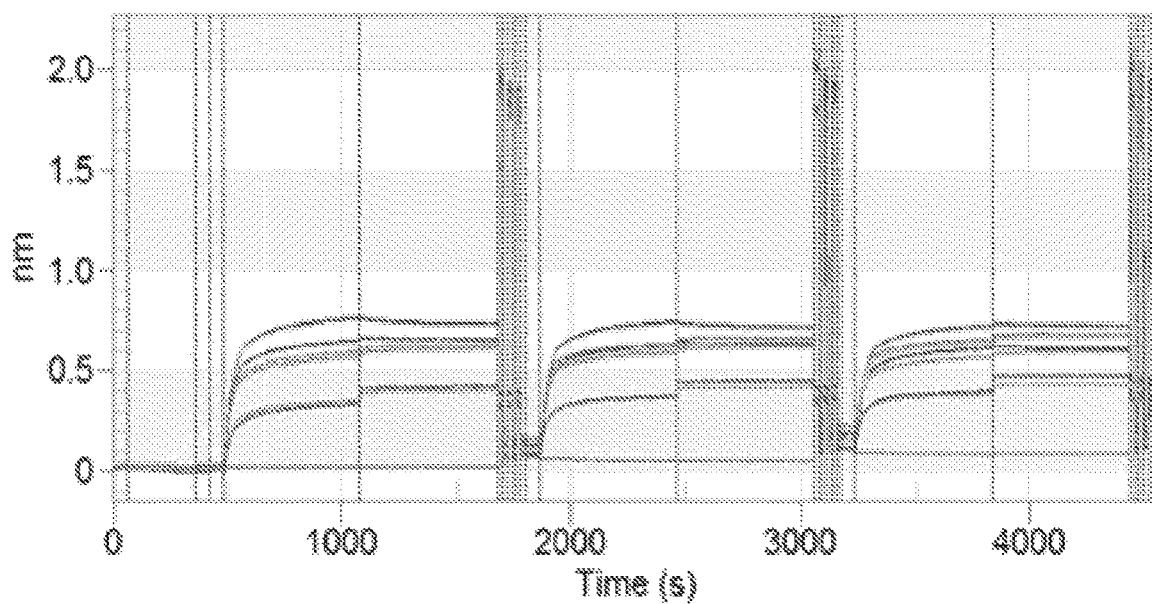

Next, heparin, compounds 50k, and fondaparinux were selected as inhibitors for competition BLI. Different concentrations of each inhibitor were mixed with FGF-2 (75 nM), and biotinylated heparin was used as the ligand (FIG. 2). Heparin showed potent inhibitory activity against heparin-FGF-2 interaction, and ~80% inhibition was achieved for 6.5 nM heparin. However, both compound 50k and fondaparinux only exhibited inhibitory activity at high concentrations (>4 uM).

Binding Studies of Pseudo-Hexasaccharides and FGF-2 Using Surface Plasmon Resonance (SPR)

Figure 3A:
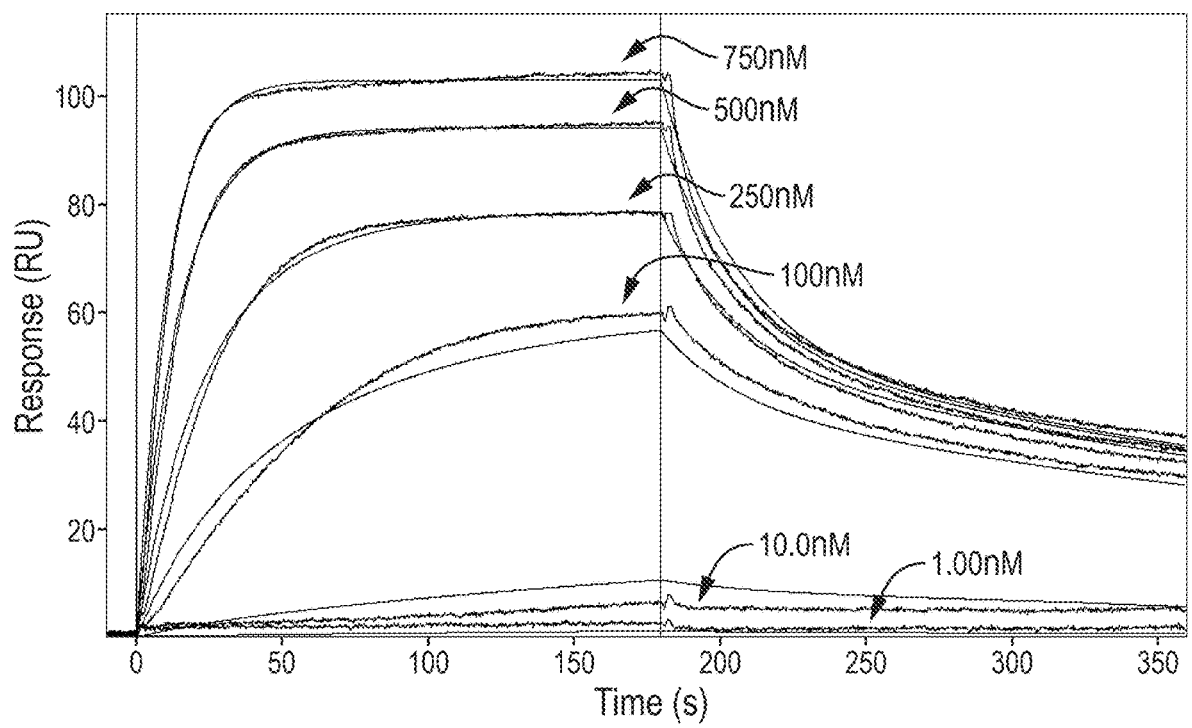
FIGS. 3A-3C show SPR sensorgrams of FGF-2 and compounds 50, 50z, and 50m interaction at different concentrations as described in Example 3.
Figure 3B:
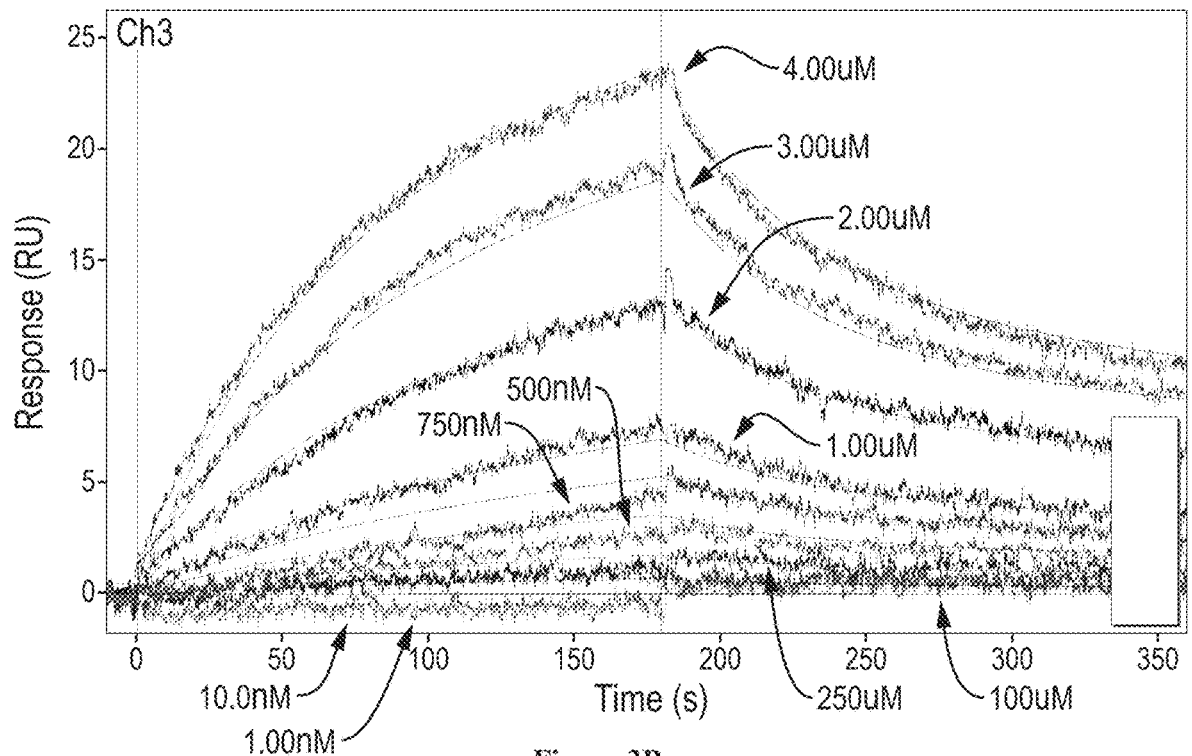
Figure 3C:
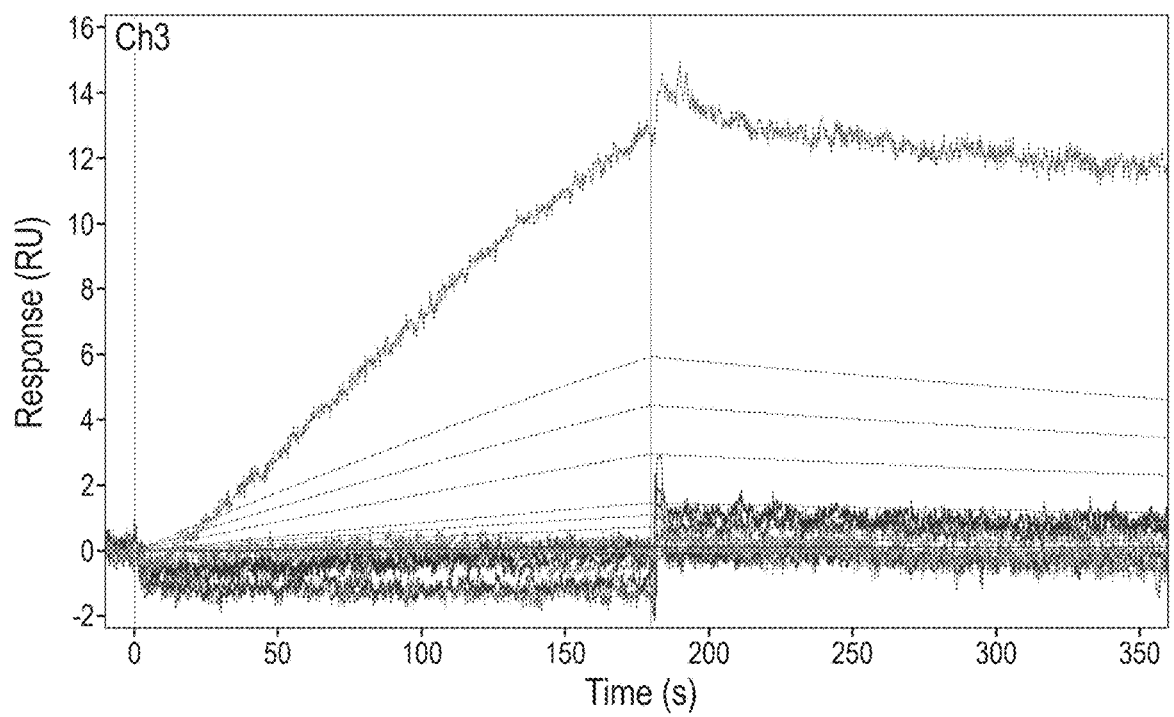

Since the pseudo-hexasaccharides did not exhibit potent inhibitory activity against heparin-FGF-2 binding through competition experiments, the direct binding studies were performed by surface plasmon resonance (SPR). FGF-2 was immobilized on CDH sensor chip surface through EDC/NHS coupling, and fully sulfated (50), O-sulfated (50z) and N-sulfated (50m) pseudo-hexasaccharides were selected as analytes. 50 and 50z showed strong and moderate binding to FGF-2 with $K_D$ values of 19.6 and 940 nM respectively, and the only weak signal was observed for 50m (FIGS. 3A-3C). The SPR results correlated well with that of heparin hexasaccharides (36, 51, 52) (*Chem. Eur. J.* 2006, 12 (34), 8664-8686). Fully sulfated hexasaccharide 36 showed comparable FGF-2 binding ability as that of heparin through microarray assay, and no significant binding signal was observed for N-sulfated hexasaccharide 52. The pseudo-hexasaccharides also exhibited much stronger FGF-2 binding ability in comparison to that of heparin di- and tetra-saccharides (54, 53) (Scheme 8) (*ACS Chem. Biol.* 2014, 9, 1712-1717; *J. Am. Chem. Soc.* 2017, 139, 9534-9543). 50 is about 20 times more potent than the strongest tetrasaccharide binder 53 based on $K_D$ values acquired from SPR assay.

Figure 4:
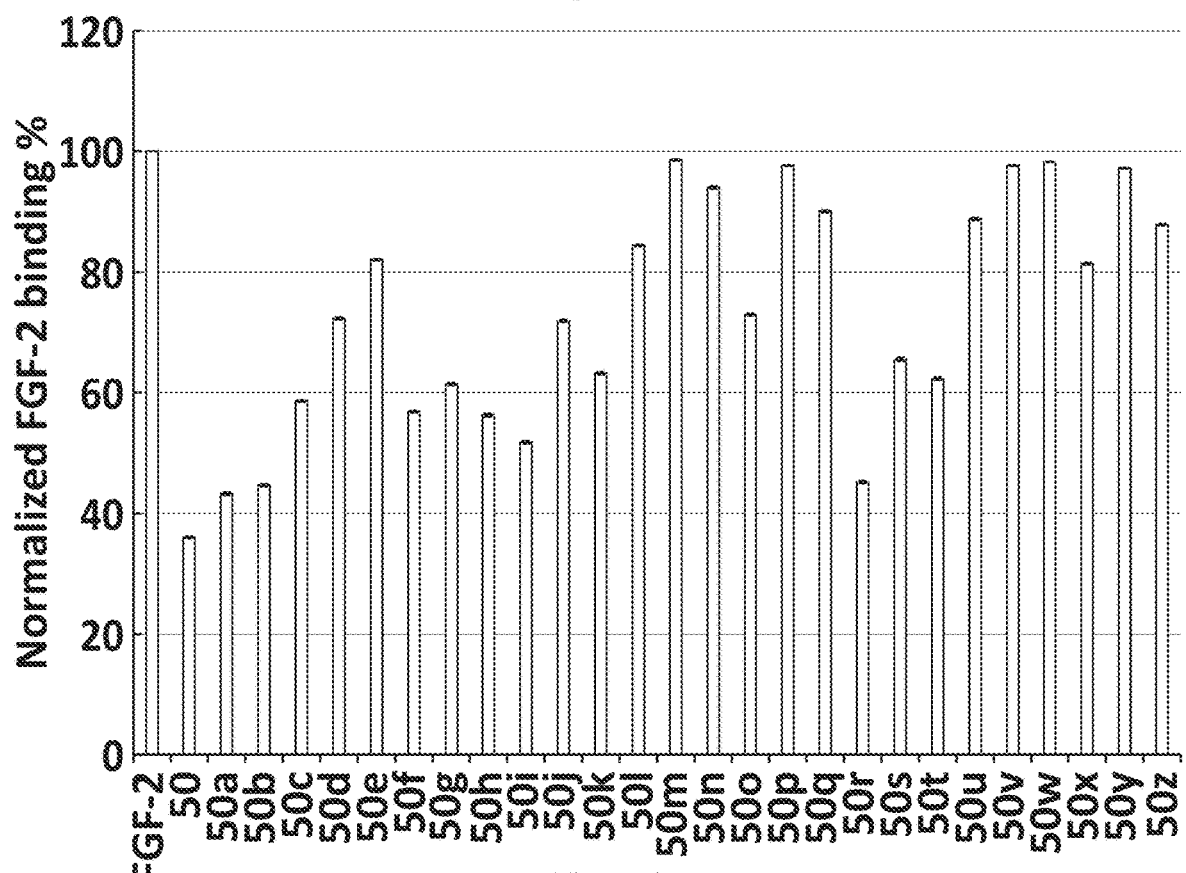
FIG. 4 shows measurement of inhibition of 27 pseudo-hexasaccharides on FGF-2-heparin interaction using competition SPR as described in Example 3.
Figure 5A:
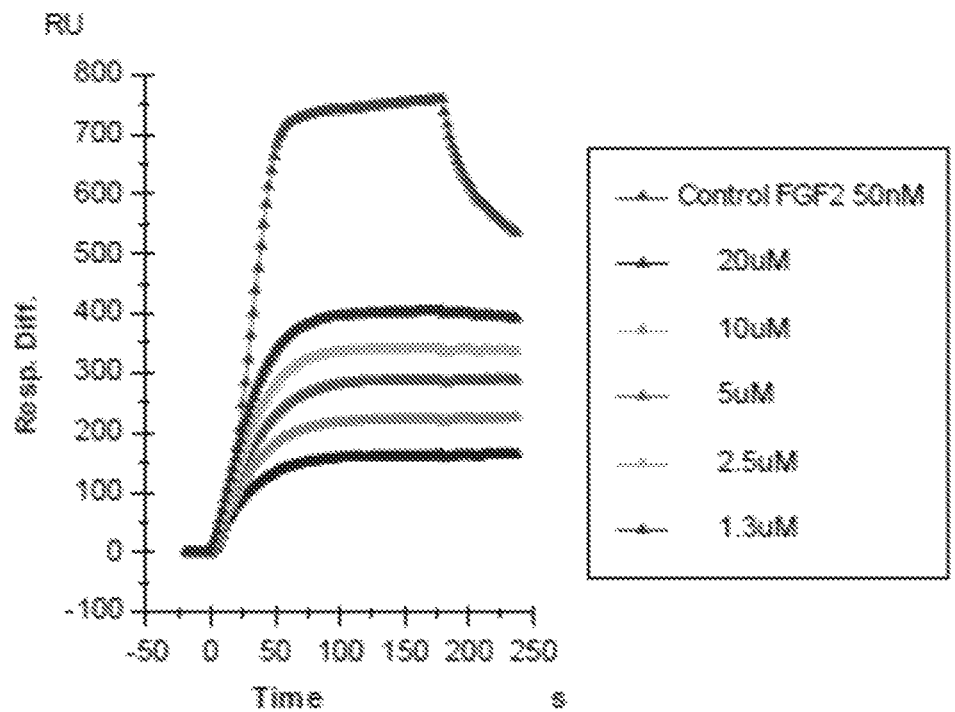
FIGS. 5A-5D shows competition SPR for $IC_{50}$ measurements for pseudo-hexasaccharides 50 (FIG. 5A), 50a (FIG. 5B), 50b (FIG. 5C), and 50r (FIG. 5D).
Figure 5B:
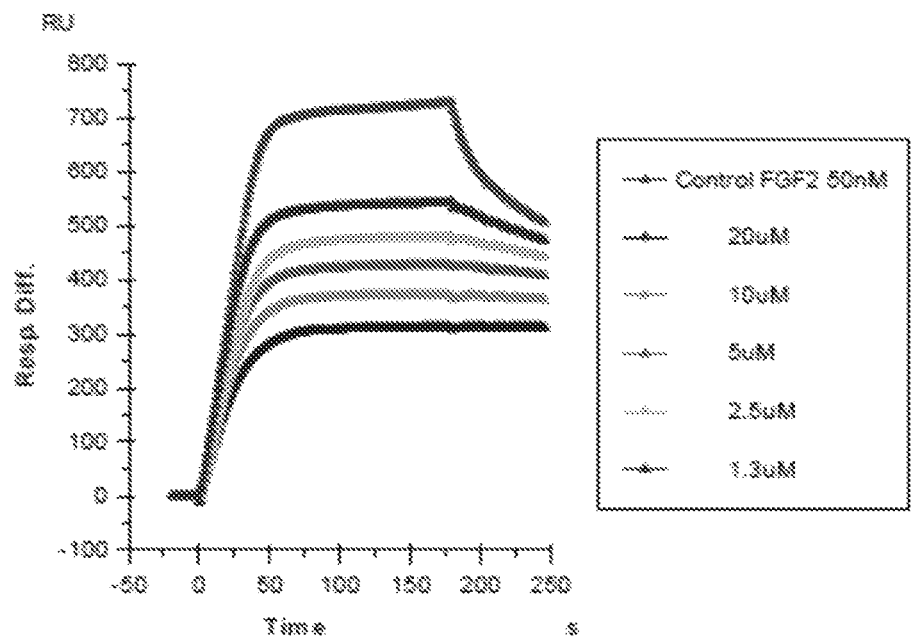
Figure 5C:
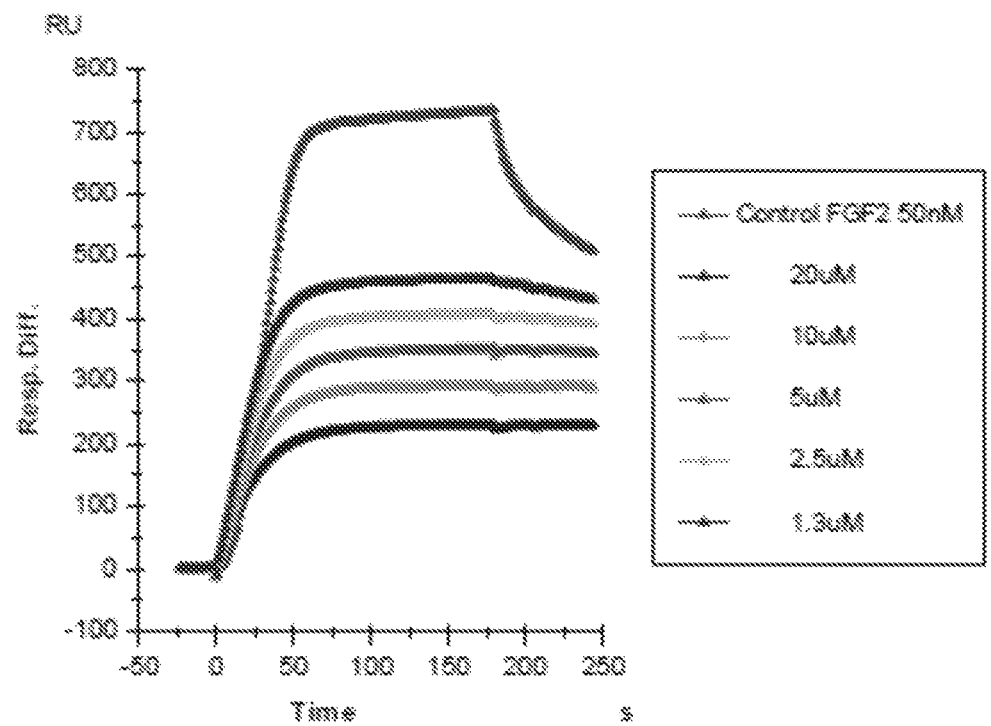
Figure 5D:
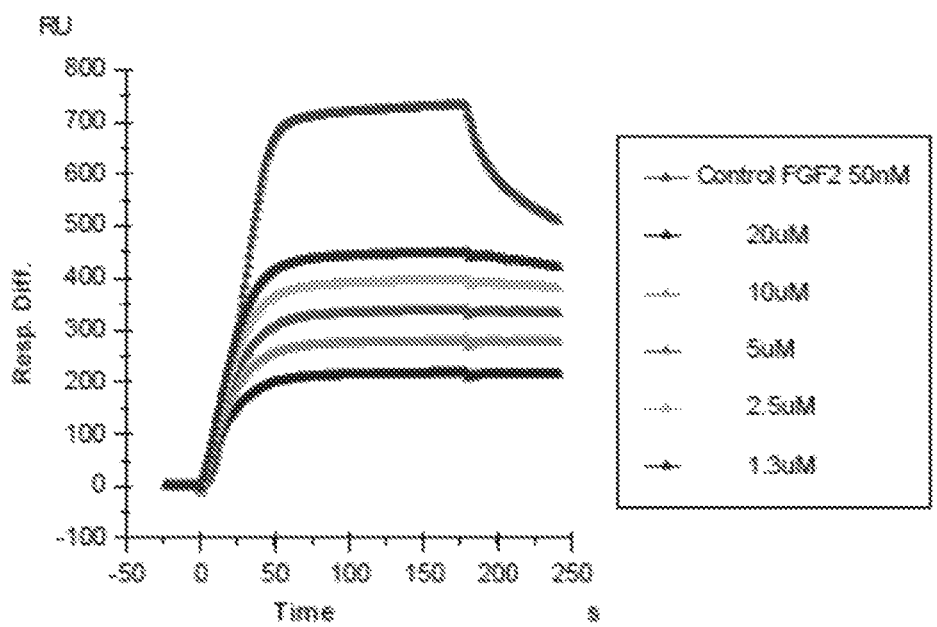

Scheme 8. Heparin hexa-, tetra- and disaccharides.
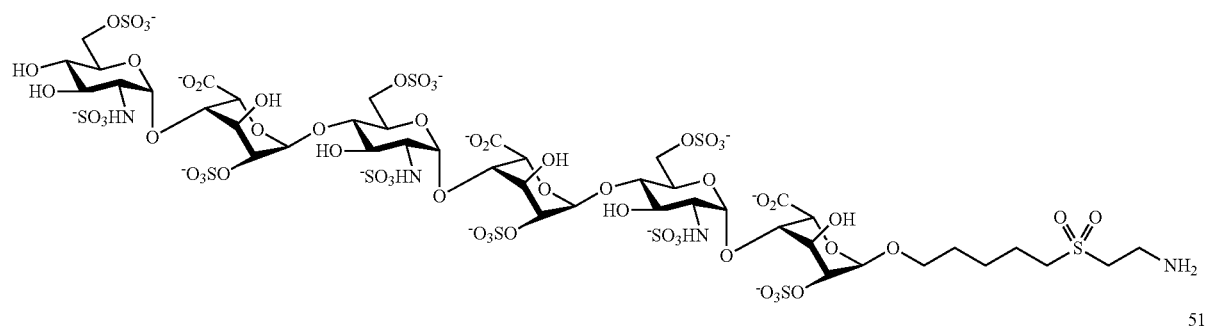
36
51
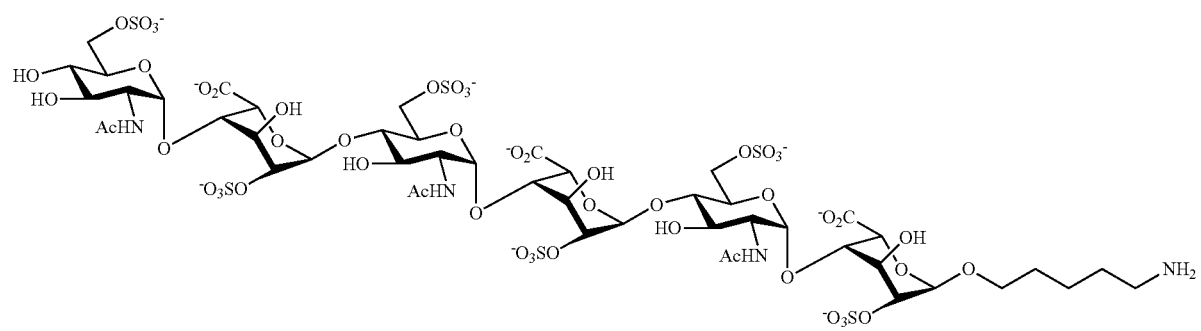
52
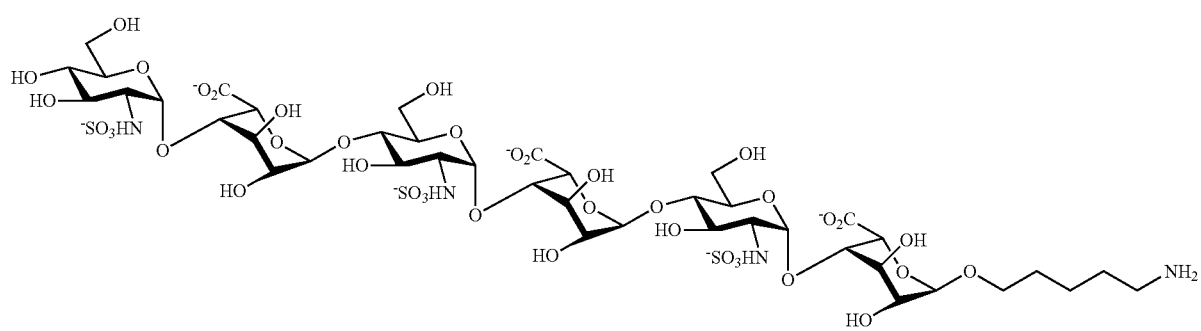
53
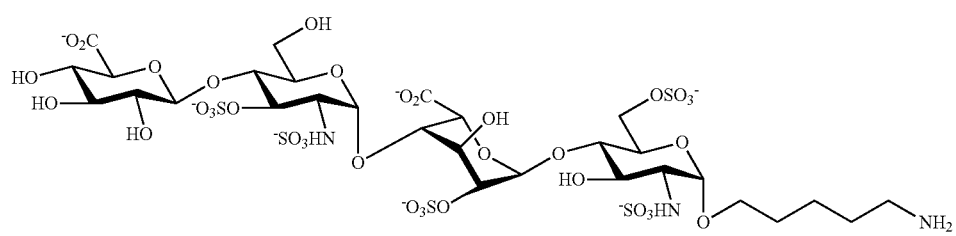
54
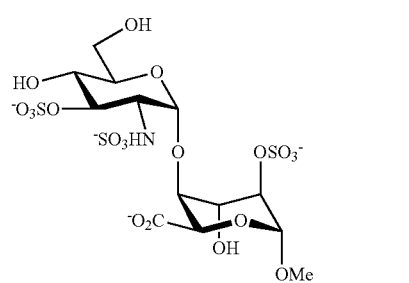
65
In order to gain more insights into the structure-activity relationship between heparin and FGF-2, the competition assay was performed by the Linhardt group (FIG. 4). Biotinylated heparin was immobilized on the biosensor, and 27 pseudo-hexasaccharides (10 uM) was mixed with FGF-2 (50 nM) individually. As expected, the fully sulfated pseudo-hexasaccharide (50) showed the most potent inhibitory activity. Compounds with more sulfate groups showed relatively higher potency. Among 27 pseudo-hexasaccharides, the best inhibitors (50, 50a, 50b, 50i, 50r), which showed about 50-65% inhibition of binding between FGF-2 and heparin contain successive fully sulfated disaccharide modules. For $IC_{50}$ measurements, biotinylated heparin was immobilized on the SA sensor chip as described above, and FGF-2 (50 nM) was pre-mixed with different concentrations of pseudo-hexasaccharides. Fully sulfated pseudo-hexasaccharide 50 displayed the highest $IC_{50}$ value of 1.7 uM, and 50a, 50b, and 50r also exhibited potent competitive effect ($IC_{50}$=10.8, 4.0, and 3.5 uM, respectively) (FIGS. 5A-5D). According to competition SPR results, successive fully sulfated disaccharide modules are required for potent competitive activity.

Heparanase Inhibitory Activity Tests Through the Colorimetric Assay

Next, we investigated the anti-tumor activity of pseudo-hexasaccharides by inhibiting heparanase enzyme that is strongly related to tumor formation, including tumor initiation, growth and metastasis (*Trends Biochem. Sci.* 2018, 43, 18-31). Proheparanase was synthesized on the endoplasmic reticulum (ER) and transported to the Golgi apparatus and secreted into the extracellular space. Proheparanase may interact with receptors on the cell surface and upregulate the expression of VEGF, resulting in cell proliferation. On the other hand, proheparanase could also be activated by internalization through binding with cell surface syndecans, and active heparanase may be translocated into the nucleus and secreted into the ECM (*Trends Biochem. Sci.* 2009, 34, 511-519; Transcription 2012, 3, 130-145). Heparanase is the sole endoglycosidase that degrades HS side chains of HSPGs. The cleavage of HS releases the sequestered growth factors and degrades the structural integrity of the basement membrane and ECM. Thus, heparanase is strongly related to tumor growth and metastasis. Since heparin and HS have the same backbone arrangement of glucosamine and uronic acid disaccharide repeating units, heparin was considered as a potential potent heparanase inhibitor (*Exp. Hematol.* 2016, 44, 1002-1012; *iScience* 2019, 15, 360-390; *Future Med. Chem.* 2016, 8, 647-680).

Figure 6:
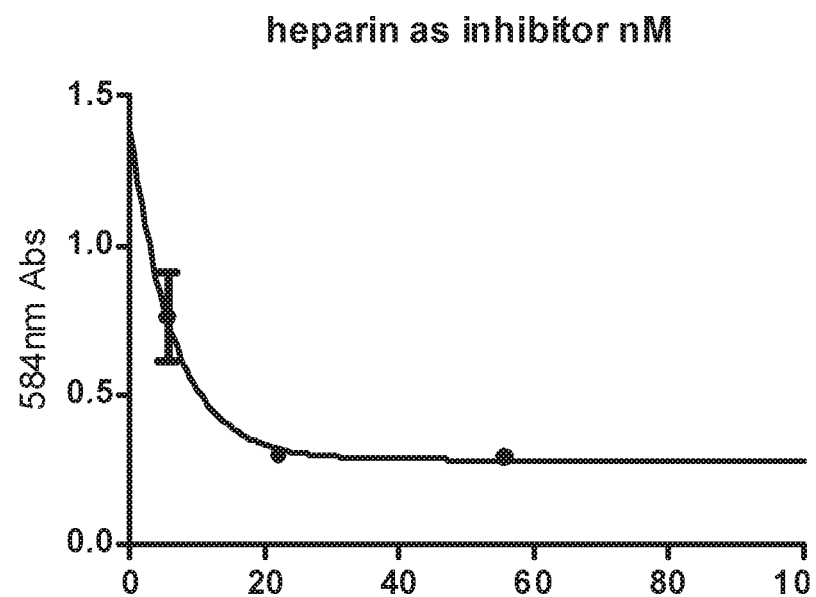
FIG. 6 shows inhibition of heparanase by heparin as described in Example 3.
Figure 7A:
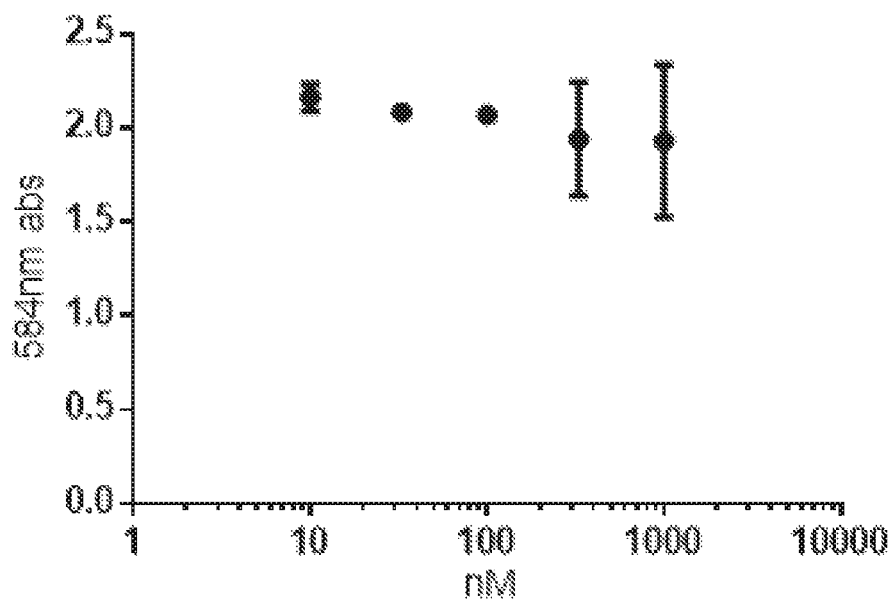
FIGS. 7A and 7B show inhibition of heparanase by compounds 50a (FIG. 7A) and 50f (FIG. 7B). Compound 50a was studied at 10-1000 nM. Compound 50f was studied at 0.1 and 10 uM.
Figure 7B:
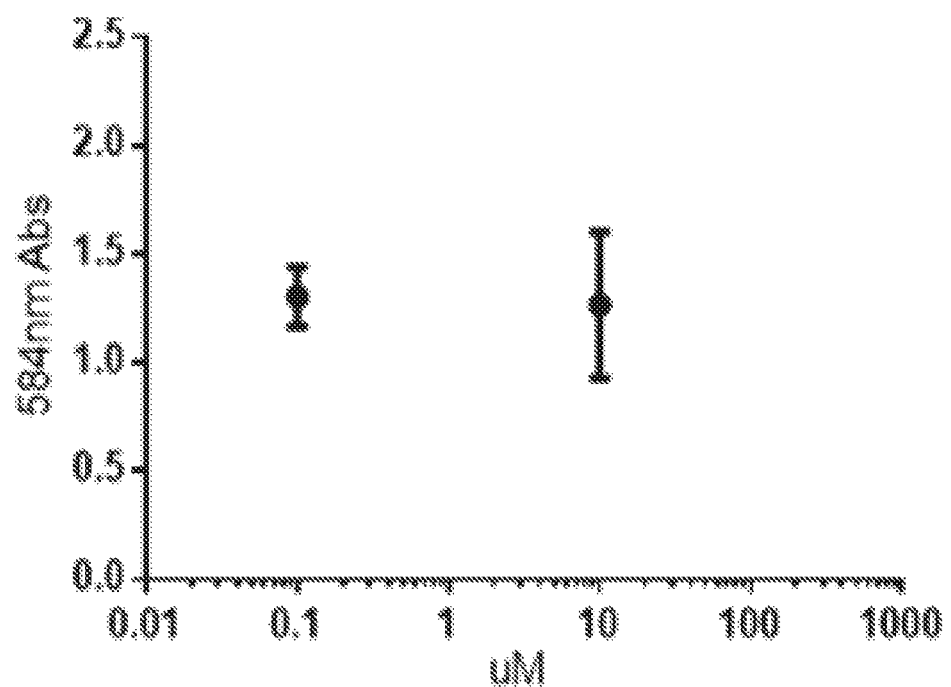

Heparanase activity was measured by a colorimetric assay. Fondaparinux 55 was used as the substrate, which would be cleaved by heparanase, and the appearance of disaccharide product 56 was measured by the tetrazolium salt WST-1 58 (Scheme 9) (*Anal. Biochem.* 2010, 396, 112-116). Heparin exhibited potent heparanase activity, and 100% inhibition was achieved with ~20 nM (FIG. 6). However, our pseudo-hexasaccharides did not exhibit significant heparanase inhibitory activity (FIGS. 7A and 7B). Compound 50a and 50f were added up to 1 and 10 uM, respectively, and the absorbance did not decrease dramatically.

Scheme 9. Heparanase colorimetric assay.

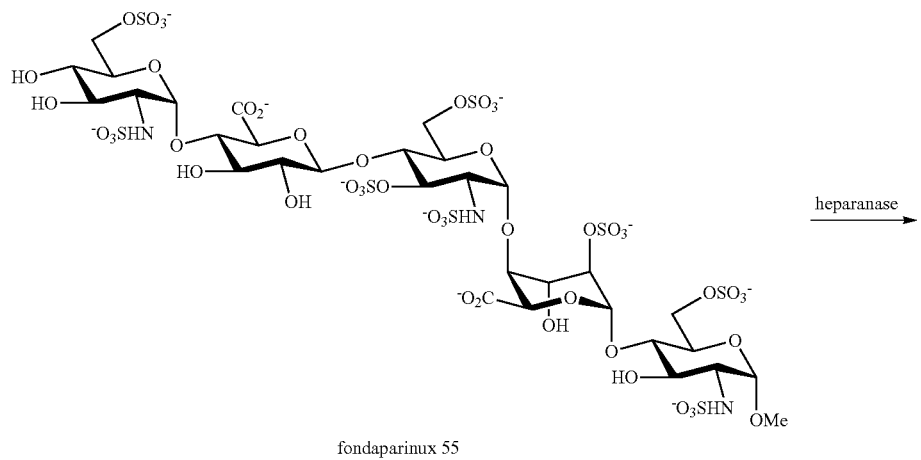

fondaparinux 55

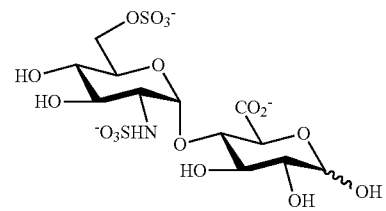

56

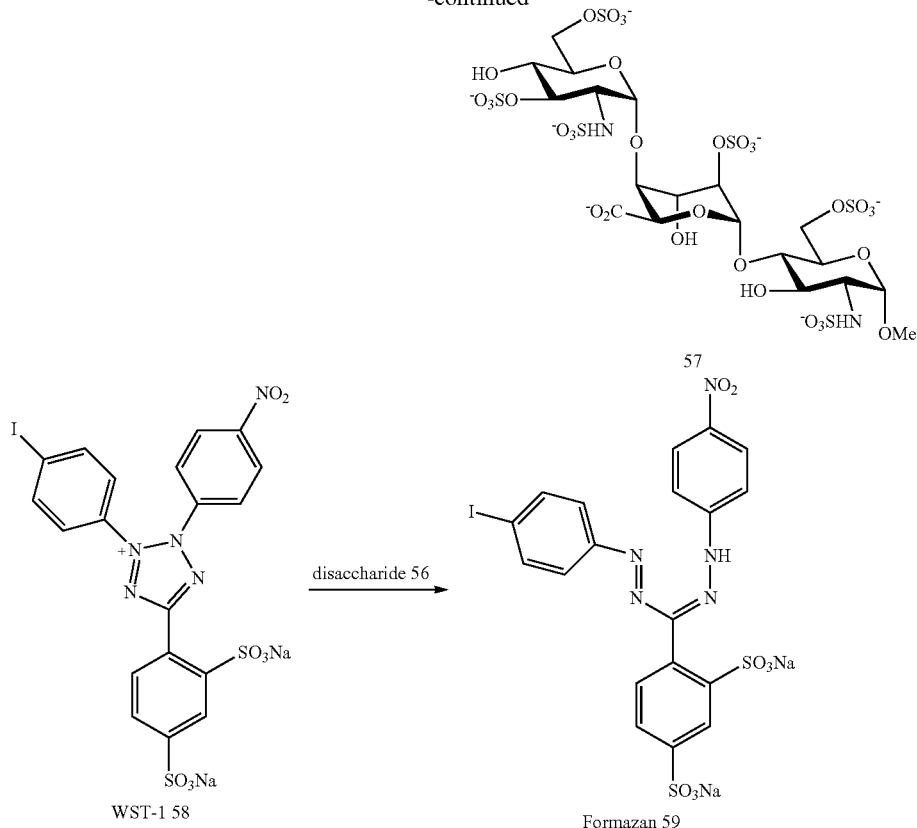

Experimental Section
Bio-Layer Interferometry (BLI).

Samples or buffers were dispensed into 96-well microtiter plates (Millipore, Billerica, MA) at a volume of 200 uL per well. The operating temperature was maintained at 30° C. Streptavidin-coated biosensor tips (FortéBio, Inc., Molecular Devices) were pre-wetted with PBS buffer for 10 min, and biotinylated heparin (27.5 nM) was loaded for 5 min. Various concentrations of analytes were then immobilized on the biosensor tips while agitating for 10 min at 1000 rpm, and biosensors was dipped into PBS buffer for 10 min for dissociation. NaCl solution (2.0 M) was employed for regeneration to achieve baseline status. All measurements were performed using 0.05% surfactant P-20 PBS buffer.

Surface Plasmon Resonance (SPR).

FGF-2 was immobilized on sensor chip by primary amine coupling reaction. The surface of a CDH sensor chip (ForteBio, Inc., Molecular Devices, USA) was activated using freshly mixed N-hydroxysuccimide (NHS; 0.05 M) and 1-(3-(dimethylamino)propyl)-ethylcarbodiimide (EDC; 0.2 M) (1/1, v/v) in water, followed by the injection of FGF-2 (50 ug/ml) in PBS buffer. The remaining active esters were quenched by ethanolamine (1.0 M). All measurements were performed using 0.01% Tween 20 PBS buffer. Aqueous NaCl (2.0 M) was employed for regeneration to achieve baseline status.

Heparanase Colorimetric Assays.

Fondaparinux colorimetric heparanase assays were carried out in 96 well microplates (NEST Scientific 96 Well Cell Culture Plate. 701002) pre-treated with a solution of 4% BSA in phosphate-buffered saline containing 0.05% Tween 20 (PBST) for 2 h at 37° C. Assay solutions (100 ul) contained sodium acetate buffer (40 mM, pH 5.0) and fondaparinux (100 mM, MedChem Express), heparanase (5 nM) and varying concentrations of compounds of interests or heparin. The mixture was kept at 37° C. for 20 h, which was followed by the addition of a solution of WST-1 (1.69 mM WST-1 in 0.1 M NaOH, 100 uL) and incubation at 60° C. for 1 h after which the absorbance at 584 nm was measured (Fluostar Optima platereader, BMG Labtech).

INCORPORATION BY REFERENCE

All publications, including but not limited to patents and patent applications, cited in this specification, to the extent that they provide exemplary procedural or other details supplementary to those set forth herein, are specifically incorporated herein by reference as if each individual publication were specifically and individually indicated to be incorporated by reference herein as though fully set forth.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A compound of Formula (I) or a pharmaceutically acceptable salt thereof:

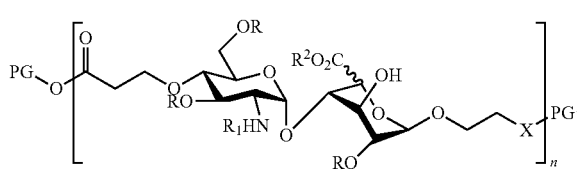
(I)

wherein, independently at each occurrence:
n is an integer from 1 to 40;
R is H, SO$_3$H, or SO$_3^-$;
R$_1$ is SO$_3$H, SO$_3^-$, or —C(O)CH$_3$;
R$^2$ is C$_{1-6}$ alkyl, H, or is a negative charge;
X is NH, S, or O;
PG$^1$ is H, Fmoc, —C(O)CH$_3$, —C(O)CF$_3$, and Boc; and
PG is H, C$_{1-6}$ alkyl, allyl or benzyl.

2. The compound of claim 1, wherein n is 1-20.
3. The compound of claim 2, wherein n is 1, 2, 3, 10, or 20.
4. The compound of claim 3, wherein the compound is:

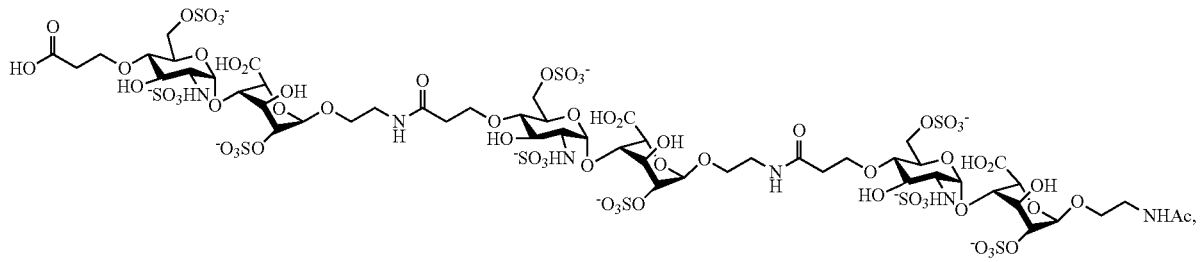
19b

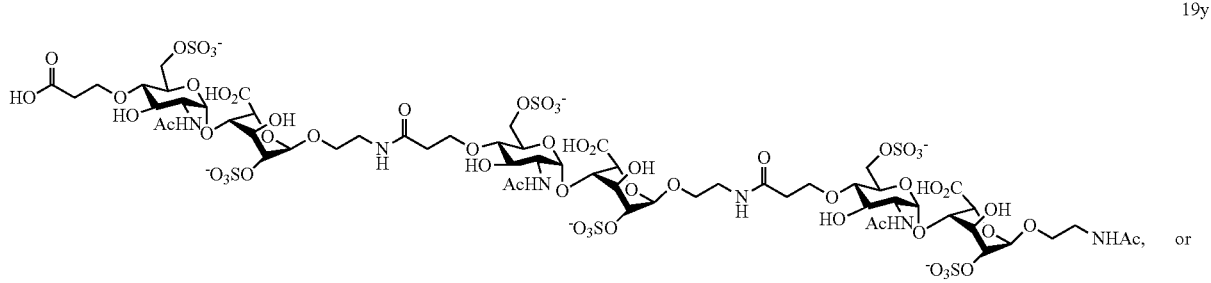
19y

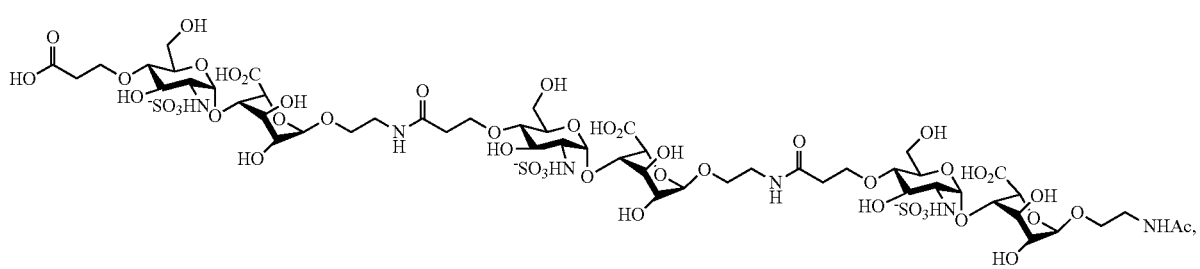
19i or a pharmaceutically acceptable salt thereof.

5. A pharmaceutical composition comprising a compound of claim 1 and a pharmaceutically acceptable excipient.

6. A method of mediating cell proliferation, cell differentiation, amyloid plaque formation, anti-coagulation, or neuronal growth in a subject in need thereof, comprising administering to the subject a therapeutically effective amount of a compound of claim 1.

7. A method of enhancing FGF-2 binding to FGF-R, the method comprising contacting a cell containing FGF-2 and FGF-R with a compound of claim 1.

8. A method of stimulating cell proliferation, the method comprising contacting a cell with a compound of claim 1.

9. A method of inhibiting blood coagulation, the method comprising the step of contacting a blood sample with a compound of claim 1.

10. A heparin mimetic comprising a compound of claim 1 or a pharmaceutically acceptable salt thereof.

11. A heparan mimetic comprising a compound of claim 1 or a pharmaceutically acceptable salt thereof.

12. A method of synthesizing a compound of formula 34

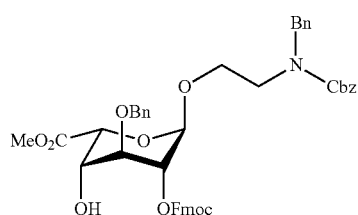
34 the method comprising:
(a1) treating a compound of formula 32

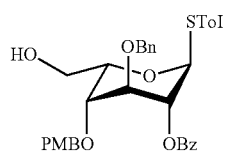
32 with TEMPO and BAIB in a first solvent, to provide a first product mixture;
(b1) treating the first product mixture with potassium carbonate and methyl iodide in a second solvent, to provide a second product mixture comprising a compound of formula 33

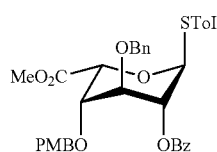
33

(c1) treating the compound of formula 33 with silver triflate, p-toluenesulfonyl chloride, and

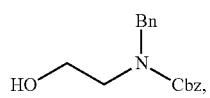

at a temperature from −78° C. to 0° C., to provide a third product mixture;
(d1) treating the third product mixture with NaOMe in a third solvent to provide a fourth product mixture;
(e1) treating the fourth product mixture with FmocCl and pyridine in a fourth solvent, to provide a fifth product mixture; and (f1) treating the fifth product mixture with DDQ in a fifth solvent to afford a sixth product mixture comprising the compound of formula 34;
or
a method of synthesizing a compound of formula 35

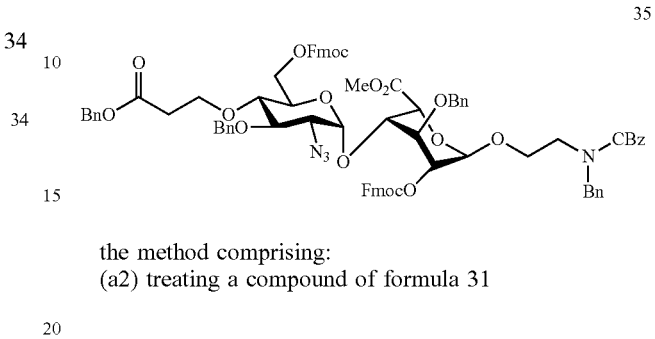
35 the method comprising:
(a2) treating a compound of formula 31

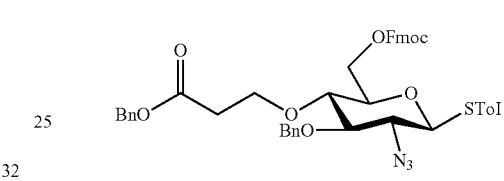
31 with a compound of formula 34

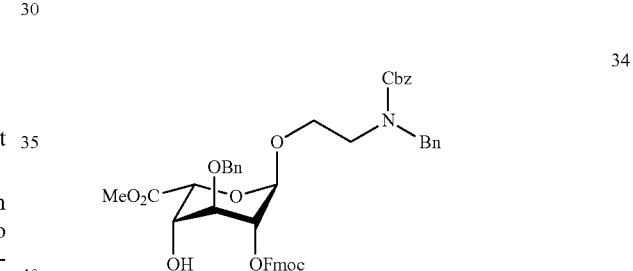
34 in the presence of silver triflate and p-toluenesulfonyl chloride, at a temperature from −78° C. to 0° C., to provide the compound of formula 35;
or
a method of synthesizing a compound of formula 31

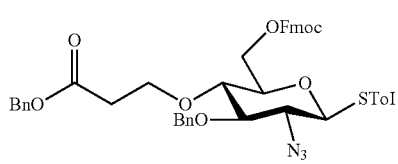
31 the method comprising:
(a3) treating a compound of formula 29

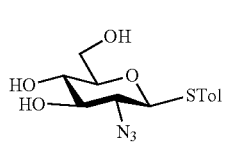
29 with anisaldehyde dimethyl acetal and CSA in acetonitrile, to afford a 23$^{rd}$ product mixture;
(b3) treating the 23$^{rd}$ product mixture with sodium hydride and BnBr in DMF, to afford a 24$^{th}$ product mixture;
(c3) treating the 24$^{th}$ product mixture with sodium cyanoborohydride and trifluoroacetic acid in DMF, to afford a 25$^{th}$ product mixture comprising a compound of formula 30

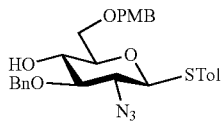

(d3) treating the 25$^{th}$ product mixture with allyl bromide and sodium hydride, to afford a 26$^{th}$ product mixture;

(e3) treating the 26$^{th}$ product mixture with 9-BBN, sodium hydroxide, and hydrogen peroxide, to afford a 27$^{th}$ product mixture;
(f3) treating the 27$^{th}$ product mixture with TEMPO and BAIB in dichloromethane and water, to afford a 28$^{th}$ product mixture;
(g3) treating the 28$^{th}$ product mixture with BnBr in DME, to afford a 29$^{th}$ product mixture;
(h3) treating the 29$^{th}$ product mixture with DDQ in dichloromethane and water to afford a 30$^{th}$ product mixture; and
(13) treating the 30$^{th}$ product mixture with FmocCl and pyridine in dichloromethane to afford a 31$^{st}$ product mixture comprising the compound of formula 31.

13. A method of making a compound of formula (Ia)

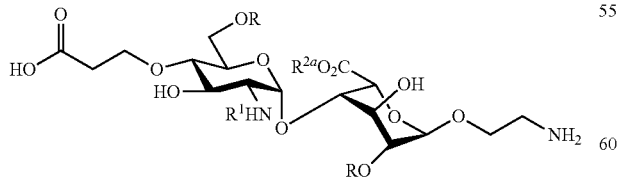

wherein, independently at each occurrence:
R is H, SO$_3$H, or SO$_3$;
R$^1$ is SO$_3$H, SO$_3^-$, or C(O) CH$_3$;
R$^{2a}$ is C$_{1-6}$ alkyl;

the method comprising:
(a1) treating a compound of formula 36

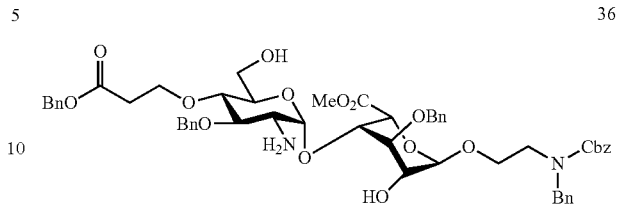

under sulfation conditions, to provide a seventh product mixture; and
(b1) treating the seventh product mixture under deprotection conditions to afford an eighth product mixture comprising the compound of formula (Ia);
or
a method of synthesizing a compound of formula (Id)

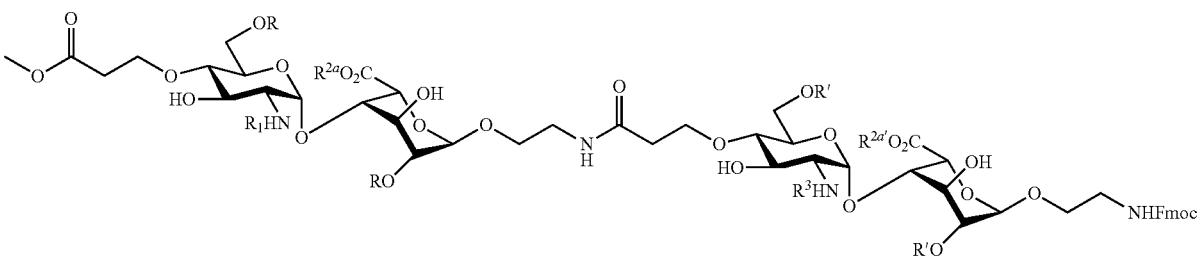

wherein, independently at each occurrence:
R is H, SO$_3$H, or SO$_3$;
R' is H, SO$_3$H, or SO$_3$;
R$^1$ is SO$_3$H, SO$_3$, or C(O) CH$_3$;
R$^3$ is SO$_3$H, SO$_3^-$, or C(O) CH$_3$;
R$^{2a}$ is C$_{1-6}$ alkyl;
R$^{2a'}$ is C$_{1-6}$ alkyl;
the method comprising:
(a2) reacting a compound of formula (Ib)

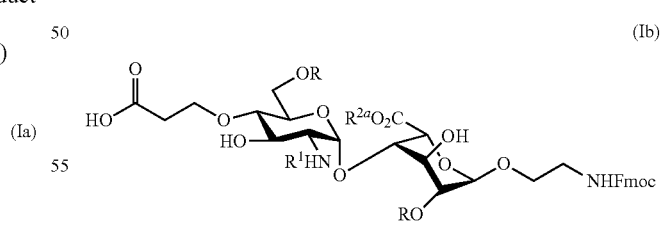

under esterification conditions to afford a thirteenth product mixture;
(b2) reacting the thirteenth product mixture under deprotection conditions, to afford a fourteenth product mixture; and
(c2) reacting the fourteenth product mixture with the compound of formula (Ib) under coupling conditions, to provide a fifteenth product mixture comprising the compound of formula (Id);

or a method of making a compound of formula (If)

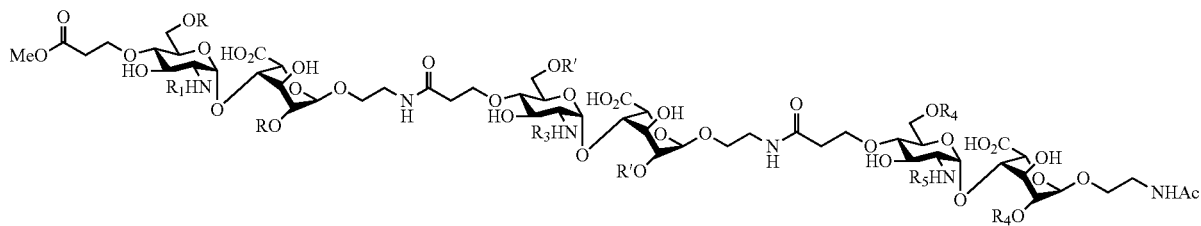

(If)

wherein, independently at each occurrence:
R is H, SO$_3$H, or SO$_3$;
R' is H, SO$_3$H, or SO$_3$;
R$^1$ is SO$_3$H, SO$_3$, or C(O) CH$_3$;
R$^3$ is SO$_3$H, SO$_3$, or C(O) CH$_3$;
the method comprising:
(a3) reacting a compound of formula (Id')

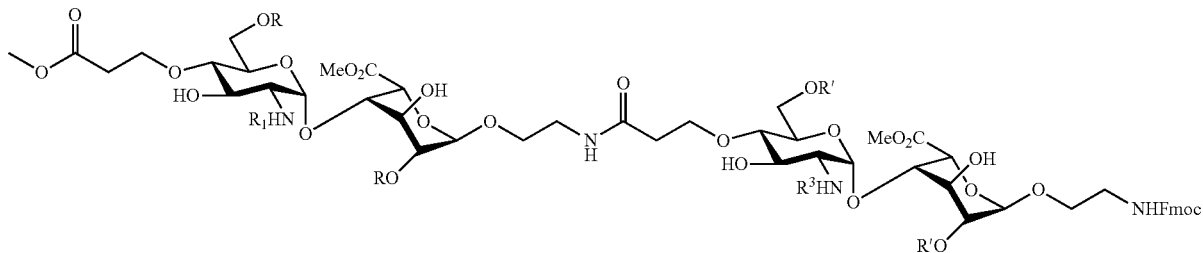

(Id')

under deprotection conditions, to afford a sixteenth product mixture comprising a compound of formula (Ie)

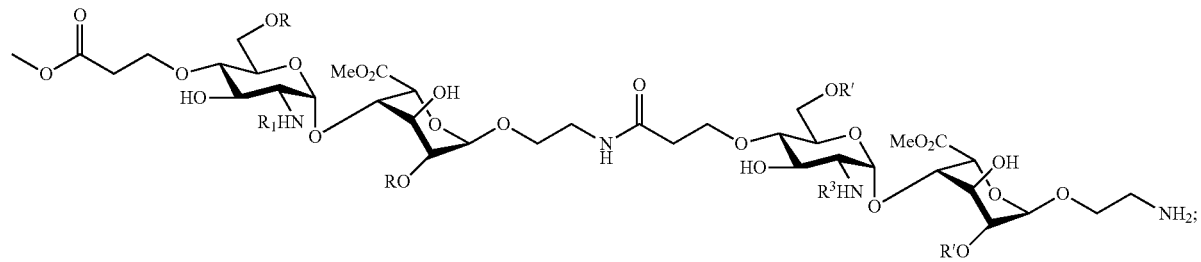

(Ie)

and (b3) reacting the sixteenth product mixture with a compound of formula (Ic)

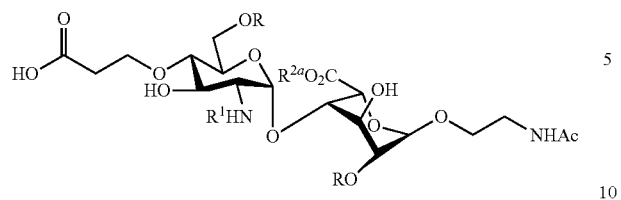

wherein $R^{2a}$ is Me,
under coupling conditions, to afford a seventeenth product mixture comprising the compound of formula (If).

14. The method of claim 13, wherein the compound of formula (Id) is a compound of formula (Id')

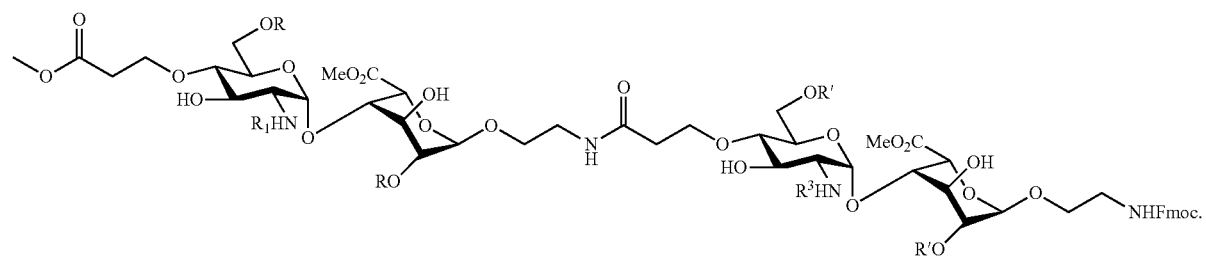

15. The method of claim 13, further comprising isolating the compound of formula (Ig) from the eighteenth product mixture, thereby obtaining substantially pure

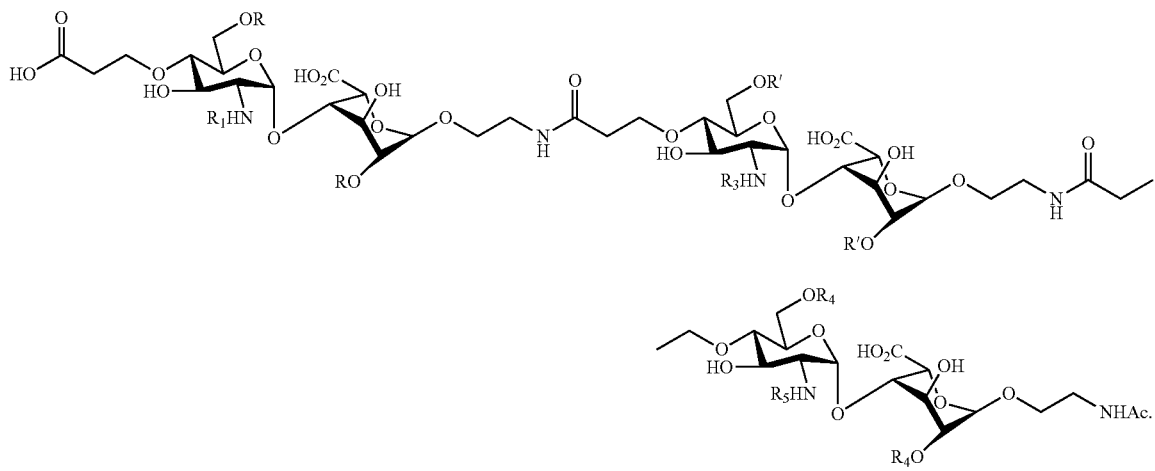

16. A method of synthesizing a compound of formula (I)

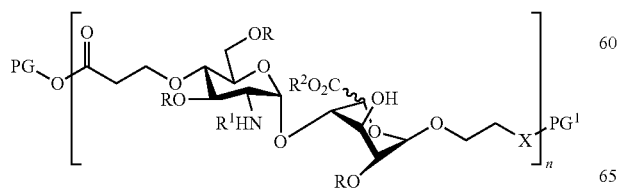

wherein, independently at each occurrence:
n is an integer from 1 to 40;
R is H, $SO_3H$, or $SO_3$;
$R^1$ is $SO_3H$, $SO_3''$, or —C(O)CH$_3$;
$R^2$ is $C_{1-6}$ alkyl, H, or is a negative charge;
X is NH, S, or O;
$PG^1$ is H, Fmoc, —C(O)CH$_3$, —C(O)CF$_3$, and Boc; and
PG is H, $C_{1-6}$ alkyl, allyl or benzyl;
the method comprising:
preparing a compound of formula (Id) according to the method of claim 13, and repeating steps (vi) and (vii) at least once, to obtain a nineteenth product mixture comprising the compound of formula (I).

* * * * *